US009006197B2

(12) United States Patent
Bumcrot et al.

(10) Patent No.: US 9,006,197 B2
(45) Date of Patent: Apr. 14, 2015

(54) COMPOSITIONS AND METHODS FOR INHIBITING EXPRESSION OF EG5 AND VEGF GENES

(75) Inventors: David Bumcrot, Belmont, MA (US);
Dinah Wen-Yee Sah, Boston, MA (US);
Ivanka Toudjarska, Medford, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/442,809

(22) Filed: Apr. 9, 2012

(65) Prior Publication Data

US 2013/0023577 A1  Jan. 24, 2013

Related U.S. Application Data

(63) Continuation of application No. 12/552,207, filed on Sep. 1, 2009, now abandoned, which is a continuation of application No. PCT/US2009/036223, filed on Mar. 5, 2009.

(60) Provisional application No. 61/150,664, filed on Feb. 6, 2009, provisional application No. 61/112,079, filed on Nov. 6, 2008, provisional application No. 61/086,381, filed on Aug. 5, 2008, provisional application No. 61/083,367, filed on Jul. 24, 2008, provisional application No. 61/034,019, filed on Mar. 5, 2008.

(51) Int. Cl.
*C12N 15/113* (2010.01)

(52) U.S. Cl.
CPC .......... *C12N 15/1136* (2013.01); *C12N 15/113* (2013.01); *C12N 2310/14* (2013.01); *C12N 2310/315* (2013.01); *C12N 2310/321* (2013.01); *C12N 2310/346* (2013.01); *C12N 2310/3515* (2013.01); *C12N 2320/31* (2013.01)

(58) Field of Classification Search
None
See application file for complete search history.

(56) References Cited

U.S. PATENT DOCUMENTS

| 7,427,605 | B2 | 9/2008 | Davis et al. |
|---|---|---|---|
| 7,718,629 | B2 | 5/2010 | Bumcrot et al. |
| 8,058,069 | B2 | 11/2011 | Yaworski et al. |
| 8,158,601 | B2 | 4/2012 | Chen et al. |
| 2003/0143732 | A1 | 7/2003 | Fosnaugh et al. |
| 2003/0170891 | A1 | 9/2003 | McSwiggen |
| 2004/0115201 | A1 | 6/2004 | Einat et al. |
| 2004/0209832 | A1 | 10/2004 | McSwiggen et al. |
| 2004/0259247 | A1 | 12/2004 | Tuschl et al. |
| 2005/0112141 | A1 | 5/2005 | Terman |
| 2006/0063751 | A1 | 3/2006 | Aquila et al. |
| 2006/0263435 | A1 | 11/2006 | Davis et al. |
| 2007/0004664 | A1 | 1/2007 | McSwiggen et al. |
| 2007/0031844 | A1 | 2/2007 | Khvorova et al. |
| 2007/0135372 | A1 | 6/2007 | MacLachlan et al. |
| 2007/0281899 | A1 | 12/2007 | Bumcrot et al. |
| 2008/0213350 | A1 | 9/2008 | Ko et al. |
| 2009/0099109 | A1 | 4/2009 | Shames et al. |
| 2009/0149403 | A1 | 6/2009 | MacLachlan |
| 2009/0291131 | A1 | 11/2009 | Maclachlan et al. |
| 2010/0267806 | A1 | 10/2010 | Bumcrot et al. |
| 2011/0015250 | A1 | 1/2011 | Bumcrot et al. |
| 2012/0244207 | A1 | 9/2012 | Fitzgerald et al. |

FOREIGN PATENT DOCUMENTS

| WO | WO 03/070918 A2 | 8/2003 |
|---|---|---|
| WO | WO 2004/065601 | 8/2004 |
| WO | WO 2004/080406 | 9/2004 |
| WO | WO 2004/090108 | 10/2004 |
| WO | WO 2005/014782 | 2/2005 |
| WO | WO 2005/089224 | 9/2005 |
| WO | WO 2007/012191 | 2/2007 |
| WO | WO 2007/115168 | 10/2007 |
| WO | WO 2010/147992 | 12/2010 |

OTHER PUBLICATIONS

Winstead, NCI Cancer Bulletin 2007, vol. 4, No. 19 [retrieved on Oct. 8, 2013]. Retrieved from the internet <URL: http://www.cancer.gov/ncicancerbulletin/archive/2007/061207/page2>.*
European Patent Office, Extended European Search Report, European Patent Application No. 12166396.7, Oct. 31, 2012, 8 Pages.
Harborth, J., et al., "Sequence, Chemical, and Structural Variation on Small Interfering RNAs and Short Hairpin RNAs and the Effect on Mammalian Gene Silencing," Antisense and Nucleic Acid Drug Development, vol. 13, pp. 83-105, 2003.
The State Intellectual Property Office of the People's Republic of China, Notification of the First Office Action, Chinese Patent Application No. 201080020483.1, Sep. 28, 2012, 14 Pages.
Agrawal, S., et al., "Antisense oligonucleotides: towards clinical trials." Trends in Biotechnology. Oct. 1996, vol. 14, pp. 376-387.
Bass, B., "The short answer," Nature, May 24, 2001, pp. 428-429, vol. 411.
Cui, W., et al., "OptiRNAi, an RNAi design tool," Computer Methods and Programs Biomedicine, 2004, vol. 75, p. 67-73.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in *Drosophila melanogaster* Embryo Lysate", The EMBO Journal, 2001, pp. 6877-6888, vol. 20, No. 23.

(Continued)

*Primary Examiner* — Tracy Vivlemore
(74) *Attorney, Agent, or Firm* — Fenwick & West LLP

(57) ABSTRACT

This invention relates to compositions containing double-stranded ribonucleic acid (dsRNA) in a SNALP formulation, and methods of using the compositions to inhibit the expression of the Eg5 and Vascular Endothelial Growth Factor (VEGF), and methods of using the compositions to treat pathological processes mediated by Eg5 and VEGF expression, such as cancer.

27 Claims, 24 Drawing Sheets

(56) References Cited

OTHER PUBLICATIONS

Elbashir, S., et al., "RNA Interference is Mediated by 21-and 22 Nucleotide RNAs," Genes & Development, 2001, pp. 188-200, vol. 15.
Examination Report for New Zealand Patent Application No. NZ 587704, Feb. 16, 2012, 2 Pages.
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in *Caenorhabditis elegans*," Nature, Feb. 19, 1998, pp. 806-811, vol. 391.
Haque, S., et al., "Monastrol, a Prototype Anti-Cancer Drug That Inhibits Mitotic Kinesin, Induces Rapid Bursts of Axonal Outgrowth From Cultured Postmitotic Neurons," Cell Motility and the Cytoskeleton, 2004, vol. 58, p. 10-16.
Japanese Patent Office, Notice of Reasons for Rejection, Japanese Patent Application No. 2009-503309, mailed Aug. 10, 2012, 10 pages.
Japanese Patent Office, Notice of Reasons for Rejection, Japanese Patent Application No. 2009-503309 mailed Mar. 28, 2012, 10 Pages.
Luo, L., et al., "Mechanism of Inhibition of Human KSP by Monastrol: Insights from Kinetic Analysis and the Effect of Ionic Strength on KSP Inhibition," Biochemistry, 2004, vol. 43, p. 15258-15266.
Office Action for U.S. Appl. No. 12/723,471, Jan. 19, 2012, 15 Pages.
Office Action for U.S. Appl. No. 12/723,471, May 22, 2012, 7 Pages.
Reynolds, et al. (2004) "Rational siRNA design for RNA interference," Nature Biotechnology, vol. 22, No. 3, pp. 326-330.
Robbins, M., et al., "Stable expression of shRNAs in human CD34[30] progenitor cells can avoid induction of interferon responses to siRNAs in vitro," Nature Biotechnology, May 2006, pp. 566-571, vol. 24, No. 5.
Rose, S., et al., "Functional polarity is introduced by Dicer processing of short substrate RNAs," Nucleic Acids Research, 2005, pp. 4140-4156, vol. 33, No. 13.
Sunder-Plassmann, N., et al., "Systhesis and biological evaluation of new tetrahydro-β-cardonlines as inhibitors of the mitotic kinesin Eg5," Bioorganic & Medicinal Chemistry, 2005, vol. 13, p. 6094-6111.
Takimoto, C., et al., "Safety and anti-tumor activity of sorafenib (Nexavar®) in combination with other anti-cancer agents: a review of clinical trials," Cancer Chemother. Pharmacol., 2008, vol. 61, pp. 535-548.
The State Intellectual Property Office of the People's Republic of China, Notification of the Third Office Action, Chinese Patent Application No. 200780018407.5, Aug. 31, 2012, 9 pages.
Tuschl T., "RNA Interference and Small Interfering RNAs" Chembiochem, 2001, pp. 239-245, vol. 2.
Tuschl, T., "Expanding small RNA interference," Nature Biotechnology, May 2002, pp. 446-448, vol. 20.
Tuschl, T., "Functional genomics: RNA sets the standard," Nature, Jan. 16, 2003, vol. 421, No. 6920, pp. 220-221.
Tuschl, T., "Mammalian RNA Interference," RNAi, A Guide to Gene Silencing, Chapter 13, G.J. Hannon (ed,), 2003, pp. 265-295.
Tuschl, T., et al., "Small Interfering RNAs: A Revolutionary Tool for the Analysis of Gene Function and Gene Therapy," Molecular Interventions, 2002, pp. 158-167, vol. 2, No. 3.
Tuschl, T., et al., "Targeted mRNA Degradation by Double-Stranded RNA In Vitro," Genes & Development, 1999, pp. 3191-3197, vol. 13.
Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.
Weil, et al (2002) "Targeting the Kinesin Eg5 to Monitor siRNA Transfection in Mammalian Cells," *Biotechniques* 33(6):1244-1248.
Zhu, A., "Development of Sorafenib and Other Molecularly Targeted Agents in Hepatocellular Carcinoma," Cancer, 2008, vol. 112, No. 2, pp. 250-259.
Zimmerman, et al. (2006) "RNAi-mediated gene silencing in non-human primates," *Nature*, vol. 441, May 4: 111-114.
Harborth, J., et al., "Identification of essential genes in cultured mammalian cells using small interfering RNAs," Journal of Cell Science, 2001, vol. 114, No. 24, pp. 4557-4565.
The State Intellectual Property Office of the People's Republic of China, Notification of Second Office Action, Chinese Patent Application No. 200980115656.5, Mar. 13, 2013, 13 pages.
Hornung, V., et al., "Sequence-specific potent induction of IFN-α by short interfering RNA in plasmacytoid dendritic cells through TLR7," Nature Medicine, Mar. 2005, pp. 263-270, vol. 11, No. 3.
NCBI, "*Homo sapiens* kinesin family member 11 (KIF11), mRNA," GenBank Accession No. NM_004523, Mar. 24, 2014, 6 Pages [online] [retrieved on Apr. 21, 204] Retrieved from the internet <URL:http://www.ncbi.nlm.nih.gov/nuccore/NM_004523>.
Office Action for U.S. Appl. No. 13/797,176 mailed on Mar. 21, 2014, 9 pages.
Office Action for U.S. Appl. No. 13/620,212 mailed on Feb. 6, 2014, 6 Pages.
Office Action for U.S. Appl. No. 12/723,471 mailed on Jan. 7, 2014, 7 pages.

\* cited by examiner

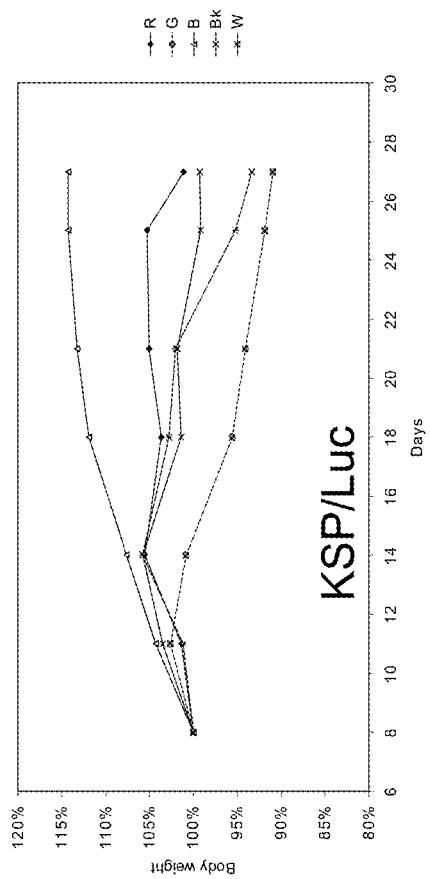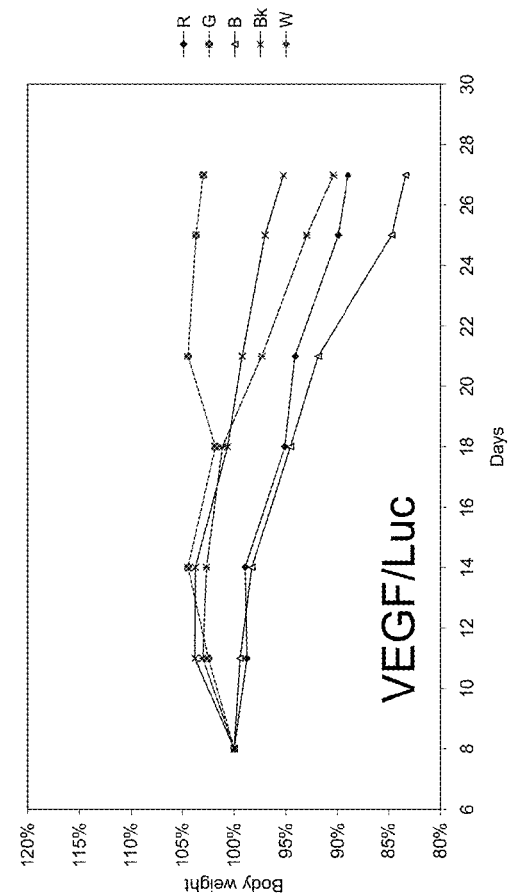
FIG. 2C
FIG. 2D

FIG. 11B
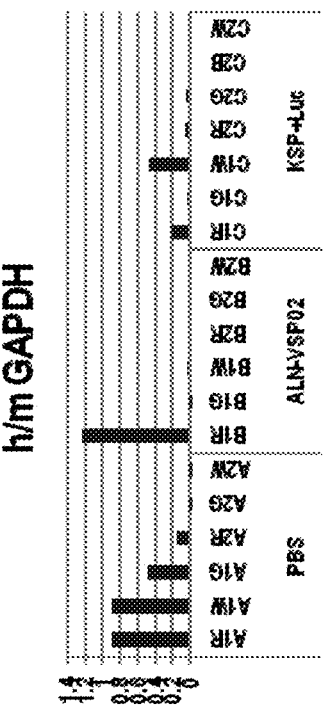
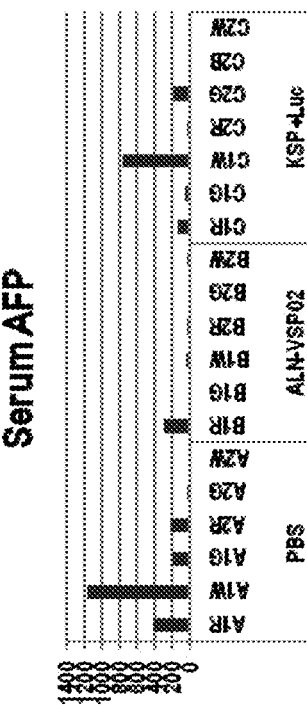
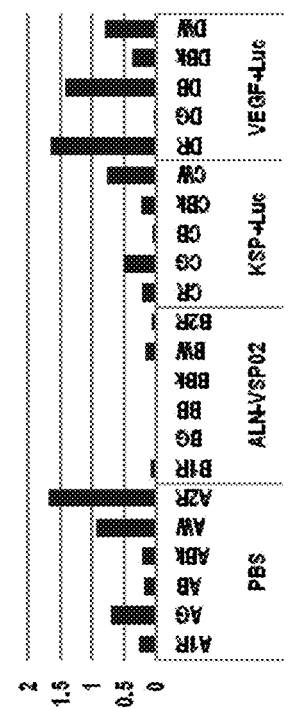
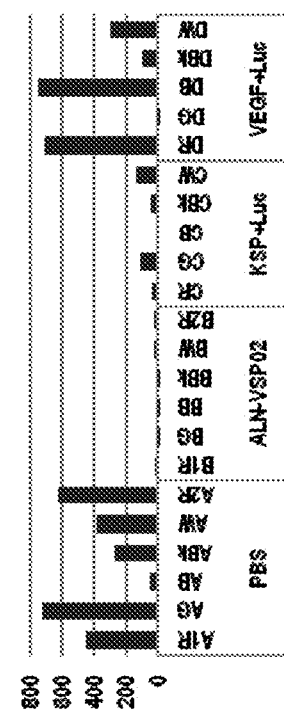

* 4 mg/kg dose
** 3 mg/kg dose

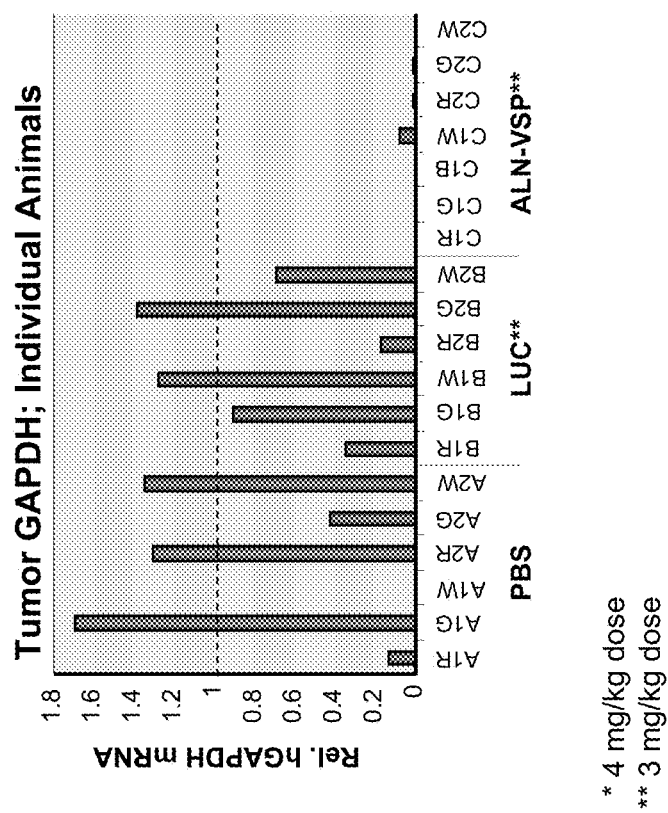

A. SNALP-VSP treated

B. SNALP-Luc treated

COMPOSITIONS AND METHODS FOR INHIBITING EXPRESSION OF EG5 AND VEGF GENES

RELATED APPLICATIONS

This application is a continuation of U.S. patent application Ser. No. 12/552,207, filed Sep. 1, 2009, which is a continuation of PCT Application No. PCT/US2009/036233, filed Mar. 5, 2009 which claims the benefit of U.S. Provisional Application No. 61/034,019, filed Mar. 5, 2008, and U.S. Provisional Application No. 61/083,367, filed Jul. 24, 2008, and U.S. Provisional Application No. 61/086,381, filed Aug. 5, 2008, and U.S. Provisional Application No. 61/112,079, filed Nov. 6, 2008, and U.S. Provisional Application No. 61/150,664, filed Feb. 6, 2009 which are hereby incorporated in their entirety by reference.

FIELD OF THE INVENTION

This invention relates to compositions containing double-stranded ribonucleic acid (dsRNA), and their use in mediating RNA interference to inhibit the expression of a combination of genes, e.g., the Eg5 and Vascular Endothelial Growth Factor (VEGF) genes formulated in SNALP, and the use of the compositions to treat pathological processes mediated by Eg5 and VEGF expression, such as cancer.

REFERENCE TO SEQUENCE LISTING

This application includes a Sequence Listing submitted electronically as a text file named 20876_sequence_listing.txt, created on Apr. 9, 2012, with a size of 640,482 bytes. The sequence listing is incorporated by reference.

BACKGROUND OF THE INVENTION

The maintenance of cell populations within an organism is governed by the cellular processes of cell division and programmed cell death. Within normal cells, the cellular events associated with the initiation and completion of each process is highly regulated. In proliferative disease such as cancer, one or both of these processes may be perturbed. For example, a cancer cell may have lost its regulation (checkpoint control) of the cell division cycle through either the overexpression of a positive regulator or the loss of a negative regulator, perhaps by mutation.

Alternatively, a cancer cell may have lost the ability to undergo programmed cell death through the overexpression of a negative regulator. Hence, there is a need to develop new chemotherapeutic drugs that will restore the processes of checkpoint control and programmed cell death to cancerous cells.

One approach to the treatment of human cancers is to target a protein that is essential for cell cycle progression. In order for the cell cycle to proceed from one phase to the next, certain prerequisite events must be completed. There are checkpoints within the cell cycle that enforce the proper order of events and phases. One such checkpoint is the spindle checkpoint that occurs during the metaphase stage of mitosis. Small molecules that target proteins with essential functions in mitosis may initiate the spindle checkpoint to arrest cells in mitosis. Of the small molecules that arrest cells in mitosis, those which display anti-tumor activity in the clinic also induce apoptosis, the morphological changes associated with programmed cell death. An effective chemotherapeutic for the treatment of cancer may thus be one which induces checkpoint control and programmed cell death. Unfortunately, there are few compounds available for controlling these processes within the cell. Most compounds known to cause mitotic arrest and apoptosis act as tubulin binding agents. These compounds alter the dynamic instability of microtubules and indirectly alter the function/structure of the mitotic spindle thereby causing mitotic arrest. Because most of these compounds specifically target the tubulin protein which is a component of all microtubules, they may also affect one or more of the numerous normal cellular processes in which microtubules have a role. Hence, there is also a need for agents that more specifically target proteins associated with proliferating cells.

Eg5 is one of several kinesin-like motor proteins that are localized to the mitotic spindle and known to be required for formation and/or function of the bipolar mitotic spindle. Recently, there was a report of a small molecule that disturbs bipolarity of the mitotic spindle (Mayer, T. U. et. al. 1999. Science 286(5441) 971-4, herein incorporated by reference). More specifically, the small molecule induced the formation of an aberrant mitotic spindle wherein a monoastral array of microtubules emanated from a central pair of centrosomes, with chromosomes attached to the distal ends of the microtubules. The small molecule was dubbed "monastrol" after the monoastral array. This monoastral array phenotype had been previously observed in mitotic cells that were immunodepleted of the Eg5 motor protein. This distinctive monoastral array phenotype facilitated identification of monastrol as a potential inhibitor of Eg5. Indeed, monastrol was further shown to inhibit the Eg5 motor-driven motility of microtubules in an in vitro assay. The Eg5 inhibitor monastrol had no apparent effect upon the related kinesin motor or upon the motor(s) responsible for golgi apparatus movement within the cell. Cells that display the monoastral array phenotype either through immunodepletion of Eg5 or monastrol inhibition of Eg5 arrest in M-phase of the cell cycle. However, the mitotic arrest induced by either immunodepletion or inhibition of Eg5 is transient (Kapoor, T. M., 2000. J Cell Biol 150(5) 975-80). Both the monoastral array phenotype and the cell cycle arrest in mitosis induced by monastrol are reversible. Cells recover to form a normal bipolar mitotic spindle, to complete mitosis and to proceed through the cell cycle and normal cell proliferation. These data suggest that an inhibitor of Eg5 which induced a transient mitotic arrest may not be effective for the treatment of cancer cell proliferation. Nonetheless, the discovery that monastrol causes mitotic arrest is intriguing and hence there is a need to further study and identify compounds which can be used to modulate the Eg5 motor protein in a manner that would be effective in the treatment of human cancers. There is also a need to explore the use of these compounds in combination with other antineoplastic agents.

VEGF (also known as vascular permeability factor, VPF) is a multifunctional cytokine that stimulates angiogenesis, epithelial cell proliferation, and endothelial cell survival. VEGF can be produced by a wide variety of tissues, and its overexpression or aberrant expression can result in a variety disorders, including cancers and retinal disorders such as age-related macular degeneration and other angiogenic disorders.

Recently, double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant or unwanted regulation of a gene.

SUMMARY OF THE INVENTION

Disclosed are compositions having two double-stranded ribonucleic acids (dsRNA) for inhibiting the expression of a human kinesin family member 11 (Eg5/KSP) and a human VEGF gene in a cell. The dsRNAs are formulated in a stable nucleic acid lipid particle (SNALP). Also disclosed are method for using the composition to decrease expression of Eg5/KSP and/or VEGF in a cell, and method of treatment of a disease, e.g., liver cancer, using the compositions of the invention.

Accordingly, disclosed herein is a composition having a first double-stranded ribonucleic acid (dsRNA) for inhibiting the expression of a human kinesin family member 11 (Eg5/KSP) gene in a cell and a second dsRNA for inhibiting expression of a human VEGF in a cell, wherein both said first and said second dsRNA are formulated in a stable nucleic acid lipid particle (SNALP); said first dsRNA consists of a first sense strand and a first antisense strand, and said first sense strand has a first sequence and said first antisense strand has a second sequence complementary to at least 15 contiguous nucleotides of SEQ ID NO: 1311 (5'-UCGAGAAUC-UAAACUAACU-3'), wherein said first sequence is complementary to said second sequence and wherein said first dsRNA is between 15 and 30 base pairs in length; and said second dsRNA consists of a second sense strand and a second antisense strand, said second sense strand having a third sequence and said second antisense strand having a fourth sequence complementary to at least 15 contiguous nucleotides of SEQ ID NO: 1538 (5'-GCACAUAG-GAGAGAUGAGCUU-3'), wherein said third sequence is complementary to said fourth sequence and wherein each strand is between 15 and 30 base pairs in length.

In some embodiments, the first antisense strand has a second sequence complementary to SEQ ID NO: 1311 (5'-UC-GAGAAUCUAAACUAACU-3') and the second antisense strand has a fourth sequence complementary to SEQ ID NO: 1538 (5'-GCACAUAGGAGAGAUGAGCUU-3'). In other embodiments, the first dsRNA consists of a sense strand consisting of SEQ ID NO: 1534 (5'-UCGAGAAUCUAAAC-UAACUTT-3') and an antisense strand consisting of SEQ ID NO: 1535 (5'-AGUUAGUUUAGAUUCUCGATT-3') and the second dsRNA consists of a sense strand consisting of SEQ ID NO:1536 (5'-GCACAUAGGAGAGAUGAGCUU-3'), and an antisense strand consisting of SEQ ID NO: 1537 (5'-AAGCUCAUCUCUCCUAUGUGCUG-3'). In further embodiments, each strand is modified as follows to include a 2'-O-methyl ribonucleotide as indicated by a lower case letter "c" or "u" and a phosphorothioate as indicated by a lower case letter "s": the first dsRNA consists of a sense strand consisting of SEQ ID NO: 1240 (5'-ucGAGAAucuAAAcuAAcuTsT-3'), and an antisense strand consisting of SEQ ID NO: 1241 (5'-AGUuAGUUuAGAUUCUCGATsT); the second dsRNA consists of a sense strand consisting of SEQ ID NO: 1242 (5'-GcAcAuAGGAGAGAuGAGCUsU-3') and an antisense strand consisting of SEQ ID NO: 1243 (5'-AAGCUcAUCU-CUCCuAuGuGCusG-3').

In some embodiments, the first dsRNA contains two overhangs and the second dsRNA contains an overhang at the 3' of the antisense and a blunt end at the 5' end of the antisense strand.

The first and second dsRNA can have at least one modified nucleotide. For example, each dsRNA can have at least one modified nucleotide chosen from the group of: a 2'-O-methyl modified nucleotide, a nucleotide having a 5'-phosphorothioate group, and a terminal nucleotide linked to a cholesteryl derivative or dodecanoic acid bisdecylamide group. The modified nucleotide can be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base having nucleotide. In some embodiments, the first and second dsRNA each comprise at least one 2'-O-methyl modified ribonucleotide and at least one nucleotide having a 5'-phosphorothioate group.

Each strand of each dsRNA can be, e.g., 19-23 bases in length, or, alternatively 21-23 bases in length. In one embodiment, each strand of the first dsRNA is 21 bases in length and the sense strand of the second dsRNA is 21 bases in length and the antisense strand of the second dsRNA is 23 bases in length.

In some embodiments, the first and second dsRNA are present in an equimolar ratio.

As described herein, the dsRNAs are formulated as SNALPS. In some embodiments, the SNALP formulation includes DLinDMA, cholesterol, DPPC, and PEG2000-C-DMA. For example, the SNALP can have the components in the proportions listed in Table 17.

The composition of the invention can be used to reduce expression of Eg5 and/or VAGF. In some embodiments, the composition of the invention, upon contact with a cell expressing Eg5, inhibits expression of Eg5 by at least 40, 50, 60, 70, 80, or by at least 90%. In other embodiments, the composition of the invention, upon contact with a cell expressing VEGF, inhibits expression of VEGF by at least 40, 50, 60, 70, 80, or by at least 90%. Administration of the composition to a cell can expression of both Eg5 and VEGF in said cell. The composition of claims 1-17, wherein the composition is administered in a nM concentration.

Administration of the composition of the invention to a cell can result in, e.g., an increase in mono-aster formation in the cell. Administration of the composition to a mammal can result in at least one effect selected from the group consisting of prevention of tumor growth, reduction in tumor growth, or prolonged survival in said mammal. The effect can be measured using at least one assay selected from the group consisting of determination of body weight, determination of organ weight, visual inspection, mRNA analysis, serum AFP analysis and survival monitoring. Included are compositions with these effect when administered in a nM concentration.

In a further embodiment the composition of the invention includes Sorafenib.

Also included in the invention are methods of suing the compositions of the invention. In one embodiment is are methods for inhibiting the expression of Eg5/KSP and VEGF in a cell by administering any of the compositions of the invention to the cell. Other embodiments are methods for preventing tumor growth, reducing tumor growth, or prolonging survival in a mammal in need of treatment for cancer by administering the composition to said mammal. In some embodiments the mammal has liver cancer, e.g., the mammal is a human with liver cancer. The method can include a further step of administering Sorafenib.

BRIEF DESCRIPTION OF THE FIGURES

FIGS. 2A-2D are graphs showing the effects of SNALP-siRNAs on body weight in a Hep3B mouse model.

FIG. 11B is a set of graphs showing the effects of SNALP-siRNAs on human GAPDH levels and serum AFP levels in a Hep3B mouse model.

FIGS. 12A-12C are graphs showing the effects of SNALP-siRNAs on tumor KSP, VEGF and GAPDH levels in a Hep3B mouse model.

DETAILED DESCRIPTION OF THE INVENTION

Figure 1:
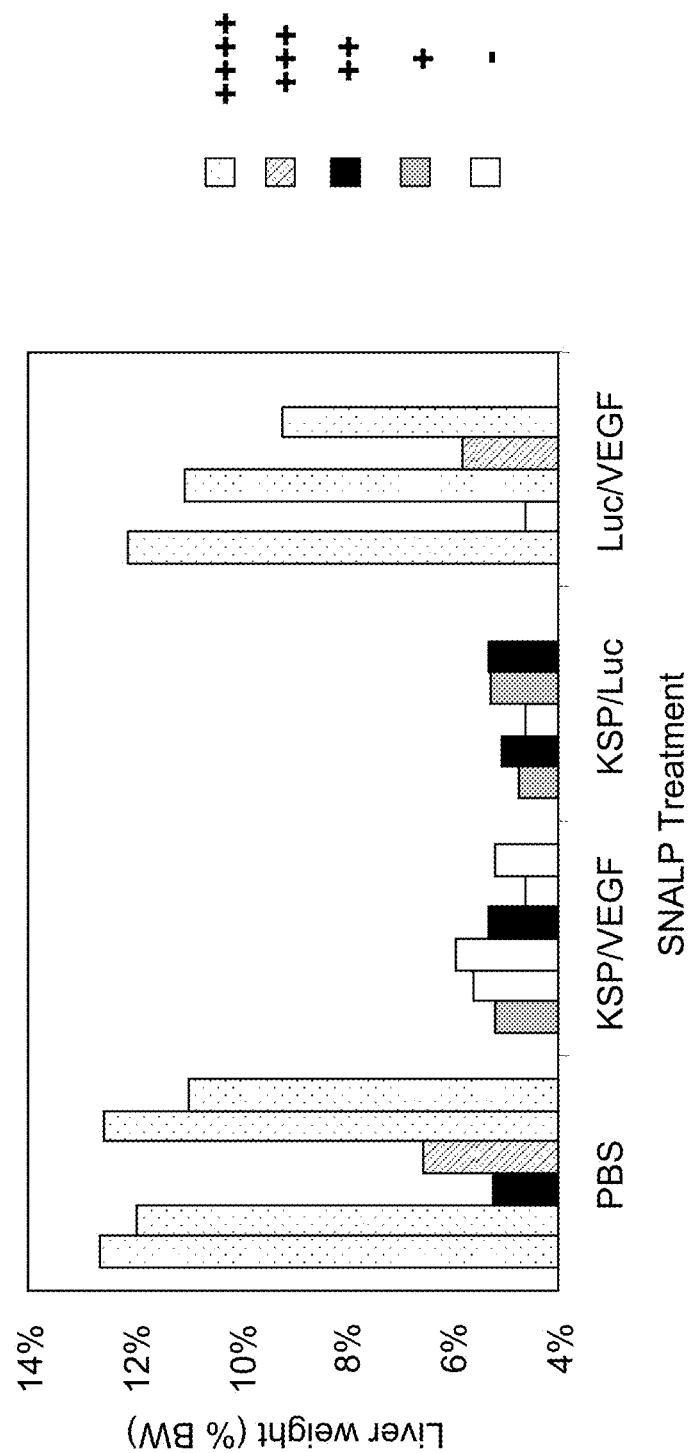
FIG. 1 is a graph showing liver weights as percentage of body weight following administration of SNALP-siRNAs in a Hep3B mouse model.
Figure 2B:
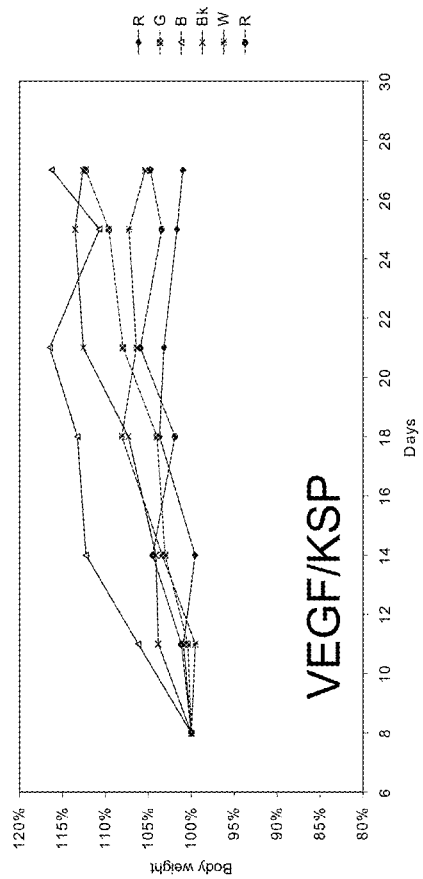
Figure 2A:
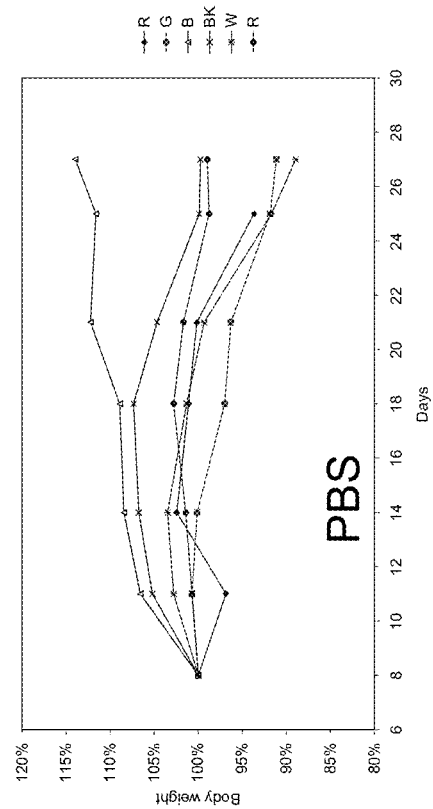

The invention provides compositions and methods for inhibiting the expression of the Eg5 gene and VEGF gene in a cell or mammal using the dsRNAs. The dsRNAs are preferably packaged in a stable nucleic acid particle (SNALP). The invention also provides compositions and methods for treating pathological conditions and diseases, such as liver cancer, in a mammal caused by the expression of the Eg5 gene and VEGF genes. The dsRNA directs the sequence-specific degradation of mRNA through a process known as RNA interference (RNAi).

The following detailed description discloses how to make and use the compositions containing dsRNAs to inhibit the expression of the Eg5 gene and VEGF genes, respectively, as well as compositions and methods for treating diseases and disorders caused by the expression of these genes, such as cancer. The pharmaceutical compositions featured in the invention include a dsRNA having an antisense strand comprising a region of complementarity which is less than 30 nucleotides in length, generally 19-24 nucleotides in length, and is substantially complementary to at least part of an RNA transcript of the Eg5 gene, together with a pharmaceutically acceptable carrier. The compositions featured in the invention also include a dsRNA having an antisense strand having a region of complementarity which is less than 30 nucleotides in length, generally 19-24 nucleotides in length, and is substantially complementary to at least part of an RNA transcript of the VEGF gene.

Accordingly, certain aspects of the invention provide pharmaceutical compositions containing the Eg5 and VEGF dsRNAs and a pharmaceutically acceptable carrier, methods of using the compositions to inhibit expression of the Eg5 gene and the VEGF gene respectively, and methods of using the pharmaceutical compositions to treat diseases caused by expression of the Eg5 and VEGF genes.

I. DEFINITIONS

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. In another example, adenine and cytosine anywhere in the oligonucleotide can be replaced with guanine and uracil, respectively to form G-U Wobble base pairing with the target mRNA. Sequences comprising such replacement moieties are embodiments of the invention.

As used herein, "Eg5" refers to the human kinesin family member 11, which is also known as KIF11, Eg5, HKSP, KSP, KNSL1 or TRIP5. Eg5 sequence can be found as NCBI GeneID:3832, HGNC ID: HGNC:6388 and RefSeq ID number:NM_004523. The terms "Eg5" and "KSP" and "Eg5/KSP are used interchangeably As used herein, VEGF, also known as vascular permeability factor, is an angiogenic growth factor. VEGF is a homodimeric 45 kDa glycoprotein that exists in at least three different isoforms. VEGF isoforms are expressed in endothelial cells. The VEGF gene contains 8 exons that express a 189-amino acid protein isoform. A 165-amino acid isoform lacks the residues encoded by exon 6, whereas a 121-amino acid isoform lacks the residues encoded by exons 6 and 7. VEGF145 is an isoform predicted to contain 145 amino acids and to lack exon 7. VEGF can act on endothelial cells by binding to an endothelial tyrosine kinase receptor, such as Flt-1 (VEGFR-1) or KDR/flk-1 (VEGFR-2). VEGFR-2 is expressed in endothelial cells and is involved in endothelial cell differentiation and vasculogenesis. A third receptor, VEGFR-3, has been implicated in lymphogenesis.

The various isoforms have different biologic activities and clinical implications. For example, VEGF145 induces angiogenesis and like VEGF189 (but unlike VEGF165) VEGF 145 binds efficiently to the extracellular matrix by a mechanism that is not dependent on extracellular matrix-associated heparin sulfates. VEGF displays activity as an endothelial cell mitogen and chemoattractant in vitro and induces vascular permeability and angiogenesis in vivo. VEGF is secreted by a wide variety of cancer cell types and promotes the growth of tumors by inducing the development of tumor-associated vasculature. Inhibition of VEGF function has been shown to limit both the growth of primary experimental tumors as well as the incidence of metastases in immunocompromised mice. Various dsRNAs directed to VEGF are described in co-pending U.S. Ser. Nos. 11/078,073 and 11/340,080, which are hereby incorporated by reference in their entirety.

As used herein, "target sequence" refers to a contiguous portion of the nucleotide sequence of an mRNA molecule formed during the transcription of the Eg5/KSP and/or VEGF gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., encoding Eg5/KSP and/or VEGF) including a 5' UTR, an open reading frame (ORF), or a 3' UTR. For example, a polynucleotide is complementary to at least a part of a Eg5 mRNA if the sequence is substantially complementary to a non-interrupted portion of a mRNA encoding Eg5.

The term "double-stranded RNA" or "dsRNA", as used herein, refers to a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs. In general, the majority of nucleotides of each strand are ribonucleotides, but as described in detail herein, each or both strands can also include at least one non-ribonucleotide, e.g., a deoxyribonucleotide and/or a modified nucleotide. In addition, as used in this specification, "dsRNA" may include chemical modifications to ribonucleotides, including substantial modifications at multiple nucleotides and including all types of modifications disclosed herein or known in the art. Any such modifications, as used in an siRNA type molecule, are encompassed by "dsRNA" for the purposes of this specification and claims.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule. In some embodiments the dsRNA can have a nucleotide overhang at one end of the duplex and a blunt end at the other end.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally the most tolerated mismatches are in the terminal regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

As used herein, the term "SNALP" refers to a stable nucleic acid-lipid particle. A SNALP represents a vesicle of lipids coating a reduced aqueous interior comprising a nucleic acid such as an iRNA agent or a plasmid from which an iRNA agent is transcribed.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of" "down-regulate the expression of," "suppress the expression of" and the like in as far as they refer to the Eg5 and/or VEGF gene, herein refer to the at least partial suppression of the expression of the Eg5 gene, as manifested by a reduction of the amount of Eg5 mRNA and/or VEGF mRNA which may be isolated from a first cell or group of cells in which the Eg5 and/or VEGF gene is transcribed and which has or have been treated such that the expression of the Eg5 and/or VEGF gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to Eg5 and/or VEGF gene expression, e.g. the amount of protein encoded by the Eg5 and/or VEGF gene which is produced by a cell, or the number of cells displaying a certain phenotype, e.g. apoptosis. In principle, target gene silencing can be determined in any cell expressing the target, either constitutively or by genomic engineering, and by any appropriate assay. However, when a reference is needed in order to determine whether a given dsRNA inhibits the expression of the Eg5 gene by a certain degree and therefore is encompassed by the instant invention, the assay provided in the Examples below shall serve as such reference.

For example, in certain instances, expression of the Eg5 gene (or VEGF gene) is suppressed by at least about 5%, 10%, 15%, 20%, 25%, 30%, 35%, 40%, 45%, or 50% by administration of the double-stranded oligonucleotide of the invention. In some embodiments, the Eg5 and/or VEGF gene is suppressed by at least about 60%, 70%, or 80% by administration of the double-stranded oligonucleotide of the invention. In other embodiments, the Eg5 and/or VEGF gene is suppressed by at least about 85%, 90%, or 95% by administration of the double-stranded oligonucleotide of the invention. The Tables and Example below provides values for inhibition of expression using various Eg5 and/or VEGF dsRNA molecules at various concentrations.

As used herein in the context of Eg5 expression (or VEGF expression), the terms "treat", "treatment", and the like, refer to relief from or alleviation of pathological processes mediated by Eg5 and/or VEGF expression. In the context of the present invention insofar as it relates to any of the other conditions recited herein below (other than pathological processes mediated by Eg5 and/or VEGF expression), the terms "treat", "treatment", and the like mean to relieve or alleviate at least one symptom associated with such condition, or to slow or reverse the progression of such condition, such as the slowing and progression of hepatic carcinoma.

As used herein, the phrases "therapeutically effective amount" and "prophylactically effective amount" refer to an amount that provides a therapeutic benefit in the treatment, prevention, or management of pathological processes mediated by Eg5 and/or VEGF expression or an overt symptom of pathological processes mediated by Eg5 and/or VEGF expression. The specific amount that is therapeutically effective can be readily determined by ordinary medical practitioner, and may vary depending on factors known in the art, such as, e.g. the type of pathological processes mediated by Eg5 and/or VEGF expression, the patient's history and age, the stage of pathological processes mediated by Eg5 and/or VEGF expression, and the administration of other anti-pathological processes mediated by Eg5 and/or VEGF expression agents.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. As described in more detail below, such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. DOUBLE-STRANDED RIBONUCLEIC ACID (DSRNA)

As described in more detail below, the invention provides double-stranded ribonucleic acid (dsRNA) molecules for inhibiting the expression of the Eg5 and/or VEGF gene in a cell or mammal, wherein the dsRNA comprises an antisense strand comprising a region of complementarity which is complementary to at least a part of an mRNA formed in the expression of the Eg5 and/or VEGF gene, and wherein the region of complementarity is less than 30 nucleotides in length, generally 19-24 nucleotides in length, and wherein said dsRNA, upon contact with a cell expressing said Eg5 and/or VEGF gene, inhibits the expression of said Eg5 and/or VEGF gene.

The dsRNA can be synthesized by standard methods known in the art as further discussed below, e.g., by use of an automated DNA synthesizer, such as are commercially available from, for example, Biosearch, Applied Biosystems, Inc.

The dsRNA comprises two strands that are sufficiently complementary to hybridize to form a duplex structure. One strand of the dsRNA (the antisense strand) comprises a region of complementarity that is substantially complementary, and generally fully complementary, to a target sequence, derived from the sequence of an mRNA formed during the expression of the Eg5 and/or VEGF gene, the other strand (the sense strand) comprises a region which is complementary to the antisense strand, such that the two strands hybridize and form a duplex structure when combined under suitable conditions. Generally, the duplex structure is between 15 and 30, more generally between 18 and 25, yet more generally between 19 and 24, and most generally between 19 and 21 base pairs in length. In other embodiments the duplex structure is 25-30 base pairs in length.

In one embodiment the duplex is 19 base pairs in length. In another embodiment the duplex is 21 base pairs in length. When two different siRNAs are used in combination, the duplex lengths can be identical or can differ. For example, a composition can include a first dsRNA targeted to Eg5 with a duplex length of 19 base pairs and a second dsRNA targeted to VEGF with a duplex length of 21 base pairs.

Similarly, the region of complementarity to the target sequence is between 15 and 30, more generally between 18 and 25, yet more generally between 19 and 24, and most generally between 19 and 21 nucleotides in length. In other embodiments the region of complementarity is 25-30 nucleotides in length.

In one embodiment the region of complementarity is 19 nucleotides in length. In another embodiment the region of complementarity is 21 nucleotides in length. When two different siRNAs are used in combination, the region of complementarity can be identical or can differ. For example, a composition can include a first dsRNA targeted to Eg5 with a region of complementarity of 19 nucleotides and a second dsRNA targeted to VEGF with a region of complementarity of 21 nucleotides.

Each strand of the dsRNA of invention is generally between 15 and 30, or between 18 and 25, or 18, 19, 20, 21, 22, 23, or 24 nucleotides in length. In other embodiments, each is strand is 25-30 base pairs in length. Each strand of the duplex can be the same length or of different lengths. When two different siRNAs are used in combination, the lengths of each strand of each siRNA can be identical or can differ. For example, a composition can include a dsRNA targeted to Eg5 with a sense strand of 21 nucleotides and an antisense strand of 21 nucleotides, and a second dsRNA targeted to VEGF with a sense strand of 21 nucleotides and an antisense strand of 23 nucleotides.

The dsRNA of the invention can include one or more single-stranded overhang(s) of one or more nucleotides. In one embodiment, at least one end of the dsRNA has a single-stranded nucleotide overhang of 1 to 4, generally 1 or 2 nucleotides. In another embodiment, the antisense strand of the dsRNA has 1-10 nucleotides overhangs each at the 3' end and the 5' end over the sense strand. In further embodiments, the sense strand of the dsRNA has 1-nucleotides overhangs each at the 3' end and the 5' end over the antisense strand.

A dsRNAs having at least one nucleotide overhang can have unexpectedly superior inhibitory properties than the blunt-ended counterpart. In some embodiments the presence of only one nucleotide overhang strengthens the interference activity of the dsRNA, without affecting its overall stability. A dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA can also have a blunt end, generally located at the 5'-end of the antisense strand. Such dsRNAs can have improved stability and inhibitory activity, thus allowing administration at low dosages, i.e., less than 5 mg/kg body weight of the recipient per day. Generally, the antisense strand of the dsRNA has a nucleotide overhang at the 3'-end, and the 5'-end is blunt. In another embodiment, one or more of the nucleotides in the overhang is replaced with a nucleoside thiophosphate.

As described in more detail herein, the composition of the invention includes a first dsRNA targeting Eg5 and a second dsRNA targeting VEGF. The first and second dsRNA can have the same overhang architecture, e.g., number of nucleotide overhangs on each strand, or each dsRNA can have a different architecture. In one embodiment, the first dsRNA targeting Eg5 includes a 2 nucleotide overhang at the 3' end of each strand and the second dsRNA targeting VEGF includes a 2 nucleotide overhang on the 3' end of the antisense strand and a blunt end at the 5' end of the antisense strand (e.g., the 3' end of the sense strand).

In one embodiment, the Eg5 gene targeted by the dsRNA of the invention is the human Eg5 gene. In one embodiment, the antisense strand of the dsRNA targeting Eg5 comprises at least 15 contiguous nucleotides of one of the antisense sequences of Table 1-3. In specific embodiments, the first sequence of the dsRNA is selected from one of the sense strands of Tables 1-3 and the second sequence is selected from the group consisting of the antisense sequences of Tables 1-3. Alternative antisense agents that target elsewhere in the target sequence provided in Tables 1-3 can readily be determined using the target sequence and the flanking Eg5 sequence. In some embodiments the dsRNA targeted to Eg5 will comprise at least two nucleotide sequence selected from the groups of sequences provided in Tables 1-3. One of the two sequences is complementary to the other of the two sequences, with one of the sequences being substantially complementary to a sequence of an mRNA generated in the expression of the Eg5 gene. As such, the dsRNA will comprises two oligonucleotides, wherein one oligonucleotide is described as the sense strand in Tables 1-3 and the second oligonucleotide is described as the antisense strand in Tables 1-3

In embodiments using a second dsRNA targeting VEGF, such agents are exemplified in the Examples, Tables 4a and 4b, and in co-pending U.S. Ser. Nos. 11/078,073 and 11/340,080, herein incorporated by reference. In one embodiment the dsRNA targeting VEGF has an antisense strand complementary to at least 15 contiguous nucleotides of the VEGF target sequences described in Table 4a. In other embodiments, the dsRNA targeting VEGF comprises one of the antisense sequences of Table 4b, or one of the sense sequences of Table 4b, or comprises one of the duplexes (sense and antisense strands) of Table 4b.

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Tables 1-3, the dsRNAs of the invention can comprise at least one strand of a length of minimally 21 nt. It can be reasonably expected that shorter dsRNAs comprising one of the sequences of Tables 1-3 minus only a few nucleotides on one or both ends may be similarly effective as compared to the dsRNAs described above. Hence, dsRNAs comprising a partial sequence of at least 15, 16, 17, 18, 19, 20, or more contiguous nucleotides from one of the sequences of Tables 1-3, and differing in their ability to inhibit the expression of the Eg5 gene in a FACS assay as described herein below by not more than 5, 10, 15, 20, 25, or 30% inhibition from a dsRNA comprising the full sequence, are contemplated by the invention. Further dsRNAs that cleave within the target sequence provided in Tables 1-3 can readily be made using the Eg5 sequence and the target sequence provided. Additional dsRNA targeting VEGF can be designed in a similar matter using the sequences disclosed in Tables 4a and 4b, the Examples and co-pending U.S. Ser. Nos. 11/078,073 and 11/340,080, herein incorporated by reference.

In addition, the RNAi agents provided in Tables 1-3 identify a site in the Eg5 mRNA that is susceptible to RNAi based cleavage. As such the present invention further includes RNAi agents, e.g., dsRNA, that target within the sequence targeted by one of the agents of the present invention. As used herein a second RNAi agent is said to target within the sequence of a first RNAi agent if the second RNAi agent cleaves the message anywhere within the mRNA that is complementary to the antisense strand of the first RNAi agent. Such a second agent will generally consist of at least 15 contiguous nucleotides from one of the sequences provided in Tables 1-3 coupled to additional nucleotide sequences taken from the region contiguous to the selected sequence in the Eg5 gene. For example, the last 15 nucleotides of SEQ ID NO: 1 combined with the next 6 nucleotides from the target Eg5 gene produces a single strand agent of 21 nucleotides that is based on one of the sequences provided in Tables 1-3. Additional RNAi agents, e.g., dsRNA, targeting VEGF can be designed in a similar matter using the sequences disclosed in Tables 4a and 4b, the Examples and co-pending U.S. Ser. Nos. 11/078,073 and 11/340,080, herein incorporated by reference.

The dsRNA of the invention can contain one or more mismatches to the target sequence. In a preferred embodiment, the dsRNA of the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the Eg5 gene, the dsRNA generally does not contain any mismatch within the central 13 nucleotides. The methods described within the invention can be used to determine whether a dsRNA containing a mismatch to a target sequence is effective in inhibiting the expression of the Eg5 gene. Consideration of the efficacy of dsRNAs with mismatches in inhibiting expression of the Eg5 gene is important, especially if the particular region of complementarity in the Eg5 gene is known to have polymorphic sequence variation within the population.

Modifications

In yet another embodiment, the dsRNA is chemically modified to enhance stability. The nucleic acids of the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Specific examples of preferred dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Preferred modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is herein incorporated by reference Preferred modified dsRNA backbones that do not include a phosphorus atom therein have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other preferred dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, an dsRNA mimetic that has been shown to have excellent hybridization properties, is referred to as a peptide nucleic acid (PNA). In PNA compounds, the sugar backbone of an dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Most preferred embodiments of the invention are dsRNAs with phosphorothioate backbones and oligonucleosides with heteroatom backbones, and in particular —$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. Also preferred are dsRNAs having morpholino backbone structures of the above-referenced U.S. Pat. No. 5,034,506.

Modified dsRNAs may also contain one or more substituted sugar moieties. Preferred dsRNAs comprise one of the following at the 2' position: OH; F; O-, S-, or N-alkyl; O-, S-, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$OCH$_3$, O($CH_2$)$_n$NH$_2$, O($CH_2$)$_n$CH$_3$, O($CH_2$)$_n$ONH$_2$, and O($CH_2$)$_n$ON[($CH_2$)$_n$CH$_3$)]$_2$, where n and m are from 1 to about 10. Other preferred dsRNAs comprise one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxy-alkoxy group. A further preferred modification includes 2'-dimethylaminooxyethoxy, i.e., a O(CH$_2$)$_2$ON (CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$, also described in examples herein below.

Other preferred modifications include 2'-methoxy (2'-OCH$_3$), 2'-aminopropoxy (2'-OCH$_2$CH$_2$CH$_2$NH$_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

DsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosine's, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., DsRNA Research and Applications, CRC Press, Boca Raton, 1993, pp. 276-278) and are presently preferred base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, each of which is herein incorporated by reference, and U.S. Pat. No. 5,750,692, also herein incorporated by reference.

Conjugates

Another modification of the dsRNAs of the invention involves chemically linking to the dsRNA one or more moieties or conjugates which enhance the activity, cellular distribution or cellular uptake of the dsRNA. Such moieties include but are not limited to lipid moieties such as a cholesterol moiety (Letsinger et al., Proc. Natl. Acid. Sci. USA, 199, 86, 6553-6556), cholic acid (Manoharan et al., Biorg. Med. Chem. Let., 1994 4 1053-1060), a thioether, e.g., beryl-5-tritylthiol (Manoharan et al., Ann. N.Y. Acad. Sci., 1992, 660, 306-309; Manoharan et al., Biorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Representative U.S. patents that teach the preparation of such dsRNA conjugates include, but are not limited to, U.S. Pat. Nos. 4,828,979; 4,948,882; 5,218,105; 5,525,465; 5,541, 313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of an dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Lett., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate.

In some cases, a ligand can be multifunctional and/or a dsRNA can be conjugated to more than one ligand. For example, the dsRNA can be conjugated to one ligand for improved uptake and to a second ligand for improved release.

Vector Encoded RNAi Agents

In another aspect of the invention, Eg5 and VEGF specific dsRNA molecules that are expressed from transcription units inserted into DNA or RNA vectors (see, e.g., Couture, A, et al., TIG. (1996), 12:5-10; Skillern, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., Proc. Natl. Acad. Sci. USA (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In a preferred embodiment, a dsRNA is expressed as an inverted repeat joined by a linker polynucleotide sequence such that the dsRNA has a stem and loop structure.

The recombinant dsRNA expression vectors are generally DNA plasmids or viral vectors. dsRNA expressing viral vectors can be constructed based on, but not limited to, adeno-associated virus (for a review, see Muzyczka, et al., *Curr. Topics Micro. Immunol.* (1992) 158:97-129)); adenovirus (see, for example, Berkner, et al., *BioTechniques* (1998) 6:616), Rosenfeld et al. (1991, *Science* 252:431-434), and Rosenfeld et al. (1992, *Cell* 68:143-155)); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, *Proc. Natl. Acad. Sci. USA* (1998) 85:6460-6464; Wilson et al., 1988, *Proc. Natl. Acad. Sci. USA* 85:3014-3018; Armentano et al., 1990, *Proc. Natl. Acad. Sci. USA* 87:61416145; Huber et al., 1991, *Proc. Natl. Acad. Sci. USA* 88:8039-8043; Ferry et al., 1991, *Proc. Natl. Acad. Sci. USA* 88:8377-8381; Chowdhury et al., 1991, *Science* 254:1802-1805; van Beusechem. et al., 1992, *Proc. Natl. Acad. Sci. USA* 89:7640-19; Kay et al., 1992, *Human Gene Therapy* 3:641-647; Dai et al., 1992, *Proc. Natl. Acad. Sci. USA* 89:10892-10895; Hwu et al., 1993, *J. Immunol.* 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

Any viral vector capable of accepting the coding sequences for the dsRNA molecule(s) to be expressed can be used, for example vectors derived from adenovirus (AV); adeno-associated virus (AAV); retroviruses (e.g., lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Preferred viral vectors are those derived from AV and AAV. In a particularly preferred embodiment, the dsRNA of the invention is expressed as two separate, complementary single-stranded RNA molecules from a recombinant AAV vector having, for example, either the U6 or H1 RNA promoters, or the cytomegalovirus (CMV) promoter.

A suitable AV vector for expressing the dsRNA of the invention, a method for constructing the recombinant AV vector, and a method for delivering the vector into target cells, are described in Xia H et al. (2002), Nat. Biotech. 20: 1006-1010.

Suitable AAV vectors for expressing the dsRNA of the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or generally RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g., the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Generally, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single EG5 gene (or VEGF gene) or multiple Eg5 genes (or VEGF genes) over a period of a week or more are also contemplated by the invention. Successful introduction of the vectors of the invention into host cells can be monitored using various known methods. For example, transient transfection. can be signaled with a reporter, such as a fluorescent marker, such as Green Fluorescent Protein (GFP). Stable transfection of ex vivo cells can be ensured using markers that provide the transfected cell with resistance to specific environmental factors (e.g., antibiotics and drugs), such as hygromycin B resistance.

The Eg5 specific dsRNA molecules and VEGF specific dsRNA molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Pharmaceutical Compositions Containing dsRNA

In one embodiment, the invention provides pharmaceutical compositions containing a dsRNA, as described herein, and a pharmaceutically acceptable carrier and methods of administering the same. The pharmaceutical composition containing the dsRNA is useful for treating a disease or disorder associated with the expression or activity of a Eg5/KSP and/or VEGF gene, such as pathological processes mediated by Eg5/KSP and/or VEGF expression, e.g., liver cancer. Such pharmaceutical compositions are formulated based on the mode of delivery.

Dosage

The pharmaceutical compositions featured herein are administered in dosages sufficient to inhibit expression of EG5/KSP and/or VEGF genes. In general, a suitable dose of dsRNA will be in the range of 0.01 to 200.0 milligrams per kilogram body weight of the recipient per day, generally in the range of 1 to 50 mg per kilogram body weight per day. For example, the dsRNA can be administered at 0.01 mg/kg, 0.05 mg/kg, 0.5 mg/kg, 1 mg/kg, 1.5 mg/kg, 2 mg/kg, 3 mg/kg, 5.0 mg/kg, 10 mg/kg, 20 mg/kg, 30 mg/kg, 40 mg/kg, or 50 mg/kg per single dose.

The pharmaceutical composition can be administered once daily, or the dsRNA may be administered as two, three, or more sub-doses at appropriate intervals throughout the day. The effect of a single dose on EG5/KSP AND/OR VEGF levels is long lasting, such that subsequent doses are administered at not more than 7 day intervals, or at not more than 1, 2, 3, or 4 week intervals.

In some embodiments the dsRNA is administered using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art and are particularly useful for delivery of agents at a particular site, such as could be used with the agents of the present invention. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by EG5/KSP AND/OR VEGF expression. Such models are used for in vivo testing of dsRNA, as well as for determining a therapeutically effective dose. A suitable mouse model is, for example, a mouse containing a plasmid expressing human EG5/KSP AND/OR VEGF. Another suitable mouse model is a transgenic mouse carrying a transgene that expresses human EG5/KSP AND/OR VEGF.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured in the invention lies generally within a range of circulating concentrations that include the ED50 with little or no toxicity. The dosage may vary within this range depending upon the dosage form employed and the route of administration utilized. For any compound used in the methods featured in the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration, as discussed above, the dsRNAs featured in the invention can be administered in combination with other known agents effective in treatment of pathological processes mediated by target gene expression. In any event, the administering physician can adjust the amount and timing of dsRNA administration on the basis of results observed using standard measures of efficacy known in the art or described herein.

Administration

The pharmaceutical compositions of the present invention may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal, and subdermal, oral or parenteral, e.g., subcutaneous.

Typically, when treating a mammal with hyperlipidemia, the dsRNA molecules are administered systemically via parental means. Parenteral administration includes intravenous, intra-arterial, subcutaneous, intraperitoneal or intramuscular injection or infusion; or intracranial, e.g., intraparenchymal, intrathecal or intraventricular, administration. For example, dsRNAs, conjugated or unconjugate or formulated with or without liposomes, can be administered intravenously to a patient. For such, a dsRNA molecule can be formulated into compositions such as sterile and non-sterile aqueous solutions, non-aqueous solutions in common solvents such as alcohols, or solutions in liquid or solid oil bases. Such solutions also can contain buffers, diluents, and other suitable additives. For parenteral, intrathecal, or intraventricular administration, a dsRNA molecule can be formulated into compositions such as sterile aqueous solutions, which also can contain buffers, diluents, and other suitable additives (e.g., penetration enhancers, carrier compounds, and other pharmaceutically acceptable carriers). Formulations are described in more detail herein.

The dsRNA can be delivered in a manner to target a particular tissue, such as the liver (e.g., the hepatocytes of the liver).

Formulations

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. In one aspect are formulations that target the liver when treating hepatic disorders such as hyperlipidemia.

In addition, dsRNA that target the EG5/KSP AND/OR VEGF gene can be formulated into compositions containing the dsRNA admixed, encapsulated, conjugated, or otherwise associated with other molecules, molecular structures, or mixtures of nucleic acids. For example, a composition containing one or more dsRNA agents that target the Eg5/KSP and/or VEGF gene can contain other therapeutic agents such as other cancer therapeutics or one or more dsRNA compounds that target non-EG5/KSP AND/OR VEGF genes.

Oral, Parenteral, Topical, and Biologic Formulations

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which dsRNAs featured in the invention are administered in conjunction with one or more penetration enhancers surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, U.S. patent publication. No. 20030027780, and U.S. Pat. No. 6,747,014, each of which is incorporated herein by reference.

Compositions and formulations for parenteral, intraparenchymal (into the brain), intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Suitable topical formulations include those in which the dsRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). DsRNAs featured in the invention may be encapsulated within liposomes or may form complexes thereto, in particular to cationic liposomes. Alternatively, dsRNAs may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference. In addition, dsRNA molecules can be administered to a mammal as biologic or abiologic means as described in, for example, U.S. Pat. No. 6,271,359. Abiologic delivery can be accomplished by a variety of methods including, without limitation, (1) loading liposomes with a dsRNA acid molecule provided herein and (2) complexing a dsRNA molecule with lipids or liposomes to form nucleic acid-lipid or nucleic acid-liposome complexes. The liposome can be composed of cationic and neutral lipids commonly used to transfect cells in vitro. Cationic lipids can complex (e.g., charge-associate) with negatively charged nucleic acids to form liposomes. Examples of cationic liposomes include, without limitation, lipofectin, lipofectamine, lipofectace, and DOTAP. Procedures for forming liposomes are well known in the art. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine. Numerous lipophilic agents are commercially available, including Lipofectin™ (Invitrogen/Life Technologies, Carlsbad, Calif.) and Effectene™ (Qiagen, Valencia, Calif.). In addition, systemic delivery methods can be optimized using commercially available cationic lipids such as DDAB or DOTAP, each of which can be mixed with a neutral lipid such as DOPE or cholesterol. In some cases, liposomes such as those described by Templeton et al. (Nature Biotechnology, 15: 647-652 (1997)) can be used. In other embodiments, polycations such as polyethyleneimine can be used to achieve delivery in vivo and ex vivo (Boletta et al., J. Am. Soc. Nephrol. 7: 1728 (1996)). Additional information regarding the use of liposomes to deliver nucleic acids can be found in U.S. Pat. No. 6,271,359, PCT Publication WO 96/40964 and Morrissey, D. et al. 2005. Nat. Biotechnol. 23(8):1002-7.

Biologic delivery can be accomplished by a variety of methods including, without limitation, the use of viral vectors. For example, viral vectors (e.g., adenovirus and herpesvirus vectors) can be used to deliver dsRNA molecules to liver cells. Standard molecular biology techniques can be used to introduce one or more of the dsRNAs provided herein into one of the many different viral vectors previously developed to deliver nucleic acid to cells. These resulting viral vectors can be used to deliver the one or more dsRNAs to cells by, for example, infection.

Characterization of Formulated dsRNAs

Formulations prepared by either the in-line mixing or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total siRNA concentration in the formulation, as well as the entrapped fraction, is estimated using a dye exclusion assay. A sample of the formulated siRNA can be incubated with an RNA-binding dye, such as Ribogreen (Molecular Probes) in the presence or absence of a formulation disrupting surfactant, e.g., 0.5% Triton-X100. The total siRNA in the formulation can be determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Liposomal Formulations

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/po-lyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_M1$ or a galactocerebroside sulfate ester. U.S. Pat. No. 5,543,152 (Webb et al.) discloses liposomes comprising sphingomyelin. Liposomes comprising 1,2-sn-dimyristoylphosphat-idylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{1215G}$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

SNALPs

In one embodiment, a dsRNA featured in the invention is fully encapsulated in the lipid formulation to form a SPLP, pSPLP, SNALP, or other nucleic acid-lipid particle. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The cationic lipid may be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA) or analogs thereof, or a mixture thereof. The cationic lipid may comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid may be from about 5 mol % to about 90 mol %, about 10 mol %, or about 58 mol % if cholesterol is included, of the total lipid present in the particle.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles may be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

LNP01

In one embodiment, the lipidoid ND98.4HCl (MW 1487) (Formula 1), Cholesterol (Sigma-Aldrich), and PEG-Ceramide C16 (Avanti Polar Lipids) can be used to prepare lipid-siRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous siRNA (e.g., in sodium acetate pH 5) such that the final ethanol concentration is about 35-45% and the final sodium acetate concentration is about 100-300 mM. Lipid-siRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

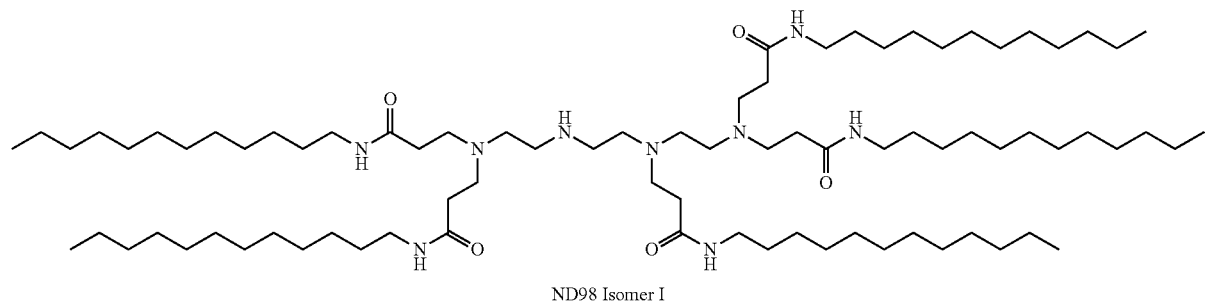

ND98 Isomer I

LNP01 formulations are described, e.g., in International Application Publication No. WO 2008/042973, which is hereby incorporated by reference.

Emulsions

The compositions of the present invention may be prepared and formulated as emulsions. Emulsions are typically heterogeneous systems of one liquid dispersed in another in the form of droplets usually exceeding 0.1 μm in diameter (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in *Remington's Pharmaceutical Sciences, Mack Publishing Co., Easton, Pa.,* 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of dsRNAs and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids.

Microemulsions of the present invention may also contain additional components and additives such as sorbitan monostearate (Grill 3), Labrasol, and penetration enhancers to improve the properties of the formulation and to enhance the absorption of the dsRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Penetration Enhancers

In one embodiment, the present invention employs various penetration enhancers to effect the efficient delivery of nucleic acids, particularly dsRNAs, to the skin of animals. Most drugs are present in solution in both ionized and non-ionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of dsRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carryier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents: Chelating agents, as used in connection with the present invention, can be defined as compounds that remove metallic ions from solution by forming complexes therewith, with the result that absorption of dsRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of dsRNAs through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of dsRNAs at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers dsRNAs of the present invention can be formulated in a pharmaceutically acceptable carrier or diluent. A "pharmaceutically acceptable carrier" (also referred to herein as an "excipient") is a pharmaceutically acceptable solvent, suspending agent, or any other pharmacologically inert vehicle. Pharmaceutically acceptable carriers can be liquid or solid, and can be selected with the planned manner of administration in mind so as to provide for the desired bulk, consistency, and other pertinent transport and chemical properties. Typical pharmaceutically acceptable carriers include, by way of example and not limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The co-administration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is co-administered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Combination Therapy

In one aspect, a composition of the invention can be used in combination therapy. The term "combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g., HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g., MET, RON, SEA, SEX); insulin receptor (e.g. IGFI-R); Eph (e.g. CEK5, CEK8, EBK, ECK, EEK, EHK-I, EHK-2, ELK, EPH, ERK, HEK, MDK2, MDK5, SEK); AxI (e.g. Mer/Nyk, Rse); RET; and platelet-derived growth factor receptor (PDGFR) (e.g. PDGFα-R, PDGβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. $p43^{abl}$, ARG); BTK (e.g. ITK/EMT, TEC); CSK, FAK, FPS, JAK, SRC, BMX, FER, CDK and SYK.

In another aspect of the invention, the subject compounds may be administered in combination with one or more agents that modulate non-kinase biological targets or processes. Such targets include histone deacetylases (HDAC), DNA methyltransferase (DNMT), heat shock proteins (e.g., HSP90), and proteosomes.

In one embodiment, subject compounds may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafenib, CNF2024, RG108, BMS387032, Affinitak, Avastin, Herceptin, Erbitux, AG24322, PD325901, ZD6474, PD 184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplasties such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA). In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more adjunctive therapeutic agents. Examples of suitable agents for adjunctive therapy include steroids, such as corticosteroids (amcinonide, betamethasone, betamethasone dipropionate, betamethasone valerate, budesonide, clobetasol, clobetasol acetate, clobetasol butyrate, clobetasol 17-propionate, cortisone, deflazacort, desoximetasone, diflucortolone valerate, dexamethasone, dexamethasone sodium phosphate, desonide, furoate, fluocinonide, fluocinolone acetonide, halcinonide, hydrocortisone, hydrocortisone butyrate, hydrocortisone sodium succinate, hydrocortisone valerate, methyl prednisolone, mometasone, prednicarbate, prednisolone, triamcinolone, triamcinolone acetonide, and halobetasol proprionate); a 5HTi agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an NKi antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilizing antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor α; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an H2-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

The compounds of the invention can be co-administered with siRNA that target other genes. For example, a compound of the invention can be co-administered with an siRNA targeted to a c-Myc gene. In one example, AD-12115 can be co-administered with a c-Myc siRNA. Examples of c-Myc targeted siRNAs are disclosed in U.S. patent application Ser. No. 12/373,039 which is herein incorporated by reference.

Methods for Treating Diseases Caused by Expression of the Eg5 and VEGF Genes

The invention relates in particular to the use of a composition containing at least two dsRNAs, one targeting an Eg5 gene, and one targeting a VEGF gene, for the treatment of a cancer, such as liver cancer, e.g., for inhibiting tumor growth and tumor metastasis. For example, a composition, such as pharmaceutical composition, may be used for the treatment of solid tumors, like intrahepatic tumors such as may occur in cancers of the liver. A composition containing a dsRNA targeting Eg5 and a dsRNA targeting VEGF may also be used to treat other tumors and cancers, such as breast cancer, lung cancer, head and neck cancer, brain cancer, abdominal cancer, colon cancer, colorectal cancer, esophagus cancer, gastrointestinal cancer, glioma, tongue cancer, neuroblastoma, osteosarcoma, ovarian cancer, pancreatic cancer, prostate cancer, retinoblastoma, Wilm's tumor, multiple myeloma and for the treatment of skin cancer, like melanoma, for the treatment of lymphomas and blood cancer. The invention further relates to the use of a composition containing an Eg5 dsRNA and a VEGF dsRNA for inhibiting accumulation of ascites fluid and pleural effusion in different types of cancer, e.g., liver cancer, breast cancer, lung cancer, head cancer, neck cancer, brain cancer, abdominal cancer, colon cancer, colorectal cancer, esophagus cancer, gastrointestinal cancer, glioma, tongue cancer, neuroblastoma, osteosarcoma, ovarian cancer, pancreatic cancer, prostate cancer, retinoblastoma, Wilm's tumor, multiple myeloma, skin cancer, melanoma, lymphomas and blood cancer. Owing to the inhibitory effects on Eg5 and VEGF expression, a composition according to the invention or a pharmaceutical composition prepared therefrom can enhance the quality of life.

In one embodiment, a patient having a tumor associated with AFP expression, or a tumor secreting AFP, e.g., a hepatoma or teratoma, is treated. In certain embodiments, the patient has a malignant teratoma, an endodermal sinus tumor (yolk sac carcinoma), a neuroblastoma, a hepatoblastoma, a heptocellular carcinoma, testicular cancer or ovarian cancer.

The invention furthermore relates to the use of a dsRNA or a pharmaceutical composition thereof, e.g., for treating cancer or for preventing tumor metastasis, in combination with other pharmaceuticals and/or other therapeutic methods, e.g., with known pharmaceuticals and/or known therapeutic methods, such as, for example, those which are currently employed for treating cancer and/or for preventing tumor metastasis. Preference is given to a combination with radiation therapy and chemotherapeutic agents, such as cisplatin, cyclophosphamide, 5-fluorouracil, adriamycin, daunorubicin or tamoxifen.

The invention can also be practiced by including with a specific RNAi agent, in combination with another anti-cancer chemotherapeutic agent, such as any conventional chemotherapeutic agent. The combination of a specific binding agent with such other agents can potentiate the chemotherapeutic protocol. Numerous chemotherapeutic protocols will present themselves in the mind of the skilled practitioner as being capable of incorporation into the method of the invention. Any chemotherapeutic agent can be used, including alkylating agents, antimetabolites, hormones and antagonists, radioisotopes, as well as natural products. For example, the compound of the invention can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of a tetracycline compound with another treatment modality, e.g., surgery, radiation, etc., also referred to herein as "adjunct antineoplastic modalities." Thus, the method of the invention can be employed with such conventional regimens with the benefit of reducing side effects and enhancing efficacy.

Methods for Inhibiting Expression of the Eg5 Gene and the VEGF Gene

In yet another aspect, the invention provides a method for inhibiting the expression of the Eg5 gene and the VEGF gene in a mammal. The method includes administering a composition featured in the invention to the mammal such that expression of the target Eg5 gene and the target VEGF gene is silenced.

In one embodiment, a method for inhibiting Eg5 gene expression and VEGF gene expression includes administering a composition containing two different dsRNA molecules, one having a nucleotide sequence that is complementary to at least a part of an RNA transcript of the Eg5 gene and the other having a nucleotide sequence that is complementary to at least a part of an RNA transcript of the VEGF gene of the mammal to be treated. When the organism to be treated is a mammal such as a human, the composition may be administered by any means known in the art including, but not limited to oral or parenteral routes, including intravenous, intramuscular, subcutaneous, transdermal, airway (aerosol), nasal, rectal, and topical (including buccal and sublingual) administration. In preferred embodiments, the compositions are administered by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1 dsRNA Synthesis

Source of Reagents

Where the source of a reagent is not specifically given herein, such reagent may be obtained from any supplier of reagents for molecular biology at a quality/purity standard for application in molecular biology.

siRNA Synthesis

For screening of dsRNA, single-stranded RNAs were produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

Conjugates

The following is a prophetic description of the synthesis of 3'-cholesterol-conjugated siRNAs (herein referred to as -Chol-3'), an appropriately modified solid support was used for RNA synthesis. The modified solid support was prepared as follows:

Diethyl-2-azabutane-1,4-dicarboxylate AA

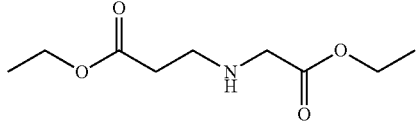

AA

A 4.7 M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until completion of the reaction was ascertained by TLC. After 19 h the solution was partitioned with dichloromethane (3×100 mL). The organic layer was dried with anhydrous sodium sulfate, filtered and evaporated. The residue was distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

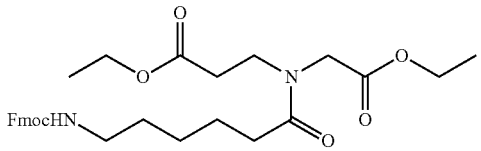

AB

Fmoc-6-amino-hexanoic acid (9.12 g, 25.83 mmol) was dissolved in dichloromethane (50 mL) and cooled with ice. Diisopropylcarbodiimde (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. Completion of the reaction was ascertained by TLC. The reaction mixture was concentrated under vacuum and ethyl acetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

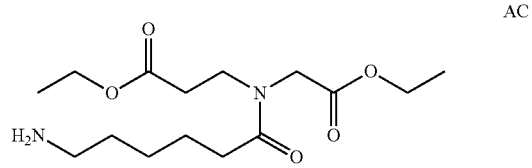 [SMILES: CCOC(=O)CCN(CC(=O)OCC)C(=O)CCCCCN]

AC

3-{Ethoxycarbonylmethyl-[6-(9H-fluoren-9-ylmethoxy-carbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated under vacuum, water was added to the residue, and the product was extracted with ethyl acetate. The crude product was purified by conversion into its hydrochloride salt.

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD

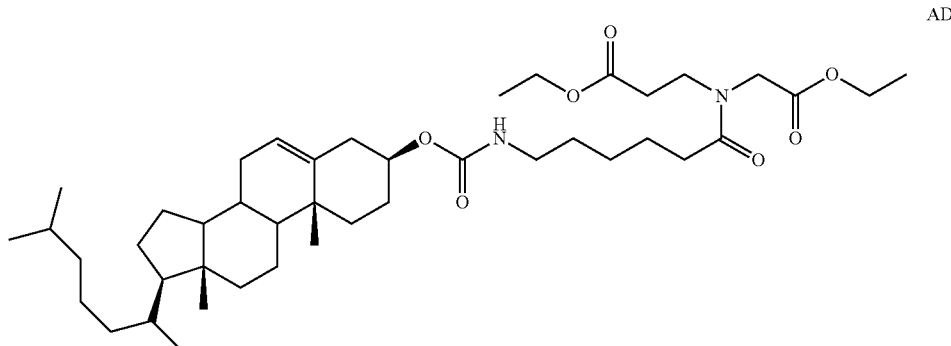

AD

The hydrochloride salt of 3-[(6-Amino-hexanoyl)-ethoxycarbonylmethyl-amino]-propionic acid ethyl ester AC (4.7 g, 14.8 mmol) was taken up in dichloromethane. The suspension was cooled to 0° C. on ice. To the suspension diisopropyl-ethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (10.3 g, 92%).

1-{6-[17-(1,5-Dimethyl-hexyl)-10,13-dimethyl-2,3,
4,7,8,9,10,11,12,13,14,15,16,17-tetradecahydro-1H-
cyclopenta[a]phenanthren-3-yloxycarbonylamino]-
hexanoyl}-4-oxo-pyrrolidine-3-carboxylic acid ethyl
ester AE

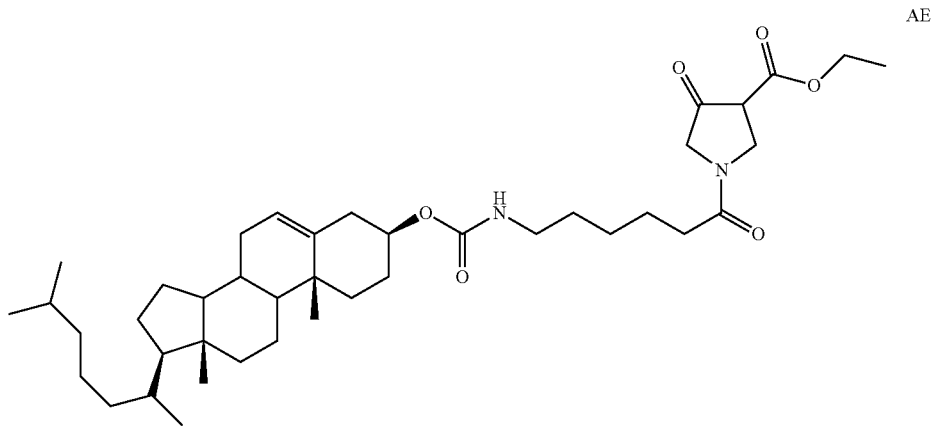 [SMILES: CCOC(=O)C1CN(C(=O)CCCCCNC(=O)O[C@H]2CC[C@@]3(C)C(=CCC4C3CC[C@@]3(C)C4CC[C@@H]3C(C)CCCC(C)C)C2)CC1=O]

Potassium t-butoxide (1.1 g, 9.8 mmol) was slurried in 30 mL of dry toluene. The mixture was cooled to 0° C. on ice and 5 g (6.6 mmol) of diester AD was added slowly with stirring within 20 mins. The temperature was kept below 5° C. during the addition. The stirring was continued for 30 mins at 0° C. and 1 mL of glacial acetic acid was added, immediately followed by 4 g of NaH$_2$PO$_4$.H$_2$O in 40 mL of water The resultant mixture was extracted twice with 100 mL of dichloromethane each and the combined organic extracts were washed twice with 10 mL of phosphate buffer each, dried, and evaporated to dryness. The residue was dissolved in 60 mL of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to dryness. The residue was purified by column chromatography using 25% ethylacetate/hexane to afford 1.9 g of b-ketoester (39%).

[6-(3-Hydroxy-4-hydroxymethyl-pyrrolidin-1-yl)-6-
oxo-hexyl]-carbamic acid 17-(1,5-dimethyl-hexyl)-
10,13-dimethyl-2,3,4,7,8,9,10,11,12,13,14,15,16,17-
tetradecahydro-1H-cyclopenta[a]phenanthren-3-yl
ester AF

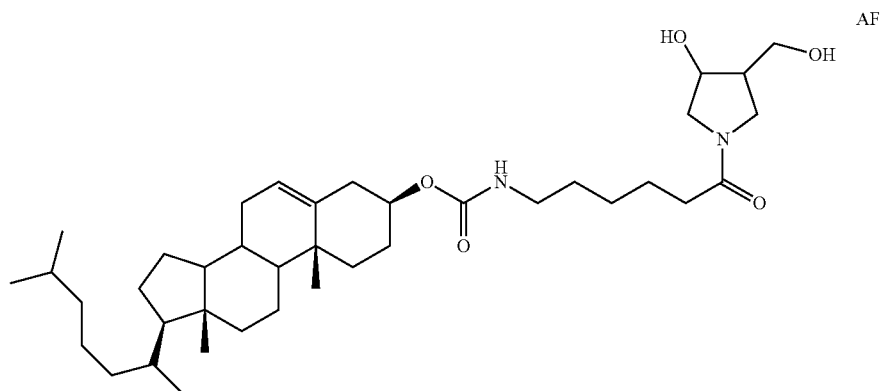 [SMILES: CC(C)CCCC(C)[C@H]1CCC2C3CC=C4C[C@@H](OC(=O)NCCCCCC(=O)N5CC(O)C(CO)C5)CC[C@]4(C)C3CC[C@@]21C]

Methanol (2 mL) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h. After cooling to room temperature, 1 N HCl (12.5 mL) was added, the mixture was extracted with ethylacetate (3×40 mL). The combined ethylacetate layer was dried over anhydrous sodium sulfate and concentrated under vacuum to yield the product which was purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

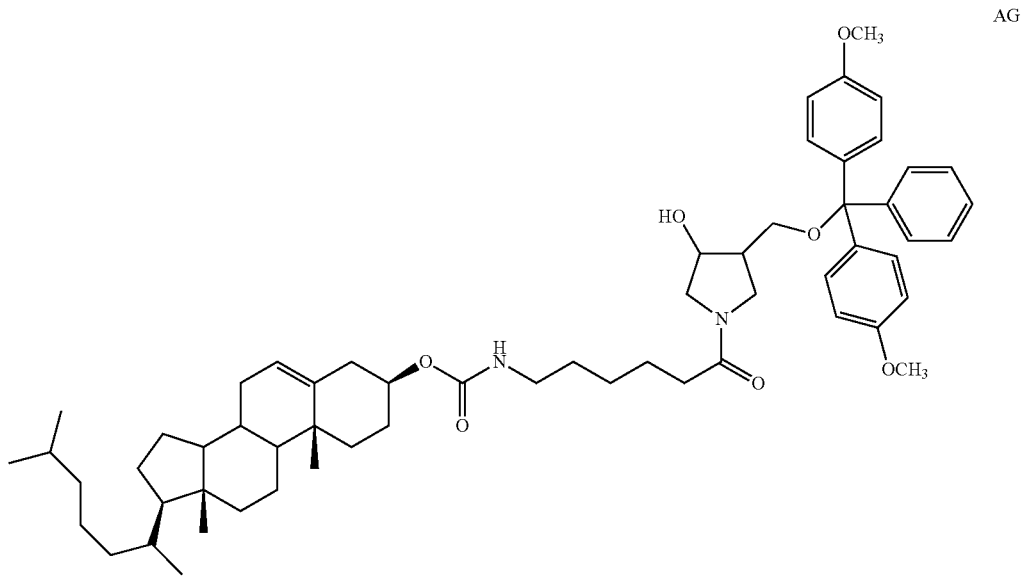 [SMILES: COc1ccc(C(OCC2CN(C(=O)CCCCCNC(=O)O[C@H]3CC[C@@]4(C)C(=CCC5C4CC[C@@]4(C)C5CC[C@@H]4C(C)CCCC(C)C)C3)CC2O)(c2ccccc2)c2ccc(OC)cc2)cc1]

Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature overnight. The reaction was quenched by the addition of methanol. The reaction mixture was concentrated under vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, Rf=0.5 in 5% MeOH/CHCl$_3$) (1.75 g, 95%).

Succinic acid mono-(4-[bis-(4-methoxy-phenyl)-phenyl-methoxymethyl]-1-{6-[17-(1,5-dimethylhexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH

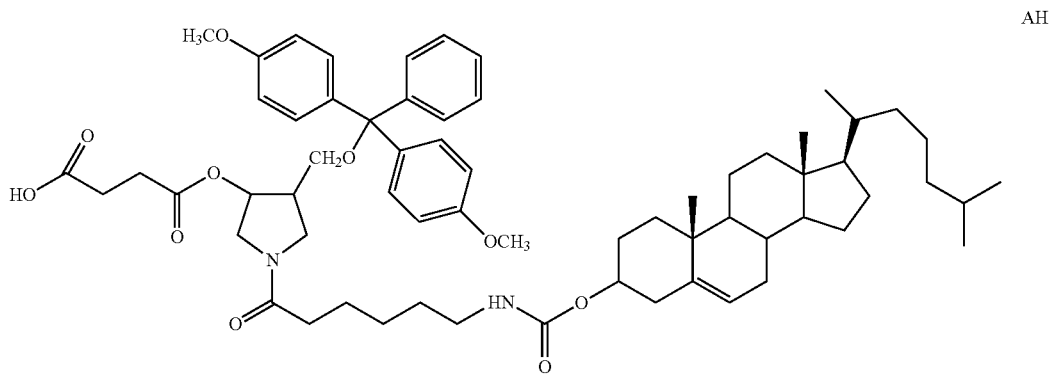

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.

Cholesterol Derivatised CPG AI

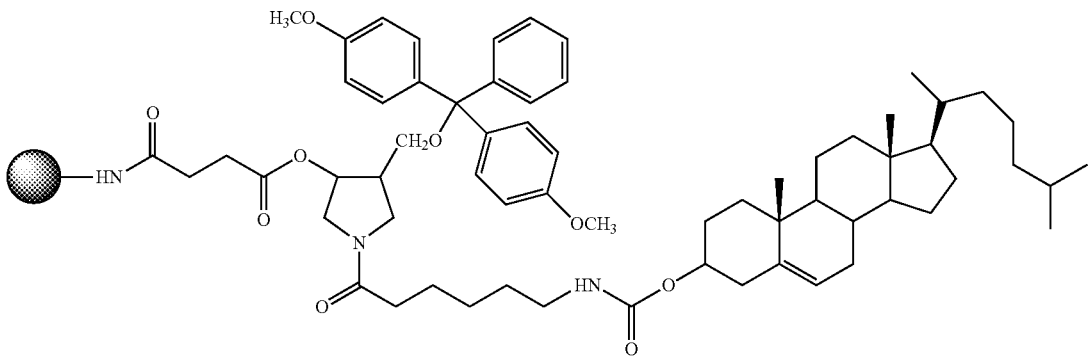

AI

Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using a wrist-action shaker (5 mins). Long chain alkyl amine-CPG (LCAA-CPG) (1.5 g, 61 mM) was added. The suspension was agitated for 2 h. The CPG was filtered through a sintered funnel and washed with acetonitrile, dichloromethane and ether successively. Unreacted amino groups were masked using acetic anhydride/pyridine. The achieved loading of the CPG was measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") was performed as described in WO 2004/065601, except that, for the cholesteryl derivative, the oxidation step was performed using the Beaucage reagent in order to introduce a phosphorothioate linkage at the 5'-end of the nucleic acid oligomer.

dsRNA Targeting the Eg5 Gene

Initial Screening Set siRNA design was carried out to identify siRNAs targeting Eg5 (also known as KIF11, HSKP, KNSL1 and TRIP5). Human mRNA sequences to Eg5, RefSeq ID number:NM_004523, was used.

siRNA duplexes cross-reactive to human and mouse Eg5 were designed. Twenty-four duplexes were synthesized for screening. (Table 1a). A second screening set was defined with 266 siRNAs targeting human Eg5, as well as its rhesus monkey ortholog (Table 2a). An expanded screening set was selected with 328 siRNA targeting human Eg5, with no necessity to hit any Eg5 mRNA of other species (Table 3a).

The sequences for human and a partial rhesus Eg5 mRNAs were downloaded from NCBI Nucleotide database and the human sequence was further on used as reference sequence (Human EG5:NM_004523.2, 4908 bp, and Rhesus EG5: XM_001087644.1, 878 bp (only 5' part of human EG5)

For the Tables: Key: A,G,C,U-ribonucleotides: T-deoxythymidine: u,c-2'-O-methyl nucleotides: s-phosphorothioate linkage.

TABLE 1a

Sequences of Eg5/KSP dsRNA duplexes

| position in human Eg5/KSP sequence | SEQ ID NO: | sequence of 23mer target site | SEQ ID NO: | sense sequence (5'-3') | SEQ ID No: | antisense sequence (5'-3') | duplex name |
|---|---|---|---|---|---|---|---|
| 385-407 | 1244 | ACCGAAGUGUUGUUUGUCCAAUU | 1 | cGAAGuGuuGuuuGuccAATsT | 2 | UUGGAcAAAcAAcACUUCGTsT | AL-DP-6226 |
| 347-369 | 1245 | UAUGGUGUUUGGAGCAUCVACUA | 3 | uGGuGuuuGGAGcAucuAcTsT | 4 | GuAGAUGCUCcAAAcACcATsT | AL-DP-6227 |
| 1078-1100 | 1246 | AAUCUAAACUAACUAGAAUCCUC | 5 | ucuAAAcuAAcuAGAAucCTsT | 6 | GGAUUCuAGUuAGUUuAGATsT | AL-DP-6228 |
| 1067-1089 | 1247 | UCCUUAUCGAGAAUCUAAACUAA | 7 | cuuAucGAGAAucuAAAcuTsT | 8 | AGUUuAGAUUCUCGAuAAGTsT | AL-DP-6229 |
| 374-396 | 1248 | GAUUGAUGUUUACCGAAGUGUUG | 9 | uuGAuGuuuAccGAAGuGuTsT | 10 | AcACUUCGGuAAAcAUcAATsT | AL-DP-6230 |
| 205-227 | 1249 | UGGUGAGAUGCAGACCAUUUAAU | 11 | GuGAGAuGcAGAccAuuuATsT | 12 | uAAAUGGUCUGcAUCUcACTsT | AL-DP-6231 |
| 1176-1198 | 1250 | ACUCUGAGUACAUUGGAAUAUGC | 13 | ucuGAGuAcAuuGGAAuAuTsT | 14 | AuAUUCcAAUGuACUcAGATsT | AL-DP-6232 |
| 386-408 | 1251 | CCGAAGUGUUGUUUGUCCAAUUC | 15 | GAAGuGuuGuuuGuccAAuTsT | 16 | AUUGGAcAAAcAAcACUUCTsT | AL-DP-6233 |
| 416-438 | 1252 | AGUUAUUAUGGGCUAUAAUUGCA | 17 | uuAuuAuGGGcuAuAAuuGTsT | 18 | cAAUuAuAGCCcAuAAuAATsT | AL-DP-6234 |
| 485-507 | 1253 | GGAAGGUGAAAGGUCACCUAAUG | 19 | AAGGuGAAAGGucAccuAATsT | 20 | UuAGGUGACCUUUcACCUUTsT | AL-DP-6235 |
| 476-498 | 1254 | UUUUACAAUGGAAGGUGAAAGGU | 21 | uuAcAAuGGAAGGuGAAAGTsT | 22 | CUUUcACCUUCcAUUGuAATsT | AL-DP-6236 |
| 486-508 | 1255 | GAAGGUGAAAGGUCACCUAAUGA | 23 | AGGuGAAAGGucAccuAAuTsT | 24 | AUuAGGUGACCUUUcACCUTsT | AL-DP-6237 |
| 487-509 | 1256 | AAGGUGAAAGGUCACCUAAUGAA | 25 | GGuGAAAGGucAccuAAuGTsT | 26 | cAUuAGGUGACCUUUcACCTsT | AL-DP-6238 |
| 1066-1088 | 1257 | UUCCUUAUCGAGAAUCUAAACUA | 27 | ccuuAucGAGAAucuAAACTsT | 28 | GUuuAGAUUCUCGAuAAGGTsT | AL-DP-6239 |
| 1256-1278 | 1258 | AGCUCUUAUUAAGGAGUAUACGG | 29 | cucuuAuuAAGGAGuAuACTsT | 30 | GuAuACUCCUuAAuAAGAGTsT | AL-DP-6240 |
| 2329-2351 | 1259 | CAGAGAGAUUCUGUGCUUUGGAG | 31 | GAGAGAuucuGuGcuuuGGTsT | 32 | CcAAAGcAcAGAAUCUCUCTsT | AL-DP-6241 |
| 1077-1099 | 1260 | GAAUCUAAACUAACUAGAAUCCU | 33 | AucuAAAcuAAcuAGAAuCTsT | 34 | GAUUCuAGUuAGUUuAGAUTsT | AL-DP-6242 |
| 1244-1266 | 1261 | ACUCACCAAAAAGCUCUUAUUA | 35 | ucAccAAAAAGcucuuAuTsT | 36 | AuAAGAGCUUUUUGGUGATsT | AL-DP-6243 |
| 637-659 | 1262 | AAGAGCUUUUUGAUCUUCUUAAU | 37 | GAGcuuuuGAucuucuuATsT | 38 | uAAGAAGAUcAAAAAGCUCTsT | AL-DP-6244 |
| 1117-1139 | 1263 | GGCGUACAAGAACAUCUAUAAUU | 39 | cGuAcAAGAAcAucuAuAATsT | 40 | UuAuAGAUGUUCUUGuACGTsT | AL-DP-6245 |
| 373-395 | 1264 | AGAUUGAUGUUUACCGAAGUGUU | 41 | AuuGAuGuuuAccGAAGuGTsT | 42 | cACUUCGGuAAAcAUcAAUTsT | AL-DP-6246 |
| 1079-1101 | 1265 | AUCUAAACUAACUAGAAUCCUCC | | cuAAAcuAAcuAGAAuccuTsT | 44 | AGGAUUCuAGUuAGUUuAGTsT | AL-DP-6247 |
| 383-405 | 1266 | UUACCGAAGUGUUGUUUGUCCAA | 45 | AccGAAGuGuuGuuuGucCTsT | 46 | GGAcAAAcAAcACUUCGGUTsT | AL-DP-6248 |
| 200-222 | 1267 | GGUGGUGGUGAGAUGCAGACCAU | 47 | uGGuGGuGAGAuGcAGAcCTsT | 48 | GGUCUGcAUCUcACcACcATsT | AL-DP-6249 |

TABLE 1b

Analysis of Eg5/KSP ds duplexes

| duplex name | single dose screen @ 25 nM [% residual mRNA] | SDs 2nd screen (among quadruplicates) |
|---|---|---|
| AL-DP-6226 | 23% | 3% |
| AL-DP-6227 | 69% | 10% |
| AL-DP-6228 | 33% | 2% |
| AL-DP-6229 | 2% | 2% |
| AL-DP-6230 | 66% | 11% |
| AL-DP-6231 | 17% | 1% |
| AL-DP-6232 | 9% | 3% |
| AL-DP-6233 | 24% | 6% |
| AL-DP-6234 | 91% | 2% |
| AL-DP-6235 | 112% | 4% |
| AL-DP-6236 | 69% | 4% |
| AL-DP-6237 | 42% | 2% |
| AL-DP-6238 | 45% | 2% |
| AL-DP-6239 | 2% | 1% |
| AL-DP-6240 | 48% | 2% |
| AL-DP-6241 | 41% | 2% |
| AL-DP-6242 | 8% | 2% |
| AL-DP-6243 | 7% | 1% |
| AL-DP-6244 | 6% | 2% |
| AL-DP-6245 | 12% | 2% |
| AL-DP-6246 | 28% | 3% |
| AL-DP-6247 | 71% | 4% |
| AL-DP-6248 | 5% | 2% |
| AL-DP-6249 | 28% | 3% |

TABLE 2a

Sequences of Eg5/ KSP dsRNA duplexes

| SEQ ID NO: | sequence of 19-mer target site | SEQ ID NO. | sense sequence (5'-3') | SEQ ID NO. | antisense sequence (5'-3') | duplex name |
|---|---|---|---|---|---|---|
| 1268 | CAUACUCUAGUCGUUCCCA | 49 | cAuAcucuAGucGuucccATsT | 50 | UGGGAACGACuAGAGuAUGTsT | AD-12072 |
| 1269 | AGCGCCCAUUCAAUAGUAG | 51 | AGcGcccAuucAAuAGuAGTsT | 52 | CuACuAUUGAAUGGGCGCUTsT | AD-12073 |
| 1270 | GGAAAGCUAGCGCCCAUUC | 53 | GGAAAGcuAGcGcccAuucTsT | 54 | GAAUGGGCGCuAGCUUUCCTsT | AD-12074 |
| 1271 | GAAAGCUAGCGCCCAUUCA | 55 | GAAAGcuAGcGcccAuucATsT | 56 | UGAAUGGGCGCuAGCUUUCTsT | AD-12075 |
| 1272 | AGAAACUACGAUUGAUGGA | 57 | AGAAAcuAcGAuuGAuGGATsT | 58 | UCcAUcAAUCGuAGUUUCUTsT | AD-12076 |
| 1273 | UGUUCCUUAUCGAGAAUCU | 59 | uGuuccuuAucGAGAAucuTsT | 60 | AGAUUCUCGAuAAGGAAcATsT | AD-12077 |
| 1274 | CAGAUUACCUCUGCGAGCC | 61 | cAGAuuAccucuGcGAGccTsT | 62 | GGCUCGcAGAGGuAAUCUGTsT | AD-12078 |
| 1275 | GCGCCCAUUCAAUAGUAGA | 63 | GcGcccAuucAAuAGuAGATsT | 64 | UCuAcuAUUGAAUGGGCGCTsT | AD-12079 |
| 1276 | UUGCACUAUCUUUGCGUAU | 65 | uuGcAcuAucuuuGcGuAuTsT | 66 | AuACGcAAAGAuAGUGcAATsT | AD-12080 |
| 1277 | CAGAGCGGAAAGCUAGCGC | 67 | cAGAGcGGAAAGcuAGcGcTsT | 68 | GCGCuAGCUUUCCGCUCUGTsT | AD-12081 |
| 1278 | AGACCUUAUUUGGUAAUCU | 69 | AGAccuuAuuuGGuAAucuTsT | 70 | AGAUuACcAAAuAAGGUCUTsT | AD-12082 |
| 1279 | AUUCUCUUGGAGGGCGUAC | 71 | AuucucuuGGAGGGcGuAcTsT | 72 | GuACGCCCUCcAAGAGAAUTsT | AD-12083 |
| 1280 | GGCUGGUAUAAUUCCACGU | 73 | GGcuGGuAuAAuuccAcGuTsT | 74 | ACGUGGAAUuAuACcAGCCTsT | AD-12084 |
| 1281 | GCGGAAAGCUAGCGCCCAU | 75 | GcGGAAAGcuAGcGcccAuTsT | 76 | AUGGGCGCuAGCUUUCCGCTsT | AD-12085 |
| 1282 | UGCACUAUCUUUGCGUAUG | 77 | uGcAcuAucuuuGcGuAuGTsT | 78 | cAuACGcAAAGAuAGUGcATsT | AD-12086 |
| 1283 | GUAUAAUUCCACGUACCCU | 79 | GuAuAAuuccAcGuAcccuTsT | 80 | AGGGuACGUGGAAUuAuACTsT | AD-12087 |
| 1284 | AGAAUCUAAACUAACUAGA | 81 | AGAAucuAAAcuAAcuAGATsT | 82 | UCuAGUuAGUUuAGAUUCUTsT | AD-12088 |
| 1285 | AGGAGCUGAAUAGGGUUAC | 83 | AGGAGcuGAAuAGGGuuAcTsT | 84 | GuAACCCuAUUcAGCUCCUTsT | AD-12089 |
| 1286 | GAAGUACAUAAGACCUUAU | 85 | GAAGuAcAuAAGAccuuAuTsT | 86 | AuAAGGUCUuAUGuACUUCTsT | AD-12090 |
| 1287 | GACAGUGGCCGAUAAGAUA | 87 | GAcAGuGGccGAuAAGAuATsT | 88 | uAUCUuAUCGGcCACUGUCTsT | AD-12091 |
| 1288 | AAACCACUUAGUAGUGUCC | 89 | AAAccAcuuAGuAGuGuccTsT | 90 | GGAcACuACuAAGUGGUUUTsT | AD-12092 |
| 1289 | UCCCUAGACUUCCCUAUUU | 91 | ucccuAGAcuucccuAuuuTsT | 92 | AAAuAGGGAAGUCuAGGGATsT | AD-12093 |
| 1290 | UAGACUUCCCUAUUUCGCU | 93 | uAGAcuucccuAuuucGcuTsT | 94 | AGCGAAAuAGGGAAGUCuATsT | AD-12094 |
| 1291 | GCGUCGCAGCCAAAUUCGU | 95 | GcGucGcAGccAAAuucGuTsT | 96 | ACGAAUUUGGCUGCGACGCTsT | AD-12095 |

TABLE 2a-continued

Sequences of Eq5/ KSP dsRNA duplexes

| SEQ ID NO: | sequence of 19-mer target site | SEQ ID NO. | sense sequence (5'-3') | SEQ ID NO. | antisense sequence (5'-3') | duplex name |
|---|---|---|---|---|---|---|
| 1292 | AGCUAGCGCCCAUUCAAUA | 97 | AGcuAGcGcccAuucAAuATsT | 98 | uAUUGAAUGGGCGCuAGCUTsT | AD-12096 |
| 1293 | GAAACUACGAUUGAUGGAG | 99 | GAAAcuAcGAuuGAuGGAGTsT | 100 | CUCcAUcAAUCGuAGUUUCTsT | AD-12097 |
| 1294 | CCGAUAAGAUAGAAGAUCA | 101 | ccGAuAAGAuAGAAGAucATsT | 102 | UGAUCUUcUAUCUuAUCGGTsT | AD-12098 |
| 1295 | UAGCGCCCAUUCAAUAGUA | 103 | uAGcGcccAuucAAuAGuATsT | 104 | uACuAUUGAAUGGGCGCuATsT | AD-12099 |
| 1296 | UUUGCGUAUGGCCAAACUG | 105 | uuuGcGuAuGGccAAAcuGTsT | 106 | cAGUUUGGCcAuACGcAAATsT | AD-12100 |
| 1297 | CACGUACCCUUCAUCAAAU | 107 | cAcGuAcccuucAucAAAuTsT | 108 | AUUUGAUGAAGGGuACGUGTsT | AD-12101 |
| 1298 | UCUUUGCGUAUGGCCAAAC | 109 | ucuuuGcGuAuGGccAAAcTsT | 110 | GUUUGGCcAuACGcAAAGATsT | AD-12102 |
| 1299 | CCGAAGUGUUGUUUGUCCA | 111 | ccGAAGuGuuGuuuGuccATsT | 112 | UGGAcAAAcAAcACUUCGGTsT | AD-12103 |
| 1300 | AGAGCGGAAAGCUAGCGCC | 113 | AGAGcGGAAAGcuAGcGccTsT | 114 | GGCGCuAGCUUUCCGCUCUTsT | AD-12104 |
| 1301 | GCUAGCGCCCAUUCAAUAG | 115 | GcuAGcGcccAuucAAuAGTsT | 116 | CuAUUGAAUGGGCGCuAGCTsT | AD-12105 |
| 1302 | AAGUUAGUGUACGAACUGG | 117 | AAGuuAGuGuAcGAAcuGGTsT | 118 | CcAGUUCGuAcACuAACUUTsT | AD-12106 |
| 1303 | GUACGAACUGGAGGAUUGG | 119 | GuAcGAAcuGGAGGAuuGGTsT | 120 | CcAAUCCUCcAGUUCGuACTsT | AD-12107 |
| 1304 | ACGAACUGGAGGAUUGGCU | 121 | AcGAAcuGGAGGAuuGGcuTsT | 122 | AGCcAAUCCUCcAGUUCGUTsT | AD-12108 |
| 1305 | AGAUUGAUGUUUACCGAAG | 123 | AGAuuGAuGuuuAccGAAGTsT | 124 | CUUCGGuAAAcAUcAAUCUTsT | AD-12109 |
| 1306 | UAUGGGCUAUAAUUGCACU | 125 | uAuGGGcuAuAAuuGcAcuTsT | 126 | AGUGcAAUuAuAGCCcAuATsT | AD-12110 |
| 1307 | AUCUUUGCGUAUGGCCAAA | 127 | AucuuuGcGuAuGGccAAATsT | 128 | UUUGGCcAuACGcAAAGAUTsT | AD-12111 |
| 1308 | ACUCUAGUCGUUCCCACUC | 129 | AcucuAGucGuucccAcucTsT | 130 | GAGUGGGAACGACuAGAGUTsT | AD-12112 |
| 1309 | AACUACGAUUGAUGGAGAA | 131 | AAcuAcGAuuGAuGGAGAATsT | 132 | UUCUCcAUcAAUCGuAGUUTsT | AD-12113 |
| 1310 | GAUAAGAGAGCUCGGGAAG | 133 | GAuAAGAGAGcucGGGAAGTsT | 134 | CUUCCCGAGCUCUCUuAUCTsT | AD-12114 |
| 1311 | UCGAGAAUCUAAACUAACU | 135 | ucGAGAAucuAAAcuAAcuTsT | 136 | AGUuAGUUuAGAUUCUCGATsT | AD-12115 |
| 1312 | AACUAACUAGAAUCCUCCA | 137 | AAcuAAcuAGAAuccuccATsT | 138 | UGGAGGAUUCuAGUuAGUUTsT | AD-12116 |
| 1313 | GGAUCGUAAGAAGGCAGUU | 139 | GGAucGuAAGAAGGcAGuuTsT | 140 | AACUGCCUUCUuACGAUCCTsT | AD-12117 |
| 1314 | AUCGUAAGAAGGCAGUUGA | 141 | AucGuAAGAAGGcAGuuGATsT | 142 | UcAACUGCCUUCUuACGAUTsT | AD-12118 |
| 1315 | AGGCAGUUGACCAACACAA | 143 | AGGcAGuuGAccAAcAcAATsT | 144 | UUGUGUUGGUcAACUGCCUTsT | AD-12119 |
| 1316 | UGGCCGAUAAGAUAGAAGA | 145 | uGGccGAuAAGAuAGAAGATsT | 146 | UCUUCuAUCUuAUCGGccATsT | AD-12120 |
| 1317 | UCUAAGGAUAUAGUCAACA | 147 | ucuAAGGAuAuAGucAAcATsT | 148 | UGUUGAcuAuAUCCUuAGATsT | AD-12121 |
| 1318 | ACUAAGCUUAAUUGCUUUC | 149 | AcuAAGcuuAAuuGcuuucTsT | 150 | GAAAGcAAUuAAGCUuAGUTsT | AD-12122 |
| 1319 | GCCCAGAUCAACCUUUAAU | 151 | GcccAGAucAAccuuuAAuTsT | 152 | AUuAAAGGUUGAUCUGGGCTsT | AD-12123 |
| 1320 | UUAAUUGGCAGAGCGGAA | 153 | uuAAuuGGcAGAGcGGAATsT | 154 | UUCCGCUCUGCcAAAUuAATsT | AD-12124 |
| 1321 | UUAUCGAGAAUCUAAACUA | 155 | uuAucGAGAAucuAAAcuATsT | 156 | uAGUUuAGAUUCUCGAuAATsT | AD-12125 |
| 1322 | CUAGCGCCCAUUCAAUAGU | 157 | cuAGcGcccAuucAAuAGuTsT | 158 | ACuAUUGAAUGGGCGCuAGTsT | AD-12126 |
| 1323 | AAUAGUAGAAUGUGAUCCU | 159 | AAuAGuAGAAuGuGAuccuTsT | 160 | AGGAUcAcAUUCuAcuAUUTsT | AD-12127 |
| 1324 | UACGAAAAGAAGUUAGUGU | 161 | uAcGAAAAGAAGuuAGuGuTsT | 162 | AcACuAACUUCUUUUCGuATsT | AD-12128 |
| 1325 | AGAAGUUAGUGUACGAACU | 163 | AGAAGuuAGuGuAcGAAcuTsT | 164 | AGUUCGuAcACuAACUUCUTsT | AD-12129 |
| 1326 | ACUAAACAGAUUGAUGUUU | 165 | AcuAAAcAGAuuGAuGuuuTsT | 166 | AAAcAUcAAUCUGUUuAGUTsT | AD-12130 |
| 1327 | CUUUGCGUAUGGCCAAACU | 167 | cuuuGcGuAuGGccAAAcuTsT | 168 | AGUUUGGCcAuACGcAAAGTsT | AD-12131 |
| 1328 | AAUGAAGAGUAUACCUGGG | 169 | AAuGAAGAGuAuAccuGGGTsT | 170 | CCcAGGuAuACUCUUcAUUTsT | AD-12132 |

TABLE 2a-continued

Sequences of Eq5/ KSP dsRNA duplexes

| SEQ ID NO: | sequence of 19-mer target site | SEQ ID NO. | sense sequence (5'-3') | SEQ ID NO. | antisense sequence (5'-3') | duplex name |
|---|---|---|---|---|---|---|
| 1329 | AUAAUUCCACGUACCCUUC | 171 | AuAAuccAcGuAcccuucTsT | 172 | GAAGGGuACGUGGAAUuAUTsT | AD-12133 |
| 1330 | ACGUACCCUUCAUCAAAUU | 173 | AcGuAcccuucAucAAAuuTsT | 174 | AAUUUGAUGAAGGGuACGUTsT | AD-12134 |
| 1331 | CGUACCCUUCAUCAAAUUU | 175 | cGuAcccuucAucAAAuuuTsT | 176 | AAAUUUGAUGAAGGGuACGTsT | AD-12135 |
| 1332 | GUACCCUUCAUCAAAUUUU | 177 | GuAcccuucAucAAAuuuuTsT | 178 | AAAAUUUGAUGAAGGGuACTsT | AD-12136 |
| 1333 | AACUUACUGAUAAUGGUAC | 179 | AAcuuAcuGAuAAuGGuAcTsT | 180 | GuACcAUuAUcAGuAAGUUTsT | AD-12137 |
| 1334 | UUCAGUCAAAGUGUCUCUG | 181 | uucAGucAAAGuGucucuGTsT | 182 | cAGAGAcACUUUGACUGAATsT | AD-12138 |
| 1335 | UUCUUAAUCCAUCAUCUGA | 183 | uucuuAAuccAucAucuGATsT | 184 | UcAGAUGAUGGAUuAAGAATsT | AD-12139 |
| 1336 | ACAGUACACAACAAGGAUG | 185 | AcAGuAcAcAAcAAGGAuGTsT | 186 | cAUCCUUGUUGUGuACUGUTsT | AD-12140 |
| 1337 | AAGAAACUACGAUUGAUGG | 187 | AAGAAAcuAcGAuuGAuGGTsT | 188 | CcAUcAAUCGuAGUUUCUUTsT | AD-12141 |
| 1338 | AAACUACGAUUGAUGGAGA | 189 | AAAcuAcGAuuGAuGGAGATsT | 190 | UCUCcAUcAAUCGuAGUUUTsT | AD-12142 |
| 1339 | UGGAGCUGUUGAUAAGAGA | 191 | uGGAGcuGuuGAuAAGAGATsT | 192 | UCUCUuAUcAAcAGCUCcATsT | AD-12143 |
| 1340 | CUAACUAGAAUCCUCCAGG | 193 | cuAAcuAGAAuccuccAGGTsT | 194 | CCUGGAGGAUUCuAGUuAGTsT | AD-12144 |
| 1341 | GAAUAUGCUCAUAGAGCAA | 195 | GAAuAuGcucAuAGAGcAATsT | 196 | UUGCUCuAUGAGcAuAUUCTsT | AD-12145 |
| 1342 | AUGCUCAUAGAGCAAAGAA | 197 | AuGcucAuAGAGcAAAGAATsT | 198 | UUCUUUGCUCuAUGAGcAUTsT | AD-12146 |
| 1343 | AAAAAUUGGUGCUGUUGAG | 199 | AAAAAuuGGuGcuGuuGAGTsT | 200 | CUcAAcAGcAccAAUUUUUTsT | AD-12147 |
| 1344 | GAGGAGCUGAAUAGGGUUA | 201 | GAGGAGcuGAAuAGGGuuATsT | 202 | uAACCCuAUUcAGCUCCUCTsT | AD-12148 |
| 1345 | GGAGCUGAAUAGGGUUACA | 203 | GGAGcuGAAuAGGGuuAcATsT | 204 | UGuAACCCuAUUcAGCUCCTsT | AD-12149 |
| 1346 | GAGCUGAAUAGGGUUACAG | 205 | GAGcuGAAuAGGGuuAcAGTsT | 206 | CUGuAACCCuAUUcAGCUCTsT | AD-12150 |
| 1347 | AGCUGAAUAGGGUUACAGA | 207 | AGcuGAAuAGGGuuAcAGATsT | 208 | UCUGuAACCCuAUUcAGCUTsT | AD-12151 |
| 1348 | GCUGAAUAGGGUUACAGAG | 209 | GcuGAAuAGGGuuAcAGAGTsT | 210 | CUCUGuAACCCuAUUcAGCTsT | AD-12152 |
| 1349 | CCAAACUGGAUCGUAAGAA | 211 | ccAAAcuGGAucGuAAGAATsT | 212 | UUCUuACGAUCcAGUUUGGTsT | AD-12153 |
| 1350 | GAUCGUAAGAAGGCAGUUG | 213 | GAucGuAAGAAGGcAGuuGTsT | 214 | cAACUGCCUUCUuACGAUCTsT | AD-12154 |
| 1351 | ACCUUAUUUGGUAAUCUGC | 215 | AccuuAuuuGGuAAucuGcTsT | 216 | GcAGAUuACcAAAuAAGGUTsT | AD-12155 |
| 1352 | UUAGAUACCAUUACUACAG | 217 | uuAGAuAccAuuAcuAcAGTsT | 218 | CUGuAGuAAUGGuAUCuAATsT | AD-12156 |
| 1353 | AUACCAUUACUACAGUAGC | 219 | AuAccAuuAcuAcAGuAGcTsT | 220 | GCuACUGuAGuAAUGGuAUTsT | AD-12157 |
| 1354 | UACUACAGUAGCACUUGGA | 221 | uAcuAcAGuAGcAcuuGGATsT | 222 | UCcAAGUGCuACUGuAGuATsT | AD-12158 |
| 1355 | AAAGUAAAACUGUACUACA | 223 | AAAGuAAAAcuGuAcuAcATsT | 224 | UGuAGuAcAGUUUuACUUUTsT | AD-12159 |
| 1356 | CUCAAGACUGAUCUUCUAA | 225 | cucAAGAcuGAucuucuAATsT | 226 | UuAGAAGAUcAGUCUUGAGTsT | AD-12160 |
| 1357 | UUGACAGUGGCCGAUAAGA | 227 | uuGAcAGuGGccGAuAAGATsT | 228 | UCUuAUCGGccACUGUcAATsT | AD-12161 |
| 1358 | UGACAGUGGCCGAUAAGAU | 229 | uGAcAGuGGccGAuAAGAuTsT | 230 | AUCUuAUCGGccACUGUcATsT | AD-12162 |
| 1359 | GCAAUGUGGAAACCUAACU | 231 | GcAAuGuGGAAAccuAAcuTsT | 232 | AGUuAGGUUUCcAcAUUGCTsT | AD-12163 |
| 1360 | CCACUUAGUAGUGUCCAGG | 233 | ccAcuuAGuAGuGuccAGGTsT | 234 | CCUGGAcACuAcuAAGUGGTsT | AD-12164 |
| 1361 | AGAAGGUACAAAAUUGGUU | 235 | AGAAGGuAcAAAAuuGGuuTsT | 236 | AAccAAUUUUGuACCUUCUTsT | AD-12165 |
| 1362 | UGGUUUGACUAAGCUUAAU | 237 | uGGuuuGAcuAAGcuuAAuTsT | 238 | AUuAAGCUuAGUcAAACcATsT | AD-12166 |
| 1363 | GGUUUGACUAAGCUUAAUU | 239 | GGuuuGAcuAAGcuuAAuuTsT | 240 | AAUuAAGCUuAGUcAAACCTsT | AD-12167 |
| 1364 | UCUAAGUCAAGAGCCAUCU | 241 | ucuAAGucAAGAGccAucuTsT | 242 | AGAUGGCUCUUGACUuAGATsT | AD-12168 |
| 1365 | UCAUCCCUAUAGUUCACUU | 243 | ucAucccuAuAGuucAcuuTsT | 244 | AAGUGAACuAuAGGGAUGATsT | AD-12169 |

TABLE 2a-continued

Sequences of Eg5/ KSP dsRNA duplexes

| SEQ ID NO: | sequence of 19-mer target site | SEQ ID NO. | sense sequence (5'-3') | SEQ ID NO. | antisense sequence (5'-3') | duplex name |
|---|---|---|---|---|---|---|
| 1366 | CAUCCCUAUAGUUCACUUU | 245 | cAucccuAuAGuucAcuuuTsT | 246 | AAAGUGAACuAuAGGGAUGTsT | AD-12170 |
| 1367 | CCCUAGACUUCCCUAUUUC | 247 | cccuAGAcuucccuAuuucTsT | 248 | GAAAuAGGGAAGUCuAGGGTsT | AD-12171 |
| 1368 | AGACUUCCCUAUUUCGCUU | 249 | AGAcuucccuAuuucGcuuTsT | 250 | AAGCGAAAuAGGGAAGUCUTsT | AD-12172 |
| 1369 | UCACCAAACCAUUUGUAGA | 251 | ucAccAAAccAuuuGuAGATsT | 252 | UCuAcAAAUGGUUUGGUGATsT | AD-12173 |
| 1370 | UCCUUUAAGAGGCCUAACU | 253 | uccuuuAAGAGGccuAAcuTsT | 254 | AGUuAGGCCUCUuAAAGGATsT | AD-12174 |
| 1371 | UUUAAGAGGCCUAACUCAU | 255 | uuuAAGAGGccuAAcucAuTsT | 256 | AUGAGUuAGGCCUCUuAAATsT | AD-12175 |
| 1372 | UUAAGAGGCCUAACUCAUU | 257 | uuAAGAGGccuAAcucAuuTsT | 258 | AAUGAGUuAGGCCUCUuAATsT | AD-12176 |
| 1373 | GGCCUAACUCAUUCACCCU | 259 | GGccuAAcucAuucAcccuTsT | 260 | AGGGUGAAUGAGUuAGGCCTsT | AD-12177 |
| 1374 | UGGUAUUUUGAUCUGGCA | 261 | uGGuAuuuuuGAucuGGcATsT | 262 | UGCcAGAUcAAAAAuACcATsT | AD-12178 |
| 1375 | AGUUUAGUGUGUAAAGUUU | 263 | AGuuuAGuGuGuAAAGuuuTsT | 264 | AAACUUuAcAcACuAAACUTsT | AD-12179 |
| 1376 | GCCAAAUUCGUCUGCGAAG | 265 | GccAAAuucGucuGcGAAGTsT | 266 | CUUCGcAGACGAAUUUGGCTsT | AD-12180 |
| 1377 | AAUUCGUCUGCGAAGAAGA | 267 | AAuucGucuGcGAAGAAGATsT | 268 | UCUUCUUCGcAGACGAAUUTsT | AD-12181 |
| 1378 | UGAAAGGUCACCUAAUGAA | 269 | uGAAAGGucAccuAAuGAATsT | 270 | UUcAUuAGGUGACCUUUcATsT | AD-12182 |
| 1379 | CAGACCAUUUAAUUUGGCA | 271 | cAGAccAuuuAAuuuGGcATsT | 272 | UGCcAAAUuAAAUGGUCUGTsT | AD-12183 |
| 1380 | AGACCAUUUAAUUUGGCAG | 273 | AGAccAuuuAAuuuGGcAGTsT | 274 | CUGCcAAAUuAAAUGGUCUTsT | AD-12184 |
| 1381 | AGUUAUUAUGGGCUAUAAU | 275 | AGuuAuuAuGGGcuAuAAuTsT | 276 | AUuAuAGCCcAuAAuAACUTsT | AD-12185 |
| 1382 | GCUGGUAUAAUUCCACGUA | 277 | GcuGGuAuAAuuccAcGuATsT | 278 | uACGUGGAAUuAuACcAGCTsT | AD-12186 |
| 1383 | AUUUAAUUUGGCAGAGCGG | 279 | AuuuAAuuuGGcAGAGcGGTsT | 280 | CCGCUCUGCcAAAUuAAAUTsT | AD-12187 |
| 1384 | UUUAAUUUGGCAGAGCGGA | 281 | uuuAAuuuGGcAGAGcGGATsT | 282 | UCCGCUCUGCcAAAUuAAATsT | AD-12188 |
| 1385 | UUUGGCAGAGCGGAAAGCU | 283 | uuuGGcAGAGcGGAAAGcuTsT | 284 | AGCUUUCCGCUCUGCcAAATsT | AD-12189 |
| 1386 | UUUUACAAUGGAAGGUGAA | 285 | uuuuAcAAuGGAAGGuGAATsT | 286 | UUcACCUUCcAUUGuAAAATsT | AD-12190 |
| 1387 | AAUGGAAGGUGAAAGGUCA | 287 | AAuGGAAGGuGAAAGGucATsT | 288 | UGACCUUUcACCUUCcAUUTsT | AD-12191 |
| 1388 | UGAGAUGCAGACCAUUUAA | 289 | uGAGAuGcAGAccAuuuAATsT | 290 | UuAAAUGGUCUGcAUCUcATsT | AD-12192 |
| 1389 | UCGCAGCCAAAUUCGUCUG | 291 | ucGcAGccAAAuucGucuGTsT | 292 | cAGACGAAUUUGGCUGCGATsT | AD-12193 |
| 1390 | GGCUAUAAUUGCACUAUCU | 293 | GGcuAuAAuuGcAcuAucuTsT | 294 | AGAuAGUGcAAUuAuAGCCTsT | AD-12194 |
| 1391 | AUUGACAGUGGCCGAUAAG | 295 | AuuGAcAGuGGccGAuAAGTsT | 296 | CUuAUCGGCcACUGUcAAUTsT | AD-12195 |
| 1392 | CUAGACUUCCCUAUUUCGC | 297 | cuAGAcuucccuAuuucGcTsT | 298 | GCGAAAuAGGGAAGUCuAGTsT | AD-12196 |
| 1393 | ACUAUCUUUGCGUAUGGCC | 299 | AcuAucuuuGcGuAuGGccTsT | 300 | GGCcAuACGcAAAGAuAGUTsT | AD-12197 |
| 1394 | AUACUCUAGUCGUUCCCAC | 301 | AuAcucuAGucGuucccAcTsT | 302 | GUGGGAACGACuAGAGuAUTsT | AD-12198 |
| 1395 | AAAGAAACUACGAUUGAUG | 303 | AAAGAAAcuAcGAuuGAuGTsT | 304 | cAUcAAUCGuAGUUUCUUUTsT | AD-12199 |
| 1396 | GCCUUGAUUUUUGGCGGG | 305 | GccuuGAuuuuuGGcGGGTsT | 306 | CCCGCcAAAAAUcAAGGCTsT | AD-12200 |
| 1397 | CGCCCAUUCAAUAGUAGAA | 307 | cGcccAuucAAuAGuAGAATsT | 308 | UUCuAcuAUUGAAuGGGCGTsT | AD-12201 |
| 1398 | CCUUAUUUGGUAAUCUGCU | 309 | ccuuAuuuGGuAAucuGcuTsT | 310 | AGcAGAUuACcAAAuAAGGTsT | AD-12202 |
| 1399 | AGAGACAAUUCCGGAUGUG | 311 | AGAGAcAAuuccGGAuGuGTsT | 312 | cAcAUCCGGAAUUGUCUCUTsT | AD-12203 |
| 1400 | UGACUUUGAUAGCUAAAUU | 313 | uGAcuuuGAuAGcuAAAuuTsT | 314 | AAUUuAGCuAUcAAAGUcATsT | AD-12204 |
| 1401 | UGGCAGAGCGGAAAGCUAG | 315 | uGGcAGAGcGGAAAGcuAGTsT | 316 | CuAGCUUUCCGCUCUGCcATsT | AD-12205 |
| 1402 | GAGCGGAAAGCUAGCGCCC | 317 | GAGcGGAAAGcuAGcGcccTsT | 318 | GGGCGCuAGCUUUCCGCUCTsT | AD-12206 |

TABLE 2a-continued

Sequences of Eg5/ KSP dsRNA duplexes

| SEQ ID NO: | sequence of 19-mer target site | SEQ ID NO. | sense sequence (5'-3') | SEQ ID NO. | antisense sequence (5'-3') | duplex name |
|---|---|---|---|---|---|---|
| 1403 | AAAGAAGUUAGUGUACGAA | 319 | AAAGAAGuuAGuGuAcGAATsT | 320 | UUCGuAcACuAACUUCUUUTsT | AD-12207 |
| 1404 | AUUGCACUAUCUUUGCGUA | 321 | AuuGcAcuAucuuuGcGuATsT | 322 | uACGcAAAGAuAGUGcAAUTsT | AD-12208 |
| 1405 | GGUAUAAUUCCACGUACCC | 323 | GGuAuAAuuccAcGuAcccTsT | 324 | GGGuACGUGGAAUuAuACCTsT | AD-12209 |
| 1406 | UACUCUAGUCGUUCCCACU | 325 | uAcucuAGucGuucccAcuTsT | 326 | AGUGGGAACGACuAGAGuATsT | AD-12210 |
| 1407 | UAUGAAAGAAACUACGAUU | 327 | uAuGAAAGAAAcuAcGAuuTsT | 328 | AAUCGuAGUUUCUUUcAuATsT | AD-12211 |
| 1408 | AUGCUAGAAGUACAUAAGA | 329 | AuGcuAGAAGuAcAuAAGATsT | 330 | UCUuAUGuACUUCuAGcAUTsT | AD-12212 |
| 1409 | AAGUACAUAAGACCUUAUU | 331 | AAGuAcAuAAGAccuuAuuTsT | 332 | AAuAAGGUCUuAUGuACUUTsT | AD-12213 |
| 1410 | ACAGCCUGAGCUGUUAAUG | 333 | AcAGccuGAGcuGuuAAuGTsT | 334 | cAUuAAcAGCUcAGGCUGUTsT | AD-12214 |
| 1411 | AAAGAAGAGACAAUUCCGG | 335 | AAAGAAGAGAcAAuuccGGTsT | 336 | CCGGAAUUGUCUCUUCUUUTsT | AD-12215 |
| 1412 | CACACUGGAGAGGUCUAAA | 337 | cAcAcuGGAGAGGucuAAATsT | 338 | UUuAGACCUCUCcAGUGUGTsT | AD-12216 |
| 1413 | CACUGGAGAGGUCUAAAGU | 339 | cAcuGGAGAGGucuAAAGuTsT | 340 | ACUuAGACCUCUCcAGUGTsT | AD-12217 |
| 1414 | ACUGGAGAGGUCUAAAGUG | 341 | AcuGGAGAGGucuAAAGuGTsT | 342 | cACUuAGACCUCUCcAGUTsT | AD-12218 |
| 1415 | CGUCGCAGCCAAAUUCGUC | 343 | cGucGcAGccAAAuucGucTsT | 344 | GACGAAUUUGGCUGCGACGTsT | AD-12219 |
| 1416 | GAAGGCAGUUGACCAACAC | 345 | GAAGGcAGuuGAccAAcAcTsT | 346 | GUGUUGGUcAACUGCCUUCTsT | AD-12220 |
| 1417 | CAUUCACCCUGACAGAGUU | 347 | cAuucAcccuGAcAGAGuuTsT | 348 | AACUCUGUcAGGGUGAAUGTsT | AD-12221 |
| 1418 | AAGAGGCCUAACUCAUUCA | 349 | AAGAGGccuAAcucAuucATsT | 350 | UGAAUGAGUuAGGCCUCUUTsT | AD-12222 |
| 1419 | GAGACAAUUCCGGAUGUGG | 351 | GAGAcAAuuccGGAuGuGGTsT | 352 | CcAcAUCCGGAAUUGUCUCTsT | AD-12223 |
| 1420 | UUCCGGAUGUGGAUGUAGA | 353 | uuccGGAuGuGGAuGuAGATsT | 354 | UCuAcAUCcAcAUCCGGAATsT | AD-12224 |
| 1421 | AAGCUAGCGCCCAUUCAAU | 355 | AAGcuAGcGcccAuucAAuTsT | 356 | AUUGAAuGGGCGCuAGCUUTsT | AD-12225 |
| 1422 | GAAGUUAGUGUACGAACUG | 357 | GAAGuuAGuGuAcGAAcuGTsT | 358 | cAGUUCGuAcACuAACUUCTsT | AD-12226 |
| 1423 | UAUAAUUCCACGUACCCUU | 359 | uAuAAuuccAcGuAcccuuTsT | 360 | AAGGGuACGUGGAAUuAuATsT | AD-12227 |
| 1424 | ACAGUGGCCGAUAAGAUAG | 361 | AcAGuGGccGAuAAGAuAGTsT | 362 | CuAUCUuAUCGGCcACUGUTsT | AD-12228 |
| 1425 | UCUGUCAUCCCUAUAGUUC | 363 | ucuGucAucccuAuAGuucTsT | 364 | GAACuAuAGGGAuGAcAGATsT | AD-12229 |
| 1426 | UUCUUGCUAUGACUUGUGU | 365 | uucuuGcuAuGAcuuGuGuTsT | 366 | AcAcAAGUcAuAGcAAGAATsT | AD-12230 |
| 1427 | GUAAGAAGGCAGUUGACCA | 367 | GuAAGAAGGcAGuuGAccATsT | 368 | UGGUcAACUGCCUUCUuACTsT | AD-12231 |
| 1428 | CAUUGACAGUGGCCGAUAA | 369 | cAuuGAcAGuGGccGAuAATsT | 370 | UuAUCGGCcACUGUcAAUGTsT | AD-12232 |
| 1429 | AGAAACCACUUAGUAGUGU | 371 | AGAAAccAcuuAGuAGuGuTsT | 372 | AcACuACuAAGUGGUUUCUTsT | AD-12233 |
| 1430 | GGAUUGUUCAUCAAUUGGC | 373 | GGAuuGuucAucAAuuGGcTsT | 374 | GCcAAUUGAUGAAcAAUCCTsT | AD-12234 |
| 1431 | UAAGAGGCCUAACUCAUUC | 375 | uAAGAGGccuAAcucAuucTsT | 376 | GAAUGAGUuAGGCCUCUuATsT | AD-12235 |
| 1432 | AGUUAGUGUACGAACUGGA | 377 | AGuuAGuGuAcGAAcuGGATsT | 378 | UCcAGUUCGuAcACuAACUTsT | AD-12236 |
| 1433 | AGUACAUAAGACCUUAUUU | 379 | AGuAcAuAAGAccuuAuuuTsT | 380 | AAAuAAGGUCUuAUGuACUTsT | AD-12237 |
| 1434 | UGAGCCUUGUGUAUAGAUU | 381 | uGAGccuuGuGuAuAGAuuTsT | 382 | AAUCuAuAcAcAAGGCUcATsT | AD-12238 |
| 1435 | CCUUUAAGAGGCCUAACUC | 383 | ccuuuAAGAGGccuAAcucTsT | 384 | GAGUuAGGCCUCUuAAAGGTsT | AD-12239 |
| 1436 | ACCACUUAGUAGUGUCCAG | 385 | AccAcuuAGuAGuGuccAGTsT | 386 | CUGGAcACuACuAAGUGGUTsT | AD-12240 |
| 1437 | GAAACUUCCAAUUAUGCUC | 387 | GAAAcuccAAuuAuGcucTsT | 388 | AGAcAAAUUGGAAGUUUCTsT | AD-12241 |
| 1438 | UGCAUACUCUAGUCGUUCC | 389 | uGcAuAcucuAGucGuuccTsT | 390 | GGAACGACuAGAGuAUGcATsT | AD-12242 |
| 1439 | AGAAGGCAGUUGACCAACA | 391 | AGAAGGcAGuuGAccAAcATsT | 392 | UGUUGGUcAACUGCCUUCUTsT | AD-12243 |

TABLE 2a-continued

Sequences of Eq5/ KSP dsRNA duplexes

| SEQ ID NO: | sequence of 19-mer target site | SEQ ID NO. | sense sequence (5'-3') | SEQ ID NO. | antisense sequence (5'-3') | duplex name |
|---|---|---|---|---|---|---|
| 1440 | GUACAUAAGACCUUAUUUG | 393 | GuAcAuAAGAccuuAuuuGTsT | 394 | cAAAuAAGGUCUuAUGuACTsT | AD-12244 |
| 1441 | UAUAAUUGCACUAUCUUUG | 395 | uAuAAuuGcAcuAucuuuGTsT | 396 | cAAAGAuAGUGcAAUuAuATsT | AD-12245 |
| 1442 | UCUCUGUUACAAUACAUAU | 397 | ucucuGuuAcAAuAcAuAuTsT | 398 | AuAUGuAUUGuAAcAGAGATsT | AD-12246 |
| 1443 | UAUGCUCAUAGAGCAAAGA | 399 | uAuGcucAuAGAGcAAAGATsT | 400 | UCUUUGCUCuAUGAGcAuATsT | AD-12247 |
| 1444 | UGUUGUUUGUCCAAUUCUG | 401 | uGuuGuuuGuccAAuucuGTsT | 402 | cAGAAUUGGAcAAAcAAcATsT | AD-12248 |
| 1445 | ACUAACUAGAAUCCUCCAG | 403 | AcuAAcuAGAAuccuccAGTsT | 404 | CUGGAGGAUUCuAGUuAGUTsT | AD-12249 |
| 1446 | UGUGGUGUCUAUACUGAAA | 405 | uGuGGuGucuAuAcuGAAATsT | 406 | UUUcAGuAuAGAcACcAcATsT | AD-12250 |
| 1447 | UAUUAUGGGAGACCACCCA | 407 | uAuuAuGGGAGAccAcccATsT | 408 | UGGGUGGUCUCCcAuAAuATsT | AD-12251 |
| 1448 | AAGGAUGAAGUCUAUCAAA | 409 | AAGGAuGAAGucuAucAAATsT | 410 | UUUGAuAGACUUcAUCCUUTsT | AD-12252 |
| 1449 | UUGAUAAGAGAGCUCGGGA | 411 | uuGAuAAGAGAGcucGGGATsT | 412 | UCCCGAGCUCUCUuAUcAATsT | AD-12253 |
| 1450 | AUGUUCCUUAUCGAGAAUC | 413 | AuGuuccuuAucGAGAAucTsT | 414 | GAUUCUCGAuAAGGAAcAUTsT | AD-12254 |
| 1451 | GGAAUAUGCUCAUAGAGCA | 415 | GGAAuAuGcucAuAGAGcATsT | 416 | UGCUCuAUGAGcAuAUUCCTsT | AD-12255 |
| 1452 | CCAUUCCAAACUGGAUCGU | 417 | ccAuuccAAAcuGGAucGuTsT | 418 | ACGAUCcAGUUUGGAAUGGTsT | AD-12256 |
| 1453 | GGCAGUUGACCAACACAAU | 419 | GGcAGuuGAccAAcAcAAuTsT | 420 | AUUGUGUUGGUcAACUGCCTsT | AD-12257 |
| 1454 | CAUGCUAGAAGUACAUAAG | 421 | cAuGcuAGAAGuAcAuAAGTsT | 422 | CUuAUGuACUUcuAGcAUGTsT | AD-12258 |
| 1455 | CUAGAAGUACAUAAGACCU | 423 | cuAGAAGuAcAuAAGAccuTsT | 424 | AGGUCUuAUGuACUUcuAGTsT | AD-12259 |
| 1456 | UUGGAUCUCUCACAUCUAU | 425 | uuGGAucucucAcAucuAuTsT | 426 | AuAGAUGUGAGAGAUCcAATsT | AD-12260 |
| 1457 | AACUGUGGUGUCUAUACUG | 427 | AAcuGuGGuGucuAuAcuGTsT | 428 | cAGuAuAGAcACcAcAGUUTsT | AD-12261 |
| 1458 | UCAUUGACAGUGGCCGAUA | 429 | ucAuuGAcAGuGGccGAuATsT | 430 | uAUCGGccACUGUcAAUGATsT | AD-12262 |
| 1459 | AUAAAGCAGACCCAUUCCC | 431 | AuAAAGcAGAcccAuucccTsT | 432 | GGGAAUGGGUCUGCUUuAUTsT | AD-12263 |
| 1460 | ACAGAAACCACUUAGUAGU | 433 | AcAGAAAccAcuuAGuAGuTsT | 434 | ACuACuAAGUGGUUUCUGUTsT | AD-12264 |
| 1461 | GAAACCACUUAGUAGUGUC | 435 | GAAAccAcuuAGuAGuGucTsT | 436 | GAcACuACuAAGUGGUUUCTsT | AD-12265 |
| 1462 | AAAUCUAAGGAUAUAGUCA | 437 | AAAucuAAGGAuAuAGucATsT | 438 | UGAcuAuAUCCUuAGAUUUTsT | AD-12266 |
| 1463 | UUAUUUAUACCCAUCAACA | 439 | uuAuuuAuAcccAucAAcATsT | 440 | UGUUGAUGGGuAuAAAuAATsT | AD-12267 |
| 1464 | ACAGAGGCAUUAACACACU | 441 | AcAGAGGcAuuAAcAcAcuTsT | 442 | AGUGUGUuAAUGCCUCUGUTsT | AD-12268 |
| 1465 | ACACACUGGAGAGGUCUAA | 443 | AcAcAcuGGAGAGGucuAATsT | 444 | UuAGACCUCUCcAGUGUGUTsT | AD-12269 |
| 1466 | ACACUGGAGAGGUCUAAAG | 445 | AcAcuGGAGAGGucuAAAGTsT | 446 | CUUuAGACCUCUCcAGUGUTsT | AD-12270 |
| 1467 | CGAGCCCAGAUCAACCUUU | 447 | cGAGcccAGAucAAccuuuTsT | 448 | AAAGGUUGAUCUGGGCUCGTsT | AD-12271 |
| 1468 | UCCCUAUUUCGCUUUCUCC | 449 | ucccuAuuucGcuuucuccTsT | 450 | GGAGAAAGCGAAAuAGGGATsT | AD-12272 |
| 1469 | UCUAAAAUCACUGUCAACA | 451 | ucuAAAAucAcuGucAAcATsT | 452 | UGUUGAcAGUGAUUUuAGATsT | AD-12273 |
| 1470 | AGCCAAAUUCGUCUGCGAA | 453 | AGccAAAuucGucuGcGAATsT | 454 | UUCGcAGACGAAUUUGGCUTsT | AD-12274 |
| 1471 | CCCAUUCAAUAGUAGAAUG | 455 | cccAuucAAuAGuAGAAuGTsT | 456 | cAUUCuACuAUUGAAUGGGTsT | AD-12275 |
| 1472 | GAUGAAUGCAUACUCUAGU | 457 | GAuGAAuGcAuAcucuAGuTsT | 458 | ACuAGAGuAUGcAUUcAUCTsT | AD-12276 |
| 1473 | CUCAUGUUCCUUAUCGAGA | 459 | cucAuGuuccuuAucGAGATsT | 460 | UCUCGAuAAGGAAcAUGAGTsT | AD-12277 |
| 1474 | GAGAAUCUAAACUAACUAG | 461 | GAGAAucuAAAcuAAcuAGTsT | 462 | CuAGUuAGUUuAGAUUCUCTsT | AD-12278 |
| 1475 | UAGAAGUACAUAAGACCUU | 463 | uAGAAGuAcAuAAGAccuuTsT | 464 | AAGGUCUuAUGuACUUcuATsT | AD-12279 |
| 1476 | CAGCCUGAGCUGUUAAUGA | 465 | cAGccuGAGcuGuIiAAuGATsT | 466 | UcAUuAAcAGCUcAGGCUGTsT | AD-12280 |

TABLE 2a-continued

Sequences of Eg5/ KSP dsRNA duplexes

| SEQ ID NO: | sequence of 19-mer target site | SEQ ID NO. | sense sequence (5'-3') | SEQ ID NO. | antisense sequence (5'-3') | duplex name |
|---|---|---|---|---|---|---|
| 1477 | AAGAAGAGACAAUUCCGGA | 467 | AAGAAGAGAcAAuuccGGATsT | 468 | UCCGGAAUUGUCUCUUCUUTsT | AD-12281 |
| 1478 | UGCUGGUGUGGAUUGUUCA | 469 | uGcuGGuGuGGAuuGuucATsT | 470 | UGAAcAAUCcAcACcAGcATsT | AD-12282 |
| 1479 | AAAUUCGUCUGCGAAGAAG | 471 | AAAuucGucuGcGAAGAAGTsT | 472 | CUUCUUCGcAGACGAAUUUTsT | AD-12283 |
| 1480 | UUUCUGGAAGUUGAGAUGU | 473 | uuucuGGAAGuuGAGAuGuTsT | 474 | AcAUCUcAACUUCcAGAAATsT | AD-12284 |
| 1481 | UACUAAACAGAUUGAUGUU | 475 | uAcuAAAcAGAuuGAuGuuTsT | 476 | AAcAUcAAUCUGUUuAGuATsT | AD-12285 |
| 1482 | GAUUGAUGUUUACCGAAGU | 477 | GAuuGAuGuuuAccGAAGuTsT | 478 | ACUUCGGuAAAcAUcAAUCTsT | AD-12286 |
| 1483 | GCACUAUCUUUGCGUAUGG | 479 | GcAcuAucuuuGcGuAuGGTsT | 480 | CcAuACGcAAAGAuAGUGCTsT | AD-12287 |
| 1484 | UGGUAUAAUUCCACGUACC | 481 | uGGuAuAAuuccAcGuAccTsT | 482 | GGuACGUGGAAUuAuACcATsT | AD-12288 |
| 1485 | AGCAAGCUGCUUAACACAG | 483 | AGcAAGcuGcuuAAcAcAGTsT | 484 | CUGUGUuAAGcAGCUUGCUTsT | AD-12289 |
| 1486 | CAGAAACCACUUAGUAGUG | 485 | cAGAAAccAcuuAGuAGuGTsT | 486 | cACuACuAAGUGGUUUCUGTsT | AD-12290 |
| 1487 | AACUUAUUGGAGGUUGUAA | 487 | AAcuuAuuGGAGGuuGuAATsT | 488 | UuAcAACCUCcAAuAAGUUTsT | AD-12291 |
| 1488 | CUGGAGAGGUCUAAAGUGG | 489 | cuGGAGAGGucuAAAGuGGTsT | 490 | CcACUUuAGACCUCUCcAGTsT | AD-12292 |
| 1489 | AAAAAAGAUAUAAGGCAGU | 491 | AAAAAAGAuAuAAGGcAGuTsT | 492 | ACUGCCUuAuAUCUUUUUUTsT | AD-12293 |
| 1490 | GAAUUUUGAUAUCUACCCA | 493 | GAAuuuuGAuAucuAcccATsT | 494 | UGGGuAGAuAUcAAAAUUCTsT | AD-12294 |
| 1491 | GUAUUUUGAUCUGGCAAC | 495 | GuAuuuuuGAucuGGcAAcTsT | 496 | GUUGCcAGAUcAAAAAuACTsT | AD-12295 |
| 1492 | AGGAUCCCUUGGCUGGUAU | 497 | AGGAucccuuGGcuGGuAuTsT | 498 | AuAcCAGCcAAGGGAUCCUTsT | AD-12296 |
| 1493 | GGAUCCCUUGGCUGGUAUA | 499 | GGAucccuuGGcuGGuAuATsT | 500 | uAuAcCAGCcAAGGGAUCCTsT | AD-12297 |
| 1494 | CAAUAGUAGAAUGUGAUCC | 501 | cAAuAGuAGAAuGuGAuccTsT | 502 | GGAUcAcAUUCuAcuAUUGTsT | AD-12298 |
| 1495 | GCUAUAAUUGCACUAUCUU | 503 | GcuAuAAuuGcAcuAucuuTsT | 504 | AAGAuAGUGcAAUuAuAGCTsT | AD-12299 |
| 1496 | UACCCUUCAUCAAAUUUUU | 505 | uAcccuucAucAAAuuuuuTsT | 506 | AAAAAUUUGAUGAAGGGuATsT | AD-12300 |
| 1497 | AGAACAUAUUGAAUAAGCC | 507 | AGAAcAuAuuGAAuAAGccTsT | 508 | GGCUuAUUcAAuAUGUUCUTsT | AD-12301 |
| 1498 | AAAUUGGUGCUGUUGAGGA | 509 | AAAuuGGuGcuGuuGAGGATsT | 510 | UCCUcAAcAGcACcAAUUUTsT | AD-12302 |
| 1499 | UGAAUAGGGUUACAGAGUU | 511 | uGAAuAGGGuuAcAGAGuuTsT | 512 | AACUCUGuAACCCuAUUcATsT | AD-12303 |
| 1500 | AAGAACUUGAAACCACUCA | 513 | AAGAAcuuGAAAccAcucATsT | 514 | UGAGUGGUUUcAAGUUCUUTsT | AD-12304 |
| 1501 | AAUAAAGCAGACCCAUUCC | 515 | AAuAAAGcAGAcccAuuccTsT | 516 | GGAAUGGGUCUGCUUuAUUTsT | AD-12305 |
| 1502 | AUACCCAUCAACACUGGUA | 517 | AuAcccAucAAcAcuGGuATsT | 518 | uACcAGUGUUGAUGGGuAUTsT | AD-12306 |
| 1503 | UGGAUUGUUCAUCAAUUGG | 519 | uGGAuuGuucAucAAuuGGTsT | 520 | CcAAUUGAuGAAcAAUCcATsT | AD-12307 |
| 1504 | UGGAGAGGUCUAAAGUGGA | 521 | uGGAGAGGucuAAAGuGGATsT | 522 | UCcACUUuAGACCUCUCcATsT | AD-12308 |
| 1505 | GUCAUCCCUAUAGUUCACU | 523 | GucAucccuAuAGuucAcuTsT | 524 | AGUGAACuAuAGGGAUGACTsT | AD-12309 |
| 1506 | AUAAUGGCUAUAAUUUCUC | 525 | AuAAuGGcuAuAAuuucucTsT | 526 | GAGAAAuuAuAGCcAUuAUTsT | AD-12310 |
| 1507 | AUCCCUUGGCUGGUAUAAU | 527 | AucccuuGGcuGGuAuAAuTsT | 528 | AUuAuAcCAGCcAAGGGAUTsT | AD-12311 |
| 1508 | GGGCUAUAAUUGCACUAUC | 529 | GGGcuAuAAuuGcAcuAucTsT | 530 | GAuAGUGcAAUuAuAGCCCTsT | AD-12312 |
| 1509 | GAUUCUCUUGGAGGGCUA | 531 | GAuucucuuGGAGGGcGuATsT | 532 | uACGCCCUCcAAGAGAAUCTsT | AD-12313 |
| 1510 | GCAUCUCUCAAUCUUGAGG | 533 | GcAucucucAAucuuGAGGTsT | 534 | CCUcAAGAUUGAGAGAUGCTsT | AD-12314 |
| 1511 | CAGCAGAAAUCUAAGGAUA | 535 | cAGcAGAAAucuAAGGAuATsT | 536 | uAUCCUuAGAUUUCUGCUGTsT | AD-12315 |
| 1512 | GUCAAGAGCCAUCUGUAGA | 537 | GucAAGAGccAucuGuAGATsT | 538 | UCuAcAGAUGGCUCUUGACTsT | AD-12316 |
| 1513 | AAACAGAGGCAUUAACACA | 539 | AAAcAGAGGcAuuAAcAcATsT | 540 | UGUGUuAAUGCCUCUGUUUTsT | AD-12317 |

TABLE 2a-continued

Sequences of Eg5/ KSP dsRNA duplexes

| SEQ ID NO. | sequence of 19-mer target site | SEQ ID NO. | sense sequence (5'-3') | SEQ ID NO. | antisense sequence (5'-3') | duplex name |
|---|---|---|---|---|---|---|
| 1514 | AGCCCAGAUCAACCUUUAA | 541 | AGcccAGAucAAccuuuAATsT | 542 | UuAAAGGUUGAUCUGGGCUTsT | AD-12318 |
| 1515 | UAUUUUUGAUCUGGCAACC | 543 | uAuuuuuGAucuGGcAAccTsT | 544 | GGUUGCcAGAUcAAAAAuATsT | AD-12319 |
| 1516 | UGUUUGGAGCAUCUACUAA | 545 | uGuuuGGAGcAucuAcuAATsT | 546 | UuAGuAGAUGCUCcAAAcATsT | AD-12320 |
| 1517 | GAAAUUACAGUACACAACA | 547 | GAAAuuAcAGuAcAcAAcATsT | 548 | UGUUGUGuACUGuAAUUUCTsT | AD-12321 |
| 1518 | ACUUGACCAGUGUAAAUCU | 549 | AcuuGAccAGuGuAAAucuTsT | 550 | AGAUUuAcACUGGUcAAGUTsT | AD-12322 |
| 1519 | ACCAGUGUAAAUCUGACCU | 551 | AccAGuGuAAAucuGAccuTsT | 552 | AGGUcAGAUUuAcACUGGUTsT | AD-12323 |
| 1520 | AGAACAAUCAUUAGCAGCA | 553 | AGAAcAAucAuuAGcAGcATsT | 554 | UGCUGCuAAUGAUUGUUCUTsT | AD-12324 |
| 1521 | CAAUGUGGAAACCUAACUG | 555 | cAAuGuGGAAAccuAAcuGTsT | 556 | cAGUuAGGUUUCcAcAUUGTsT | AD-12325 |
| 1522 | ACCAAGAAGGUACAAAAUU | 557 | AccAAGAAGGuAcAAAAuuTsT | 558 | AAUUUUGuACCUUCUUGGUTsT | AD-12326 |
| 1523 | GGUACAAAAUUGGUUGAAG | 559 | GGuAcAAAAuuGGuuGAAGTsT | 560 | CUUcAACcAAUUUUGuACCTsT | AD-12327 |
| 1524 | GGUGUGGAUUGUUCAUCAA | 561 | GGuGuGGAuuGuucAucAATsT | 562 | UUGAUGAAcAAUCcAcACCTsT | AD-12328 |
| 1525 | AGAGUUCACAAAAAGCCCA | 563 | AGAGuucAcAAAAAGcccATsT | 564 | UGGGCUUUUUGUGAACUCUTsT | AD-12329 |
| 1526 | UGAUAGCUAAAUUAAACCA | 565 | uGAuAGcuAAAuuAAAccATsT | 566 | UGGUUuAAUUuAGCuAUcATsT | AD-12330 |
| 1527 | AAUAAGCCUGAAGUGAAUC | 567 | AAuAAGccuGAAGuGAAucTsT | 568 | GAUUcACUUcAGGCUuAUUTsT | AD-12331 |
| 1528 | CAGUUGACCAACACAAUGC | 569 | cAGuuGAccAAcAcAAuGcTsT | 570 | GcAUUGUGUUGGUcAACUGTsT | AD-12332 |
| 1529 | UGGUGUGGAUUGUUCAUCA | 571 | uGGuGuGGAuuGuucAucATsT | 572 | UGAUGAAcAAUCcAcACCATsT | AD-12333 |
| 1530 | AUUCACCCUGACAGAGUUC | 573 | AuucAcccuGAcAGAGuucTsT | 574 | GAACUCUGUcAGGGUGAAUTsT | AD-12334 |
| 1531 | UAAGACCUUAUUUGGUAAU | 575 | uAAGAccuuAuuuGGuAAuTsT | 576 | AUuACcAAAuAAGGUCUuATsT | AD-12335 |
| 1532 | AAGCAAUGUGGAAACCUAA | 577 | AAGcAAuGuGGAAAccuAATsT | 578 | UuAGGUUUCcAcAUUGCUUTsT | AD-12336 |
| 1533 | UCUGAAACUGGAUAUCCCA | 579 | ucuGAAAcuGGAuAucccATsT | 580 | UGGGAuAUCcAGUUUcAGATsT | AD-12337 |

TABLE 2b

Analysis of Eg5/KSP dsRNA duplexes

| Eg5/KSP duplex name | 1st single dose screen @ 50 nM [% residual mRNA] | SDs 1st screen (among quadruplicates) | 2nd single dose screen @ 25 nM [% residual mRNA] | SDs 2nd screen (among quadruplicates) | 3rd single dose screen @ 25 nM | SDs 3rd screen (among quadruplicates) |
|---|---|---|---|---|---|---|
| AD-12072 | 65% | 2% | 82% | 5% | | |
| AD-12073 | 84% | 1% | 61% | 6% | | |
| AD-12074 | 51% | 3% | 36% | 9% | | |
| AD-12075 | 56% | 4% | 36% | 4% | | |
| AD-12076 | 21% | 4% | 13% | 3% | | |
| AD-12077 | 11% | 2% | 6% | 1% | | |
| AD-12078 | 22% | 3% | 9% | 2% | | |
| AD-12079 | 22% | 10% | 15% | 7% | | |
| AD-12080 | 68% | 4% | 52% | 13% | | |
| AD-12081 | 34% | 8% | 35% | 24% | | |
| AD-12082 | 20% | 2% | 92% | 5% | | |
| AD-12083 | 85% | 6% | 63% | 10% | | |
| AD-12084 | 18% | 6% | 17% | 4% | | |
| AD-12085 | 13% | 4% | 12% | 4% | | |
| AD-12086 | 26% | 5% | 17% | 3% | | |
| AD-12087 | 95% | 4% | 80% | 4% | | |
| AD-12088 | 29% | 6% | 29% | 2% | | |
| AD-12089 | 69% | 5% | 64% | 7% | | |
| AD-12090 | 46% | 15% | 34% | 5% | | |

TABLE 2b-continued

Analysis of Eg5/KSP dsRNA duplexes

| Eg5/KSP duplex name | 1st single dose screen @ 50 nM [% resudual mRNA] | SDs 1st screen (among quadruplicates) | 2nd single dose screen @ 25 nM [% resudual mRNA] | SDs 2nd screen (among quadruplicates) | 3rd single dose screen @ 25 nM | SDs 3rd screen (among quadruplicates) |
|---|---|---|---|---|---|---|
| AD-12091 | 16% | 6% | 17% | 3% | | |
| AD-12092 | 82% | 26% | 63% | 5% | | |
| AD-12093 | 84% | 4% | 70% | 4% | | |
| AD-12094 | 46% | 3% | 34% | 1% | | |
| AD-12095 | 14% | 2% | 13% | 1% | | |
| AD-12096 | 26% | 11% | 17% | 1% | | |
| AD-12097 | 23% | 2% | 21% | 1% | | |
| AD-12098 | 41% | 14% | 17% | 3% | | |
| AD-12099 | 57% | 2% | 48% | 6% | | |
| AD-12100 | 101% | 11% | 98% | 8% | | |
| AD-12101 | 46% | 7% | 32% | 2% | | |
| AD-12102 | 96% | 17% | 88% | 18% | | |
| AD-12103 | 19% | 5% | 20% | 2% | | |
| AD-12104 | 40% | 8% | 24% | 2% | | |
| AD-12105 | 39% | 2% | 36% | 10% | | |
| AD-12106 | 87% | 6% | 79% | 19% | | |
| AD-12107 | 29% | 2% | 32% | 16% | | |
| AD-12108 | 38% | 4% | 39% | 8% | | |
| AD-12109 | 49% | 3% | 44% | 10% | | |
| AD-12110 | 85% | 5% | 80% | 14% | | |
| AD-12111 | 64% | 6% | 71% | 18% | | |
| AD-12112 | 48% | 4% | 41% | 5% | | |
| AD-12113 | 13% | 0% | 14% | 3% | | |
| AD-12114 | 32% | 6% | 16% | 4% | | |
| AD-12115 | 8% | 4% | 7% | 5% | | |
| AD-12116 | 74% | 5% | 61% | 7% | | |
| AD-12117 | 21% | 4% | 20% | 2% | | |
| AD-12118 | 44% | 4% | 42% | 6% | | |
| AD-12119 | 37% | 4% | 24% | 3% | | |
| AD-12120 | 22% | 2% | 15% | 4% | | |
| AD-12121 | 32% | 1% | 22% | 2% | | |
| AD-12122 | 36% | 16% | 19% | 5% | | |
| AD-12123 | 28% | 1% | 16% | | | |
| AD-12124 | 28% | 2% | 16% | | | |
| AD-12125 | 15% | 1% | 14% | | | |
| AD-12126 | 51% | 22% | 27% | | | |
| AD-12127 | 54% | 4% | 42% | 9% | | |
| AD-12128 | 29% | 1% | 20% | 2% | | |
| AD-12129 | 22% | 3% | 19% | 3% | | |
| AD-12130 | 53% | 6% | 42% | 7% | | |
| AD-12131 | 28% | 5% | 22% | 3% | | |
| AD-12132 | 88% | 2% | 90% | 18% | | |
| AD-12133 | 34% | 2% | 26% | 6% | | |
| AD-12134 | 18% | 3% | 14% | 2% | | |
| AD-12135 | 50% | 6% | 37% | 4% | | |
| AD-12136 | 42% | 19% | 22% | 2% | | |
| AD-12137 | 85% | 12% | 92% | 4% | | |
| AD-12138 | 47% | 6% | 49% | 1% | | |
| AD-12139 | 80% | 5% | 72% | 4% | | |
| AD-12140 | 97% | 22% | 67% | 9% | | |
| AD-12141 | 120% | 4% | 107% | 10% | | |
| AD-12142 | 55% | 8% | 33% | 4% | | |
| AD-12143 | 64% | 34% | 19% | 2% | | |
| AD-12144 | 58% | 29% | 17% | 2% | | |
| AD-12145 | 27% | 8% | 18% | 2% | | |
| AD-12146 | 19% | 20% | 15% | 1% | | |
| AD-12147 | 29% | 9% | 35% | 3% | | |
| AD-12148 | 30% | 3% | 56% | 5% | | |
| AD-12149 | 8% | 2% | 12% | 3% | | |
| AD-12150 | 31% | 2% | 31% | 7% | | |
| AD-12151 | 9% | 5% | 14% | 2% | | |
| AD-12152 | 3% | 3% | 23% | 3% | | |
| AD-12153 | 20% | 6% | 34% | 4% | | |
| AD-12154 | 24% | 7% | 44% | 3% | | |
| AD-12155 | 33% | 6% | 53% | 11% | | |
| AD-12156 | 35% | 5% | 40% | 5% | | |
| AD-12157 | 8% | 3% | 23% | 4% | | |
| AD-12158 | 13% | 2% | 22% | 5% | | |
| AD-12159 | 34% | 6% | 46% | 5% | | |
| AD-12160 | 19% | 3% | 31% | 4% | | |

TABLE 2b-continued

Analysis of Eg5/KSP dsRNA duplexes

| Eg5/KSP duplex name | 1st single dose screen @ 50 nM [% resudual mRNA] | SDs 1st screen (among quadruplicates) | 2nd single dose screen @ 25 nM [% resudual mRNA] | SDs 2nd screen (among quadruplicates) | 3rd single dose screen @ 25 nM | SDs 3rd screen (among quadruplicates) |
|---|---|---|---|---|---|---|
| AD-12161 | 88% | 4% | 83% | 7% | | |
| AD-12162 | 26% | 7% | 32% | 7% | | |
| AD-12163 | 55% | 9% | 40% | 3% | | |
| AD-12164 | | | 21% | 3% | | |
| AD-12165 | 30% | 3% | 41% | 4% | | |
| AD-12166 | 9% | 10% | 22% | 9% | | |
| AD-12167 | 26% | 3% | 30% | 2% | | |
| AD-12168 | 54% | 4% | 59% | 20% | | |
| AD-12169 | 41% | 4% | 51% | 16% | | |
| AD-12170 | 43% | 4% | 52% | 20% | | |
| AD-12171 | 67% | 3% | 73% | 25% | | |
| AD-12172 | 53% | 15% | 37% | 2% | | |
| AD-12173 | 39% | 0% | 39% | 0% | | |
| AD-12174 | 41% | 5% | 27% | 0% | | |
| AD-12175 | 29% | 0% | 38% | 14% | | |
| AD-12176 | 43% | 2% | 56% | 25% | | |
| AD-12177 | 68% | 6% | 74% | 30% | | |
| AD-12178 | 41% | 4% | 41% | 6% | | |
| AD-12179 | 53% | 5% | 44% | 5% | | |
| AD-12180 | 16% | 2% | 13% | 4% | | |
| AD-12181 | 19% | 3% | 14% | 2% | | |
| AD-12182 | 16% | 4% | 18% | 8% | | |
| AD-12183 | 26% | 3% | 19% | 4% | | |
| AD-12184 | 54% | 2% | 77% | 8% | | |
| AD-12185 | 8% | 1% | 9% | 1% | | |
| AD-12186 | 36% | 3% | 41% | 6% | | |
| AD-12187 | 34% | 17% | 27% | 1% | | |
| AD-12188 | 30% | 3% | 27% | 4% | | |
| AD-12189 | 51% | 4% | 48% | 5% | | |
| AD-12190 | 33% | 2% | 26% | 4% | | |
| AD-12191 | 20% | 2% | 13% | 0% | | |
| AD-12192 | 21% | 1% | 23% | 10% | | |
| AD-12193 | 64% | 8% | 98% | 6% | | |
| AD-12194 | 8% | 2% | 15% | 4% | | |
| AD-12195 | 34% | 2% | 48% | 3% | | |
| AD-12196 | 34% | 2% | 51% | 3% | | |
| AD-12197 | 75% | 4% | 93% | 6% | | |
| AD-12198 | 55% | 5% | 48% | 2% | | |
| AD-12199 | 102% | 6% | 118% | 9% | | |
| AD-12200 | 75% | 6% | 60% | 12% | | |
| AD-12201 | 42% | 3% | 16% | 4% | | |
| AD-12202 | 29% | 4% | 9% | 3% | | |
| AD-12203 | 114% | 14% | 89% | 20% | | |
| AD-12204 | 64% | 7% | 26% | 5% | | |
| AD-12205 | 66% | 12% | 35% | 4% | | |
| AD-12206 | 46% | 3% | 32% | 12% | | |
| AD-12207 | 57% | 5% | 40% | 6% | | |
| AD-12208 | 30% | 8% | 10% | 5% | | |
| AD-12209 | 101% | 6% | 102% | 23% | | |
| AD-12210 | 38% | 11% | 27% | 14% | | |
| AD-12211 | 16% | 6% | 10% | 5% | | |
| AD-12212 | 59% | 8% | 65% | 5% | | |
| AD-12213 | 24% | 9% | 12% | 2% | | |
| AD-12214 | 67% | 14% | 70% | 12% | | |
| AD-12215 | 29% | 13% | 13% | 4% | | |
| AD-12216 | 36% | 4% | 13% | 1% | | |
| AD-12217 | 36% | 9% | 11% | 2% | | |
| AD-12218 | 35% | 5% | 17% | 3% | | |
| AD-12219 | 41% | 9% | 14% | 1% | | |
| AD-12220 | 37% | 5% | 23% | 3% | | |
| AD-12221 | 58% | 7% | 39% | 6% | | |
| AD-12222 | 74% | 9% | 53% | 3% | | |
| AD-12223 | 74% | 10% | 67% | 7% | | |
| AD-12224 | 24% | 2% | 11% | 2% | | |
| AD-12225 | 75% | 5% | 76% | 14% | | |
| AD-12226 | 45% | 8% | 40% | 3% | | |
| AD-12227 | 61% | 6% | 47% | 5% | | |
| AD-12228 | 28% | 3% | 25% | 5% | | |
| AD-12229 | 54% | 13% | 37% | 6% | | |
| AD-12230 | 70% | 17% | 65% | 4% | | |

TABLE 2b-continued

Analysis of Eg5/KSP dsRNA duplexes

| Eg5/KSP duplex name | 1st single dose screen @ 50 nM [% resudual mRNA] | SDs 1st screen (among quadruplicates) | 2nd single dose screen @ 25 nM [% resudual mRNA] | SDs 2nd screen (among quadruplicates) | 3rd single dose screen @ 25 nM | SDs 3rd screen (among quadruplicates) |
|---|---|---|---|---|---|---|
| AD-12231 | 32% | 12% | 22% | 6% | | |
| AD-12232 | 30% | 3% | 17% | 2% | | |
| AD-12233 | 38% | 2% | 32% | 3% | | |
| AD-12234 | 90% | 5% | 95% | 7% | | |
| AD-12235 | 57% | 7% | 46% | 3% | | |
| AD-12236 | 34% | 8% | 16% | 2% | | |
| AD-12237 | 42% | 9% | 32% | 8% | | |
| AD-12238 | 42% | 6% | 34% | 6% | | |
| AD-12239 | 42% | 3% | 40% | 4% | | |
| AD-12240 | 47% | 6% | 36% | 5% | | |
| AD-12241 | 69% | 5% | 70% | 8% | | |
| AD-12242 | 61% | 2% | 47% | 3% | | |
| AD-12243 | 26% | 7% | 15% | 1% | | |
| AD-12244 | 25% | 6% | 15% | 1% | | |
| AD-12245 | 65% | 6% | 83% | 13% | | |
| AD-12246 | 29% | 7% | 31% | 6% | | |
| AD-12247 | 57% | 13% | 50% | 3% | | |
| AD-12248 | 36% | 8% | 20% | 3% | 15% | 7% |
| AD-12249 | 44% | 3% | 70% | 11% | 103% | 34% |
| AD-12250 | 47% | 5% | 18% | 5% | 17% | 4% |
| AD-12251 | 121% | 28% | 35% | 8% | 60% | 42% |
| AD-12252 | 94% | 19% | 8% | 3% | 5% | 3% |
| AD-12253 | 94% | 33% | 42% | 8% | 49% | 27% |
| AD-12254 | 101% | 58% | 70% | 5% | 80% | 32% |
| AD-12255 | 163% | 27% | 28% | 6% | 36% | 10% |
| AD-12256 | 112% | 62% | 18% | 3% | 9% | 4% |
| AD-12257 | 10% | 4% | 9% | 2% | 6% | 2% |
| AD-12258 | 27% | 9% | 18% | 3% | 20% | 6% |
| AD-12259 | 20% | 5% | 12% | 2% | 13% | 5% |
| AD-12260 | 22% | 7% | 81% | 7% | 65% | 13% |
| AD-12261 | 122% | 11% | 66% | 7% | 80% | 22% |
| AD-12262 | 97% | 30% | 33% | 6% | 44% | 18% |
| AD-12263 | 177% | 57% | 85% | 11% | 84% | 15% |
| AD-12264 | 37% | 6% | 10% | 1% | 10% | 4% |
| AD-12265 | 40% | 8% | 17% | 1% | 20% | 10% |
| AD-12266 | 33% | 9% | 9% | 1% | 8% | 4% |
| AD-12267 | 34% | 13% | 11% | 1% | 6% | 2% |
| AD-12268 | 34% | 6% | 11% | 1% | 9% | 2% |
| AD-12269 | 54% | 6% | 33% | 4% | 29% | 7% |
| AD-12270 | 52% | 5% | 29% | 4% | 27% | 6% |
| AD-12271 | 53% | 7% | 27% | 3% | 19% | 6% |
| AD-12272 | 85% | 15% | 57% | 7% | 51% | 16% |
| AD-12273 | 36% | 6% | 26% | 2% | 30% | 5% |
| AD-12274 | 75% | 21% | 40% | 2% | 50% | 19% |
| AD-12275 | 29% | 9% | 8% | 1% | 8% | 4% |
| AD-12276 | 45% | 19% | 15% | 2% | 16% | 12% |
| AD-12277 | 58% | 17% | 32% | 2% | 55% | 14% |
| AD-12278 | 120% | 35% | 96% | 10% | 124% | 38% |
| AD-12279 | 47% | 29% | 17% | 1% | 12% | 4% |
| AD-12280 | 2% | 0% | 3% | 1% | | |
| AD-12281 | 2% | 0% | 5% | 2% | | |
| AD-12282 | 3% | 0% | 25% | 5% | | |
| AD-12283 | 3% | 1% | 35% | 4% | | |
| AD-12284 | 5% | 2% | 49% | 8% | | |
| AD-12285 | 7% | 7% | 21% | 26% | | |
| AD-12286 | 28% | 34% | 12% | 7% | | |
| AD-12287 | 40% | 21% | 51% | 23% | | |
| AD-12288 | 26% | 7% | 155% | 146% | | |
| AD-12289 | 43% | 21% | 220% | 131% | | |
| AD-12290 | 2% | 1% | 81% | 23% | | |
| AD-12291 | 4% | 1% | 70% | 3% | | |
| AD-12292 | 2% | 1% | 6% | 2% | | |
| AD-12293 | 4% | 2% | 36% | 3% | | |
| AD-12294 | 10% | 6% | 38% | 3% | | |
| AD-12295 | 29% | 31% | 37% | 3% | | |
| AD-12296 | 82% | 4% | 89% | 2% | | |
| AD-12297 | 75% | 3% | 65% | 2% | | |
| AD-12298 | 73% | 4% | 60% | 3% | | |
| AD-12299 | 76% | 4% | 66% | 4% | | |
| AD-12300 | 36% | 4% | 15% | 1% | | |

TABLE 2b-continued

Analysis of Eg5/KSP dsRNA duplexes

| Eg5/KSP duplex name | 1st single dose screen @ 50 nM [% resudual mRNA] | SDs 1st screen (among quadruplicates) | 2nd single dose screen @ 25 nM [% residual mRNA] | SDs 2nd screen (among quadruplicates) | 3rd single dose screen @ 25 nM | SDs 3rd screen (among quadruplicates) |
|---|---|---|---|---|---|---|
| AD-12301 | 33% | 4% | 18% | 2% | | |
| AD-12302 | 66% | 5% | 65% | 3% | | |
| AD-12303 | 35% | 6% | 17% | 2% | | |
| AD-12304 | 70% | 8% | 70% | 6% | | |
| AD-12305 | 63% | 8% | 80% | 7% | | |
| AD-12306 | 23% | 6% | 20% | 3% | | |
| AD-12307 | 78% | 10% | 58% | 5% | | |
| AD-12308 | 27% | 8% | 15% | 2% | | |
| AD-12309 | 58% | 11% | 42% | 3% | | |
| AD-12310 | 106% | 23% | 80% | 2% | | |
| AD-12311 | 73% | 12% | 60% | 2% | | |
| AD-12312 | 39% | 3% | 36% | 3% | | |
| AD-12313 | 64% | 9% | 49% | 6% | | |
| AD-12314 | 28% | 7% | 14% | 6% | | |
| AD-12315 | 31% | 7% | 13% | 2% | | |
| AD-12316 | 42% | 5% | 14% | 2% | | |
| AD-12317 | 34% | 9% | 15% | 5% | | |
| AD-12318 | 46% | 4% | 28% | 4% | | |
| AD-12319 | 77% | 3% | 56% | 4% | | |
| AD-12320 | 55% | 7% | 41% | 3% | | |
| AD-12321 | 21% | 3% | 10% | 2% | | |
| AD-12322 | 27% | 8% | 30% | 12% | | |
| AD-12323 | 26% | 7% | 35% | 18% | | |
| AD-12324 | 27% | 8% | 27% | 14% | | |
| AD-12325 | 32% | 12% | 32% | 22% | | |
| AD-12326 | 42% | 22% | 45% | 41% | | |
| AD-12327 | 36% | 14% | 37% | 32% | | |
| AD-12328 | 45% | 2% | 31% | 3% | | |
| AD-12329 | 61% | 4% | 34% | 3% | | |
| AD-12330 | 63% | 5% | 38% | 4% | | |
| AD-12331 | 50% | 2% | 26% | 5% | | |
| AD-12332 | 80% | 4% | 51% | 7% | | |
| AD-12333 | 34% | 6% | 12% | 2% | | |
| AD-12334 | 27% | 2% | 18% | 3% | | |
| AD-12335 | 84% | 6% | 60% | 7% | | |
| AD-12336 | 45% | 4% | 36% | 4% | | |
| AD-12337 | 30% | 7% | 19% | 2% | | |

TABLE 3

Sequences and analysis of Eg5/KSP dsRNA duplexes

| Sense sequence (5'-3') | SEQ ID NO. | Antisense sequence (5'-3') | SEQ ID NO. | duplex name | single dose screen @ 25 nM [% residual mRNA] | SDs 2nd screen (among quadru-plicates) |
|---|---|---|---|---|---|---|
| ccAuuAcuAcAGuAGcAcuTsT | 582 | AGUGCuACUGuAGuAAUGGTsT | 583 | AD-14085 | 19% | 1% |
| AucuGGcAAccAuAuuucuTsT | 584 | AGAAAuAUGGUUGCcAGAUTsT | 585 | AD-14086 | 38% | 1% |
| GAuAGcuAAAuuAAAccAATsT | 586 | UUGGUUuAAUUuAGCuAUCTsT | 587 | AD-14087 | 75% | 10% |
| AGAuAccAuuAcuAcAGuATsT | 588 | uACUGuAGuAAUGGuAUCUTsT | 589 | AD-14088 | 22% | 8% |
| GAuuGuucAucAAuuGGcGTsT | 590 | CGCcAAUUGAUGAAcAAUCTsT | 591 | AD-14089 | 70% | 12% |
| GcuuucccucGGcucAcuTsT | 592 | AGuGAGCCGAGGAGAAAGCTsT | 593 | AD-14090 | 79% | 11% |
| GGAGGAuuGGcuGAcAAGATsT | 594 | UCUUGUcAGCcAAUCCUCCTsT | 595 | AD-14091 | 29% | 3% |
| uAAuGAAGAGuAuAccGGTsT | 596 | CcAGGuAuACUCUUcAUuATsT | 597 | AD-14092 | 23% | 2% |
| uuucAccAAAccAuuuGuATsT | 598 | uAcAAAUGGUUUGGUGAAATsT | 599 | AD-14093 | 60% | 2% |

TABLE 3-continued

Sequences and analysis of Eg5/KSP dsRNA duplexes

| Sense sequence (5'-3') | SEQ ID NO. | Antisense sequence (5'-3') | SEQ ID NO. | duplex name | single dose screen @ 25 nM [% residual mRNA] | SDs 2nd screen (among quadru-plicates) |
|---|---|---|---|---|---|---|
| cuuAuuAAGGAGuAuAcGGTsT | 600 | CCGuAuACUCCUuAAuAAGTsT | 601 | AD-14094 | 11% | 3% |
| GAAAucAGAuGGAcGuAAGTsT | 602 | CUuACGUCcAUCUGAUUUCTsT | 603 | AD-14095 | 10% | 2% |
| cAGAuGucAGcAuAAGcGATsT | 604 | UCGCUuAUGCUGAcAUCUGTsT | 605 | AD-14096 | 27% | 2% |
| AucuAAcccuAGuuGuAucTsT | 606 | GAuAcAACuAGGGUuAGAUTsT | 607 | AD-14097 | 45% | 6% |
| AAGAGcuuGuuAAAAucGGTsT | 608 | CCGAUUUuAAcAAGCUCUUTsT | 609 | AD-14098 | 50% | 10% |
| uuAAGGAGuAuAcGGAGGATsT | 610 | UCCUCCGuAuACUCCUuAATsT | 611 | AD-14099 | 12% | 4% |
| uuGcAAuGuAAAuAcGAuTsT | 612 | AuACGuAUUuAcAUUGcAATsT | 613 | AD-14100 | 49% | 7% |
| ucuAAcccuAGuuGuAuccTsT | 614 | GGAuAcAACuAGGGUuAGATsT | 615 | AD-14101 | 36% | 1% |
| cAuGuAucuuuuucucGAuTsT | 616 | AUCGAGAAAAAGAuAcAUGTsT | 617 | AD-14102 | 49% | 3% |
| GAuGucAGcAuAAGcGAuGTsT | 618 | cAUCGCUuAUGCUGAcAUCTsT | 619 | AD-14103 | 74% | 5% |
| ucccAAcAGGuAcGAcAccTsT | 620 | GGGuGUCGuACCUGUUGGGATsT | 621 | AD-14104 | 27% | 3% |
| uGcucAcGAuGAGuuuAGuTsT | 622 | ACuAAACUcAUCGUGAGcATsT | 623 | AD-14105 | 34% | 4% |
| AGAGcuuGuuAAAAucGGATsT | 624 | UCCGAUUUuAAcAAGCUCUTsT | 625 | AD-14106 | 9% | 2% |
| GcGuAcAAGAAcAucuAuATsT | 626 | uAuAGAUGUUCUUGuACGCTsT | 627 | AD-14107 | 5% | 1% |
| GAGGuuGuAAGccAAuGuuTsT | 628 | AAcAUUGGCUuAcAACCUCTsT | 629 | AD-14108 | 15% | 1% |
| AAcAGGuAcGAcAccAcAGTsT | 630 | CUGUGGUGUCGuACCUGUUTsT | 631 | AD-14109 | 91% | 2% |
| AAcccuAGuuGuAucccucTsT | 632 | GAGGGAuAcAACuAGGGUUTsT | 633 | AD-14110 | 66% | 5% |
| GcAuAAGcGAuGGAuAAuATsT | 634 | uAUuAUCcAUCGCUuAUGCTsT | 635 | AD-14111 | 33% | 3% |
| AAGcGAuGGAuAAuAccuATsT | 636 | uAGGuAUuAUCcAUCGCUUTsT | 637 | AD-14112 | 51% | 3% |
| uGAuccuGuAcGAAAAGAATsT | 638 | UUCUUUUCGuAcAGGAUcATsT | 639 | AD-14113 | 22% | 3% |
| AAAAcAuuGGccGuucuGGTsT | 640 | CcAGAACGGCcAAUGUUUUTsT | 641 | AD-14114 | 117% | 8% |
| cuuGGAGGGcGuAcAAGAATsT | 642 | UUCUUGuACGCCCUCCAAGTsT | 643 | AD-14115 | 50% | 8% |
| GGcGuAcAAGAAcAucuAuTsT | 644 | AuAGAUGUUCUUGuACGCCTsT | 645 | AD-14116 | 14% | 3% |
| AcucuGAGuAcAuuGGAAuTsT | 646 | AUUCcAAUGuACUcAGAGUTsT | 647 | AD-14117 | 12% | 4% |
| uuAuuAAGGAGuAuAcGGATsT | 648 | UCCGuAuACUCCUuAAuAATsT | 649 | AD-14118 | 26% | 4% |
| uAAGGAGuAuAcGGAGGAGTsT | 650 | CUCCUCCGuAuACUCCUuATsT | 651 | AD-14119 | 24% | 5% |
| AAAucAAuAGucAAcuAAATsT | 652 | UUuAGUUGACuAUUGAUUUTsT | 653 | AD-14120 | 8% | 1% |
| AAucAAuAGucAAcuAAAGTsT | 654 | CUUuAGUUGACuAUUGAUUTsT | 655 | AD-14121 | 24% | 2% |
| uucucAGuAuAcuGuGuAATsT | 656 | UuAcAcAGuAuACUGAGAATsT | 657 | AD-14122 | 10% | 1% |
| uGuGAAAcAcucuGAuAAATsT | 658 | UUuAUcAGAGUGUUUcAcATsT | 659 | AD-14123 | 8% | 1% |
| AGAuGuGAAucucuGAAcATsT | 660 | UGUUcAGAGAUUcAcAUCUTsT | 661 | AD-14124 | 9% | 2% |
| AGGuuGuAAGccAAuGuuGTsT | 662 | cAAcAUUGGCUuAcAACCUTsT | 663 | AD-14125 | 114% | 6% |
| uGAGAAucAGAuGGAcGuTsT | 664 | ACGUCcAUCUGAUUUCuATsT | 665 | AD-14126 | 9% | 1% |
| AGAAucAGAuGGAcGuAATsT | 666 | UuACGUCcAUCUGAUUUCUTsT | 667 | AD-14127 | 57% | 6% |
| AuAucccAAcAGGuAcGAcTsT | 668 | GUCGuACCUGUUGGGAuAUTsT | 669 | AD-14128 | 104% | 6% |

TABLE 3-continued

Sequences and analysis of Eg5/KSP dsRNA duplexes

| Sense sequence (5'-3') | SEQ ID NO. | Antisense sequence (5'-3') | SEQ ID NO. | duplex name | single dose screen @ 25 nM [% residual mRNA] | SDs 2nd screen (among quadruplicates) |
|---|---|---|---|---|---|---|
| cccAAcAGGuAcGAcAccATsT | 670 | UGGUGUCGuACCUGUUGGGTsT | 671 | AD-14129 | 21% | 2% |
| AGuAuAcuGAAGAAccucuTsT | 672 | AGAGGUUCUUcAGuAuACUTsT | 673 | AD-14130 | 57% | 6% |
| AuAuAuAucAGccGGGcGcTsT | 674 | GCGCCCGGCUGAuAuAuAUTsT | 675 | AD-14131 | 93% | 6% |
| AAucuAAcccuAGuuGuAuTsT | 676 | AuAcAACuAGGGUuAGAUUTsT | 677 | AD-14132 | 75% | 8% |
| cuAAcccuAGuuGuAucccTsT | 678 | GGGAuAcAACuAGGGUuAGTsT | 679 | AD-14133 | 66% | 4% |
| cuAGuuGuAucccuccuuuTsT | 680 | AAAGGAGGGAuAcAACuAGTsT | 681 | AD-14134 | 44% | 6% |
| AGAcAucuGAcuAAuGGcuTsT | 682 | AGCcAUuAGUcAGAUGUCUTsT | 683 | AD-14135 | 55% | 6% |
| GAAGcucAcAAuGAuuuAATsT | 684 | UuAAAUcAUUGUGAGCUUCTsT | 685 | AD-14136 | 29% | 3% |
| AcAuGuAucuuuucucGATsT | 686 | UCGAGAAAAGAuAcAUGUTsT | 687 | AD-14137 | 40% | 3% |
| ucGAuucAAAucuuAAcccTsT | 688 | GGGUuAAGAUUUGAAUCGATsT | 689 | AD-14138 | 39% | 5% |
| ucuuAAcccuuAGGAcucuTsT | 690 | AGAGUCCuAAGGGUuAAGATsT | 691 | AD-14139 | 71% | 11% |
| GcucAcGAuGAGuuuAGuGTsT | 692 | cACuAAACUcAUCGUGAGCTsT | 693 | AD-14140 | 43% | 15% |
| cAuAAGcGAuGGAuAAuAcTsT | 694 | GuAUuAUCcAUCGCUuAUGTsT | 695 | AD-14141 | 33% | 6% |
| AuAAGcGAuGGAuAAuAccTsT | 696 | GGuAUuAUCcAUCGCUuAUTsT | 697 | AD-14142 | 51% | 14% |
| ccuAuAAAcuGcccucAGTsT | 698 | CUGAGGGcAGUUuAUuAGGTsT | 699 | AD-14143 | 42% | 1% |
| ucGGAAAGuuGAAcuuGGuTsT | 700 | ACcAAGUUcAACUUUCCGATsT | 701 | AD-14144 | 4% | 4% |
| GAAAAcAuuGGccGuucuGTsT | 702 | cAGAACGGCcAAUGUUUUCTsT | 703 | AD-14145 | 92% | 5% |
| AAGAcuGAucuucuAAGuuTsT | 704 | AACuuAGAAGAUcAGUCUUTsT | 705 | AD-14146 | 13% | 2% |
| GAGcuuGuuAAAAucGGAATsT | 706 | UUCCGAUUUuAAcAAGCUCTsT | 707 | AD-14147 | 8% | 1% |
| AcAuuGGccGuucuGGAGcTsT | 708 | GCUCcAGAACGGCcAAUGUTsT | 709 | AD-14148 | 80% | 7% |
| AAGAAcAucuAuAuuGcATsT | 710 | UGcAAUuAuAGAUGUUCUUTsT | 711 | AD-14149 | 44% | 7% |
| AAAuGucucAcucAuGuuTsT | 712 | AAcAUGAGuGAGAcAcAUUUTsT | 713 | AD-14150 | 32% | 29% |
| uGucuAcucAuGuuucucATsT | 714 | UGAGAAAcAUGAGuAGAcATsT | 715 | AD-14151 | 75% | 11% |
| GuAuAcuGuGuAAcAAucuTsT | 716 | AGAUUGUuAcAcAGuAuACTsT | 717 | AD-14152 | 8% | 5% |
| uAuAcuGuGuAAcAAucuATsT | 718 | uAGAUUGUuAcAcAGuAuATsT | 719 | AD-14153 | 17% | 11% |
| cuuAGuAGuGuccAGGAAATsT | 720 | UUUCCUGGAcACuACuAAGTsT | 721 | AD-14154 | 16% | 4% |
| ucAGAuGGAcGuAAGGcAGTsT | 722 | CUGCCUuACGUCcAUCUGATsT | 723 | AD-14155 | 11% | 1% |
| AGAuAAAuuGAuAGcAcAATsT | 724 | UUGUGCuAUcAAUUuAUCUTsT | 725 | AD-14156 | 10% | 1% |
| cAAcAGGuAcGAcAccAcATsT | 726 | UGUGGUGUCGuACCUGUUGTsT | 727 | AD-14157 | 29% | 3% |
| uGcAAuGuAAAuAcGuAuuTsT | 728 | AAuACGuAUUuAcAUUGcATsT | 729 | AD-14158 | 51% | 3% |
| AGucAGAAuuuuAucuAGATsT | 730 | UCuAGAuAAAAUUCUGACUTsT | 731 | AD-14159 | 53% | 5% |
| cuAGAAucuuuuAAcAccTsT | 732 | GGUGUuAAAAGAUUUCuAGTsT | 733 | AD-14160 | 40% | 3% |
| AAuAAAucuAAcccuAGuuTsT | 734 | AACuAGGGUuAGAUUuAUUTsT | 735 | AD-14161 | 83% | 7% |
| AAuuucuGcucAcGAuGATsT | 736 | UcAUCGUGAGcAGAAAUUTsT | 737 | AD-14162 | 44% | 6% |
| GcccucAGuAAAuccAuGGTsT | 738 | CcAUGGAUUuACUGAGGGCTsT | 739 | AD-14163 | 57% | 3% |

TABLE 3-continued

Sequences and analysis of Eg5/KSP dsRNA duplexes

| Sense sequence (5'-3') | SEQ ID NO. | Antisense sequence (5'-3') | SEQ ID NO. | duplex name | single dose screen @ 25 nM [% residual mRNA] | SDs 2nd screen (among quadruplicates) |
|---|---|---|---|---|---|---|
| AcGuuuAAAAcGAGAucuuTsT | 740 | AAGAUCUCGUUUuAAACGUTsT | 741 | AD-14164 | 4% | 1% |
| AGGAGAuAGAAcGuuuAAATsT | 742 | UUuAAACGUUCuAUCUCCUTsT | 743 | AD-14165 | 11% | 1% |
| GAccGucAuGGcGucGcAGTsT | 744 | CUGCGACGCcAUGACGGUCTsT | 745 | AD-14166 | 90% | 5% |
| AccGucAuGGcGucGcAGcTsT | 746 | GCUGCGACGCcAUGACGGUTsT | 747 | AD-14167 | 49% | 1% |
| GAAcGuuuAAAAcGAGAucTsT | 748 | GAUCUCGUUUuAAACGUUCTsT | 749 | AD-14168 | 12% | 2% |
| uuGAGcuuAAcAuAGGuAATsT | 750 | UuACCuAUGUuAAGCUcAATsT | 751 | AD-14169 | 66% | 4% |
| AcuAAAuuGAucucGuAGATsT | 752 | UCuACGAGAUcAAUUuAGUTsT | 753 | AD-14170 | 52% | 6% |
| ucGuAGAAuuAucuuAAuATsT | 754 | uAUuAAGAuAAUUCuACGATsT | 755 | AD-14171 | 42% | 4% |
| GGAGAuAGAAcGuuuAAAATsT | 756 | UUUuAAACGUUCuAUCUCCTsT | 757 | AD-14172 | 3% | 1% |
| AcAAcuuAuuGGAGGuuGuTsT | 758 | AcAACCUCcAAuAAGUUGUTsT | 759 | AD-14173 | 29% | 2% |
| uGAGcuuAAcAuAGGuAAATsT | 760 | UUuACCuAUGUuAAGCUcATsT | 761 | AD-14174 | 69% | 2% |
| AucucGuAGAAuuAucuuATsT | 762 | uAAGAuAAUUCuACGAGAUTsT | 763 | AD-14175 | 53% | 3% |
| cuGcGuGcAGucGGuccucTsT | 764 | GAGGACCGACUGCACGCAGTsT | 765 | AD-14176 | 111% | 4% |
| cAcGcAGcGcccGAGAGuATsT | 766 | uACUCUCGGGCGCUGCGUGTsT | 767 | AD-14177 | 87% | 6% |
| AGuAccAGGGAGAcuccGGTsT | 768 | CCGGAGUCUCCCUGGuACUTsT | 769 | AD-14178 | 59% | 2% |
| AcGGAGGAGAuAGAAcGuuTsT | 770 | AACGUUCuAUCUCCUCCGUTsT | 771 | AD-14179 | 9% | 2% |
| AGAAcGuuuAAAAcGAGAuTsT | 772 | AUCUCGUUUuAAACGUUCUTsT | 773 | AD-14180 | 43% | 2% |
| AAcGuuuAAAAcGAGAucuTsT | 774 | AGAUCUCGUUUuAAACGUUTsT | 775 | AD-14181 | 70% | 10% |
| AGcuuGAGcuuAAcAuAGGTsT | 776 | CCuAUGUuAAGCUcAAGCUTsT | 777 | AD-14182 | 100% | 7% |
| AGcuuAAcAuAGGuAAAuATsT | 778 | uAUUuACCuAUGUuAAGCUTsT | 779 | AD-14183 | 60% | 5% |
| uAGcuAcAAAAccuAucTsT | 780 | GAuAGGUUUUGuAGCUCuATsT | 781 | AD-14184 | 129% | 6% |
| uAGuuGuAucccuccuuuATsT | 782 | uAAAGGAGGGAuAcAACuATsT | 783 | AD-14185 | 62% | 4% |
| AccAcccAGAcAucuGAcuTsT | 784 | AGUcAGAUGUCUGGGUGGUTsT | 785 | AD-14186 | 42% | 3% |
| AGAAAcuAAAuuGAucucGTsT | 786 | CGAGAUcAAUUuAGUUUCUTsT | 787 | AD-14187 | 123% | 12% |
| ucucGuAGAAuuAucuuAATsT | 788 | UuAAGAuAAUUCuACGAGATsT | 789 | AD-14188 | 38% | 2% |
| cAAcuuAuuGGAGGuuGuATsT | 790 | uAcAACCUCcAAuAAGUUGTsT | 791 | AD-14189 | 13% | 1% |
| uuGuAucccuccuuuAAGuTsT | 792 | ACUuAAAGGAGGGAuAcAATsT | 793 | AD-14190 | 59% | 3% |
| ucAcAAcuuAuuGGAGGuuTsT | 794 | AACCUCcAAuAAGUUGUGATsT | 795 | AD-14191 | 93% | 3% |
| AGAAcuGuAcucuucucAGTsT | 796 | CUGAGAAGAGuAcAGUUCUTsT | 797 | AD-14192 | 45% | 5% |
| GAGcuuAAcAuAGGuAAAuTsT | 798 | AUUuACCuAUGUuAAGCUCTsT | 799 | AD-14193 | 57% | 3% |
| cAccAAcucuGuccuuAGTsT | 800 | CuAAGGAcAGAUGUUGGUGTsT | 801 | AD-14194 | 51% | 4% |
| AAAGcccAcuuuAGAGuAuTsT | 802 | AuACUCuAAAGUGGGCUUUTsT | 803 | AD-14195 | 77% | 5% |
| AAGcccAcuuuAGAGuAuATsT | 804 | uAuACUCuAAAGUGGGCUUTsT | 805 | AD-14196 | 42% | 6% |
| GAccuuAuuuGGuAAucuGTsT | 806 | cAGAUuACcAAAuAAGGUCTsT | 807 | AD-14197 | 15% | 2% |
| GAuuAAuGuAcucAAGAcuTsT | 808 | AGUCUUGAGuAcAUuAAUCTsT | 809 | AD-14198 | 12% | 2% |

TABLE 3-continued

Sequences and analysis of Eg5/KSP dsRNA duplexes

| Sense sequence (5'-3') | SEQ ID NO. | Antisense sequence (5'-3') | SEQ ID NO. | duplex name | single dose screen @ 25 nM [% residual mRNA] | SDs 2nd screen (among quadruplicates) |
|---|---|---|---|---|---|---|
| cuuuAAGAGGccuAAcucATsT | 810 | UGAGUuAGGCCUCUuAAAGTsT | 811 | AD-14199 | 18% | 2% |
| uuAAAccAAAcccuAuuGATsT | 812 | UcAAuAGGGUUUGGUUuAATsT | 813 | AD-14200 | 72% | 9% |
| ucuGuuGGAGAucuAuAAuTsT | 814 | AUuAuAGAUCUCcAAcAGATsT | 815 | AD-14201 | 9% | 3% |
| cuGAuGuuucuGAGAGAcuTsT | 816 | AGUCUCUcAGAAAcAUcAGTsT | 817 | AD-14202 | 25% | 3% |
| GcAuAcucuAGucGuucccTsT | 818 | GGGAACGACuAGAGuAUGCTsT | 819 | AD-14203 | 21% | 1% |
| GuuccuuAucGAGAAucuATsT | 820 | uAGAUUCUCGAuAAGGAACTsT | 821 | AD-14204 | 4% | 2% |
| GcAcuuGGAucucucAcAuTsT | 822 | AUGUGAGAGAUCcAAGUGCTsT | 823 | AD-14205 | 5% | 1% |
| AAAAAAGGAAcuAGAuGGcTsT | 824 | GCcAUCuAGUUCCUUUUUUTsT | 825 | AD-14206 | 79% | 6% |
| AGAGcAGAuuAccucuGcGTsT | 826 | CGcAGAGGuAAUCUGCUCUTsT | 827 | AD-14207 | 55% | 2% |
| AGcAGAuuAccucuGcGAGTsT | 828 | CUCGcAGAGGuAAUCUGCUTsT | 829 | AD-14208 | 100% | 4% |
| cccuGAcAGAGuucAcAAATsT | 830 | UUUGUGAACUCUGUcAGGGTsT | 831 | AD-14209 | 34% | 3% |
| GuuuAccGAAGuGuuGuuuTsT | 832 | AAAcAAcACUUCGGuAAACTsT | 833 | AD-14210 | 13% | 2% |
| uuAcAGuAcAcAAcAAGGATsT | 834 | UCCUUGUUGUGuACGuAATsT | 835 | AD-14211 | 9% | 1% |
| AcuGGAucGuAAGAAGGcATsT | 836 | UGCCUUCUuACGAUCcAGUTsT | 837 | AD-14212 | 20% | 3% |
| GAGcAGAuuAccucuGcGATsT | 838 | UCGcAGAGGuAAUCUGCUCTsT | 839 | AD-14213 | 48% | 5% |
| AAAAGAAGuuAGuGuAcGATsT | 840 | UCGuAcACuAACUUCUUUUTsT | 841 | AD-14214 | 28% | 18% |
| GAccAuuuAAuuuGGcAGATsT | 842 | UCUGCcAAAUuAAAUGGUCTsT | 843 | AD-14215 | 132% | 0% |
| GAGAGGAGuGAuAAuuAAATsT | 844 | UUuAAUuAUcACUCCUCUCTsT | 845 | AD-14216 | 3% | 0% |
| cuGGAGGAuuGGcuGAcAATsT | 846 | UUGUcAGCcAAUCCUCcAGTsT | 847 | AD-14217 | 19% | 1% |
| cucuAGucGuucccAcucATsT | 848 | UGAGUGGGAACGACuAGAGTsT | 849 | AD-14218 | 67% | 8% |
| GAuAccAuuAcAcAGuAGTsT | 850 | CuACUGuAGuAAUGGuAUCTsT | 851 | AD-14219 | 76% | 4% |
| uucGucuGcGAAGAAGAAATsT | 852 | UUUCUUCUUCGcAGACGAATsT | 853 | AD-14220 | 33% | 8% |
| GAAAGAAGuuAGuGuAcGTsT | 854 | CGuAcACuAACUUCUUUUCTsT | 855 | AD-14221 | 25% | 2% |
| uGAuGuuuAccGAAGuGuuTsT | 856 | AAcACUUCGGuAAAcAUcATsT | 857 | AD-14222 | 7% | 2% |
| uGuuuGuccAAuucuGGAuTsT | 858 | AUCcAGAAUUGGAcAAAcATsT | 859 | AD-14223 | 19% | 2% |
| AuGAAGAGuAuAccGGGATsT | 860 | UCCcAGGuAuACUCUUcAUTsT | 861 | AD-14224 | 13% | 1% |
| GcuAcucuGAuGAAuGcAuTsT | 862 | AUGcAUUcAUcAGAGuAGCTsT | 863 | AD-14225 | 15% | 2% |
| GcccuuGuAGAAAGAAcAcTsT | 864 | GUGUUCUUUCuAcAAGGGCTsT | 865 | AD-14226 | 11% | 0% |
| ucAuGuuccuuAucGAGAATsT | 866 | UUCUCGAuAAGGAAcAUGATsT | 867 | AD-14227 | 5% | 1% |
| GAAuAGGGuuAcAGAGuuGTsT | 868 | cAACUCUGuAACCCuAUUCTsT | 869 | AD-14228 | 34% | 3% |
| cAAAcuGGAucGuAAGAAGTsT | 870 | CUUCUuACGAUCcAGUUUGTsT | 871 | AD-14229 | 15% | 2% |
| cuuAuuuGGuAAucuGcuGTsT | 872 | cAGcAGAUuACcAAAuAAGTsT | 873 | AD-14230 | 20% | 1% |
| AGcAAuGuGGAAAccuAAcTsT | 874 | GUuAGGUUUCcAcAUUGCUTsT | 875 | AD-14231 | 18% | 1% |
| AcAAuAAAGcAGAcccAuuTsT | 876 | AAUGGGUCUGCUUuAUUGUTsT | 877 | AD-14232 | 21% | 1% |
| AAccAcuuAGuAGuGuccATsT | 878 | UGGAcACuACuAAGUGGUUTsT | 879 | AD-14233 | 106% | 12% |

TABLE 3-continued

Sequences and analysis of Eg5/KSP dsRNA duplexes

| Sense sequence (5'-3') | SEQ ID NO. | Antisense sequence (5'-3') | SEQ ID NO. | duplex name | single dose screen @ 25 nM [% residual mRNA] | SDs 2nd screen (among quadruplicates) |
|---|---|---|---|---|---|---|
| AGucAAGAGccAucuGuAGTsT | 880 | CuAcAGAUGGCUCUUGACUTsT | 881 | AD-14234 | 35% | 3% |
| cucccuAGAcuucccuAuuTsT | 882 | AAuAGGGAAGUCuAGGGAGTsT | 883 | AD-14235 | 48% | 4% |
| AuAGcuAAAuuAAAccAAATsT | 884 | UUUGGUUuAAUUuAGCuAUTsT | 885 | AD-14236 | 23% | 3% |
| uGGcuGGuAuAAuuccAcGTsT | 886 | CGUGGAAUuAuACcAGCcATsT | 887 | AD-14237 | 79% | 9% |
| uuAuuuGGuAAucuGcuGuTsT | 888 | AcAGcAGAUuACcAAAuAATsT | 889 | AD-14238 | 92% | 7% |
| AAcuAGAuGGcuuucucAGTsT | 890 | CUGAGAAAGCcAUCuAGUUTsT | 891 | AD-14239 | 20% | 2% |
| ucAuGGcGucGcAGccAAATsT | 892 | UUUGGCUGCGACGCcAUGATsT | 893 | AD-14240 | 71% | 6% |
| AcuGGAGGAuuGGcuGAcATsT | 894 | UGUcAGCcAAUCCUCcAGUTsT | 895 | AD-14241 | 14% | 1% |
| cuAuAAuuGcAcuAucuuuTsT | 896 | AAAGAuAGUGcAAUuAuAGTsT | 897 | AD-14242 | 11% | 2% |
| AAAGGucAccuAAuGAAGATsT | 898 | UCUUcAUuAGGUGACCUUUTsT | 899 | AD-14243 | 11% | 1% |
| AuGAAuGcAuAcucuAGucTsT | 900 | GACuAGAGuAUGcAUUcAUTsT | 901 | AD-14244 | 15% | 2% |
| AAcAuAuuGAAuAAGccuGTsT | 902 | cAGGCUuAUUcAAuAUGUUTsT | 903 | AD-14245 | 50% | 7% |
| AAGAAGGcAGuuGAccAAcTsT | 904 | GUUGGUcAACUGCCUUCUUTsT | 905 | AD-14246 | 57% | 5% |
| GAuAcuAAAAGAAcAAucATsT | 906 | UGAUUGUUCUUUuAGuAUCTsT | 907 | AD-14247 | 9% | 3% |
| AuAcuGAAAAucAAuAGucTsT | 908 | GACuAUUGAUUUUcAGuAUTsT | 909 | AD-14248 | 39% | 4% |
| AAAAAGGAAcuAGAuGGcuTsT | 910 | AGCcAUCuAGUUCCUUUUUTsT | 911 | AD-14249 | 64% | 2% |
| GAAcuAGAuGGcuuucucATsT | 912 | UGAGAAAGCcAUCuAGUUCTsT | 913 | AD-14250 | 18% | 2% |
| GAAAccuAAcuGAAGAccuTsT | 914 | AGGUCUUCAGUuAGGUUUCTsT | 915 | AD-14251 | 56% | 6% |
| uAcccAucAAcAcuGGuAATsT | 916 | UuACcAGUGUUGAUGGGuATsT | 917 | AD-14252 | 48% | 6% |
| AuuuuGAuAucuAcccAuuTsT | 918 | AAUGGGuAGAuAUcAAAAUTsT | 919 | AD-14253 | 39% | 5% |
| AucccuAuGuucAcuuuGTsT | 920 | cAAAGUGAACuAuAGGGAUTsT | 921 | AD-14254 | 44% | 8% |
| AuGGGcuAuAAuuGcAcuATsT | 922 | uAGUGcAAUuAuAGCCcAUTsT | 923 | AD-14255 | 108% | 8% |
| AGAuuAccucuGcGAGcccTsT | 924 | GGGCUCGcAGAGGuAAUCUTsT | 925 | AD-14256 | 108% | 6% |
| uAAuccAcGuAcccuucATsT | 926 | UGAAGGGuACGUGGAAUuATsT | 927 | AD-14257 | 23% | 2% |
| GucGuucccAcucAGuuuuTsT | 928 | AAAACuGAGuGGGAACGACTsT | 929 | AD-14258 | 21% | 3% |
| AAAucAAucccuGuuGAcuTsT | 930 | AGUcAAcAGGGAUUGAUUUTsT | 931 | AD-14259 | 19% | 2% |
| ucAuAGAGcAAAGAAcAuATsT | 932 | uAUGUUCUUUGCUCuAUGATsT | 933 | AD-14260 | 10% | 1% |
| uuAcuAcAGuAGcAcuuGGTsT | 934 | CcAAGUGCuACUGuAGuAATsT | 935 | AD-14261 | 76% | 3% |
| AuGuGGAAAccuAAcuGAATsT | 936 | UUcAGUuAGGUUUCcAcAUTsT | 937 | AD-14262 | 13% | 2% |
| uGuGGAAAccuAAcuGAAGTsT | 938 | CUUcAGUuAGGUUUCcAcATsT | 939 | AD-14263 | 14% | 2% |
| ucuuccuuAAAuGAAAGGGTsT | 940 | CCCUUUcAUUuAAGGAAGATsT | 941 | AD-14264 | 65% | 3% |
| uGAAGAAccucuAAGucAATsT | 942 | UUGACUuAGAGGUUCUUcATsT | 943 | AD-14265 | 13% | 1% |
| AGAGGucuAAAGuGGAAGATsT | 944 | UCUUCcACUUuAGACCUCUTsT | 945 | AD-14266 | 18% | 3% |
| AuAucuAcccAuuuuucuGTsT | 946 | cAGAAAAAUGGGuAGAuAUTsT | 947 | AD-14267 | 50% | 9% |
| uAAGccuGAAGuGAAucAGTsT | 948 | CUGAUUcACUUcAGGCUuATsT | 949 | AD-14268 | 13% | 3% |

TABLE 3-continued

Sequences and analysis of Eg5/KSP dsRNA duplexes

| Sense sequence (5'-3') | SEQ ID NO. | Antisense sequence (5'-3') | SEQ ID NO. | duplex name | single dose screen @ 25 nM [% residual mRNA] | SDs 2nd screen (among quadru- plicates) |
|---|---|---|---|---|---|---|
| AGAuGcAGAccAuuuAAuuTsT | 950 | AAUuAAAUGGUCUGcAUCUTsT | 951 | AD-14269 | 19% | 4% |
| AGuGuuGuuuGuccAAuucTsT | 952 | GAAUUGGAcAAAcAACACUTsT | 953 | AD-14270 | 11% | 2% |
| cuAuAAuGAAGAGcuuuuuTsT | 954 | AAAAAGCUCUUcAUuAuAGTsT | 955 | AD-14271 | 11% | 1% |
| AGAGGAGuGAuAAuuAAAGTsT | 956 | CUUuAAUuAUcACUCCUCUTsT | 957 | AD-14272 | 7% | 1% |
| uuucucuGuuAcAAuAcAuTsT | 958 | AUGuAUUGuAAcAGAGAAATsT | 959 | AD-14273 | 14% | 2% |
| AAcAucuAuAAuuGcAAcATsT | 960 | UGUUGcAAUuAuAGAUGUUTsT | 961 | AD-14274 | 73% | 4% |
| uGcuAGAAGuAcAuAAGAcTsT | 962 | GUCUuAUGuACUUCuAGcATsT | 963 | AD-14275 | 10% | 1% |
| AAuGuAcucAAGAcuGAucTsT | 964 | GAUcAGUCUUGAGuAcAUUTsT | 965 | AD-14276 | 89% | 2% |
| GuAcucAAGAcuGAucuucTsT | 966 | GAAGAUcAGUCUUGAGuACTsT | 967 | AD-14277 | 7% | 1% |
| cAcucuGAuAAAcucAAuGTsT | 968 | cAUUGAGUUuAUcAGAGUGTsT | 969 | AD-14278 | 12% | 1% |
| AAGAGcAGAuuAccucuGcTsT | 970 | GcAGAGGuAAUCUGCUCUUTsT | 971 | AD-14279 | 104% | 3% |
| ucuGcGAGcccAGAucAAcTsT | 972 | GUUGAUCUGGGCUCGcAGATsT | 973 | AD-14280 | 21% | 2% |
| AAcuuGAGccuuGuGuAuATsT | 974 | uAuAcAcAAGGCUcAAGUUTsT | 975 | AD-14281 | 43% | 3% |
| GAAuAuAuAucAGccGGTsT | 976 | CCGGCUGAuAuAuAuAUUCTsT | 977 | AD-14282 | 45% | 6% |
| uGucAucccuAuAGuucAcTsT | 978 | GUGAACuAuAGGGAUGAcATsT | 979 | AD-14283 | 35% | 5% |
| GAucuGGcAAccAuAuuucTsT | 980 | GAAAuAUGGUUGCcAGAUCTsT | 981 | AD-14284 | 58% | 3% |
| uGGcAAccAuAuuucuGGATsT | 982 | UCcAGAAAuAUGGUUGCcATsT | 983 | AD-14285 | 48% | 3% |
| GAuGuuuAccGAAGuGuuGTsT | 984 | cAAcACUUCGGuAAAcAUCTsT | 985 | AD-14286 | 49% | 3% |
| uuccuuAucGAGAAucuAATsT | 986 | UuAGAUUCUCGAuAAGGAATsT | 987 | AD-14287 | 6% | 1% |
| AGcuuAAuuGcuuucuGGATsT | 988 | UCcAGAAAGcAAUuAAGCUTsT | 989 | AD-14288 | 50% | 2% |
| uuGcuAuuAuGGGAGAccATsT | 990 | UGGUCUCCcAuAAuAGcAATsT | 991 | AD-14289 | 48% | 1% |
| GucAuGGcGucGcAGccAATsT | 992 | UUGGCUGCGACGCcAUGACTsT | 993 | AD-14290 | 112% | 7% |
| uAAuuGcAcuAucuuuGcGTsT | 994 | CGcAAAGAuAGUGcAAUuATsT | 995 | AD-14291 | 77% | 2% |
| cuAucuuuGcGAuGGccATsT | 996 | UGGCcAuACGcAAAGAuAGTsT | 997 | AD-14292 | 80% | 6% |
| ucccuAuAGuucAcuuuGuTsT | 998 | AcAAAGUGAAcuAuAGGGATsT | 999 | AD-14293 | 58% | 2% |
| ucAAccuuuAAuucAcuuGTsT | 1000 | cAAGUGAAUuAAAGGUUGATsT | 1001 | AD-14294 | 77% | 2% |
| GGcAAccAuAuuucuGGAATsT | 1002 | UUCcAGAAAuAUGGUUGCCTsT | 1003 | AD-14295 | 62% | 2% |
| AuGuAcucAAGAcuGAucuTsT | 1004 | AGAUcAGUCUUGAGuAcAUTsT | 1005 | AD-14296 | 59% | 4% |
| GcAGAccAuuuAAuuuGGcTsT | 1006 | GCcAAAUuAAAUGGUCUGCTsT | 1007 | AD-14297 | 37% | 1% |
| ucuGAGAGAcuAcAGAuGuTsT | 1008 | AcAUCUGuAGUCUCucAGATsT | 1009 | AD-14298 | 21% | 1% |
| uGcucAuAGAGcAAAGAAcTsT | 1010 | GUUCUUUGCUCuAUGAGcATsT | 1011 | AD-14299 | 6% | 1% |
| AcAuAAGAccuuAuuuGGuTsT | 1012 | ACcAAAuAAGGUCUuAUGUTsT | 1013 | AD-14300 | 17% | 2% |
| uuuGcucAuuucuGAuGGTsT | 1014 | CcAUcAGAAAUcAGcAcAAATsT | 1015 | AD-14301 | 97% | 6% |
| ccAucAAcAcuGGuAAGAATsT | 1016 | UUCUuACcAGUGUUGAUGGTsT | 1017 | AD-14302 | 13% | 1% |
| AGAcAAuuccGGAuGuGGATsT | 1018 | UCcAcAUCCGGAAUUGUCUTsT | 1019 | AD-14303 | 13% | 3% |

TABLE 3-continued

Sequences and analysis of Eg5/KSP dsRNA duplexes

| Sense sequence (5'-3') | SEQ ID NO. | Antisense sequence (5'-3') | SEQ ID NO. | duplex name | single dose screen @ 25 nM [% residual mRNA] | SDs 2nd screen (among quadruplicates) |
|---|---|---|---|---|---|---|
| GAAcuuGAGccuuGuGuAuTsT | 1020 | AuAcAcAAGGCUcAAGUUCTsT | 1021 | AD-14304 | 38% | 2% |
| uAAuuuGGcAGAGcGGAAATsT | 1022 | UUUCCGCUCUGCcAAAUuATsT | 1023 | AD-14305 | 14% | 2% |
| uGGAuGAAGuuAuuAuGGGTsT | 1024 | CCcAuAAuAACUUcAUCcATsT | 1025 | AD-14306 | 22% | 4% |
| AucuAcAuGAAcuAcAAGATsT | 1026 | UCUUGuAGUUcAUGuAGAUTsT | 1027 | AD-14307 | 26% | 6% |
| GGuAuuuuGAucuGGcAATsT | 1028 | UUGCcAGAUcAAAAAuACCTsT | 1029 | AD-14308 | 62% | 8% |
| cuAAuGAAGAGuAuAccuGTsT | 1030 | cAGGuAuACUCUUcAUuAGTsT | 1031 | AD-14309 | 52% | 5% |
| uuuGAGAAAcuuAcuGAuATsT | 1032 | uAUcAGuAAGUUUCUcAAATsT | 1033 | AD-14310 | 32% | 3% |
| cGAuAAGAuAGAAGAucAATsT | 1034 | UUGAUCUUCuAUCUuAUCGTsT | 1035 | AD-14311 | 23% | 2% |
| cuGGcAAccAuAuuucuGGTsT | 1036 | CcAGAAAuAUGGUUGCcAGTsT | 1037 | AD-14312 | 49% | 6% |
| uAGAuAccAuuAcuAcAGuTsT | 1038 | ACUGuAGuAAUGGuAUCuATsT | 1039 | AD-14313 | 69% | 4% |
| GuAuuAAAuuGGGuuucAuTsT | 1040 | AUGAAACCcAAUUuAAuACTsT | 1041 | AD-14314 | 52% | 3% |
| AAGAccuuAuuuGGuAAucTsT | 1042 | GAUuACcAAAuAAGGUCUUTsT | 1043 | AD-14315 | 66% | 4% |
| GcuGuuGAuAAGAGAGcucTsT | 1044 | GAGCUCUCUuAUcAAcAGCTsT | 1045 | AD-14316 | 19% | 4% |
| uAcucAuGuuucucAGAuuTsT | 1046 | AAUCUGAGAAAcAUGAGuATsT | 1047 | AD-14317 | 16% | 5% |
| cAGAuGGAcGuAAGGcAGcTsT | 1048 | GCUGCCUuACGUCcAUCUGTsT | 1049 | AD-14318 | 52% | 11% |
| uAucccAAcAGGuAcGAcATsT | 1050 | UGUCGuACCUGUUGGGAuATsT | 1051 | AD-14319 | 28% | 11% |
| cAuuGcuAuuAuGGGAGAcTsT | 1052 | GUCUCCcAuAuAGcAAUGTsT | 1053 | AD-14320 | 52% | 10% |
| cccucAGuAAAuccAuGGuTsT | 1054 | ACcAUGGAUUuACUGAGGGTsT | 1055 | AD-14321 | 53% | 6% |
| GGucAuuAcuGcccuuGATsT | 1056 | uAcAAGGGcAGuAAUGACCTsT | 1057 | AD-14322 | 20% | 2% |
| AAccAcucAAAAAcAuuuGTsT | 1058 | cAAAUGUUUUUGAGUGGUUTsT | 1059 | AD-14323 | 116% | 6% |
| uuuGcAAGuuAAuGAAucuTsT | 1060 | AGAUUcAUuAACUUGcAAATsT | 1061 | AD-14324 | 14% | 2% |
| uuAuuuucAGuAGucAGAATsT | 1062 | UUCUGACuACUGAAAAuAATsT | 1063 | AD-14325 | 50% | 2% |
| uuuucucGAuucAAAucuuTsT | 1064 | AAGAUUuGAAUCGAGAAAATsT | 1065 | AD-14326 | 47% | 3% |
| GuAcGAAAAGAAGuuAGuGTsT | 1066 | cACuAACUUCUUUUCGuACTsT | 1067 | AD-14327 | 18% | 2% |
| uuuAAAAcGAGAucuuGcuTsT | 1068 | AGcAAGAUCUCGUUUuAAATsT | 1069 | AD-14328 | 19% | 1% |
| GAAuuGAuuAAuGuAcucATsT | 1070 | UGAGuAcAUuAAUcAAUUCTsT | 1071 | AD-14329 | 94% | 10% |
| GAuGGAcGuAAGGcAGcucTsT | 1072 | GAGCUGCCUuACGUCcAUCTsT | 1073 | AD-14330 | 60% | 4% |
| cAucuGAcuAAuGGcucuGTsT | 1074 | cAGAGCcAUuAGUcAGAUGTsT | 1075 | AD-14331 | 54% | 7% |
| GuGAuccuGuAcGAAAAGATsT | 1076 | UCUUUUCGuAcAGGAUcACTsT | 1077 | AD-14332 | 22% | 4% |
| AGcucuuAuuAAGGAGuAuTsT | 1078 | AuACUCCUuAAuAAGAGCUTsT | 1079 | AD-14333 | 70% | 10% |
| GcucuuAuuAAGGAGuAuATsT | 1080 | uAuACUCCUuAAuAAGAGCTsT | 1081 | AD-14334 | 18% | 3% |
| ucuuAuuAAGGAGuAuAcGTsT | 1082 | CGuAuACUCCUuAAuAAGATsT | 1083 | AD-14335 | 38% | 6% |
| uAuuAAGGAGuAuAcGGATsT | 1084 | CUCCGuAuACUCCUuAAuATsT | 1085 | AD-14336 | 16% | 3% |
| cuGcAGcccGuGAGAAAAATsT | 1086 | UUUUUCUcACGGGCUGcAGTsT | 1087 | AD-14337 | 65% | 4% |
| ucAAGAcuGAucuucuAAGTsT | 1088 | CUuAGAAGAUcAGUCUUGATsT | 1089 | AD-14338 | 18% | 0% |

TABLE 3-continued

Sequences and analysis of Eg5/KSP dsRNA duplexes

| Sense sequence (5'-3') | SEQ ID NO. | Antisense sequence (5'-3') | SEQ ID NO. | duplex name | single dose screen @ 25 nM [% residual mRNA] | SDs 2nd screen (among quadru-plicates) |
|---|---|---|---|---|---|---|
| cuucuAAGuucAcuGGAAATsT | 1090 | UUUCcAGUGAACUuAGAAGTsT | 1091 | AD-14339 | 20% | 4% |
| uGcAAGuuAAuGAAucuuuTsT | 1092 | AAAGAUUcAUuAACUUGcATsT | 1093 | AD-14340 | 24% | 1% |
| AAucuAAGGAuAuAGucAATsT | 1094 | UUGACuAuAUCCUuAGAUUTsT | 1095 | AD-14341 | 27% | 3% |
| AucucuGAAcAcAAGAAcATsT | 1096 | UGUUCUUGUGUUcAGAGAUTsT | 1097 | AD-14342 | 13% | 1% |
| uucuGAAcAGuGGGuAucuTsT | 1098 | AGAuACCcACUGUUcAGAATsT | 1099 | AD-14343 | 19% | 1% |
| AGuuAuuuAuAcccAucAATsT | 1100 | UUGAUGGGuAuAAAuAACUTsT | 1101 | AD-14344 | 23% | 2% |
| AuGcuAAAcuGuucAGAAATsT | 1102 | UUUCUGAAcAGUUuAGcAUTsT | 1103 | AD-14345 | 21% | 4% |
| cuAcAGAGcAcuuGGuuAcTsT | 1104 | GuAACcAAGUGCUCUGuAGTsT | 1105 | AD-14346 | 18% | 2% |
| uAuAucAGccGGGcGcGTsT | 1106 | CGCGCCCGGCUGAuAuAuATsT | 1107 | AD-14347 | 67% | 2% |
| AuGuAAAuAcGuAuuucuATsT | 1108 | uAGAAAuACGuAUUuAcAUTsT | 1109 | AD-14348 | 39% | 3% |
| uuuuucucGAuucAAAucuTsT | 1110 | AGAUUuGAAUCGAGAAAAATsT | 1111 | AD-14349 | 83% | 6% |
| AAucuuAAcccuuAGGAcuTsT | 1112 | AGUCCuAAGGGUuAAGAUUTsT | 1113 | AD-14350 | 54% | 2% |
| ccuuAGGAcucuGGuAuuuTsT | 1114 | AAAuAccAGAGUCCuAAGGTsT | 1115 | AD-14351 | 57% | 8% |
| AAuAAAcuGcccucAGuAATsT | 1116 | UuACUGAGGGcAGUuAUUTsT | 1117 | AD-14352 | 82% | 3% |
| GAuccuGuAcGAAAAGAAGTsT | 1118 | CUUCUUUUCGuAcAGGAUCTsT | 1119 | AD-14353 | 2% | 1% |
| AAuGuGAuccuGuAcGAAATsT | 1120 | UUUCGuAcAGGAUcAcAUUTsT | 1121 | AD-14354 | 18% | 11% |
| GuGAAAcAuuGGccGuucTsT | 1122 | GAACGGCcAAUGUUUuCACTsT | 1123 | AD-14355 | 2% | 1% |
| cuuGAGGAAAcucuGAGuATsT | 1124 | uACUcAGAGUUUCCUcAAGTsT | 1125 | AD-14356 | 8% | 2% |
| cGuuuAAAAcGAGAucuuGTsT | 1126 | cAAGAUCUCGUUUuAAACGTsT | 1127 | AD-14357 | 6% | 3% |
| uuAAAAcGAGAucuuGcuGTsT | 1128 | cAGcAAGAUCUCGUUUuAATsT | 1129 | AD-14358 | 98% | 17% |
| AAAGAuGuAucGGucuccTsT | 1130 | GGAGACcAGAuAcAUCUUUTsT | 1131 | AD-14359 | 10% | 1% |
| cAGAAAAuGuGucuAcucATsT | 1132 | UGAGuAGAcAcAUUUUCUGTsT | 1133 | AD-14360 | 6% | 4% |
| cAGGAAuuGAuuAAuGuAcTsT | 1134 | GuAcAUuAAUcAAUUCCUGTsT | 1135 | AD-14361 | 30% | 5% |
| AGucAAcuAAAGcAuAuuuTsT | 1136 | AAAuAUGCUUuAGUUGACUTsT | 1137 | AD-14362 | 28% | 2% |
| uGuGuAAcAAucuAcAuGATsT | 1138 | UcAUGuAGAUUGUuAcAcATsT | 1139 | AD-14363 | 60% | 6% |
| AuAccAuuuGuuccuuGGuTsT | 1140 | ACcAAGGAAcAAAUGGuAUTsT | 1141 | AD-14364 | 12% | 9% |
| GcAGAAAucuAAGGAuAuATsT | 1142 | uAuAUCCUuAGAUUUCUGCTsT | 1143 | AD-14365 | 5% | 2% |
| uGGcuucucAcAGGAAcucTsT | 1144 | GAGUUCCUGUGAGAAGCcATsT | 1145 | AD-14366 | 28% | 5% |
| GAGAuGuGAAucucuGAAcTsT | 1146 | GUUcAGAGAUUcAcAUCUCTsT | 1147 | AD-14367 | 42% | 4% |
| uGuAAGccAAuGuuGuGAGTsT | 1148 | CUcAcAAcAUUGGCUuAcATsT | 1149 | AD-14368 | 93% | 12% |
| AGccAAuGuuGuGAGGcuuTsT | 1150 | AAGCCUcAcAAcAUUGGCUTsT | 1151 | AD-14369 | 65% | 4% |
| uuGuGAGGcuucAAGuucATsT | 1152 | UGAACUUGAAGCCUcAcAATsT | 1153 | AD-14370 | 5% | 2% |
| AGGcAGcucAuGAGAAAcATsT | 1154 | UGUUUCUcAUGAGCUGCCUTsT | 1155 | AD-14371 | 54% | 5% |
| AuAAAuuGAuAGcAcAAAATsT | 1156 | UUUUGUGCuAUcAAUUuAUTsT | 1157 | AD-14372 | 4% | 1% |
| AcAAAucuAGAAcuuAAuTsT | 1158 | AUuAAGUUCuAGAUUUUGUTsT | 1159 | AD-14373 | 5% | 1% |

TABLE 3-continued

Sequences and analysis of Eg5/KSP dsRNA duplexes

| Sense sequence (5'-3') | SEQ ID NO. | Antisense sequence (5'-3') | SEQ ID NO. | duplex name | single dose screen @ 25 nM [% residual mRNA] | SDs 2nd screen (among quadruplicates) |
|---|---|---|---|---|---|---|
| GAuAucccAAcAGGuAcGATsT | 1160 | UCGuACCUGUUGGGAuAUCTsT | 1161 | AD-14374 | 92% | 6% |
| AAGuuAuuuAuAcccAucATsT | 1162 | UGAUGGGuAuAAAuAACUUTsT | 1163 | AD-14375 | 76% | 4% |
| uGuAAAuAcGuAuuucuAGTsT | 1164 | CuAGAAAuACGuAUUuAcATsT | 1165 | AD-14376 | 70% | 5% |
| ucuAGuuuucAuAuAAAGuTsT | 1166 | ACUUuAuAUGAAAACuAGATsT | 1167 | AD-14377 | 48% | 4% |
| AuAAAGuAGuucuuuuAuATsT | 1168 | uAuAAAAGAACuACUUuAUTsT | 1169 | AD-14378 | 48% | 3% |
| ccAuuuGuAGAGcuAcAAATsT | 1170 | UUUGuAGCUCuAcAAAUGGTsT | 1171 | AD-14379 | 44% | 5% |
| uAuuucAGuAGucAGAAuTsT | 1172 | AUUCUGACuACUGAAAAuATsT | 1173 | AD-14380 | 35% | 16% |
| AAAucuAAccuAGuuGuATsT | 1174 | uAcAACuAGGGUuAGAUUUTsT | 1175 | AD-14381 | 44% | 5% |
| cuuuAGAGuAuAcAuuGcuTsT | 1176 | AGcAAUGuAuACUCuAAAGTsT | 1177 | AD-14382 | 28% | 1% |
| AucuGAcuAAuGGcucuGuTsT | 1178 | AcAGAGCcAUuAGUcAGAUTsT | 1179 | AD-14383 | 55% | 11% |
| cAcAAuGAuuuAAGGAcuGTsT | 1180 | cAGUCCUuAAAUcAUUGUGTsT | 1181 | AD-14384 | 48% | 9% |
| ucuuuuucucGAuucAAAuTsT | 1182 | AUUuGAAUCGAGAAAAAGATsT | 1183 | AD-14385 | 36% | 2% |
| cuuuuucucGAuucAAAucTsT | 1184 | GAUUuGAAUCGAGAAAAAGTsT | 1185 | AD-14386 | 41% | 7% |
| AuuuucuGcucAcGAuGAGTsT | 1186 | CUcAUCGUGAGcAGAAAAUTsT | 1187 | AD-14387 | 38% | 3% |
| uuucuGcucAcGAuGAGuuTsT | 1188 | AACUcAUCGUGAGcAGAAATsT | 1189 | AD-14388 | 50% | 4% |
| AGAGcuAcAAAAccuAuccTsT | 1190 | GGAuAGGUUUUGuAGCUCUTsT | 1191 | AD-14389 | 98% | 6% |
| GAGccAAAGGuAcAccAcuTsT | 1192 | AGUGGUGuACCUUUGGCUCTsT | 1193 | AD-14390 | 43% | 8% |
| GccAAAGGuAcAccAcuAcTsT | 1194 | GuAGUGGUGuACCUUUGGCTsT | 1195 | AD-14391 | 48% | 4% |
| GAAcuGuAcucuucucAGcTsT | 1196 | GCUGAGAAGAGuACAGUUCTsT | 1197 | AD-14392 | 44% | 3% |
| AGGuAAAuAucAccAAcAuTsT | 1198 | AUGUUGGUGAuAUUuACCUTsT | 1199 | AD-14393 | 37% | 2% |
| AGcuAcAAAAccuAuccuuTsT | 1200 | AAGGAuAGGUUUUGuAGCUTsT | 1201 | AD-14394 | 114% | 7% |
| uGuGAAAGcAuuuAAuuccTsT | 1202 | GGAAUuAAAUGCUUUcAcATsT | 1203 | AD-14395 | 55% | 4% |
| GcccAcuuuAGAGuAuAcATsT | 1204 | UGuAuACUCuAAAGUGGGCTsT | 1205 | AD-14396 | 49% | 5% |
| uGuGccAcAcuccAAGAccTsT | 1206 | GGUCUUGGAGUGUGGcAcATsT | 1207 | AD-14397 | 71% | 6% |
| AAAcuAAAuuGAucucGuATsT | 1208 | uACGAGAUcAAUUuAGUUUTsT | 1209 | AD-14398 | 81% | 7% |
| uGAucucGuAGAAuuAucuTsT | 1210 | AGAuAAUUCuACGAGAUcATsT | 1211 | AD-14399 | 38% | 4% |
| GcGuGcAGucGGuccuccATsT | 1212 | UGGAGGACCGACUGcACGCTsT | 1213 | AD-14400 | 106% | 8% |
| AAAGuuuAGAGAcucuGATsT | 1214 | UcAGAUGUCUCuAAACUUUTsT | 1215 | AD-14401 | 47% | 3% |
| cAGAAGGAAuAuGuAcAAATsT | 1216 | UUUGuAcAuAUUCCUUCUGTsT | 1217 | AD-14402 | 31% | 1% |
| cGcccGAGAGuAccAGGGATsT | 1218 | UCCCUGGuACUCUCGGGCGTsT | 1219 | AD-14403 | 105% | 4% |
| cGGAGGAGAuAGAAcGuuuTsT | 1220 | AAACGUUCuAUCUCCUCCGTsT | 1221 | AD-14404 | 3% | 1% |
| AGAuAGAAcGuuuAAAAcGTsT | 1222 | CGUUUuAAACGUUCuAUCUTsT | 1223 | AD-14405 | 15% | 1% |
| GGAAcAGGAAcuucAcAAcTsT | 1224 | GUuGuGAAGUUCCuGUUCCTsT | 1225 | AD-14406 | 44% | 5% |
| GuGAGccAAAGGuAcAccATsT | 1226 | UGGUGuACCUUUGGCUcACTsT | 1227 | AD-14407 | 41% | 4% |
| AuccucccuAGAcuucccuTsT | 1228 | AGGGAAGUCuAGGGAGGAUTsT | 1229 | AD-14408 | 104% | 3% |

TABLE 3-continued

Sequences and analysis of Eg5/KSP dsRNA duplexes

| Sense sequence (5'-3') | SEQ ID NO. | Antisense sequence (5'-3') | SEQ ID NO. | duplex name | single dose screen @ 25 nM [% residual mRNA] | SDs 2nd screen (among quadru-plicates) |
|---|---|---|---|---|---|---|
| cAcAcuccAAGAccuGuGcTsT | 1230 | GcAcAGGUCUUGGAGUGUGTsT | 1231 | AD-14409 | 67% | 4% |
| AcAGAAGGAAuAuGuAcAATsT | 1232 | UUGuAcAuAUUCCUUCUGUTsT | 1233 | AD-14410 | 22% | 1% |
| uuAGAGAcAucuGAcuuuGTsT | 1234 | cAAAGUcAGAUGUCUCuAATsT | 1235 | AD-14411 | 29% | 3% |
| AAuuGAucucGuAGAAuuATsT | 1236 | uAAUUCuACGAGAUcAAUUTsT | 1237 | AD-14412 | 31% | 4% | dsRNA Targeting the VEGF Gene

Four hundred target sequences were identified within exons 1-5 of the VEGF-A121 mRNA sequence. reference transcript is: NM_003376.

(SEQ ID NO: 1539)
```
  1 augaacuuuc ugcugucuug ggugcauugg agccuugccu ugcugcucua ccuccaccau
 61 gccaaguggu cccaggcugc acccauggca gaaggaggag ggcagaauca ucacgaagug
121 gugaaguuca uggaugucua ucagcgcagc uacugccauc caaucgagac ccugguggac
181 aucuuccagg aguacccuga ugagaucgag uacaucuuca agccauccug ugugccccug
241 augcgaugcg ggggcugcug caaugacgag ggccuggagu gugugcccac ugaggaguccc
301 aacaucacca ugcagauuau gcggaucaaa ccucaccaag gccagcacau aggagagaug
361 agcuuccuac agcacaacaa augugaaugc agaccaaaga aagauagagc aagacaagaa
421 aaaugugaca agccgaggcg guga
```

Table 4a includes the identified target sequences. Corresponding siRNAs targeting these sequences were subjected to a bioinformatics screen.

To ensure that the sequences were specific to VEGF sequence and not to sequences from any other genes, the target sequences were checked against the sequences in Genbank using the BLAST search engine provided by NCBI. The use of the BLAST algorithm is described in Altschul et al., J. Mol. Biol. 215:403, 1990; and Altschul and Gish, Meth. Enzymol. 266:460, 1996.

siRNAs were also prioritized for their ability to cross react with monkey, rat and human VEGF sequences.

Of these 400 potential target sequences 80 were selected for analysis by experimental screening in order to identify a small number of lead candidates. A total of 114 siRNA molecules were designed for these 80 target sequences 114 (Table 4b).

TABLE 4a

| Target sequences in VEGF-121 | | |
|---|---|---|
| SEQ ID NO: | position in VEGF-121 ORF | TARGET SEQUENCE IN VEGF121 mRNA 5' to 3' |
| 1540 | 1 | AUGAACUUUCUGCUGUCUUGGGU |
| 1541 | 2 | UGAACUUUCUGCUGUCUUGGGUG |

TABLE 4a-continued

| Target sequences in VEGF-121 | | |
|---|---|---|
| SEQ ID NO: | position in VEGF-121 ORF | TARGET SEQUENCE IN VEGF121 mRNA 5' to 3' |
| 1542 | 3 | GAACUUUCUGCUGUCUUGGGUGC |
| 1543 | 4 | AACUUUCUGCUGUCUUGGGUGCA |
| 1544 | 5 | ACUUUCUGCUGUCUUGGGUGCAU |
| 1545 | 6 | CUUUCUGCUGUCUUGGGUGCAUU |
| 1546 | 7 | UUUCUGCUGUCUUGGGUGCAUUG |
| 1547 | 8 | UUCUGCUGUCUUGGGUGCAUUGG |
| 1548 | 9 | UCUGCUGUCUUGGGUGCAUUGGA |
| 1549 | 10 | CUGCUGUCUUGGGUGCAUUGGAG |
| 1550 | 11 | UGCUGUCUUGGGUGCAUUGGAGC |
| 1551 | 12 | GCUGUCUUGGGUGCAUUGGAGCC |
| 1552 | 13 | CUGUCUUGGGUGCAUUGGAGCCU |
| 1553 | 14 | UGUCUUGGGUGCAUUGGAGCCUU |
| 1554 | 15 | GUCUUGGGUGCAUUGGAGCCUUG |
| 1555 | 16 | UCUUGGGUGCAUUGGAGCCUUGC |

TABLE 4a-continued

Target sequences in VEGF-121

| SEQ ID NO: | position in VEGF-121 ORF | TARGET SEQUENCE IN VEGF121 mRNA 5' to 3' |
|---|---|---|
| 1556 | 17 | CUUGGGUGCAUUGGAGCCUUGCC |
| 1557 | 18 | UUGGGUGCAUUGGAGCCUUGCCU |
| 1558 | 19 | UGGGUGCAUUGGAGCCUUGCCUU |
| 1559 | 20 | GGGUGCAUUGGAGCCUUGCCUUG |
| 1560 | 21 | GGUGCAUUGGAGCCUUGCCUUGC |
| 1561 | 22 | GUGCAUUGGAGCCUUGCCUUGCU |
| 1562 | 23 | UGCAUUGGAGCCUUGCCUUGCUG |
| 1563 | 24 | GCAUUGGAGCCUUGCCUUGCUGC |
| 1564 | 25 | CAUUGGAGCCUUGCCUUGCUGCU |
| 1565 | 26 | AUUGGAGCCUUGCCUUGCUGCUC |
| 1566 | 27 | UUGGAGCCUUGCCUUGCUGCUCU |
| 1567 | 28 | UGGAGCCUUGCCUUGCUGCUCUA |
| 1568 | 29 | GGAGCCUUGCCUUGCUGCUCUAC |
| 1569 | 30 | GAGCCUUGCCUUGCUGCUCUACC |
| 1570 | 31 | AGCCUUGCCUUGCUGCUCUACCU |
| 1571 | 32 | GCCUUGCCUUGCUGCUCUACCUC |
| 1572 | 33 | CCUUGCCUUGCUGCUCUACCUCC |
| 1573 | 34 | CUUGCCUUGCUGCUCUACCUCCA |
| 1574 | 35 | UUGCCUUGCUGCUCUACCUCCAC |
| 1575 | 36 | UGCCUUGCUGCUCUACCUCCACC |
| 1576 | 37 | GCCUUGCUGCUCUACCUCCACCA |
| 1577 | 38 | CCUUGCUGCUCUACCUCCACCAU |
| 1578 | 39 | CUUGCUGCUCUACCUCCACCAUG |
| 1579 | 40 | UUGCUGCUCUACCUCCACCAUGC |
| 1580 | 41 | UGCUGCUCUACCUCCACCAUGCC |
| 1581 | 42 | GCUGCUCUACCUCCACCAUGCCA |
| 1582 | 43 | CUGCUCUACCUCCACCAUGCCAA |
| 1583 | 44 | UGCUCUACCUCCACCAUGCCAAG |
| 1584 | 45 | GCUCUACCUCCACCAUGCCAAGU |
| 1585 | 46 | CUCUACCUCCACCAUGCCAAGUG |
| 1586 | 47 | UCUACCUCCACCAUGCCAAGUGG |
| 1587 | 48 | CUACCUCCACCAUGCCAAGUGGU |
| 1588 | 49 | UACCUCCACCAUGCCAAGUGGUC |
| 1589 | 50 | ACCUCCACCAUGCCAAGUGGUCC |
| 1590 | 51 | CCUCCACCAUGCCAAGUGGUCCC |
| 1591 | 52 | CUCCACCAUGCCAAGUGGUCCCA |
| 1592 | 53 | UCCACCAUGCCAAGUGGUCCCAG |
| 1593 | 54 | CCACCAUGCCAAGUGGUCCCAGG |
| 1594 | 55 | CACCAUGCCAAGUGGUCCCAGGC |
| 1595 | 56 | ACCAUGCCAAGUGGUCCCAGGCU |
| 1596 | 57 | CCAUGCCAAGUGGUCCCAGGCUG |
| 1597 | 58 | CAUGCCAAGUGGUCCCAGGCUGC |
| 1598 | 59 | AUGCCAAGUGGUCCCAGGCUGCA |
| 1599 | 60 | UGCCAAGUGGUCCCAGGCUGCAC |
| 1600 | 61 | GCCAAGUGGUCCCAGGCUGCACC |
| 1601 | 62 | CCAAGUGGUCCCAGGCUGCACCC |
| 1602 | 63 | CAAGUGGUCCCAGGCUGCACCCA |
| 1603 | 64 | AAGUGGUCCCAGGCUGCACCCAU |
| 1604 | 65 | AGUGGUCCCAGGCUGCACCCAUG |
| 1605 | 66 | GUGGUCCCAGGCUGCACCCAUGG |
| 1606 | 67 | UGGUCCCAGGCUGCACCCAUGGC |
| 1607 | 68 | GGUCCCAGGCUGCACCCAUGGCA |
| 1608 | 69 | GUCCCAGGCUGCACCCAUGGCAG |
| 1609 | 70 | UCCCAGGCUGCACCCAUGGCAGA |
| 1610 | 71 | CCCAGGCUGCACCCAUGGCAGAA |
| 1611 | 72 | CCAGGCUGCACCCAUGGCAGAAG |
| 1612 | 73 | CAGGCUGCACCCAUGGCAGAAGG |
| 1613 | 74 | AGGCUGCACCCAUGGCAGAAGGA |
| 1614 | 75 | GGCUGCACCCAUGGCAGAAGGAG |
| 1615 | 76 | GCUGCACCCAUGGCAGAAGGAGG |
| 1616 | 77 | CUGCACCCAUGGCAGAAGGAGGA |
| 1617 | 78 | UGCACCCAUGGCAGAAGGAGGAG |
| 1618 | 79 | GCACCCAUGGCAGAAGGAGGAGG |
| 1619 | 80 | CACCCAUGGCAGAAGGAGGAGGG |
| 1620 | 81 | ACCCAUGGCAGAAGGAGGAGGGC |
| 1621 | 82 | CCCAUGGCAGAAGGAGGAGGGCA |
| 1622 | 83 | CCAUGGCAGAAGGAGGAGGGCAG |
| 1623 | 84 | CAUGGCAGAAGGAGGAGGGCAGA |
| 1624 | 85 | AUGGCAGAAGGAGGAGGGCAGAA |
| 1625 | 86 | UGGCAGAAGGAGGAGGGCAGAAU |
| 1626 | 87 | GGCAGAAGGAGGAGGGCAGAAUC |
| 1627 | 88 | GCAGAAGGAGGAGGGCAGAAUCA |
| 1628 | 89 | CAGAAGGAGGAGGGCAGAAUCAU |
| 1629 | 90 | AGAAGGAGGAGGGCAGAAUCAUC |

TABLE 4a-continued

Target sequences in VEGF-121

| SEQ ID NO: | position in VEGF-121 ORF | TARGET SEQUENCE IN VEGF121 mRNA 5' to 3' |
|---|---|---|
| 1630 | 91 | GAAGGAGGAGGGCAGAAUCAUCA |
| 1631 | 92 | AAGGAGGAGGGCAGAAUCAUCAC |
| 1632 | 93 | AGGAGGAGGGCAGAAUCAUCACG |
| 1633 | 94 | GGAGGAGGGCAGAAUCAUCACGA |
| 1634 | 95 | GAGGAGGGCAGAAUCAUCACGAA |
| 1635 | 96 | AGGAGGGCAGAAUCAUCACGAAG |
| 1636 | 97 | GGAGGGCAGAAUCAUCACGAAGU |
| 1637 | 98 | GAGGGCAGAAUCAUCACGAAGUG |
| 1638 | 99 | AGGGCAGAAUCAUCACGAAGUGG |
| 1639 | 100 | GGGCAGAAUCAUCACGAAGUGGU |
| 1640 | 101 | GGCAGAAUCAUCACGAAGUGGUG |
| 1641 | 102 | GCAGAAUCAUCACGAAGUGGUGA |
| 1642 | 103 | CAGAAUCAUCACGAAGUGGUGAA |
| 1643 | 104 | AGAAUCAUCACGAAGUGGUGAAG |
| 1644 | 105 | GAAUCAUCACGAAGUGGUGAAGU |
| 1645 | 106 | AAUCAUCACGAAGUGGUGAAGUU |
| 1646 | 107 | AUCAUCACGAAGUGGUGAAGUUC |
| 1647 | 108 | UCAUCACGAAGUGGUGAAGUUCA |
| 1648 | 109 | CAUCACGAAGUGGUGAAGUUCAU |
| 1649 | 110 | AUCACGAAGUGGUGAAGUUCAUG |
| 1650 | 111 | UCACGAAGUGGUGAAGUUCAUGG |
| 1651 | 112 | CACGAAGUGGUGAAGUUCAUGGA |
| 1652 | 113 | ACGAAGUGGUGAAGUUCAUGGAU |
| 1653 | 114 | CGAAGUGGUGAAGUUCAUGGAUG |
| 1654 | 115 | GAAGUGGUGAAGUUCAUGGAUGU |
| 1655 | 116 | AAGUGGUGAAGUUCAUGGAUGUC |
| 1656 | 117 | AGUGGUGAAGUUCAUGGAUGUCU |
| 1657 | 118 | GUGGUGAAGUUCAUGGAUGUCUA |
| 1658 | 119 | UGGUGAAGUUCAUGGAUGUCUAU |
| 1659 | 120 | GGUGAAGUUCAUGGAUGUCUAUC |
| 1660 | 121 | GUGAAGUUCAUGGAUGUCUAUCA |
| 1661 | 122 | UGAAGUUCAUGGAUGUCUAUCAG |
| 1662 | 123 | GAAGUUCAUGGAUGUCUAUCAGC |
| 1663 | 124 | AAGUUCAUGGAUGUCUAUCAGCG |
| 1664 | 125 | AGUUCAUGGAUGUCUAUCAGCGC |
| 1665 | 126 | GUUCAUGGAUGUCUAUCAGCGCA |
| 1666 | 127 | UUCAUGGAUGUCUAUCAGCGCAG |
| 1667 | 128 | UCAUGGAUGUCUAUCAGCGCAGC |
| 1668 | 129 | CAUGGAUGUCUAUCAGCGCAGCU |
| 1669 | 130 | AUGGAUGUCUAUCAGCGCAGCUA |
| 1670 | 131 | UGGAUGUCUAUCAGCGCAGCUAC |
| 1671 | 132 | GGAUGUCUAUCAGCGCAGCUACU |
| 1672 | 133 | GAUGUCUAUCAGCGCAGCUACUG |
| 1673 | 134 | AUGUCUAUCAGCGCAGCUACUGC |
| 1674 | 135 | UGUCUAUCAGCGCAGCUACUGCC |
| 1675 | 136 | GUCUAUCAGCGCAGCUACUGCCA |
| 1676 | 137 | UCUAUCAGCGCAGCUACUGCCAU |
| 1677 | 138 | CUAUCAGCGCAGCUACUGCCAUC |
| 1678 | 139 | UAUCAGCGCAGCUACUGCCAUCC |
| 1679 | 140 | AUCAGCGCAGCUACUGCCAUCCA |
| 1680 | 141 | UCAGCGCAGCUACUGCCAUCCAA |
| 1681 | 142 | CAGCGCAGCUACUGCCAUCCAAU |
| 1682 | 143 | AGCGCAGCUACUGCCAUCCAAUC |
| 1683 | 144 | GCGCAGCUACUGCCAUCCAAUCG |
| 1684 | 145 | CGCAGCUACUGCCAUCCAAUCGA |
| 1685 | 146 | GCAGCUACUGCCAUCCAAUCGAG |
| 1686 | 147 | CAGCUACUGCCAUCCAAUCGAGA |
| 1687 | 148 | AGCUACUGCCAUCCAAUCGAGAC |
| 1688 | 149 | GCUACUGCCAUCCAAUCGAGACC |
| 1689 | 150 | CUACUGCCAUCCAAUCGAGACCC |
| 1690 | 151 | UACUGCCAUCCAAUCGAGACCCU |
| 1691 | 152 | ACUGCCAUCCAAUCGAGACCCUG |
| 1692 | 153 | CUGCCAUCCAAUCGAGACCCUGG |
| 1693 | 154 | UGCCAUCCAAUCGAGACCCUGGU |
| 1694 | 155 | GCCAUCCAAUCGAGACCCUGGUG |
| 1695 | 156 | CCAUCCAAUCGAGACCCUGGUGG |
| 1696 | 157 | CAUCCAAUCGAGACCCUGGUGGA |
| 1697 | 158 | AUCCAAUCGAGACCCUGGUGGAC |
| 1698 | 159 | UCCAAUCGAGACCCUGGUGGACA |
| 1699 | 160 | CCAAUCGAGACCCUGGUGGACAU |
| 1700 | 161 | CAAUCGAGACCCUGGUGGACAUC |
| 1701 | 162 | AAUCGAGACCCUGGUGGACAUCU |
| 1702 | 163 | AUCGAGACCCUGGUGGACAUCUU |
| 1703 | 164 | UCGAGACCCUGGUGGACAUCUUC |

TABLE 4a-continued

Target sequences in VEGF-121

| SEQ ID NO: | position in VEGF-121 ORF | TARGET SEQUENCE IN VEGF121 mRNA 5' to 3' |
|---|---|---|
| 1704 | 165 | CGAGACCCUGGUGGACAUCUUCC |
| 1705 | 166 | GAGACCCUGGUGGACAUCUUCCA |
| 1706 | 167 | AGACCCUGGUGGACAUCUUCCAG |
| 1707 | 168 | GACCCUGGUGGACAUCUUCCAGG |
| 1708 | 169 | ACCCUGGUGGACAUCUUCCAGGA |
| 1709 | 170 | CCCUGGUGGACAUCUUCCAGGAG |
| 1710 | 171 | CCUGGUGGACAUCUUCCAGGAGU |
| 1711 | 172 | CUGGUGGACAUCUUCCAGGAGUA |
| 1712 | 173 | UGGUGGACAUCUUCCAGGAGUAC |
| 1713 | 174 | GGUGGACAUCUUCCAGGAGUACC |
| 1714 | 175 | GUGGACAUCUUCCAGGAGUACCC |
| 1715 | 176 | UGGACAUCUUCCAGGAGUACCCU |
| 1716 | 177 | GGACAUCUUCCAGGAGUACCCUG |
| 1717 | 178 | GACAUCUUCCAGGAGUACCCUGA |
| 1718 | 179 | ACAUCUUCCAGGAGUACCCUGAU |
| 1719 | 180 | CAUCUUCCAGGAGUACCCUGAUG |
| 1720 | 181 | AUCUUCCAGGAGUACCCUGAUGA |
| 1721 | 182 | UCUUCCAGGAGUACCCUGAUGAG |
| 1722 | 183 | CUUCCAGGAGUACCCUGAUGAGA |
| 1723 | 184 | UUCCAGGAGUACCCUGAUGAGAU |
| 1724 | 185 | UCCAGGAGUACCCUGAUGAGAUC |
| 1725 | 186 | CCAGGAGUACCCUGAUGAGAUCG |
| 1726 | 187 | CAGGAGUACCCUGAUGAGAUCGA |
| 1727 | 188 | AGGAGUACCCUGAUGAGAUCGAG |
| 1728 | 189 | GGAGUACCCUGAUGAGAUCGAGU |
| 1729 | 190 | GAGUACCCUGAUGAGAUCGAGUA |
| 1730 | 191 | AGUACCCUGAUGAGAUCGAGUAC |
| 1731 | 192 | GUACCCUGAUGAGAUCGAGUACA |
| 1732 | 193 | UACCCUGAUGAGAUCGAGUACAU |
| 1733 | 194 | ACCCUGAUGAGAUCGAGUACAUC |
| 1734 | 195 | CCCUGAUGAGAUCGAGUACAUCU |
| 1735 | 196 | CCUGAUGAGAUCGAGUACAUCUU |
| 1736 | 197 | CUGAUGAGAUCGAGUACAUCUUC |
| 1737 | 198 | UGAUGAGAUCGAGUACAUCUUCA |
| 1738 | 199 | GAUGAGAUCGAGUACAUCUUCAA |
| 1739 | 200 | AUGAGAUCGAGUACAUCUUCAAG |
| 1740 | 201 | UGAGAUCGAGUACAUCUUCAAGC |
| 1741 | 202 | GAGAUCGAGUACAUCUUCAAGCC |
| 1742 | 203 | AGAUCGAGUACAUCUUCAAGCCA |
| 1743 | 204 | GAUCGAGUACAUCUUCAAGCCAU |
| 1744 | 205 | AUCGAGUACAUCUUCAAGCCAUC |
| 1745 | 206 | UCGAGUACAUCUUCAAGCCAUCC |
| 1746 | 207 | CGAGUACAUCUUCAAGCCAUCCU |
| 1747 | 208 | GAGUACAUCUUCAAGCCAUCCUG |
| 1748 | 209 | AGUACAUCUUCAAGCCAUCCUGU |
| 1749 | 210 | GUACAUCUUCAAGCCAUCCUGUG |
| 1750 | 211 | UACAUCUUCAAGCCAUCCUGUGU |
| 1751 | 212 | ACAUCUUCAAGCCAUCCUGUGUG |
| 1752 | 213 | CAUCUUCAAGCCAUCCUGUGUGC |
| 1753 | 214 | AUCUUCAAGCCAUCCUGUGUGCC |
| 1754 | 215 | UCUUCAAGCCAUCCUGUGUGCCC |
| 1755 | 216 | CUUCAAGCCAUCCUGUGUGCCCC |
| 1756 | 217 | UUCAAGCCAUCCUGUGUGCCCCU |
| 1757 | 218 | UCAAGCCAUCCUGUGUGCCCCUG |
| 1758 | 219 | CAAGCCAUCCUGUGUGCCCCUGA |
| 1759 | 220 | AAGCCAUCCUGUGUGCCCCUGAU |
| 1760 | 221 | AGCCAUCCUGUGUGCCCCUGAUG |
| 1761 | 222 | GCCAUCCUGUGUGCCCCUGAUGC |
| 1762 | 223 | CCAUCCUGUGUGCCCCUGAUGCG |
| 1763 | 224 | CAUCCUGUGUGCCCCUGAUGCGA |
| 1764 | 225 | AUCCUGUGUGCCCCUGAUGCGAU |
| 1765 | 226 | UCCUGUGUGCCCCUGAUGCGAUG |
| 1766 | 227 | CCUGUGUGCCCCUGAUGCGAUGC |
| 1767 | 228 | CUGUGUGCCCCUGAUGCGAUGCG |
| 1768 | 229 | UGUGUGCCCCUGAUGCGAUGCGG |
| 1769 | 230 | GUGUGCCCCUGAUGCGAUGCGGG |
| 1770 | 231 | UGUGCCCCUGAUGCGAUGCGGGG |
| 1771 | 232 | GUGCCCCUGAUGCGAUGCGGGGG |
| 1772 | 233 | UGCCCCUGAUGCGAUGCGGGGGC |
| 1773 | 234 | GCCCCUGAUGCGAUGCGGGGCU |
| 1774 | 235 | CCCCUGAUGCGAUGCGGGGCUG |
| 1775 | 236 | CCCUGAUGCGAUGCGGGGCUGC |
| 1776 | 237 | CCUGAUGCGAUGCGGGGCUGCU |
| 1777 | 238 | CUGAUGCGAUGCGGGGCUGCUG |

TABLE 4a-continued

Target sequences in VEGF-121

| SEQ ID NO: | position in VEGF-121 ORF | TARGET SEQUENCE IN VEGF121 mRNA 5' to 3' |
|---|---|---|
| 1778 | 239 | UGAUGCGAUGCGGGGCUGCUGC |
| 1779 | 240 | GAUGCGAUGCGGGGCUGCUGCA |
| 1780 | 241 | AUGCGAUGCGGGGCUGCUGCAA |
| 1781 | 242 | UGCGAUGCGGGGCUGCUGCAAU |
| 1782 | 243 | GCGAUGCGGGGCUGCUGCAAUG |
| 1783 | 244 | CGAUGCGGGGCUGCUGCAAUGA |
| 1784 | 245 | GAUGCGGGGCUGCUGCAAUGAC |
| 1785 | 246 | AUGCGGGGCUGCUGCAAUGACG |
| 1786 | 247 | UGCGGGGCUGCUGCAAUGACGA |
| 1787 | 248 | GCGGGGCUGCUGCAAUGACGAG |
| 1788 | 249 | CGGGGCUGCUGCAAUGACGAGG |
| 1789 | 250 | GGGGCUGCUGCAAUGACGAGGG |
| 1790 | 251 | GGGCUGCUGCAAUGACGAGGGC |
| 1791 | 252 | GGCUGCUGCAAUGACGAGGGCC |
| 1792 | 253 | GCUGCUGCAAUGACGAGGGCCU |
| 1793 | 254 | CUGCUGCAAUGACGAGGGCCUG |
| 1794 | 255 | UGCUGCAAUGACGAGGGCCUGG |
| 1795 | 256 | GCUGCAAUGACGAGGGCCUGGA |
| 1796 | 257 | CUGCAAUGACGAGGGCCUGGAG |
| 1797 | 258 | UGCAAUGACGAGGGCCUGGAGU |
| 1798 | 259 | GCAAUGACGAGGGCCUGGAGUG |
| 1799 | 260 | CAAUGACGAGGGCCUGGAGUGU |
| 1800 | 261 | AAUGACGAGGGCCUGGAGUGUG |
| 1801 | 262 | AUGACGAGGGCCUGGAGUGUGU |
| 1802 | 263 | UGACGAGGGCCUGGAGUGUGUG |
| 1803 | 264 | GACGAGGGCCUGGAGUGUGUGC |
| 1804 | 265 | ACGAGGGCCUGGAGUGUGUGCC |
| 1805 | 266 | CGAGGGCCUGGAGUGUGUGCCC |
| 1806 | 267 | GAGGGCCUGGAGUGUGUGCCCA |
| 1807 | 268 | AGGGCCUGGAGUGUGUGCCCAC |
| 1808 | 269 | GGGCCUGGAGUGUGUGCCCACU |
| 1809 | 270 | GGCCUGGAGUGUGUGCCCACUG |
| 1810 | 271 | GCCUGGAGUGUGUGCCCACUGA |
| 1811 | 272 | CCUGGAGUGUGUGCCCACUGAG |
| 1812 | 273 | CUGGAGUGUGUGCCCACUGAGG |
| 1813 | 274 | UGGAGUGUGUGCCCACUGAGGA |
| 1814 | 275 | GGAGUGUGUGCCCACUGAGGAG |
| 1815 | 276 | GAGUGUGUGCCCACUGAGGAGU |
| 1816 | 277 | AGUGUGUGCCCACUGAGGAGUC |
| 1817 | 278 | GUGUGUGCCCACUGAGGAGUCC |
| 1818 | 279 | UGUGUGCCCACUGAGGAGUCCA |
| 1819 | 280 | GUGUGCCCACUGAGGAGUCCAA |
| 1820 | 281 | UGUGCCCACUGAGGAGUCCAAC |
| 1821 | 282 | GUGCCCACUGAGGAGUCCAACA |
| 1822 | 283 | UGCCCACUGAGGAGUCCAACAU |
| 1823 | 284 | GCCCACUGAGGAGUCCAACAUC |
| 1824 | 285 | CCCACUGAGGAGUCCAACAUCA |
| 1825 | 286 | CCACUGAGGAGUCCAACAUCAC |
| 1826 | 287 | CACUGAGGAGUCCAACAUCACC |
| 1827 | 288 | ACUGAGGAGUCCAACAUCACCA |
| 1828 | 289 | CUGAGGAGUCCAACAUCACCAU |
| 1829 | 290 | UGAGGAGUCCAACAUCACCAUG |
| 1830 | 291 | GAGGAGUCCAACAUCACCAUGC |
| 1831 | 292 | AGGAGUCCAACAUCACCAUGCA |
| 1832 | 293 | GGAGUCCAACAUCACCAUGCAG |
| 1833 | 294 | GAGUCCAACAUCACCAUGCAGA |
| 1834 | 295 | AGUCCAACAUCACCAUGCAGAU |
| 1835 | 296 | GUCCAACAUCACCAUGCAGAUU |
| 1836 | 297 | UCCAACAUCACCAUGCAGAUUA |
| 1837 | 298 | CCAACAUCACCAUGCAGAUUAU |
| 1838 | 299 | CAACAUCACCAUGCAGAUUAUG |
| 1839 | 300 | AACAUCACCAUGCAGAUUAUGC |
| 1840 | 301 | ACAUCACCAUGCAGAUUAUGCG |
| 1841 | 302 | CAUCACCAUGCAGAUUAUGCGG |
| 1842 | 303 | AUCACCAUGCAGAUUAUGCGGA |
| 1843 | 304 | UCACCAUGCAGAUUAUGCGGAU |
| 1844 | 305 | CACCAUGCAGAUUAUGCGGAUC |
| 1845 | 306 | ACCAUGCAGAUUAUGCGGAUCA |
| 1846 | 307 | CCAUGCAGAUUAUGCGGAUCAA |
| 1847 | 308 | CAUGCAGAUUAUGCGGAUCAAA |
| 1848 | 309 | AUGCAGAUUAUGCGGAUCAAAC |
| 1849 | 310 | UGCAGAUUAUGCGGAUCAAACC |
| 1850 | 311 | GCAGAUUAUGCGGAUCAAACCU |
| 1851 | 312 | CAGAUUAUGCGGAUCAAACCUC |

TABLE 4a-continued

Target sequences in VEGF-121

| SEQ ID NO: | position in VEGF-121 ORF | TARGET SEQUENCE IN VEGF121 mRNA 5' to 3' |
|---|---|---|
| 1852 | 313 | CAGAUUAUGCGGAUCAAACCUCA |
| 1853 | 314 | AGAUUAUGCGGAUCAAACCUCAC |
| 1854 | 315 | GAUUAUGCGGAUCAAACCUCACC |
| 1855 | 316 | AUUAUGCGGAUCAAACCUCACCA |
| 1856 | 317 | UUAUGCGGAUCAAACCUCACCAA |
| 1857 | 318 | UAUGCGGAUCAAACCUCACCAAG |
| 1858 | 319 | AUGCGGAUCAAACCUCACCAAGG |
| 1859 | 320 | UGCGGAUCAAACCUCACCAAGGC |
| 1860 | 321 | GCGGAUCAAACCUCACCAAGGCC |
| 1861 | 322 | CGGAUCAAACCUCACCAAGGCCA |
| 1862 | 323 | GGAUCAAACCUCACCAAGGCCAG |
| 1863 | 324 | GAUCAAACCUCACCAAGGCCAGC |
| 1864 | 325 | AUCAAACCUCACCAAGGCCAGCA |
| 1865 | 326 | UCAAACCUCACCAAGGCCAGCAC |
| 1866 | 327 | CAAACCUCACCAAGGCCAGCACA |
| 1867 | 328 | AAACCUCACCAAGGCCAGCACAU |
| 1868 | 329 | AACCUCACCAAGGCCAGCACAUA |
| 1869 | 330 | ACCUCACCAAGGCCAGCACAUAG |
| 1870 | 331 | CCUCACCAAGGCCAGCACAUAGG |
| 1871 | 332 | CUCACCAAGGCCAGCACAUAGGA |
| 1872 | 333 | UCACCAAGGCCAGCACAUAGGAG |
| 1873 | 334 | CACCAAGGCCAGCACAUAGGAGA |
| 1874 | 335 | ACCAAGGCCAGCACAUAGGAGAG |
| 1875 | 336 | CCAAGGCCAGCACAUAGGAGAGA |
| 1876 | 337 | CAAGGCCAGCACAUAGGAGAGAU |
| 1877 | 338 | AAGGCCAGCACAUAGGAGAGAUG |
| 1878 | 339 | AGGCCAGCACAUAGGAGAGAUGA |
| 1879 | 340 | GGCCAGCACAUAGGAGAGAUGAG |
| 1880 | 341 | GCCAGCACAUAGGAGAGAUGAGC |
| 1881 | 342 | CCAGCACAUAGGAGAGAUGAGCU |
| 1882 | 343 | CAGCACAUAGGAGAGAUGAGCUU |
| 1883 | 344 | AGCACAUAGGAGAGAUGAGCUUC |
| 1884 | 345 | GCACAUAGGAGAGAUGAGCUUCC |
| 1885 | 346 | CACAUAGGAGAGAUGAGCUUCCU |
| 1886 | 347 | ACAUAGGAGAGAUGAGCUUCCUA |
| 1887 | 348 | CAUAGGAGAGAUGAGCUUCCUAC |
| 1888 | 349 | AUAGGAGAGAUGAGCUUCCUACA |
| 1889 | 350 | UAGGAGAGAUGAGCUUCCUACAG |
| 1890 | 351 | AGGAGAGAUGAGCUUCCUACAGC |
| 1891 | 352 | GGAGAGAUGAGCUUCCUACAGCA |
| 1892 | 353 | GAGAGAUGAGCUUCCUACAGCAC |
| 1893 | 354 | AGAGAUGAGCUUCCUACAGCACA |
| 1894 | 355 | GAGAUGAGCUUCCUACAGCACAA |
| 1895 | 356 | AGAUGAGCUUCCUACAGCACAAC |
| 1896 | 357 | GAUGAGCUUCCUACAGCACAACA |
| 1897 | 358 | AUGAGCUUCCUACAGCACAACAA |
| 1898 | 359 | UGAGCUUCCUACAGCACAACAAA |
| 1899 | 360 | GAGCUUCCUACAGCACAACAAAU |
| 1900 | 361 | AGCUUCCUACAGCACAACAAAUG |
| 1901 | 362 | GCUUCCUACAGCACAACAAAUGU |
| 1902 | 363 | CUUCCUACAGCACAACAAAUGUG |
| 1903 | 364 | UUCCUACAGCACAACAAAUGUGA |
| 1904 | 365 | UCCUACAGCACAACAAAUGUGAA |
| 1905 | 366 | CCUACAGCACAACAAAUGUGAAU |
| 1906 | 367 | CUACAGCACAACAAAUGUGAAUG |
| 1907 | 368 | UACAGCACAACAAAUGUGAAUGC |
| 1908 | 369 | ACAGCACAACAAAUGUGAAUGCA |
| 1909 | 370 | CAGCACAACAAAUGUGAAUGCAG |
| 1910 | 371 | AGCACAACAAAUGUGAAUGCAGA |
| 1911 | 372 | GCACAACAAAUGUGAAUGCAGAC |
| 1912 | 373 | CACAACAAAUGUGAAUGCAGACC |
| 1913 | 374 | ACAACAAAUGUGAAUGCAGACCA |
| 1914 | 375 | CAACAAAUGUGAAUGCAGACCAA |
| 1915 | 376 | AACAAAUGUGAAUGCAGACCAAA |
| 1916 | 377 | ACAAAUGUGAAUGCAGACCAAAG |
| 1917 | 378 | CAAAUGUGAAUGCAGACCAAAGA |
| 1918 | 379 | AAAUGUGAAUGCAGACCAAAGAA |
| 1919 | 380 | AAUGUGAAUGCAGACCAAAGAAA |
| 1920 | 381 | AUGUGAAUGCAGACCAAAGAAAG |
| 1921 | 382 | UGUGAAUGCAGACCAAAGAAAGA |
| 1922 | 383 | GUGAAUGCAGACCAAAGAAAGAU |
| 1923 | 384 | UGAAUGCAGACCAAAGAAAGAUA |
| 1924 | 385 | GAAUGCAGACCAAAGAAAGAUAG |
| 1925 | 386 | AAUGCAGACCAAAGAAAGAUAGA |

TABLE 4a-continued

Target sequences in VEGF-121

| SEQ ID NO: | position in VEGF-121 ORF | TARGET SEQUENCE IN VEGF121 mRNA 5' to 3' |
|---|---|---|
| 1926 | 387 | AUGCAGACCAAAGAAAGAUAGAG |
| 1927 | 388 | UGCAGACCAAAGAAAGAUAGAGC |
| 1928 | 389 | GCAGACCAAAGAAAGAUAGAGCA |
| 1929 | 390 | CAGACCAAAGAAAGAUAGAGCAA |
| 1930 | 391 | AGACCAAAGAAAGAUAGAGCAAG |
| 1931 | 392 | GACCAAAGAAAGAUAGAGCAAGA |
| 1932 | 393 | ACCAAAGAAAGAUAGAGCAAGAC |
| 1933 | 394 | CCAAAGAAAGAUAGAGCAAGACA |
| 1934 | 395 | CAAAGAAAGAUAGAGCAAGACAA |
| 1935 | 396 | AAAGAAAGAUAGAGCAAGACAAG |
| 1936 | 397 | AAGAAAGAUAGAGCAAGACAAGA |
| 1937 | 398 | AGAAAGAUAGAGCAAGACAAGAA |
| 1938 | 399 | GAAAGAUAGAGCAAGACAAGAAA |
| 1939 | 400 | AAAGAUAGAGCAAGACAAGAAAA |

TABLE 4b

VEGF targeted duplexes

| position in ORF | SEQ ID NO: | Target sequence (5'-3') | Duplex ID | Strand | SEQ ID NO: | Strand Sequences |
|---|---|---|---|---|---|---|
| 1 | 2184 | AUGAACUUUCUGCUGUCUUGGGU | AL-DP-4043 | S | 1940 | 5 GAACUUUCUGCUGUCUUGGGU 3 |
| | | | | AS | 1941 | 3 UACUUGAAAGACGACAGAACCCA 5 |
| 22 | 2185 | GUGCAUUGGAGCCUUGCCUUGCU | AL-DP-4077 | S | 1942 | 5 GCAUUGGAGCCUUGCCUUGCU 3 |
| | | | | AS | 1943 | 3 CACGUAACCUCGGAACGGAACGA 5 |
| 47 | 2186 | UCUACCUCCACCAUGCCAAGUGG | AL-DP-4021 | S | 1944 | 5 UACCUCCACCAUGCCAAGUTT 3 |
| | | | | AS | 1945 | 3 TTAUGGAGGUGGUACGGUUCA 5 |
| 48 | 2187 | CUACCUCCACCAUGCCAAGUGGU | AL-DP-4109 | S | 1946 | 5 ACCUCCACCAUGCCAAGUGT T 3 |
| | | | | AS | 1947 | 3 TTUGGAGGUGGUACGGUUCAC 5 |
| 50 | 2188 | ACCUCCACCAUGCCAAGUGGUCC | AL-DP-4006 | S | 1948 | 5 CUCCACCAUGCCAAGUGGUCC 3 |
| | | | | AS | 1949 | 3 UGGAGGUGGUACGGUUCACCAGG 5 |
| | | | AL-DP-4083 | S | 1950 | 5 CUCCACCAUGCCAAGUGGUTT 3 |
| | | | | AS | 1951 | 3 TTGAGGUGGUACGGUUCACCA 5 |
| 51 | 2189 | CCUCCACCAUGCCAAGUGGUCCC | AL-DP-4047 | S | 1952 | 5 UCCACCAUGCCAAGUGGUCCC 3 |
| | | | | AS | 1953 | 3 GGAGGUGGUACGGUUCACCAGGG 5 |
| | | | AL-DP-4017 | S | 1954 | 5 UCCACCAUGCCAAGUGGUCTT 3 |
| | | | | AS | 1955 | 3 TTAGGUGGUACGGUUCACCAG 5 |
| 52 | 2190 | CUCCACCAUGCCAAGUGGUCCCA | AL-DP-4048 | S | 1956 | 5 CCACCAUGCCAAGUGGUCCCA 3 |
| | | | | AS | 1957 | 3 GAGGUGGUACGGUUCACCAGGGU 5 |
| | | | AL-DP-4103 | S | 1958 | 5 CCACCAUGCCAAGUGGUCCTT 3 |
| | | | | AS | 1959 | 3 TTGGUGGUACGGUUCACCAGG 5 |
| 53 | 2191 | UCCACCAUGCCAAGUGGUCCCAG | AL-DP-4035 | S | 1960 | 5 CACCAUGCCAAGUGGUCCCAG 3 |
| | | | | AS | 1961 | 3 AGGUGGUACGGUUCACCAGGGUC 5 |
| | | | AL-DP-4018 | S | 1962 | 5 CACCAUGCCAAGUGGUCCCTT 3 |
| | | | | AS | 1963 | 3 TTGUGGUACGGUUCACCAGGG 5 |
| 54 | 2192 | CCACCAUGCCAAGUGGUCCCAGG | AL-DP-4036 | S | 1964 | 5 ACCAUGCCAAGUGGUCCCAGG 3 |
| | | | | AS | 1965 | 3 GGUGGUACGGUUCACCAGGGUCC 5 |
| | | | AL-DP-4084 | S | 1966 | 5 ACCAUGCCAAGUGGUCCCATT 3 |
| | | | | AS | 1967 | 3 TTUGGUACGGUUCACCAGGGU 5 |
| 55 | 2193 | CACCAUGCCAAGUGGUCCCAGGC | AL-DP-4093 | S | 1968 | 5 CCAUGCCAAGUGGUCCCAGGC 3 |
| | | | | AS | 1969 | 3 GUGGUACGGUUCACCAGGGUCCG 5 |
| | | | AL-DP-4085 | S | 1970 | 5 CCAUGCCAAGUGGUCCCAGTT 3 |
| | | | | AS | 1971 | 3 TTGGUACGGUUCACCAGGGUC 5 |
| 56 | 2194 | ACCAUGCCAAGUGGUCCCAGGCU | AL-DP-4037 | S | 1972 | 5 CAUGCCAAGUGGUCCCAGGCU 3 |
| | | | | AS | 1973 | 3 UGGUACGGUUCACCAGGGUCCGA 5 |
| | | | AL-DP-4054 | S | 1974 | 5 CAUGCCAAGUGGUCCCAGGTT 3 |
| | | | | AS | 1975 | 3 TTGUACGGUUCACCAGGGUCC 5 |

TABLE 4b-continued

VEGF targeted duplexes

| position in ORF | SEQ ID NO: | Target sequence (5'-3') | Duplex ID | Strand | SEQ ID NO: | Strand Sequences |
|---|---|---|---|---|---|---|
| 57 | 2195 | CCAUGCCAAGUGGUCCCAGGCUG | AL-DP-4038 | S | 1976 | 5 AUGCCAAGUGGUCCCAGGCUG 3 |
| | | | | AS | 1977 | 3 GGUACGGUUCACCAGGGUCCGAC 5 |
| | | | AL-DP-4086 | S | 1978 | 5 AUGCCAAGUGGUCCCAGGCUT 3 |
| | | | | AS | 1979 | 3 TTUACGGUUCACCAGGGUCCG 5 |
| 58 | 2196 | CAUGCCAAGUGGUCCCAGGCUGC | AL-DP-4049 | S | 1980 | 5 UGCCAAGUGGUCCCAGGCUGC 3 |
| | | | | AS | 1981 | 3 GUACGGUUCACCAGGGUCCGACG 5 |
| | | | AL-DP-4087 | S | 1982 | 5 UGCCAAGUGGUCCCAGGCUT 3 |
| | | | | AS | 1983 | 3 TTACGGUUCACCAGGGUCCGA 5 |
| 59 | 2197 | AUGCCAAGUGGUCCCAGGCUGCA | AL-DP-4001 | S | 1984 | 5 GCCAAGUGGUCCCAGGCUGCA 3 |
| | | | | AS | 1985 | 3 UACGGUUCACCAGGGUCCGACGU 5 |
| | | | AL-DP-4052 | A | 1986 | 5 GCCAAGUGGUCCCAGGCUT 3 |
| | | | | AS | 1987 | 3 TTCGGUUCACCAGGGUCCGAC 5 |
| 60 | 2198 | UGCCAAGUGGUCCCAGGCUGCAC | AL-DP-4007 | S | 1988 | 5 CCAAGUGGUCCCAGGCUGCAC 3 |
| | | | | AS | 1989 | 3 ACGGUUCACCAGGGUCCGACGUG 5 |
| | | | AL-DP-4088 | S | 1990 | 5 CCAAGUGGUCCCAGGCUGCTT 3 |
| | | | | AS | 1991 | 3 TTGGUUCACCAGGGUCCGACG 5 |
| 61 | 2199 | GCCAAGUGGUCCCAGGCUGCACC | AL-DP-4070 | S | 1992 | 5 CAAGUGGUCCCAGGCUGCACC 3 |
| | | | | AS | 1993 | 3 CGGUUCACCAGGGUCCGACGUGG 5 |
| | | | AL-DP-4055 | S | 1994 | 5 CAAGUGGUCCCAGGCUGCATT 3 |
| | | | | AS | 1995 | 3 TTGUUCACCAGGGUCCGACGU 5 |
| 62 | 2200 | CCAAGUGGUCCCAGGCUGCACCC | AL-DP-4071 | S | 1996 | 5 AAGUGGUCCCAGGCUGCACCC 3 |
| | | | | AS | 1997 | 3 GGUUCACCAGGGUCCGACGUGGG 5 |
| | | | AL-DP-4056 | S | 1998 | 5 AAGUGGUCCCAGGCUGCACTT 3 |
| | | | | AS | 1999 | 3 TTUUCACCAGGGUCCGACGUG 5 |
| 63 | 2201 | CAAGUGGUCCCAGGCUGCACCCA | AL-DP-4072 | S | 2000 | 5 AGUGGUCCCAGGCUGCACCCA 3 |
| | | | | AS | 2001 | 3 GUUCACCAGGGUCCGACGUGGGU 5 |
| | | | AL-DP-4057 | S | 2002 | 5 AGUGGUCCCAGGCUGCACCTT 3 |
| | | | | AS | 2003 | 3 TTUCACCAGGGUCCGACGUGG 5 |
| 64 | 2202 | AAGUGGUCCCAGGCUGCACCCAU | AL-DP-4066 | S | 2004 | 5 GUGGUCCCAGGCUGCACCCTT 3 |
| | | | | AS | 2005 | 3 TTCACCAGGGUCCGACGUGGG 5 |
| 99 | 2203 | AGGGCAGAAUCAUCACGAAGUGG | AL-DP-4022 | S | 2006 | 5 GGCAGAAUCAUCACGAAGUTT 3 |
| | | | | AS | 2007 | 3 TTCCGUCUUAGUAGUGCUUCA 5 |
| 100 | 2204 | GGGCAGAAUCAUCACGAAGUGGU | AL-DP-4023 | S | 2008 | 5 GCAGAAUCAUCACGAAGUGTT 3 |
| | | | | AS | 2009 | 3 TTCGUCUUAGUAGUGCUUCAC 5 |
| 101 | 2205 | GGCAGAAUCAUCACGAAGUGGUG | AL-DP-4024 | S | 2010 | 5 CAGAAUCAUCACGAAGUGGTT 3 |
| | | | | AS | 2011 | 3 TTGUCUUAGUAGUGCUUCACC 5 |
| 102 | 2206 | GCAGAAUCAUCACGAAGUGGUGA | AL-DP-4076 | S | 2012 | 5 AGAAUCAUCACGAAGUGGUGA 3 |
| | | | | AS | 2013 | 3 CGUCUUAGUAGUGCUUCACCACU 5 |
| | | | AL-DP-4019 | S | 2014 | 5 AGAAUCAUCACGAAGUGGUTT 3 |
| | | | | AS | 2015 | 3 TTUCUUAGUAGUGCUUCACCA 5 |
| 103 | 2207 | CAGAAUCAUCACGAAGUGGUGAA | AL-DP-4025 | S | 2016 | 5 GAAUCAUCACGAAGUGGUGTT 3 |
| | | | | AS | 2017 | 3 TTCUUAGUAGUGCUUCACCAC 5 |
| 104 | 2208 | AGAAUCAUCACGAAGUGGUGAAG | AL-DP-4110 | S | 2018 | 5 AAUCAUCACGAAGUGGUGATT 3 |
| | | | | AS | 2019 | 3 TTUUAGUAGUGCUUCACCACU 5 |
| 105 | 2209 | GAAUCAUCACGAAGUGGUGAAGU | AL-DP-4068 | S | 2020 | 5 AUCAUCACGAAGUGGUGAATT 3 |
| | | | | AS | 2021 | 3 TTUAGUAGUGCUUCACCACUU 5 |
| 113 | 2210 | ACGAAGUGGUGAAGUUCAUGGAU | AL-DP-4078 | S | 2022 | 5 GAAGUGGUGAAGUUCAUGGAU 3 |
| | | | | AS | 2023 | 3 UGCUUCACCACUUCAAGUACCUA 5 |
| 121 | 2211 | GUGAAGUUCAUGGAUGUCUAUCA | AL-DP-4080 | S | 2024 | 5 GAAGUUCAUGGAUGUCUAUCA 3 |
| | | | | AS | 2025 | 3 CACUUCAAGUACCUACAGAUAGU 5 |
| 129 | 2212 | CAUGGAUGUCUAUCAGCGCAGCU | AL-DP-4111 | S | 2026 | 5 UGGAUGUCUAUCAGCGCAGTT 3 |
| | | | | AS | 2027 | 3 TTACCUACAGAUAGUCGCGUC 5 |
| 130 | 2213 | AUGGAUGUCUAUCAGCGCAGCUA | AL-DP-4041 | S | 2028 | 5 GGAUGUCUAUCAGCGCAGCUA 3 |
| | | | | AS | 2029 | 3 UACCUACAGAUAGUCGCGUCGAU 5 |
| | | | AL-DP-4062 | S | 2030 | 5 GGAUGUCUAUCAGCGCAGCTT 3 |
| | | | | AS | 2031 | 3 TTCCUACAGAUAGUCGCGUCG 5 |

TABLE 4b-continued

VEGF targeted duplexes

| position in ORF | SEQ ID NO: | Target sequence (5'-3') | Duplex ID | Strand | SEQ ID NO: | Strand Sequences |
|---|---|---|---|---|---|---|
| 131 | 2214 | UGGAUGUCUAUCAGCGCAGCUAC | AL-DP-4069 | S | 2032 | 5 GAUGUCUAUCAGCGCAGCUTT 3 |
| | | | | AS | 2033 | 3 TTCUACAGAUAGUCGCGUCGA 5 |
| 132 | 2215 | GGAUGUCUAUCAGCGCAGCUACU | AL-DP-4112 | S | 2034 | 5 AUGUCUAUCAGCGCAGCUATT 3 |
| | | | | AS | 2035 | 3 TTUACAGAUAGUCGCGUCGAU 5 |
| 133 | 2216 | GAUGUCUAUCAGCGCAGCUACUG | AL-DP-4026 | S | 2036 | 5 UGUCUAUCAGCGCAGCUACTT 3 |
| | | | | AS | 2037 | 3 TTACAGAUAGUCGCGUCGAUG 5 |
| 134 | 2217 | AUGUCUAUCAGCGCAGCUACUGC | AL-DP-4095 | S | 2038 | 5 GUCUAUCAGCGCAGCUACUGC 3 |
| | | | | AS | 2039 | 3 UACAGAUAGUCGCGUCGAUGACG 5 |
| | | | AL-DP-4020 | S | 2040 | 5 GUCUAUCAGCGCAGCUACUTT 3 |
| | | | | AS | 2041 | 3 TTCAGAUAGUCGCGUCGAUGA 5 |
| 135 | 2218 | UGUCUAUCAGCGCAGCUACUGCC | AL-DP-4027 | S | 2042 | 5 UCUAUCAGCGCAGCUACUGTT 3 |
| | | | | AS | 2043 | 3 TTAGAUAGUCGCGUCGAUGAC 5 |
| 144 | 2219 | GCGCAGCUACUGCCAUCCAAUCG | AL-DP-4081 | S | 2044 | 5 GCAGCUACUGCCAUCCAAUCG 3 |
| | | | | AS | 2045 | 3 CGCGUCGAUGACGGUAGGUUAGC 5 |
| 146 | 2220 | GCAGCUACUGCCAUCCAAUCGAG | AL-DP-4098 | S | 2046 | 5 AGCUACUGCCAUCCAAUCGAG 3 |
| | | | | AS | 2047 | 3 CGUCGAUGACGGUAGGUUAGCUC 5 |
| 149 | 2221 | GCUACUGCCAUCCAAUCGAGACC | AL-DP-4028 | S | 2048 | 5 UACUGCCAUCCAAUCGAGATT 3 |
| | | | | AS | 2049 | 3 TTAUGACGGUAGGUUAGCUCU 5 |
| 150 | 2222 | CUACUGCCAUCCAAUCGAGACCC | AL-DP-4029 | S | 2050 | 5 ACUGCCAUCCAAUCGAGACTT 3 |
| | | | | AS | 2051 | 3 TTUGACGGUAGGUUAGCUCUG 5 |
| 151 | 2223 | UACUGCCAUCCAAUCGAGACCCU | AL-DP-4030 | S | 2052 | 5 CUGCCAUCCAAUCGAGACCTT 3 |
| | | | | AS | 2053 | 3 TTGACGGUAGGUUAGCUCUGG 5 |
| 152 | 2224 | ACUGCCAUCCAAUCGAGACCCUG | AL-DP-4031 | S | 2054 | 5 UGCCAUCCAAUCGAGACCCTT 3 |
| | | | | AS | 2055 | 3 TTACGGUAGGUUAGCUCUGGG 5 |
| 166 | 2225 | GAGACCCUGGUGGACAUCUUCCA | AL-DP-4008 | S | 2056 | 5 GACCCUGGUGGACAUCUUCCA 3 |
| | | | | AS | 2057 | 3 CUCUGGGACCACCUGUAGAAGGU 5 |
| | | | AL-DP-4058 | S | 2058 | 5 GACCCUGGUGGACAUCUUCTT 3 |
| | | | | AS | 2059 | 3 TTCUGGGACCACCUGUAGAAG 5 |
| 167 | 2226 | AGACCCUGGUGGACAUCUUCCAG | AL-DP-4009 | S | 2060 | 5 ACCCUGGUGGACAUCUUCCAG 3 |
| | | | | AS | 2061 | 3 UCUGGGACCACCUGUAGAAGGUC 5 |
| | | | AL-DP-4059 | S | 2062 | 5 ACCCUGGUGGACAUCUUCCTT 3 |
| | | | | AS | 2063 | 3 TTUGGGACCACCUGUAGAAGG 5 |
| 168 | 2227 | GACCCUGGUGGACAUCUUCCAGG | AL-DP-4010 | S | 2064 | 5 CCCUGGUGGACAUCUUCCAGG 3 |
| | | | | AS | 2065 | 3 CUGGGACCACCUGUAGAAGGUCC 5 |
| | | | AL-DP-4060 | S | 2066 | 5 CCCUGGUGGACAUCUUCCATT 3 |
| | | | | AS | 2067 | 3 TTGGGACCACCUGUAGAAGGU 5 |
| 169 | 2228 | ACCCUGGUGGACAUCUUCCAGGA | AL-DP-4073 | S | 2068 | 5 CCUGGUGGACAUCUUCCAGGA 3 |
| | | | | AS | 2069 | 3 UGGGACCACCUGUAGAAGGUCCU 5 |
| | | | AL-DP-4104 | S | 2070 | 5 CCUGGUGGACAUCUUCCAGTT 3 |
| | | | | AS | 2071 | 3 TTGGACCACCUGUAGAAGGUC 5 |
| 170 | 2229 | CCCUGGUGGACAUCUUCCAGGAG | AL-DP-4011 | S | 2072 | 5 CUGGUGGACAUCUUCCAGGAG 3 |
| | | | | AS | 2073 | 3 GGGACCACCUGUAGAAGGUCCUC 5 |
| | | | AL-DP-4089 | S | 2074 | 5 CUGGUGGACAUCUUCCAGGTT 3 |
| | | | | AS | 2075 | 3 TTGACCACCUGUAGAAGGUCC 5 |
| 171 | 2230 | CCUGGUGGACAUCUUCCAGGAGU | AL-DP-4074 | S | 2076 | 5 UGGUGGACAUCUUCCAGGAGU 3 |
| | | | | AS | 2077 | 3 GGACCACCUGUAGAAGGUCCUCA 5 |
| | | | AL-DP-4090 | S | 2078 | 5 UGGUGGACAUCUUCCAGGATT 3 |
| | | | | AS | 2079 | 3 TTACCACCUGUAGAAGGUCCU 5 |
| 172 | 2231 | CUGGUGGACAUCUUCCAGGAGUA | AL-DP-4039 | S | 2080 | 5 GGUGGACAUCUUCCAGGAGUA 3 |
| | | | | AS | 2081 | 3 GACCACCUGUAGAAGGUCCUCAU 5 |
| | | | AL-DP-4091 | S | 2082 | 5 GGUGGACAUCUUCCAGGAGTT 3 |
| | | | | AS | 2083 | 3 TTCCACCUGUAGAAGGUCCUC 5 |

TABLE 4b-continued

VEGF targeted duplexes

| position in ORF | SEQ ID NO: | Target sequence (5'-3') | Duplex ID | Strand | SEQ ID NO: | Strand Sequences |
|---|---|---|---|---|---|---|
| 175 | 2232 | GUGGACAUCUUCCAGGAGUACCC | AL-DP-4003 | S | 2084 | 5 GGACAUCUUCCAGGAGUACCC 3 |
| | | | | AS | 2085 | 3 CCUGUAGAAGGUCCUCAUGGG 5 |
| | | | AL-DP-4116 | S | 2086 | 5 GGACAUCUUCCAGGAGUACCC 3 |
| | | | | AS | 2087 | 3 CCUGUAGAAGGUCCUCAUGGG 5 |
| | | | AL-DP-4015 | S | 2088 | 5 GGACAUCUUCCAGGAGUACTT 3 |
| | | | | AS | 2089 | 3 TTCCUGUAGAAGGUCCUCAUG 5 |
| | | | AL-DP-4120 | S | 2090 | 5 GGACAUCUUCCAGGAGUAC 3 |
| | | | | AS | 2091 | 3 CCUGUAGAAGGUCCUCAUG 5 |
| 179 | 2233 | ACAUCUUCCAGGAGUACCCUGAU | AL-DP-4099 | S | 2092 | 5 AUCUUCCAGGAGUACCCUGAU 3 |
| | | | | AS | 2093 | 3 UGUAGAAGGUCCUCAUGGGACUA 5 |
| 191 | 2234 | AGUACCCUGAUGAGAUCGAGUAC | AL-DP-4032 | S | 2094 | 5 UACCCUGAUGAGAUCGAGUTT 3 |
| | | | | AS | 2095 | 3 TTAUGGGACUACUCUAGCUCA 5 |
| 192 | 2235 | GUACCCUGAUGAGAUCGAGUACA | AL-DP-4042 | S | 2096 | 5 ACCCUGAUGAGAUCGAGUACA 3 |
| | | | | AS | 2097 | 3 CAUGGGACUACUCUAGCUCAUGU 5 |
| | | | AL-DP-4063 | S | 2098 | 5 ACCCUGAUGAGAUCGAGUAT T 3 |
| | | | | AS | 2099 | 3 TTGGGACUACUCUAGCUCAU 5 |
| 209 | 2236 | AGUACAUCUUCAAGCCAUCCUGU | AL-DP-4064 | S | 2100 | 5 UACAUCUUCAAGCCAUCCUTT 3 |
| | | | | AS | 2101 | 3 TTAUGUAGAAGUUCGGUAGGA 5 |
| 260 | 2237 | GCAAUGACGAGGGCCUGGAGUGU | AL-DP-4044 | S | 2102 | 5 AAUGACGAGGGCCUGGAGUGU 3 |
| | | | | AS | 2103 | 3 CGUUACUGCUCCCGGACCUCACA 5 |
| 263 | 2238 | AUGACGAGGGCCUGGAGUGUGUG | AL-DP-4045 | S | 2104 | 5 GACGAGGGCCUGGAGUGUGUG 3 |
| | | | | AS | 2105 | 3 UACUGCUCCCGGACCUCACACAC 5 |
| 279 | 2239 | GUGUGUGCCCACUGAGGAGUCCA | AL-DP-4046 | S | 2106 | 5 GUGUGCCCACUGAGGAGUCCA 3 |
| | | | | AS | 2107 | 3 CACACACGGGUGACUCCUCAGGU 5 |
| 281 | 2240 | GUGUGCCCACUGAGGAGUCCAAC | AL-DP-4096 | S | 2108 | 5 GUGCCCACUGAGGAGUCCAAC 3 |
| | | | | AS | 2109 | 3 CACACGGGUGACUCCUCAGGUUG 5 |
| 283 | 2241 | GUGCCCACUGAGGAGUCCAACAU | AL-DP-4040 | S | 2110 | 5 GCCCACUGAGGAGUCCAACAU 3 |
| | | | | AS | 2111 | 3 CACGGGUGACUCCUCAGGUUGUA 5 |
| 289 | 2242 | ACUGAGGAGUCCAACAUCACCAU | AL-DP-4065 | S | 2112 | 5 UGAGGAGUCCAACAUCACCTT 3 |
| | | | | AS | 2113 | 3 TTACUCCUCAGGUUGUAGUGG 5 |
| 302 | 2243 | ACAUCACCAUGCAGAUUAUGCGG | AL-DP-4100 | S | 2114 | 5 AUCACCAUGCAGAUUAUGCGG 3 |
| | | | | AS | 2115 | 3 UGUAGUGGUACGUCUAAUACGCC 5 |
| 305 | 2244 | UCACCAUGCAGAUUAUGCGGAUC | AL-DP-4033 | S | 2116 | 5 ACCAUGCAGAUUAUGCGGATT 3 |
| | | | | AS | 2117 | 3 TTUGGUACGUCUAAUACGCCU 5 |
| 310 | 2245 | AUGCAGAUUAUGCGGAUCAAACC | AL-DP-4101 | S | 2118 | 5 GCAGAUUAUGCGGAUCAAACC 3 |
| | | | | AS | 2119 | 3 UACGUCUAAUACGCCUAGUUUGG 5 |
| 312 | 2246 | GCAGAUUAUGCGGAUCAAACCUC | AL-DP-4102 | S | 2120 | 5 AGAUUAUGCGGAUCAAACCUC 3 |
| | | | | AS | 2121 | 3 CGUCUAAUACGCCUAGUUUGGAG 5 |
| 315 | 2247 | GAUUAUGCGGAUCAAACCUCACC | AL-DP-4034 | S | 2122 | 5 UUAUGCGGAUCAAACCUCATT 3 |
| | | | | AS | 2123 | 3 TTAAUACGCCUAGUUUGGAGU 5 |
| 316 | 2248 | AUUAUGCGGAUCAAACCUCACCA | AL-DP-4113 | S | 2124 | 5 UAUGCGGAUCAAACCUCACTT 3 |
| | | | | AS | 2125 | 3 TTAUACGCCUAGUUUGGAGUG 5 |
| 317 | 2249 | UUAUGCGGAUCAAACCUCACCAA | AL-DP-4114 | S | 2126 | 5 AUGCGGAUCAAACCUCACCTT 3 |
| | | | | AS | 2127 | 3 TTUACGCCUAGUUUGGAGUGG 5 |
| 319 | 2250 | AUGCGGAUCAAACCUCACCAAGG | AL-DP-4002 | S | 2128 | 5 GCGGAUCAAACCUCACCAAGG 3 |
| | | | | AS | 2129 | 3 UACGCCUAGUUUGGAGUGGUUCC 5 |
| | | | AL-DP-4115 | S | 2130 | 5 GCGGAUCAAACCUCACCAA 3 |
| | | | | AS | 2131 | 3 CGCCUAGUUUGGAGUGGUU 5 |
| | | | AL-DP-4014 | S | 2132 | 5 GCGGAUCAAACCUCACCAATT 3 |
| | | | | AS | 2133 | 3 TTCGCCUAGUUUGGAGUGGUU 5 |
| | | | AL-DP-4119 | S | 2134 | 5 GCGGAUCAAACCUCACCAA 3 |
| | | | | AS | 2135 | 3 CGCCUAGUUUGGAGUGGUU 5 |

TABLE 4b-continued

VEGF targeted duplexes

| position in ORF | SEQ ID NO: | Target sequence (5'-3') | Duplex ID | Strand | SEQ ID NO: | Strand Sequences |
|---|---|---|---|---|---|---|
| 321 | 2251 | GCGGAUCAAACCUCACCAAGGCC | AL-DP-4013 | S | 2136 | 5 GGAUCAAACCUCACCAAGGCC 3 |
| | | | | AS | 2137 | 3 CGCCUAGUUUGGAGUGGUUCCGG 5 |
| 341 | 2252 | GCCAGCACAUAGGAGAGAUGAGC | AL-DP-4075 | S | 2138 | 5 CAGCACAUAGGAGAGAUGAGC 3 |
| | | | | AS | 2139 | 3 CGGUCGUGUAUCCUCUCUACUCG 5 |
| | | | AL-DP-4105 | S | 2140 | 5 CAGCACAUAGGAGAGAUGAUT 3 |
| | | | | AS | 2141 | 3 TTGUCGUGUAUCCUCUCUACU 5 |
| 342 | 2253 | CCAGCACAUAGGAGAGAUGAGCU | AL-DP-4050 | S | 2142 | 5 AGCACAUAGGAGAGAUGAGCU 3 |
| | | | | AS | 2143 | 3 GGUCGUGUAUCCUCUCUACUCGA 5 |
| | | | AL-DP-4106 | S | 2144 | 5 AGCACAUAGGAGAGAUGAGT T 3 |
| | | | | AS | 2145 | 3 TTUCGUGUAUCCUCUCUACUC 5 |
| 343 | 2254 | CAGCACAUAGGAGAGAUGAGCUU | AL-DP-4094 | S | 2146 | 5 GCACAUAGGAGAGAUGAGCUU 3 |
| | | | | AS | 2147 | 3 GUCGUGUAUCCUCUCUACUCGAA 5 |
| | | | AL-DP-4118 | S | 2148 | 5 GCACAUAGGAGAGAUGAGCUU 3 |
| | | | | AS | 2149 | 3 CGUGUAUCCUCUCUACUCGAA 5 |
| | | | AL-DP-4107 | S | 2150 | 5 GCACAUAGGAGAGAUGAGCTT 3 |
| | | | | AS | 2151 | 3 TTCGUGUAUCCUCUCUACUCG 5 |
| | | | AL-DP-4122 | S | 2152 | 5 GCACAUAGGAGAGAUGAGC 3 |
| | | | | AS | 2153 | 3 CGUGUAUCCUCUCUACUCG 5 |
| 344 | 2255 | AGCACAUAGGAGAGAUGAGCUUC | AL-DP-4012 | S | 2154 | 5 CACAUAGGAGAGAUGAGCUUC 3 |
| | | | | AS | 2155 | 3 UCGUGUAUCCUCUCUACUCGAAG 5 |
| | | | AL-DP-4108 | S | 2156 | 5 CACAUAGGAGAGAUGAGCUTT 3 |
| | | | | AS | 2157 | 3 TTGUGUAUCCUCUCUACUCGA 5 |
| 346 | 2256 | CACAUAGGAGAGAUGAGCUUCCU | AL-DP-4051 | S | 2158 | 5 CAUAGGAGAGAUGAGCUUCCU 3 |
| | | | | AS | 2159 | 3 GUGUAUCCUCUCUACUCGAAGGA 5 |
| | | | AL-DP-4061 | S | 2160 | 5 CAUAGGAGAGAUGAGCUUCTT 3 |
| | | | | AS | 2161 | 3 TTGUAUCCUCUCUACUCGAAG 5 |
| 349 | 2257 | AUAGGAGAGAUGAGCUUCCUACA | AL-DP-4082 | S | 2162 | 5 AGGAGAGAUGAGCUUCCUACA 3 |
| | | | | AS | 2163 | 3 UAUCCUCUCUACUCGAAGGAUGU 5 |
| 369 | 2258 | ACAGCACAACAAAUGUGAAUGCA | AL-DP-4079 | S | 2164 | 5 AGCACAACAAAUGUGAAUGCA 3 |
| | | | | AS | 2165 | 3 UGUCGUGUUGUUUACACUUACGU 5 |
| 372 | 2259 | GCACAACAAAUGUGAAUGCAGAC | AL-DP-4097 | S | 2166 | 5 ACAACAAAUGUGAAUGCAGAC 3 |
| | | | | AS | 2167 | 3 CGUGUUGUUUACACUUACGUCUG 5 |
| 379 | 2260 | AAAUGUGAAUGCAGACCAAAGAA | AL-DP-4067 | S | 2168 | 5 AUGUGAAUGCAGACCAAAGTT 3 |
| | | | | AS | 2169 | 3 TTUACACUUACGUCUGGUUUC 5 |
| 380 | 2261 | AAUGUGAAUGCAGACCAAAGAAA | AL-DP-4092 | S | 2170 | 5 UGUGAAUGCAGACCAAAGAUU 3 |
| | | | | AS | 2171 | 3 TTACACUUACGUCUGGUUUCU 5 |
| 381 | 2262 | AUGUGAAUGCAGACCAAAGAAAG | AL-DP-4004 | S | 2172 | 5 GUGAAUGCAGACCAAAGAAAG 3 |
| | | | | AS | 2173 | 3 UACACUUACGUCUGGUUUCUUUC 5 |
| | | | AL-DP-4117 | S | 2174 | 5 GUGAAUGCAGACCAAAGAAAG 3 |
| | | | | AS | 2175 | 3 CACUUACGUCUGGUUUCUUUC 5 |
| | | | AL-DP-4016 | S | 2176 | 5 GUGAAUGCAGACCAAAGAATT 3 |
| | | | | AS | 2177 | 3 TTCACUUACGUCUGGUUUCUU 5 |
| | | | AL-DP-4121 | S | 2178 | 5 GUGAAUGCAGACCAAAGAA 3 |
| | | | | AS | 2179 | 3 CACUUACGUCUGGUUUCUU 5 |
| 383 | 2263 | GUGAAUGCAGACCAAAGAAAGAU | AL-DP-4005 | S | 2180 | 5 GAAUGCAGACCAAAGAAAGAU 3 |
| | | | | AS | 2181 | 3 CACUUACGUCUGGUUUCUUUCUA 5 |
| | | | AL-DP-4053 | S | 2182 | 5 GAAUGCAGACCAAAGAAAGTT 3 |
| | | | | AS | 2183 | 3 TTCUUACGUCUGGUUUCUUUC 5 |

Strand:
S = sense,
AS = Antisense

Example 2

Eg5 siRNA In Vitro Screening Via Cell Proliferation

As silencing of Eg5 has been shown to cause mitotic arrest (Weil, D, et al [2002] Biotechniques 33: 1244-8), a cell viability assay was used for siRNA activity screening. HeLa cells (14000 per well [Screens 1 and 3] or 10000 per well [Screen2])) were seeded in 96-well plates and simultaneously transfected with Lipofectamine 2000 (Invitrogen) at a final siRNA concentration in the well of 30 nM and at final concentrations of 50 nM ($1^{st}$ screen) and 25 nM ($2^{nd}$ screen). A subset of duplexes was tested at 25 nM in a third screen (Table 5).

Seventy-two hours post-transfection, cell proliferation was assayed the addition of WST-1 reagent (Roche) to the culture medium, and subsequent absorbance measurement at 450 nm. The absorbance value for control (non-transfected) cells was considered 100 percent, and absorbances for the siRNA transfected wells were compared to the control value. Assays were performed in sextuplicate for each of three screens. A subset of the siRNAs was further tested at a range of siRNA concentrations. Assays were performed in HeLa cells (14000 per well; method same as above, Table 5).

TABLE 5

Effects of Eg5 targeted duplexes on cell viability at 25 nM.

Relative absorbance at 450 nm

| Duplex | Screen I mean | sd | Screen II Mean | sd | Screen III mean | Sd |
|---|---|---|---|---|---|---|
| AL-DP-6226 | 20 | 10 | 28 | 11 | 43 | 9 |
| AL-DP-6227 | 66 | 27 | 96 | 41 | 108 | 33 |
| AL-DP-6228 | 56 | 28 | 76 | 22 | 78 | 18 |
| AL-DP-6229 | 17 | 3 | 31 | 9 | 48 | 13 |
| AL-DP-6230 | 48 | 8 | 75 | 11 | 73 | 7 |
| AL-DP-6231 | 8 | 1 | 21 | 4 | 41 | 10 |
| AL-DP-6232 | 16 | 2 | 37 | 7 | 52 | 14 |
| AL-DP-6233 | 31 | 9 | 37 | 6 | 49 | 12 |
| AL-DP-6234 | 103 | 40 | 141 | 29 | 164 | 45 |
| AL-DP-6235 | 107 | 34 | 140 | 27 | 195 | 75 |
| AL-DP-6236 | 48 | 12 | 54 | 12 | 56 | 12 |
| AL-DP-6237 | 73 | 14 | 108 | 18 | 154 | 37 |
| AL-DP-6238 | 64 | 9 | 103 | 10 | 105 | 24 |
| AL-DP-6239 | 9 | 1 | 20 | 4 | 31 | 11 |
| AL-DP-6240 | 99 | 7 | 139 | 16 | 194 | 43 |
| AL-DP-6241 | 43 | 9 | 54 | 12 | 66 | 19 |
| AL-DP-6242 | 6 | 1 | 15 | 7 | 36 | 8 |
| AL-DP-6243 | 7 | 2 | 19 | 5 | 33 | 13 |
| AL-DP-6244 | 7 | 2 | 19 | 3 | 37 | 13 |
| AL-DP-6245 | 25 | 4 | 45 | 10 | 58 | 9 |
| AL-DP-6246 | 34 | 8 | 65 | 10 | 66 | 13 |
| AL-DP-6247 | 53 | 6 | 78 | 14 | 105 | 20 |
| AL-DP-6248 | 7 | 0 | 22 | 7 | 39 | 12 |
| AL-DP-6249 | 36 | 8 | 48 | 13 | 61 | 7 |

The nine siRNA duplexes that showed the greatest growth inhibition in Table 5 were re-tested at a range of siRNA concentrations in HeLa cells. The siRNA concentrations tested were 100 nM, 33.3 nM, 11.1 nM, 3.70 nM, 1.23 nM, 0.41 nM, 0.14 nM and 0.046 nM. Assays were performed in sextuplicate, and the concentration of each siRNA resulting in fifty percent inhibition of cell proliferation ($IC_{50}$) was calculated. This dose-response analysis was performed between two and four times for each duplex. Mean $IC_{50}$ values (nM) are given in Table 6.

TABLE 6

IC50 of siRNA: cell proliferation in HeLa cells

| Duplex | Mean $IC_{50}$ |
|---|---|
| AL-DP-6226 | 15.5 |
| AL-DP-6229 | 3.4 |
| AL-DP-6231 | 4.2 |
| AL-DP-6232 | 17.5 |
| AL-DP-6239 | 4.4 |
| AL-DP-6242 | 5.2 |
| AL-DP-6243 | 2.6 |
| AL-DP-6244 | 8.3 |
| AL-DP-6248 | 1.9 |

Example 3

Eg5 siRNA in Vitro Screening Via mRNA Inhibition

Directly before transfection, HeLa S3 (ATCC-Number: CCL-2.2, LCG Promochem GmbH, Wesel, Germany) cells were seeded at $1.5 \times 10^4$ cells/well on 96-well plates (Greiner Bio-One GmbH, Frickenhausen, Germany) in 75 µl of growth medium (Ham's F12, 10% fetal calf serum, 100 u penicillin/100 µg/ml streptomycin, all from Bookroom AG, Berlin, Germany). Transfections were performed in quadruplicates. For each well 0.5 µl Lipofectamine-2000 (Invitrogen GmbH, Karlsruhe, Germany) were mixed with 12 µl Opti-MEM (Invitrogen) and incubated for 15 min at room temperature. For the siRNA concentration being 50 nM in the 100 µl transfection volume, 1 µl of a 5 µM siRNA were mixed with 11.5 µl Opti-MEM per well, combined with the Lipofectamine-2000-Opti-MEM mixture and again incubated for 15 minutes at room temperature. siRNA-Lipofectamine-2000-complexes were applied completely (25 µl each per well) to the cells and cells were incubated for 24 h at 37° C. and 5% $CO_2$ in a humidified incubator (Heroes GmbH, Hanau). The single dose screen was done once at 50 nM and at 25 nM, respectively.

Cells were harvested by applying 50 µl of lysis mixture (content of the QuantiGene bDNA-kit from Genospectra, Fremont, USA) to each well containing 100 µl of growth medium and were lysed at 53° C. for 30 min. Afterwards, 50 µl of the lists were incubated with probesets specific to human Eg5 and human GAPDH and proceeded according to the manufacturer's protocol for QuantiGene. In the end chemoluminescence was measured in a Victor2-Light (Perkin Elmer, Wiesbaden, Germany) as RLUs (relative light units) and values obtained with the hEg5 probeset were normalized to the respective GAPDH values for each well. Values obtained with siRNAs directed against Eg5 were related to the value obtained with an unspecific siRNA (directed against HCV) which was set to 100% (Tables 1b, 2b and 3b).

Effective siRNAs from the screen were further characterized by dose response curves.

Transfections of dose response curves were performed at the following concentrations: 100 nM, 16.7 nM, 2.8 nM, 0.46 nM, 77 picoM, 12.8 picoM, 2.1 picoM, 0.35 picoM, 59.5 fM, 9.9 fM and mock (no siRNA) and diluted with Opti-MEM to a final concentration of 12.5 µl according to the above protocol. Data analysis was performed by using the Microsoft Excel add-in software XL-fit 4.2 (IDBS, Guildford, Surrey, UK) and applying the dose response model number 205 (Tables 1b, 2b and 3b).

The lead siRNA AD 12115 was additionally analyzed by applying the WST-proliferation assay from Roche (as previously described).

A subset of 34 duplexes from Table 2 that showed greatest activity was assayed by transfection in HeLa cells at final concentrations ranging from 100 nM to 10 fM. Transfections were performed in quadruplicate. Two dose-response assays were performed for each duplex. The concentration giving 20% (IC20), 50% (IC50) and 80% (IC80) reduction of KSP mRNA was calculated for each duplex (Table 7).

TABLE 7

Dose response mRNA inhibition of Eg5/KSP duplexes in HeLa cells
Concentrations given in pM

| Duplex name | IC20s 1st screen | IC20s 2nd screen | IC50s 1st screen | IC50s 2nd screen | IC80s 1st screen | IC80s 2nd screen |
|---|---|---|---|---|---|---|
| AD12077 | 1.19 | 0.80 | 6.14 | 10.16 | 38.63 | 76.16 |
| AD12078 | 25.43 | 25.43 | 156.18 | 156.18 | ND | ND |
| AD12085 | 9.08 | 1.24 | 40.57 | 8.52 | 257.68 | 81.26 |
| AD12095 | 1.03 | 0.97 | 9.84 | 4.94 | 90.31 | 60.47 |
| AD12113 | 4.00 | 5.94 | 17.18 | 28.14 | 490.83 | 441.30 |
| AD12115 | 0.60 | 0.41 | 3.79 | 3.39 | 23.45 | 23.45 |
| AD12125 | 31.21 | 22.02 | 184.28 | 166.15 | 896.85 | 1008.11 |
| AD12134 | 2.59 | 5.51 | 17.87 | 22.00 | 116.36 | 107.03 |
| AD12149 | 0.72 | 0.50 | 4.51 | 3.91 | 30.29 | 40.89 |
| AD12151 | 0.53 | 6.84 | 4.27 | 10.72 | 22.88 | 43.01 |
| AD12152 | 155.45 | 7.56 | 867.36 | 66.69 | 13165.27 | ND |
| AD12157 | 0.30 | 26.23 | 14.60 | 92.08 | 14399.22 | 693.31 |
| AD12166 | 0.20 | 0.93 | 3.71 | 3.86 | 46.28 | 20.59 |
| AD12180 | 28.85 | 28.85 | 101.06 | 101.06 | 847.21 | 847.21 |
| AD12185 | 2.60 | 0.42 | 15.55 | 13.91 | 109.80 | 120.63 |
| AD12194 | 2.08 | 1.11 | 5.37 | 5.09 | 53.03 | 30.92 |
| AD12211 | 5.27 | 4.52 | 11.73 | 18.93 | 26.74 | 191.07 |
| AD12257 | 4.56 | 5.20 | 21.68 | 22.75 | 124.69 | 135.82 |
| AD12280 | 2.37 | 4.53 | 6.89 | 20.23 | 64.80 | 104.82 |
| AD12281 | 8.81 | 8.65 | 19.68 | 42.89 | 119.01 | 356.08 |
| AD12282 | 7.71 | 456.42 | 20.09 | 558.00 | ND | ND |
| AD12285 | ND | 1.28 | 57.30 | 7.31 | 261.79 | 42.53 |
| AD12292 | 40.23 | 12.00 | 929.11 | 109.10 | ND | ND |
| AD12252 | 0.02 | 18.63 | 6.35 | 68.24 | 138.09 | 404.91 |
| AD12275 | 25.76 | 25.04 | 123.89 | 133.10 | 1054.54 | 776.25 |
| AD12266 | 4.85 | 7.80 | 10.00 | 32.94 | 41.67 | 162.65 |
| AD12267 | 1.39 | 1.21 | 12.00 | 4.67 | 283.03 | 51.12 |
| AD12264 | 0.92 | 2.07 | 8.56 | 15.12 | 56.36 | 196.78 |
| AD12268 | 2.29 | 3.67 | 22.16 | 25.64 | 258.27 | 150.84 |
| AD12279 | 1.11 | 28.54 | 23.19 | 96.87 | 327.28 | 607.27 |
| AD12256 | 7.20 | 33.52 | 46.49 | 138.04 | 775.54 | 1076.76 |
| AD12259 | 2.16 | 8.31 | 8.96 | 40.12 | 50.05 | 219.42 |
| AD12276 | 19.49 | 6.14 | 89.60 | 59.60 | 672.51 | 736.72 |
| AD12321 | 4.67 | 4.91 | 24.88 | 19.43 | 139.50 | 89.49 |

(ND—not determined)

Example 4

Silencing of Liver Eg5/KSP in Juvenile Rats Following Single-Bolus Administration of LNP01 Formulated siRNA From birth until approximately 23 days of age, Eg5/KSP expression can be detected in the growing rat liver. Target silencing with a formulated Eg5/KSP siRNA was evaluated in juvenile rats using duplex AD-6248.

KSP Duplex Tested

| Duplex ID | Target | Sense | Antisense |
|---|---|---|---|
| AD6248 | KSP | AccGAAGuGuuGuuu GuccTsT (SEQ ID NO: 1238) | GGAcAAAcAAcACUUC GGUTsT (SEQ ID NO: 1239) |

Methods

Dosing of Animals.

Male, juvenile Sprague-Dawley rats (19 days old) were administered single doses of lipidoid ("LNP01") formulated siRNA via tail vein injection. Groups often animals received doses of 10 milligrams per kilogram (mg/kg) bodyweight of either AD6248 or an unspecific siRNA. Dose level refers to the amount of siRNA duplex administered in the formulation. A third group received phosphate-buffered saline. Animals were sacrificed two days after siRNA administration. Livers were dissected, flash frozen in liquid Nitrogen and pulverized into powders.

mRNA Measurements.

Levels of Eg5/KSP mRNA were measured in livers from all treatment groups. Samples of each liver powder (approximately ten milligrams) were homogenized in tissue lysis buffer containing proteinase K. Levels of Eg5/KSP and GAPDH mRNA were measured in triplicate for each sample using the Quantigene branched DNA assay (GenoSpectra). Mean values for Eg5/KSP were normalized to mean GAPDH values for each sample. Group means were determined and normalized to the PBS group for each experiment.

Statistical Analysis.

Significance was determined by ANOVA followed by the Tukey post-hoc test.

Results

Data Summary

Mean values (±standard deviation) for Eg5/KSP mRNA are given. Statistical significance (p value) versus the PBS group is shown (ns, not significant [p>0.05]).

TABLE 8

| | Experiment 1 | | |
|---|---|---|---|
| | | KSP/GAPDH | p value |
| PBS | | 1.0 ± 0.47 | |
| AD6248 | 10 mg/kg | 0.47 ± 0.12 | <0.001 |
| unspec | 10 mg/kg | 1.0 ± 0.26 | ns |

A statistically significant reduction in liver Eg5/KSP mRNA was obtained following treatment with formulated AD6248 at a dose of 10 mg/kg.

Example 5

Silencing of Rat Liver VEGF Following Intravenous Infusion of LNP01 Formulated VSP A "lipidoid" formulation comprising an equimolar mixture of two siRNAs was administered to rats. As used herein, VSP refers to a composition having two siRNAs, one directed to Eg5/KSP and one directed to VEGF. For this experiment the duplex AD3133 directed towards VEGF and AD12115 directed towards Eg5/KSP were used. Since Eg5/KSP expression is nearly undetectable in the adult rat liver, only VEGF levels were measured following siRNA treatment.

siRNA Duplexes Administered (VSP)

| Duplex ID | Target | Sense | Antisense |
|---|---|---|---|
| AD12115 | Eg5/KSP | ucGAGAAucuAAA cuAAcuTsT (SEQ ID NO: 1240) | AGUuAGUUuAGAU UCUCGATsT (SEQ ID NO: 1241) |
| AD3133 | VEGF | GcAcAuAGGAGA GAuGAGCUsU (SEQ ID NO: 1242) | AAGCUcAUCUCU CCuAuGuGCusG (SEQ ID NO: 1243) |

Key
A,G,C,U-ribonucleotides;
c,u-2'-O-Me ribonucleotides;
s-phosphorothioate.

Unmodified versions of each strand and the targets for each siRNA are as follows

| | | | |
|---|---|---|---|
| Eg5/KSP | unmod sense | 5' UCGAGAAUCUAAACUAACUTT 3' | SEQ ID NO: 1534 |
| | unmod antisense | 3' TTAGUCCUUAGAUUUGAUUGA 5' | SEQ ID NO: 1535 |
| | target | 5' UCGAGAAUCUAAACUAACU 3' | SEQ ID NO: 1311 |
| VEGF | unmod sense | 5' GCACAUAGGAGAGAUGAGCUU 3' | SEQ ID NO: 1536 |
| | unmod antisense | 3' GUCGUGUAUCCUCUCUACUCGAA 5' | SEQ ID NO: 1537 |
| | target | 5' GCACAUAGGAGAGAUGAGCUU 3' | SEQ ID NO: 1538 |

Methods

Dosing of animals. Adult, female Sprague-Dawley rats were administered lipidoid ("LNP01") formulated siRNA by a two-hour infusion into the femoral vein. Groups of four animals received doses of 5, 10 and 15 milligrams per kilogram (mg/kg) bodyweight of formulated siRNA. Dose level refers to the total amount of siRNA duplex administered in the formulation. A fourth group received phosphate-buffered saline. Animals were sacrificed 72 hours after the end of the siRNA infusion. Livers were dissected, flash frozen in liquid Nitrogen and pulverized into powders.

Formulation Procedure

The lipidoid ND98.4HCl (MW 1487) (Formula 1, above), Cholesterol (Sigma-Aldrich), and PEG-Ceramide C16 (Avanti Polar Lipids) were used to prepare lipid-siRNA nanoparticles. Stock solutions of each in ethanol were prepared: ND98, 133 mg/mL; Cholesterol, 25 mg/mL, PEG-Ceramide C16, 100 mg/mL. ND98, Cholesterol, and PEG-Ceramide C16 stock solutions were then combined in a 42:48:10 molar ratio. Combined lipid solution was mixed rapidly with aqueous siRNA (in sodium acetate pH 5) such that the final ethanol concentration was 35-45% and the final sodium acetate concentration was 100-300 mM. Lipid-siRNA nanoparticles formed spontaneously upon mixing. Depending on the desired particle size distribution, the resultant nanoparticle mixture was in some cases extruded through a polycarbonate membrane (100 nm cut-off) using a thermobarrel extruder (Lipex Extruder, Northern Lipids, Inc). In other cases, the extrusion step was omitted. Ethanol removal and simultaneous buffer exchange was accomplished by either dialysis or tangential flow filtration. Buffer was exchanged to phosphate buffered saline (PBS) pH 7.2.

Characterization of Formulations

Formulations prepared by either the standard or extrusion-free method are characterized in a similar manner. Formulations are first characterized by visual inspection.

They should be whitish translucent solutions free from aggregates or sediment. Particle size and particle size distribution of lipid-nanoparticles are measured by dynamic light scattering using a Malvern Zetasizer Nano ZS (Malvern, USA). Particles should be 20-300 nm, and ideally, 40-100 nm in size. The particle size distribution should be unimodal. The total siRNA concentration in the formulation, as well as the entrapped fraction, is estimated using a dye exclusion assay. A sample of the formulated siRNA is incubated with the RNA-binding dye Ribogreen (Molecular Probes) in the presence or absence of a formulation disrupting surfactant, 0.5% Triton-X100. The total siRNA in the formulation is determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The preferred range is about at least 50 nm to about at least 110 nm, preferably about at least 60 nm to about at least 100 nm, most preferably about at least 80 nm to about at least 90 nm. In one example, each of the particle size comprises at least about 1:1 ratio of Eg5 dsRNA to VEGF dsRNA.

mRNA Measurements.

Samples of each liver powder (approximately ten milligrams) were homogenized in tissue lysis buffer containing proteinase K. Levels of VEGF and GAPDH mRNA were measured in triplicate for each sample using the Quantigene branched DNA assay (GenoSpectra). Mean values for VEGF were normalized to mean GAPDH values for each sample. Group means were determined and normalized to the PBS group for each experiment.

Protein Measurements.

Samples of each liver powder (approximately 60 milligrams) were homogenized in 1 ml RIPA buffer. Total protein concentrations were determined using the Micro BCA protein assay kit (Pierce). Samples of total protein from each animal was used to determine VEGF protein levels using a VEGF ELISA assay (R&D systems). Group means were determined and normalized to the PBS group for each experiment.

Statistical Analysis.

Significance was determined by ANOVA followed by the Tukey post-hoc test

Results

Data Summary

Mean values (±standard deviation) for mRNA (VEGF/GAPDH) and protein (rel. VEGF) are shown for each treatment group. Statistical significance (p value) versus the PBS group for each experiment is shown.

TABLE 9

|  | VEGF/GAPDH | p value | rel VEGF | p value |
| --- | --- | --- | --- | --- |
| PBS | 1.0 ± 0.17 |  | 1.0 ± 0.17 |  |
| 5 mg/kg | 0.74 ± 0.12 | <0.05 | 0.23 ± 0.03 | <0.001 |
| 10 mg/kg | 0.65 ± 0.12 | <0.005 | 0.22 ± 0.03 | <0.001 |
| 15 mg/kg | 0.49 ± 0.17 | <0.001 | 0.20 ± 0.04 | <0.001 |

Statistically significant reductions in liver VEGF mRNA and protein were measured at all three siRNA dose levels.

Example 6

Assessment of VSP SNALP in Mouse Models of Human Hepatic Tumors

These studies utilized a VSP siRNA cocktail containing dsRNAs targeting KSP/Eg5 and dsRNAs targeting VEGF. As used herein, VSP refers to a composition having two siRNAs, one directed to Eg5/KSP and one directed to VEGF. For this experiment the duplexes AD3133 (directed towards VEGF) and AD12115 (directed towards Eg5/KSP) were used. The siRNA cocktail was formulated in SNALPs.

The maximum study size utilized 20-25 mice. To test the efficacy of the siRNA SNALP cocktail to treat liver cancer, $1 \times 10^6$ tumor cells were injected directly into the left lateral lobe of test mice. The incisions were closed by sutures, and the mice allowed to recover for 2-5 hours. The mice were fully recovered within 48-72 hours. The SNALP siRNA treatment was initiated 8-11 days after tumor seeding.

The SNALP formulations utilized were (i) VSP (KSP+VEGF siRNA cocktail (1:1 molar ratio)); (ii) KSP (KSP+Luc siRNA cocktail); and (iii) VEGF (VEGF+Luc siRNA cocktail). All formulations contained equal amounts (mg) of each active siRNA. All mice received a total siRNA/lipid dose, and each cocktail was formulated into 1:57 cDMA SNALP (1.4% PEG-cDMA; 57.1% DLinDMA; 7.1% DPPC; and 34.3% cholesterol), 6:1 lipid:drug using original citrate buffer conditions.

Human Hep3B Study A: Anti-Tumor Activity of VSP-SNALP

Human Hepatoma Hep3B tumors were established in scid/beige mice by intrahepatic seeding. Group A (n=6) animals were administered PBS; Group B (n=6) animals were administered VSP SNALP; Group C (n=5) animals were administered KSP/Luc SNALP; and Group D (n=5) animals were administered VEGF/Luc SNALP.

SNALP treatment was initiated eight days after tumor seeding. The SNALP was dosed at 3 mg/kg total siRNA, twice weekly (Monday and Thursday), for a total of six doses (cumulative 18 mg/kg siRNA). The final dose was administered at day 25, and the terminal endpoint was at day 27.

Tumor burden was assayed by (a) body weight; (b) liver weight; (c) visual inspection+photography at day 27; (d) human-specific mRNA analysis; and (e) blood alpha-fetoprotein levels measured at day 27.

Table 10 below illustrates the results of visual scoring of tumor burden measured in the seeded (left lateral) liver lobe. Score: "−"=no visible tumor; "+"=evidence of tumor tissue at injection site; "++"=Discrete tumor nodule protruding from liver lobe; "+++"=large tumor protruding on both sides of liver lobe; "++++"=large tumor, multiple nodules throughout liver lobe.

TABLE 10

|  | Mouse | Tumor Burden |
| --- | --- | --- |
| Group A: PBS, day 27 | 1 | ++++ |
|  | 2 | ++++ |
|  | 3 | ++ |
|  | 4 | +++ |
|  | 5 | ++++ |
|  | 6 | ++++ |
| Group B: VSP (VEGF + KSP/Eg5, d. 27 | 1 | + |
|  | 2 | − |
|  | 3 | − |
|  | 4 | − |
|  | 5 | ++ |
|  | 6 | − |
| Group C: KSP (Luc + KSP), d. 27 | 1 | + |
|  | 2 | ++ |
|  | 3 | − |
|  | 4 | + |
|  | 5 | ++ |
| Group D: VEGF (Luc + VEGF), d. 27 | 1 | ++++ |
|  | 2 | − |
|  | 3 | ++++ |
|  | 4 | +++ |
|  | 5 | ++++ |

Liver weights, as percentage of body weight, are shown in FIG. 1.

Body weights are shown in FIGS. 2A-2D.

From this study, the following conclusions were made. (1) VSP SNALP demonstrated potent anti-tumor effects in Hep3B 1H model; (2) the anti-tumor activity of the VSP cocktail appeared largely associated with the KSP component; (3) anti-KSP activity was confirmed by single dose histological analysis; and (4) VEGF siRNA showed no measurable effect on inhibition of tumor growth in this model.

Human Hep3B Study B: Prolonged Survival with VSP Treatment

In a second Hep3B study, human hepatoma Hep3B tumors were established by intrahepatic seeding into scid/beige mice. These mice were deficient for lymphocytes and natural killer (NK) cells, which is the minimal scope for immune-mediated anti-tumor effects. Group A (n=6) mice were untreated; Group B (n=6) mice were administered luciferase (luc) 1955 SNALP (Lot No. AP10-02); and Group C (n=7) mice were administered VSP SNALP (Lot No. AP10-01). SNALP was 1:57 cDMA SNALP, and 6:1 lipid:drug.

SNALP treatment was initiated eight days after tumor seeding. SNALP was dosed at 3 mg/kg siRNA, twice weekly (Mondays and Thursdays), for a total of six doses (cumulative 18 mg/kg siRNA). The final dose was delivered at day 25, and the terminal endpoint of the study was at day 27.

Tumor burden was assayed by (1) body weight; (2) visual inspection+photography at day 27; (3) human-specific mRNA analysis; and (4) blood alpha-fetoprotein measured at day 27.

Figure 3:
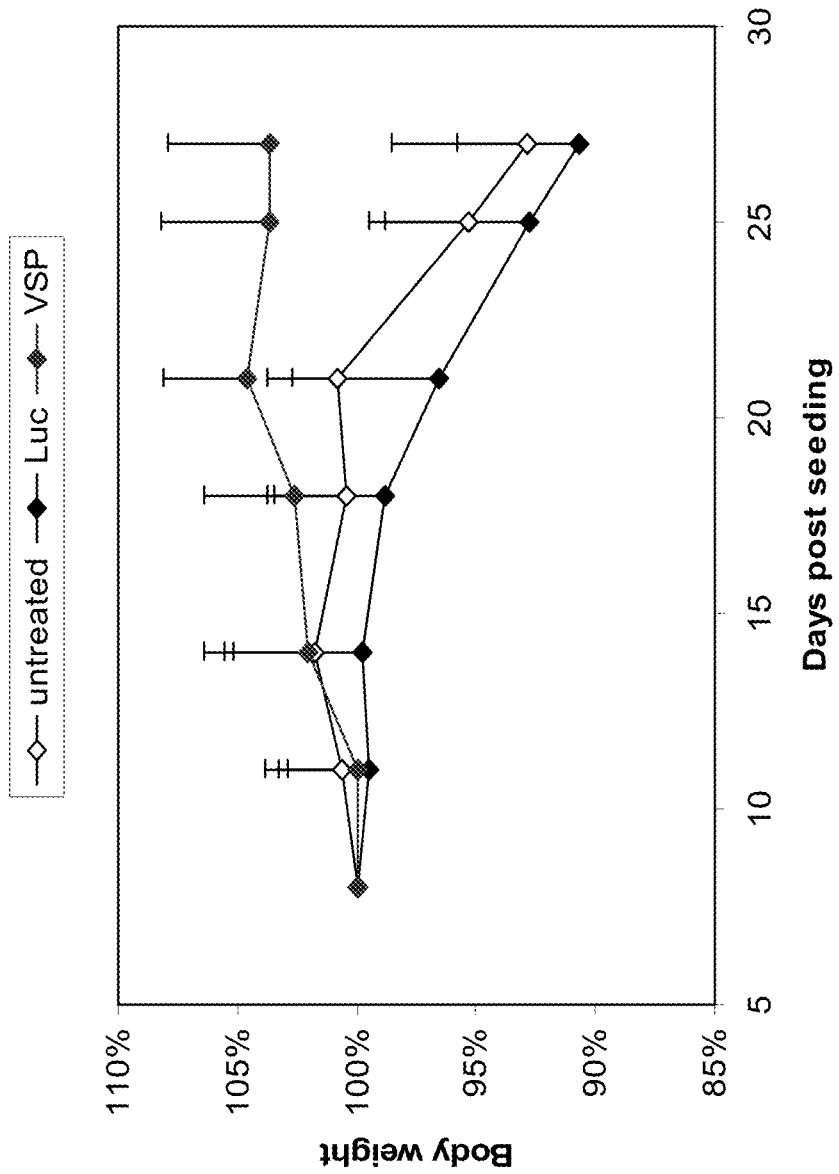
FIG. 3 is a graph showing the effects of SNALP-siRNAs on body weight in a Hep3B mouse model.

Body weights were measured at each day of dosing (days 8, 11, 14, 18, 21, and 25) and on the day of sacrifice (FIG. 3).

TABLE 11

|  | Mouse | Tumor Burden by macroscopic observation |
| --- | --- | --- |
| Group A: untreated, day 27 | A1R | ++ |
|  | A1G | ++++ |
|  | A1W | − |
|  | A2R | ++++ |
|  | A2G | +++ |
|  | A2W | ++++ |

TABLE 11-continued

|  | Mouse | Tumor Burden by macroscopic observation |
|---|---|---|
| Group B: | B1R | ++++ |
| 1955 Luc SNALP, day 27 | B1G | ++++ |
|  | B1W | +++ |
|  | B2R | ++ |
|  | B2G | +++ |
|  | B2W | ++++ |
| Group C: | C1R | − |
| VSP SNALP, day 27 | C1G | − |
|  | C1B | − |
|  | C1W | + |
|  | C2R | + |
|  | C2G | + |
|  | C2W | − |

Score: "−"=no visible tumor; "+"=evidence of tumor tissue at injection site; "++"=Discrete tumor nodule protruding from liver lobe; "+++"=large tumor protruding on both sides of liver lobe; "++++"=large tumor, multiple nodules throughout liver lobe.

Figure 4:
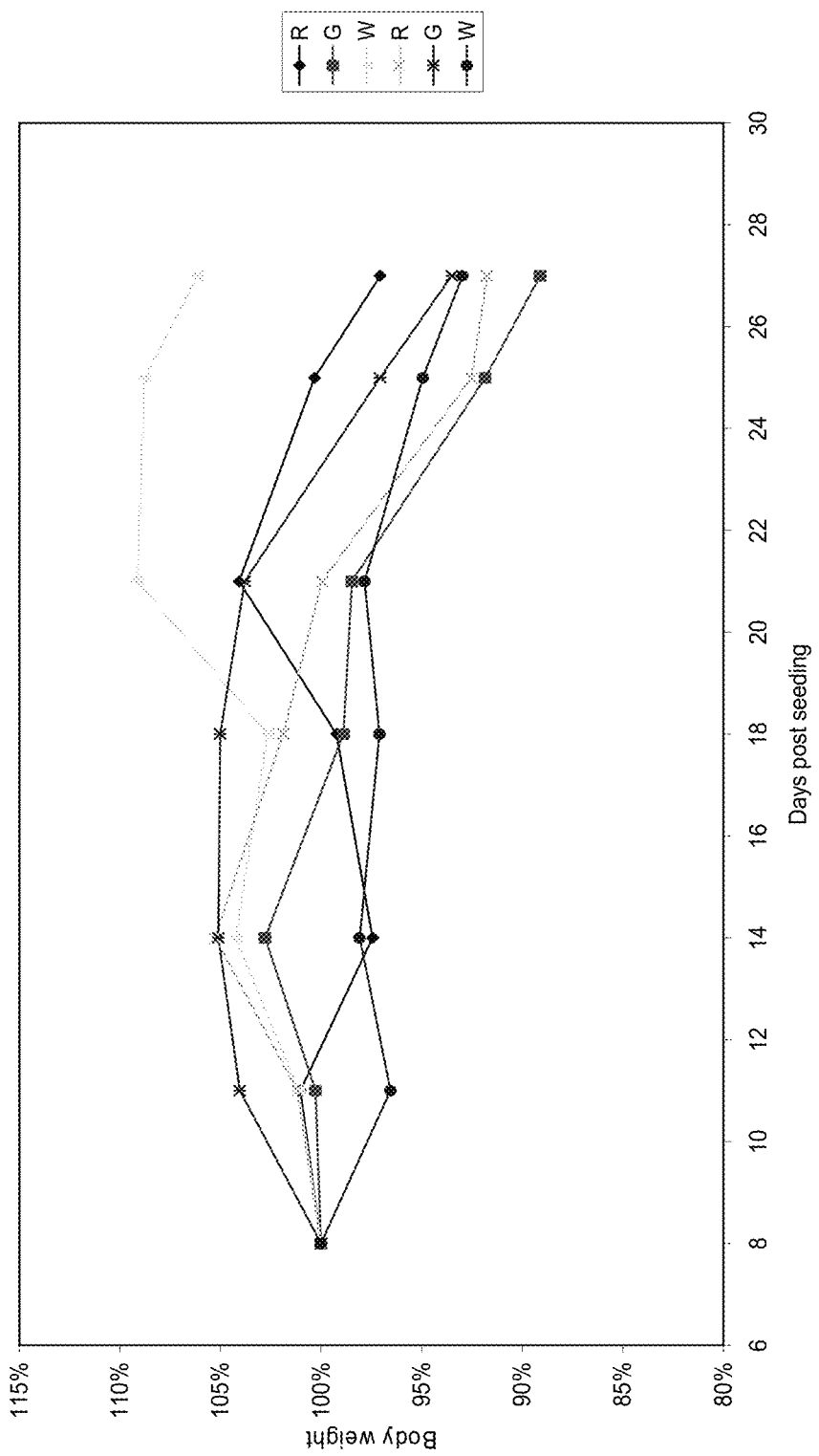
FIG. 4 is a graph showing the body weight in untreated control animals.
Figure 5:
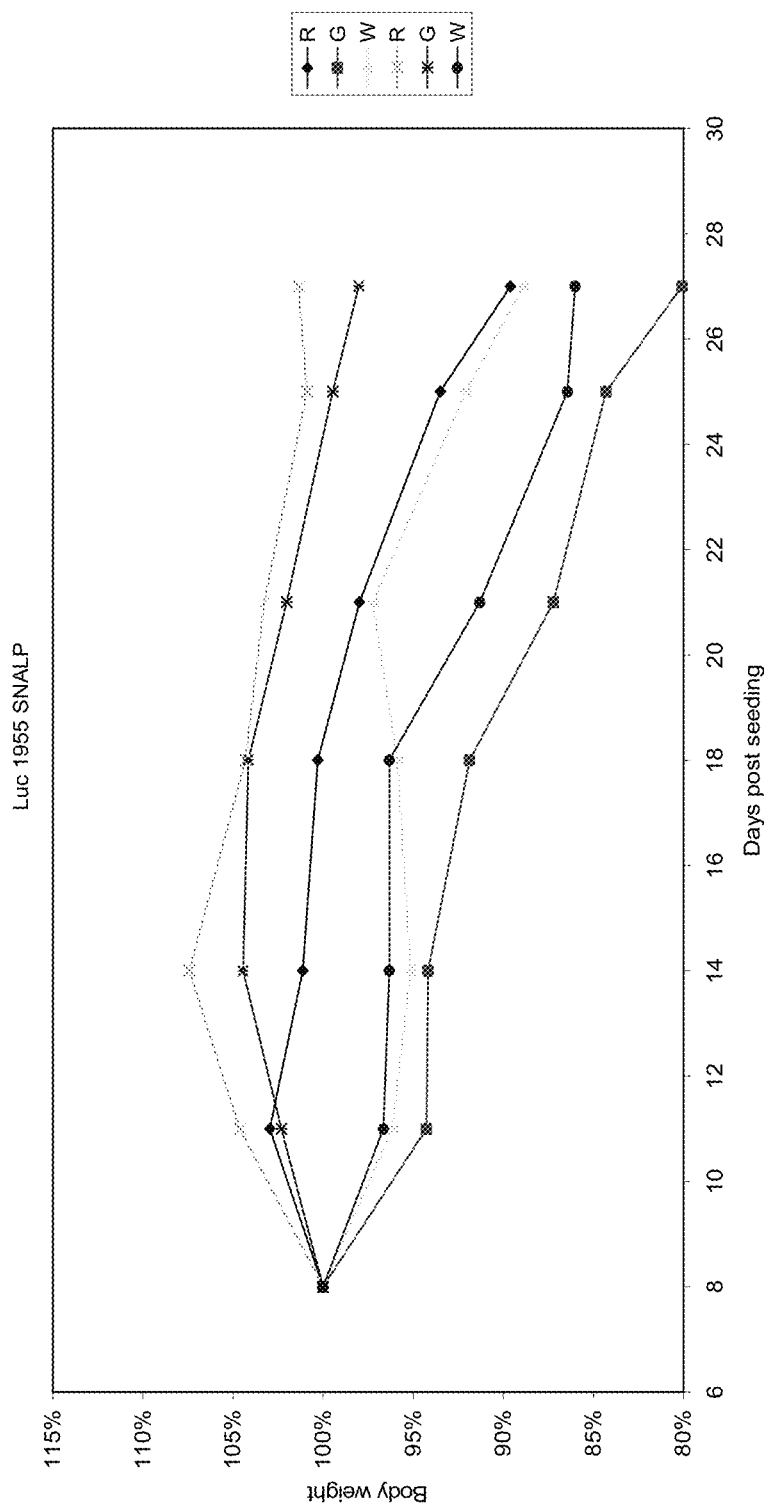
FIG. 5 is a graph showing the effects of control luciferase-SNALP siRNAs on body weight in a Hep3B mouse model.
Figure 6:
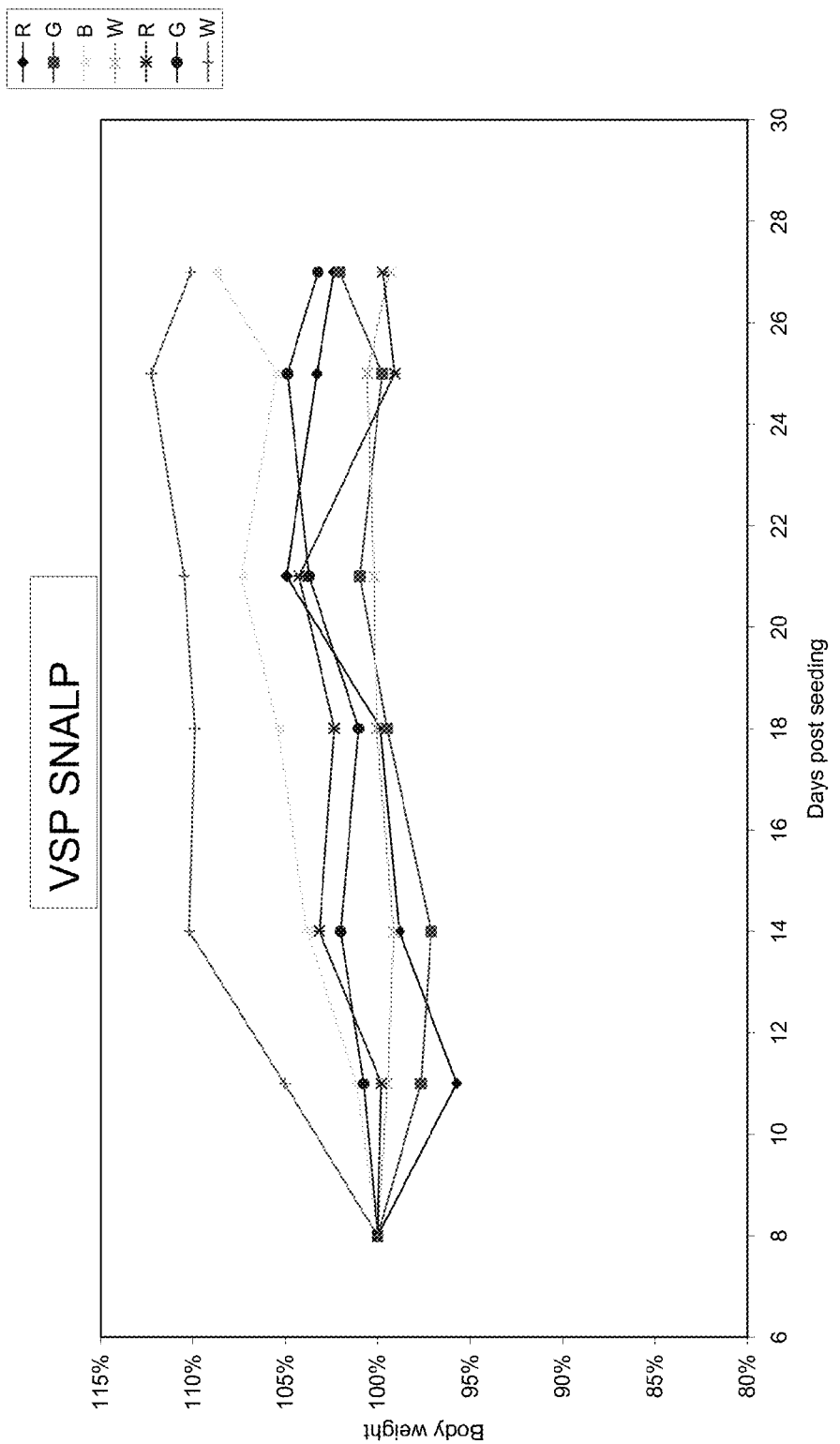
FIG. 6 is a graph showing the effects of VSP-SNALP siRNAs on body weight in a Hep3B mouse model.

The correlation between body weights and tumor burden are shown in FIGS. 4, 5 and 6.

A single dose of VSP SNALP (2 mg/kg) to Hep3B mice also resulted in the formation of mitotic spindles in liver tissue samples examined by histological staining.

Figure 7A:
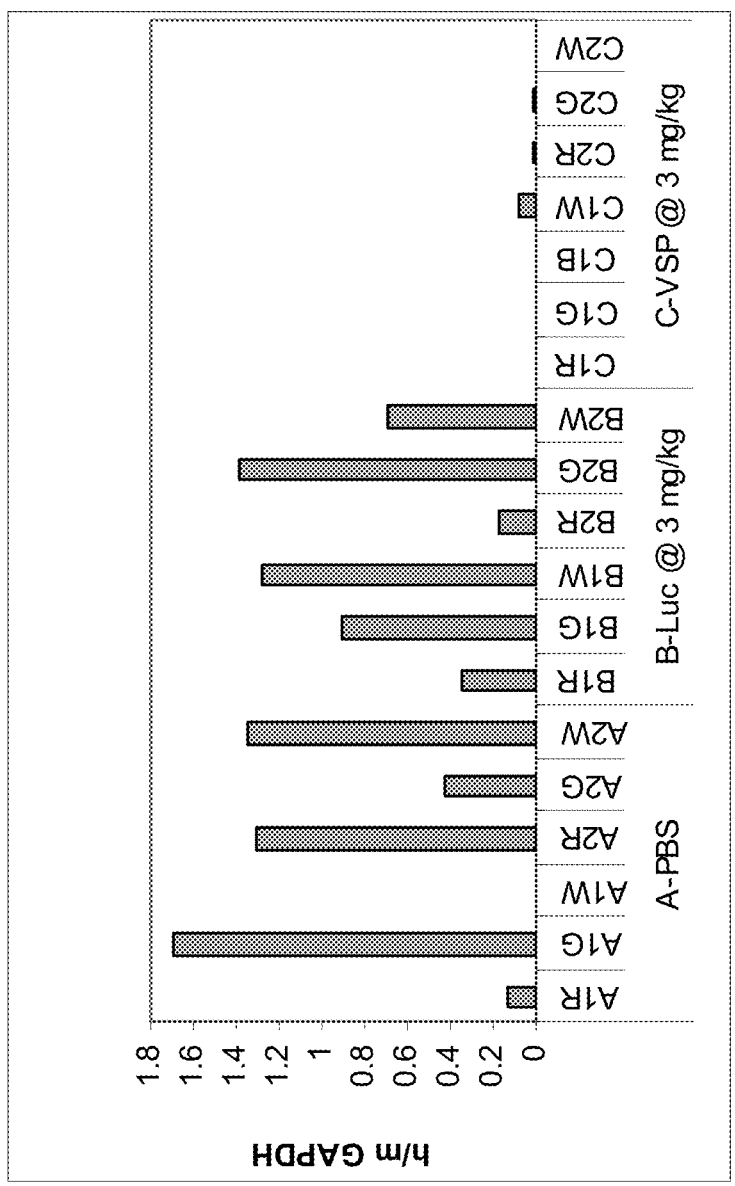
FIG. 7A is a graph showing the effects of SNALP-siRNAs on human GAPDH levels normalized to mouse GAPDH levels in a Hep3B mouse model.

Tumor burden was quantified by quantitative RT-PCR (pRT-PCR) (Taqman). Human GAPDH was normalized to mouse GAPDH via species-specific Taqman assays. Tumor score as shown by macroscopic observation in the table above correlated with GADPH levels (FIG. 7A).

Figure 7B:
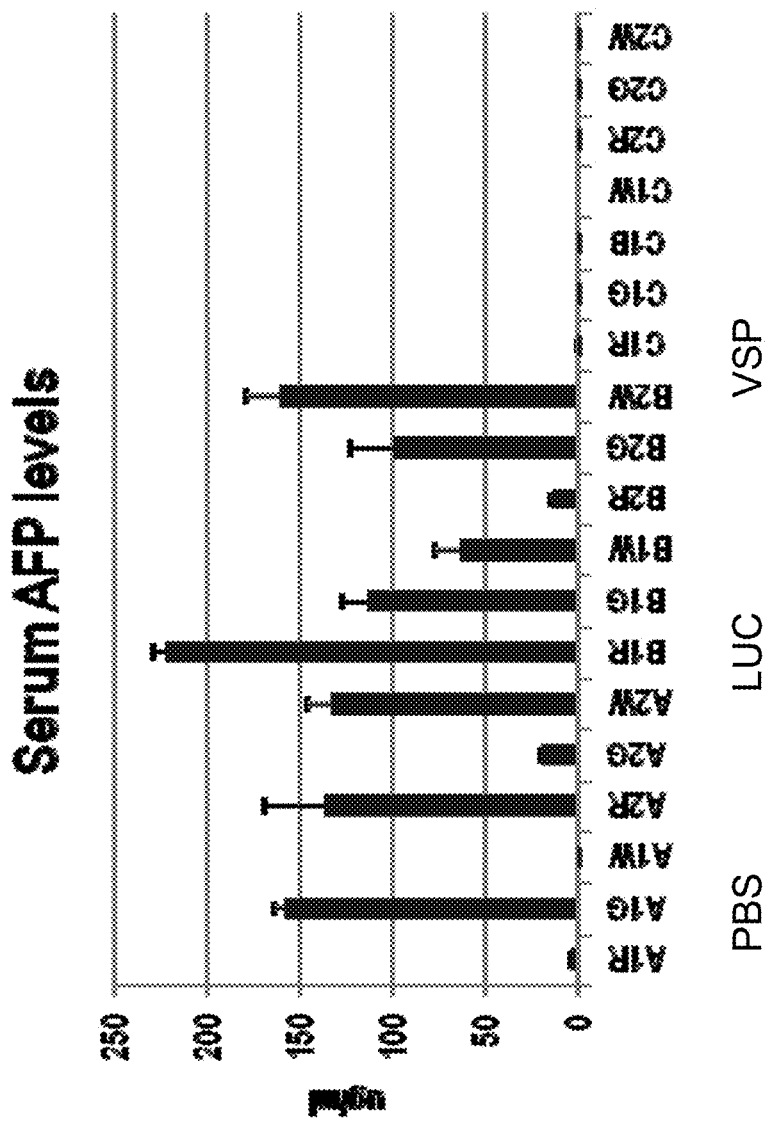
FIG. 7B is a graph showing the effects of SNALP-siRNAs on serum AFP levels as measured by serum ELISA in a Hep3B mouse model.

Serum ELISA was performed to measure alpha-fetoprotein (AFP) secreted by the tumor. As described below, if levels of AFP go down after treatment, the tumor is not growing. Treatment with VSP lowered AFP levels in some animals compared to treatment with controls (FIG. 7B).

Human HepB3 Study C:

In a third study, human HCC cells (HepB3) were injected directly into the liver of SCID/beige mice, and treatment was initiated 20 days later. Group A animals were administered PBS; Group B animals were administered 4 mg/kg Luc-1955 SNALP; Group C animals were administered 4 mg/kg SNALP-VSP; Group D animals were administered 2 mg/kg SNALP-VSP; and Group E animals were administered 1 mg/kg SNALP-VSP. Treatment was with a single intravenous (iv) dose, and mice were sacrificed 24 hr. later.

Figure 8:
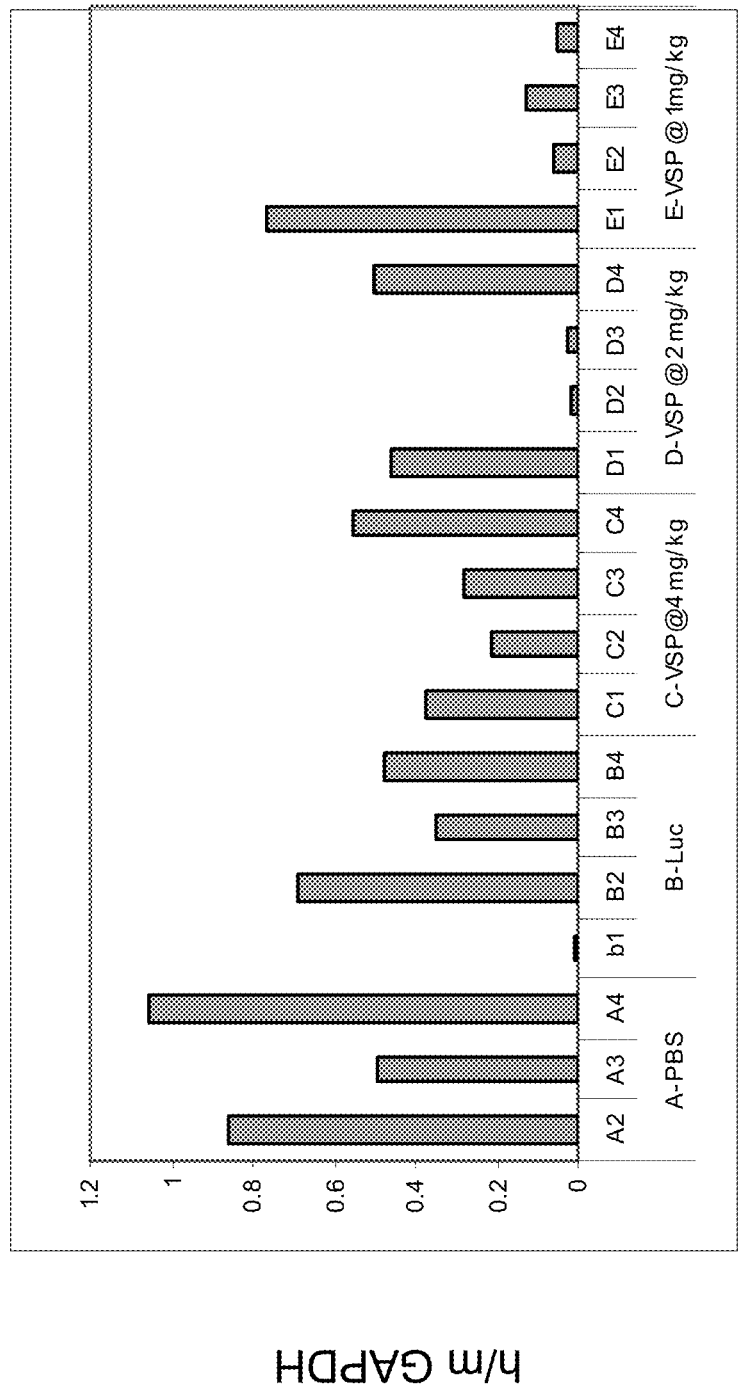
FIG. 8 is a graph showing the effects of SNALP-siRNAs on human GAPDH levels normalized to mouse GAPDH levels in a Hep3B mouse model.

Tumor burden and target silencing was assayed by qRT-PCR (Taqman). Tumor score was also measured visually as described above, and the results are shown in the following table. hGAPDH levels, as shown in FIG. 8, correlates with macroscopic tumor score as shown in the table below.

TABLE 12

|  | Mouse | Tumor Burden by macroscopic observation |
|---|---|---|
| Group A: PBS | A2 | +++ |
|  | A3 | +++ |
|  | A4 | +++ |
| Group B: 4 mg/kg Luc-1955 SNALP | B1 | + |
|  | B2 | +++ |
|  | B3 | +++ |
|  | B4 | +++ |
| Group C: 4 mg/kg SNALP-VSP | C1 | ++ |
|  | C2 | ++ |
|  | C3 | ++ |
|  | C4 | +++ |
| Group D: 2 mg/kg SNALP-VSP | D1 | ++ |
|  | D2 | + |
|  | D3 | + |
|  | D4 | ++ |
| Group E: 1 mg/kg SNALP-VSP | E1 | +++ |
|  | E2 | + |
|  | E3 | ++ |
|  | E4 | + |

Figure 9:
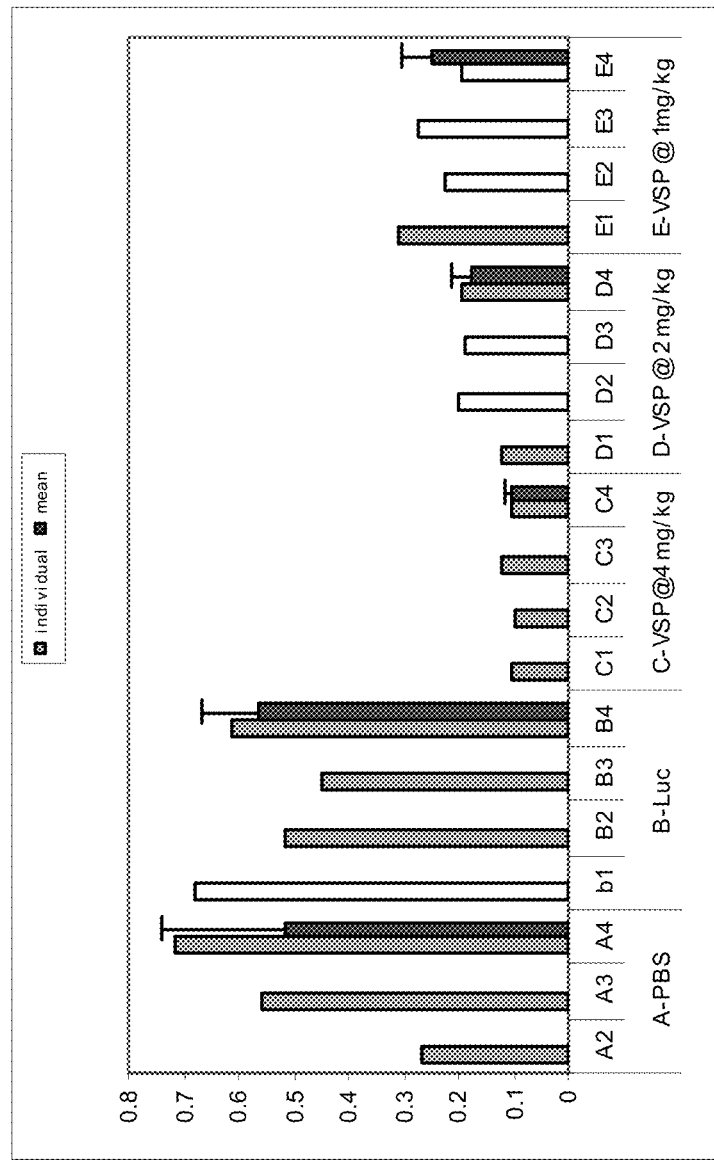
FIG. 9 is a graph showing the effects of SNALP-siRNAs on human KSP levels normalized to human GAPDH levels in a Hep3B mouse model.
Figure 10:
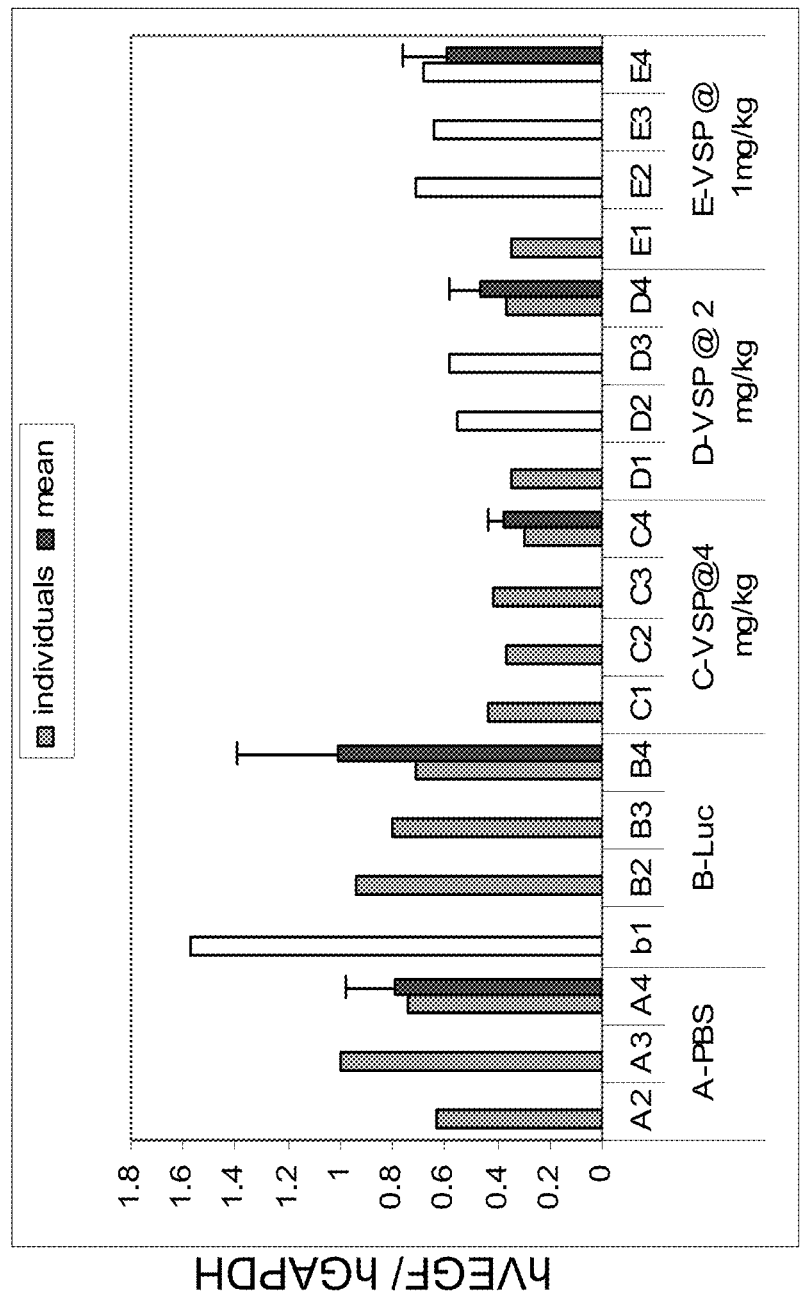
FIG. 10 is a graph showing the effects of SNALP-siRNAs on human VEGF levels normalized to human GAPDH levels in a Hep3B mouse model.

Score:
"+" = variable tumor take/some small tumors;
"++" = Discrete tumor nodule protruding from liver lobe;
"+++" = large tumor protruding on both sides of liver lobe Human (tumor-derived) KSP silencing was assayed by Taqman analysis and the results are shown in FIG. 10. hKSP expression was normalized to hGAPDH. About 80% tumor KSP silencing was observed at 4 mg/kg SNALP-VSP, and efficacy was evident at 1 mg/kg. The clear bars in FIG. 9 represent the results from small (low GAPDH) tumors.

Human (tumor-derived) VEGF silencing was assayed by Taqman analysis and the results are shown in FIG. 10. hVEGF expression was normalized to hGAPDH. About 60% tumor VEGF silencing was observed at 4 mg/kg SNALP-VSP, and efficacy was evident at 1 mg/kg. The clear bars in FIG. 10 represent the results from small (low GAPDH) tumors.

Figure 11A:
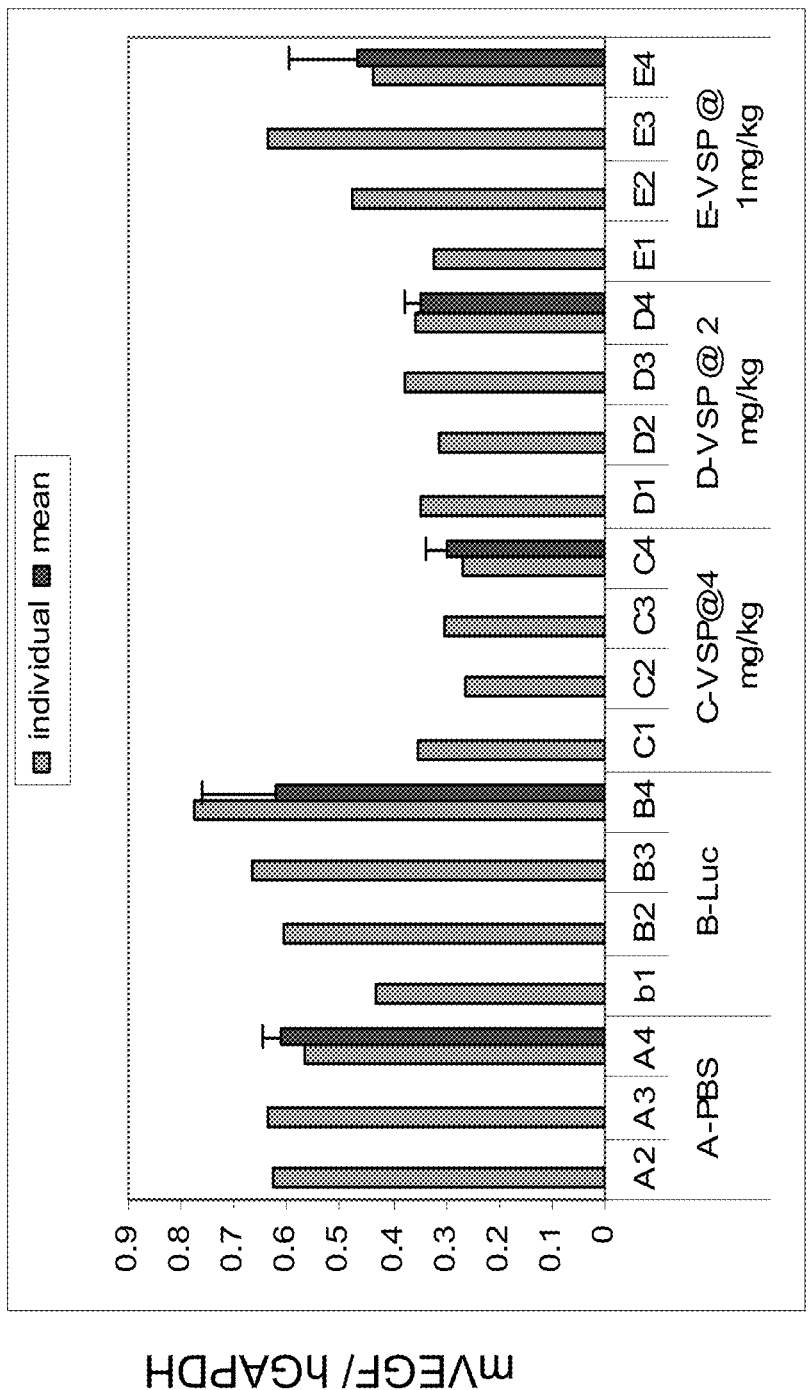
FIG. 11A is a graph showing the effects of SNALP-siRNAs on mouse VEGF levels normalized to human GAPDH levels in a Hep3B mouse model.

Mouse (liver-derived) VEGF silencing was assayed by Taqman analysis and the results are shown in FIG. 11A. mVEGF expression was normalized to hGAPDH. About 50% liver VEGF silencing was observed at 4 mg/kg SNALP-VSP, and efficacy was evident at 1 mg/kg.

Human HepB3 Study D: Contribution of Each dsRNA to Tumor Growth

In a fourth study, human HCC cells (HepB3) were injected directly into the liver of SCID/beige mice, and treatment was initiated 8 days later. Treatment was with intravenous (iv) bolus injections, twice weekly, for a total of six does. The final dose was administered at day 25, and the terminal endpoint was at day 27.

Tumor burden was assayed by gross histology, human-specific mRNA analysis (hGAPDH qPCR), and blood alpha-fetoprotein levels (serum AFP via ELISA).

In Study 1, Group A was treated with PBS, Group B was treated with SNALP-KSP+Luc (3 mg/kg), Group C was treated with SNALP-VEGF+Luc (3 mg/kg), and Group D was treated with ALN-VSP02 (3 mg/kg).

In Study 2, Group A was treated with PBS; Group B was treated with SNALP-KSP+Luc (1 mg/kg), Group C was treated with ALN-VSP02 (1 mg/kg).

Both GAPDH mRNA levels and serum AFP levels were shown to decrease after treatment with ALN-VSP02 (FIG. 11B).

Histology Studies:

Human hepatoma Hep3B tumors were established by intrahepatic seeding in mice. SNALP treatment was initiated 20 days after tumor seeding. Tumor-bearing mice (three per group) were treated with a single intravenous (IV) dose of (i) VSP SNALP or (ii) control (Luc) SNALP at 2 mg/kg total siRNA.

Liver/tumor samples were collected for conventional H&E histology 24 hours after single SNALP administration.

Large macroscopic tumor nodules (5-10 mm) were evident at necroscopy.

Figure 12B:
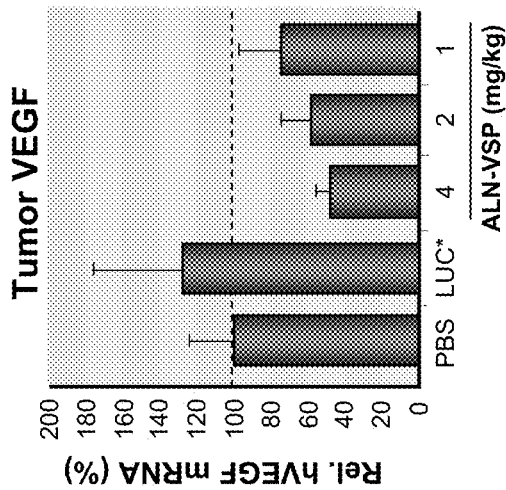
Figure 12A:
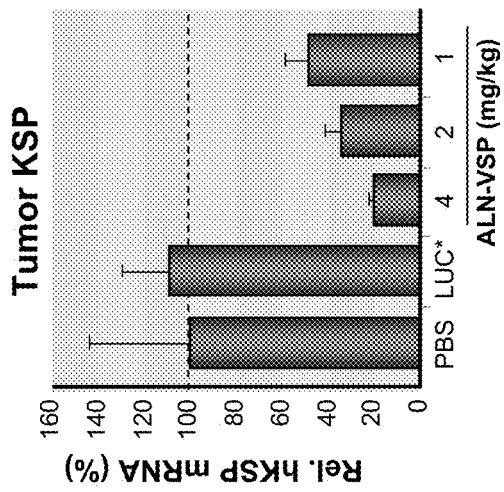

Effect of ALN-VSP in Hep3B Mice:

ALN-VSP (a cocktail of KSP dsRNA and VEGF dsRNA) treatment reduced tumor burden and expression of tumor-derived KSP and VEGF. GAPDH mRNA levels, a measure of tumor burden, were also observed to decline following administration of ALN-VSP dsRNA (see FIGS. 12A-12C). A decrease in tumor burden by visual macroscopic observation was also evident following administration of ALN-VSP.

A single IV bolus injection of ALN-VSP also resulted in mitotic spindle formation that was clearly detected in liver tissue samples from Hep3B mice. This observation indicated cell cycle arrest.

Example 7

Survival of SNALP-VSP Animals Versus SNALP-Luc Treated Animals

To test the effect of siRNA SNALP on survival rates of cancer subjects, tumors were established by intrahepatic seeding in mice and the mice were treated with SNALP-siRNA. These studies utilized a VSP siRNA cocktail containing dsRNAs targeting KSP/Eg5 and VEGF. Control was dsRNA targeting Luc. The siRNA cocktail was formulated in SNALPs.

Tumor cells (Human Hepatoma Hep3B, 1×10^6) were injected directly into the left lateral lobe of scid/beige mice. These mice were deficient for lymphocytes and natural killer (NK) cells, which is the minimal scope for immune-mediated anti-tumor effects. The incisions were closed by sutures, and the mice allowed to recover for 2-5 hours. The mice were fully recovered within 48-72 hours.

All mice received a total siRNA/lipid intravenous (iv) dose, and each cocktail was formulated into 1:57 cDMA SNALP (1.4% PEG-cDMA; 57.1% DLinDMA; 7.1% DPPC; and 34.3% cholesterol), 6:1 lipid:drug using original citrate buffer conditions.

siRNA-SNALP treatment was initiated on the day indicated below (18 or 26 days) after tumor seeding. siRNA-SNALP were administered twice a week for three weeks after 18 or 26 day is at a dose of 4 mg/kg. Survival was monitored and animals were euthanized based on humane surrogate endpoints (e.g., animal body weight, abdominal distension/discoloration, and overall health).

Figure 13A:
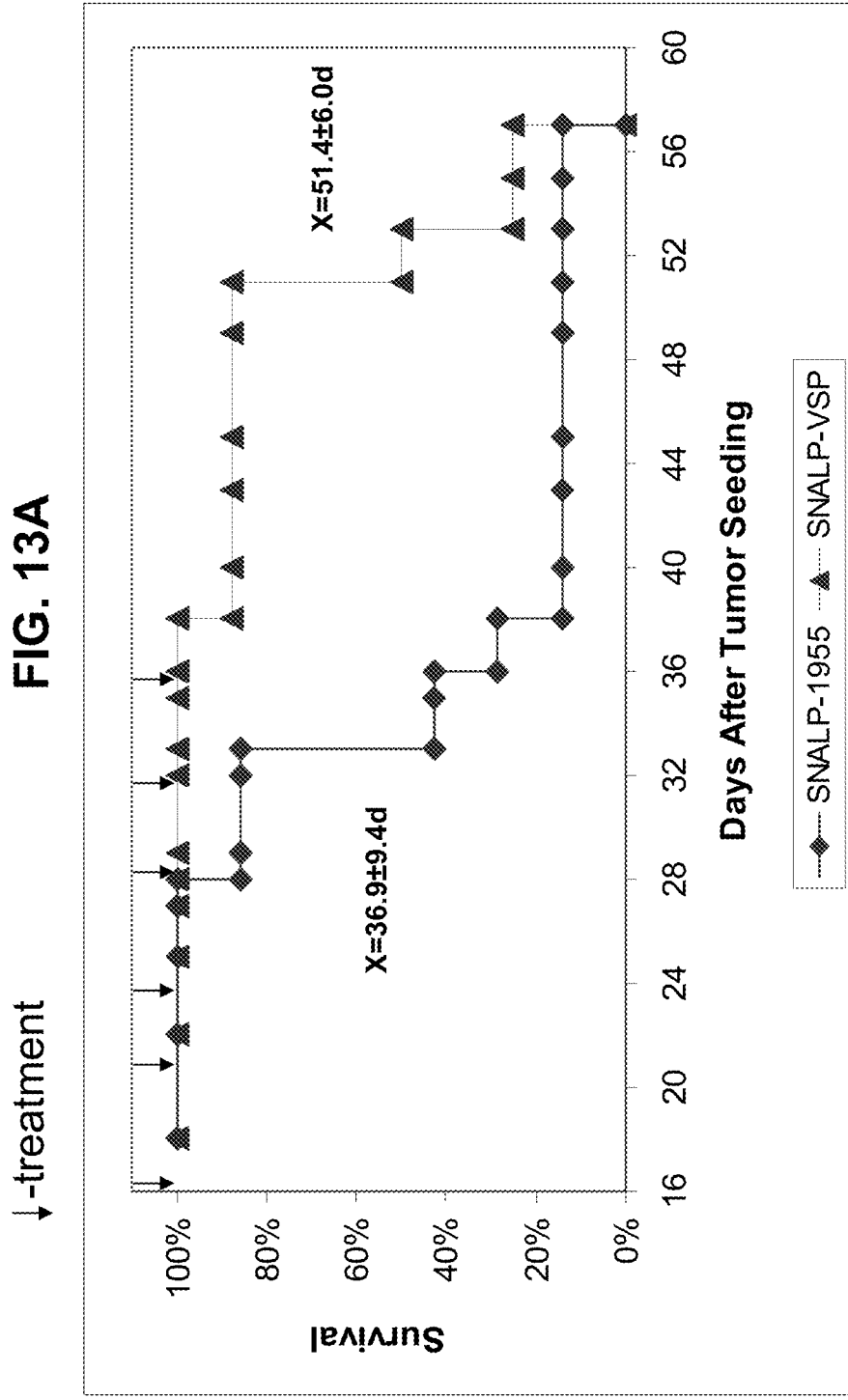
FIG. 13A and FIG. 13B are graphs showing the effects of SNALP-siRNAs on survival in mice with hepatic tumors. Treatment was started at 18 days (FIG. 13A) and 26 days (FIG. 13B) after tumor cell seeding.

The survival data for treatment initiated 18 days after tumor seeing is summarized in Table 13, Table 14, and FIG. 13A.

TABLE 13

Kaplan-Meier (survival) data (% Surviving)

| Day | SNALP-Luc | SNALP-VSP |
|---|---|---|
| 18 | 100% | 100% |
| 22 | 100% | 100% |
| 25 | 100% | 100% |
| 27 | 100% | 100% |
| 28 | 100% | 100% |
| 28 | 86% | 100% |
| 29 | 86% | 100% |
| 32 | 86% | 100% |
| 33 | 86% | 100% |
| 33 | 43% | 100% |
| 35 | 43% | 100% |
| 36 | 43% | 100% |

TABLE 13-continued

Kaplan-Meier (survival) data (% Surviving)

| Day | SNALP-Luc | SNALP-VSP |
|---|---|---|
| 36 | 29% | 100% |
| 38 | 29% | 100% |
| 38 | 14% | 100% |
| 38 | 14% | 88% |
| 40 | 14% | 88% |
| 43 | 14% | 88% |
| 45 | 14% | 88% |
| 49 | 14% | 88% |
| 51 | 14% | 88% |
| 51 | 14% | 50% |
| 53 | 14% | 50% |
| 53 | 14% | 25% |
| 55 | 14% | 25% |
| 57 | 14% | 25% |
| 57 | 0% | 0% |

TABLE 14

Survival in days, for each animal.

| Animal | Treatment group | Survival | |
|---|---|---|---|
| 1 | SNALP-Luc | 28 | days |
| 2 | SNALP-Luc | 33 | days |
| 3 | SNALP-Luc | 33 | days |
| 4 | SNALP-Luc | 33 | days |
| 5 | SNALP-Luc | 36 | days |
| 6 | SNALP-Luc | 38 | days |
| 7 | SNALP-Luc | 57 | days |
| 8 | SNALP-VSP | 38 | days |
| 9 | SNALP-VSP | 51 | days |
| 10 | SNALP-VSP | 51 | days |
| 11 | SNALP-VSP | 51 | days |
| 12 | SNALP-VSP | 53 | days |
| 13 | SNALP-VSP | 53 | days |
| 14 | SNALP-VSP | 57 | days |
| 15 | SNALP-VSP | 57 | days |

FIG. 13A shows the mean survival of SNALP-VSP animals and SNALP-Luc treated animals versus days after tumor seeding. The mean survival of SNALP-VSP animals was extended by approximately 15 days versus SNALP-Luc treated animals.

TABLE 15

Serum alpha fetoprotein (AFP) concentration, for each animal, at a time pre-treatment and at end of treatment (concentration in µg/ml)

| | | pre-Rx | End of Rx |
|---|---|---|---|
| 1 | SNALP-Luc | 30.858 | 454.454 |
| 2 | SNALP-Luc | 10.088 | 202.082 |
| 3 | SNALP-Luc | 23.736 | 648.952 |
| 4 | SNALP-Luc | 1.696 | 13.308 |
| 5 | SNALP-Luc | 4.778 | 338.688 |
| 6 | SNALP-Luc | 15.004 | 826.972 |
| 7 | SNALP-Luc | 11.036 | 245.01 |
| 8 | SNALP-VSP | 37.514 | 182.35 |
| 9 | SNALP-VSP | 91.516 | 248.06 |
| 10 | SNALP-VSP | 25.448 | 243.13 |
| 11 | SNALP-VSP | 24.862 | 45.514 |
| 12 | SNALP-VSP | 57.774 | 149.352 |
| 13 | SNALP-VSP | 12.446 | 78.724 |
| 14 | SNALP-VSP | 2.912 | 9.61 |
| 15 | SNALP-VSP | 4.516 | 11.524 |

Figure 14:
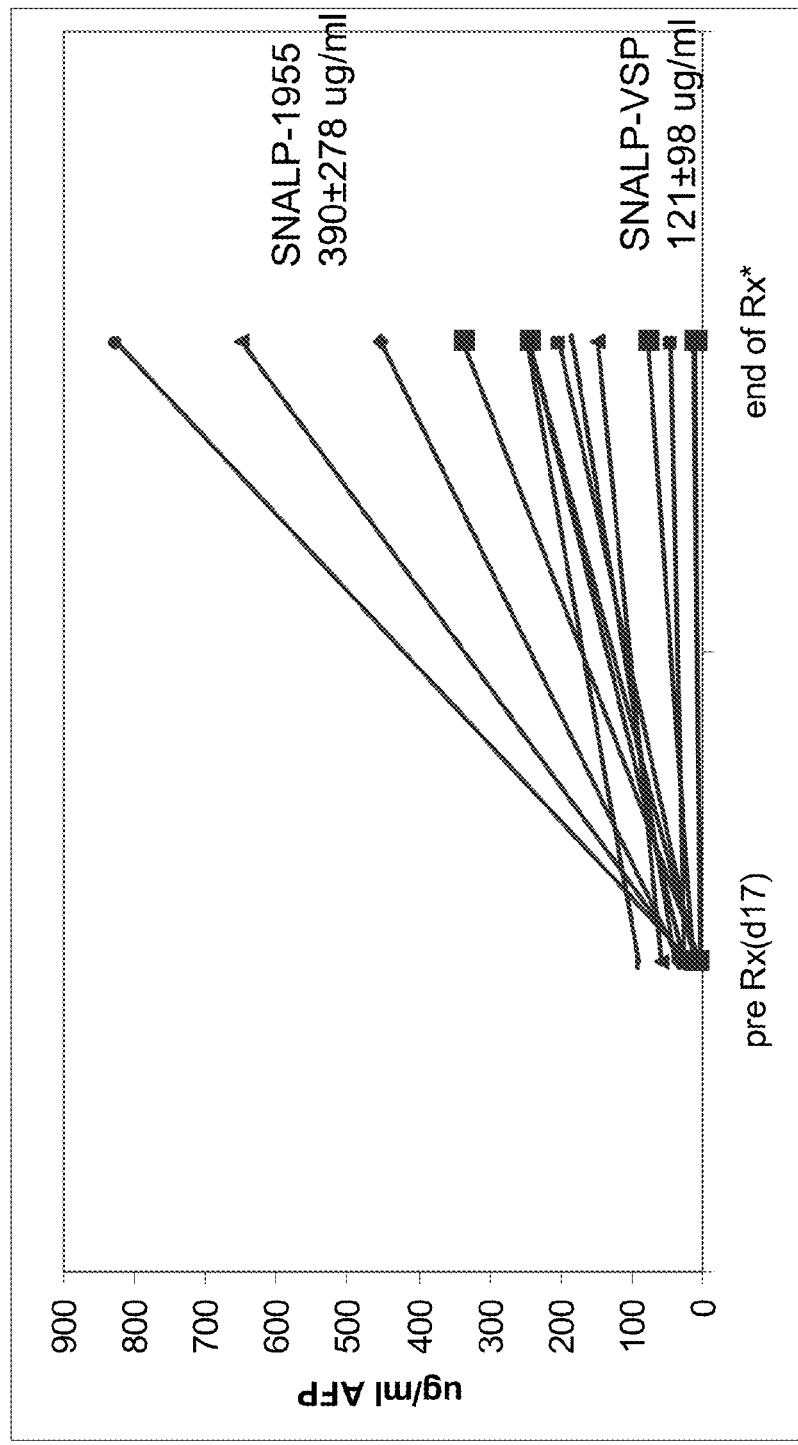
FIG. 14 is a graph showing the effects of SNALP-siRNAs on serum alpha fetoprotein (AFP) levels.

Tumor burden was monitored using serum AFP levels during the course of the experiment. Alpha-fetoprotein (AFP) is a major plasma protein produced by the yolk sac and the liver during fetal life. The protein is thought to be the fetal counterpart of serum albumin, and human AFP and albumin gene are present in tandem in the same transcriptional orientation on chromosome 4. AFP is found in monomeric as well as dimeric and trimeric forms, and binds copper, nickel, fatty acids and bilirubin. AFP levels decrease gradually after birth, reaching adult levels by 8-12 months. Normal adult AFP levels are low, but detectable. AFP has no known function in normal adults and AFP expression in adults is often associated with a subset of tumors such as hepatoma and teratoma. AFP is a tumor marker used to monitor testicular cancer, ovarian cancer, and malignant teratoma. Principle tumors that secrete AFP include endodermal sinus tumor (yolk sac carcinoma), neuroblastoma, hepatoblastoma, and heptocellular carcinoma. In patients with AFP-secreting tumors, serum levels of AFP often correlate with tumor size. Serum levels are useful in assessing response to treatment. Typically, if levels of AFP go down after treatment, the tumor is not growing. A temporary increase in AFP immediately following chemotherapy may indicate not that the tumor is growing but rather that it is shrinking (and releasing AFP as the tumor cells die). Resection is usually associated with a fall in serum levels. As shown in FIG. 14, tumor burden in SNALP-VSP treated animals was significantly reduced.

Figure 13B:
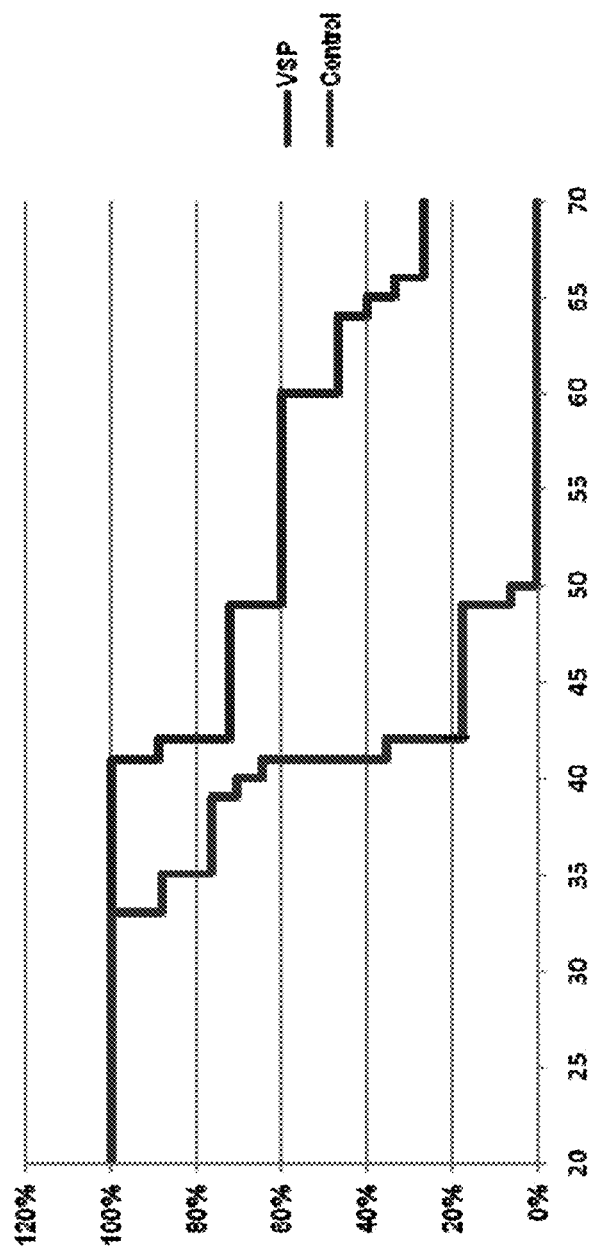

The experiment was repeated with SNALP-siRNA treatment at 26, 29, 32 35, 39, and 42 days after implantation. The data is shown in FIG. 13B. The mean survival of SNALP-VSP animals was extended by approximately 15 days versus SNALP-Luc treated animals by approximately 19 days, or 38%.

Example 8

Induction of Mono-asters in Established Tumors

Figure 15:
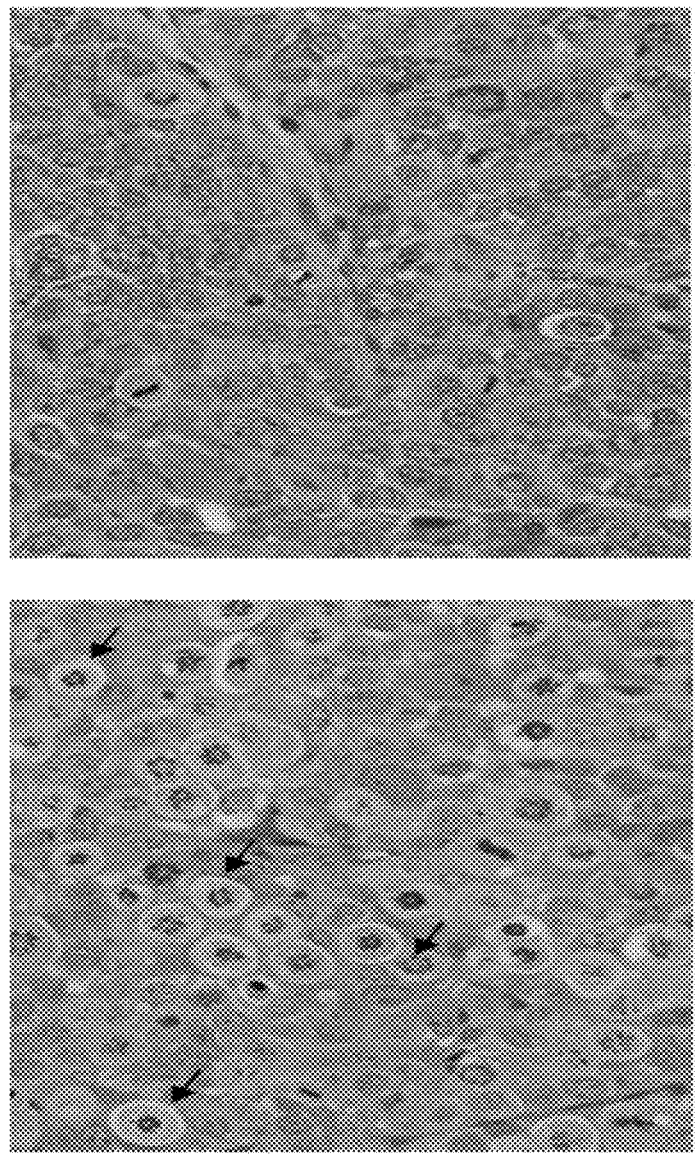
FIGS. 15A and 15B are images of H&E stained sections in tumor bearing animals (three weeks after Hep3B cell implantation) were administered 2 mg/kg SNALP-VSP (A) or 2 mg/kg SNALP-Luc (B). Twenty four hours later, tumor bearing liver lobes were processed for histological analysis. Arrows indicate mono asters.

Inhibition of KSP in dividing cells leads to the formation of mono asters that are readily observable in histological sections. To determine whether mono aster formation occurred in SNALP-VSP treated tumors, tumor bearing animals (three weeks after Hep3B cell implantation) were administered 2 mg/kg SNALP-VSP via tail vein injection. Control animals received 2 mg/kg SNALP-Luc. Twenty four hours later, animals were sacrificed, and tumor bearing liver lobes were processed for histological analysis. Representative images of H&E stained tissue sections are shown in FIG. 15. Extensive mono aster formation was evident in ALN VSP02 treated (A), but not SNALP-Luc treated (B), tumors. In the latter, normal mitotic figures were evident. The generation of mono asters is a characteristic feature of KSP inhibition and provides further evidence that SNALP-VSP has significant activity in established liver tumors.

Example 9

Manufacturing Process and Product Specification of ALN-VSP02 (SNALP-VSP)

ALN-VSP02 product contains 2 mg/mL of drug substance ALN-VSPDS01 formulated in a sterile lipid particle formulation (referred to as SNALP) for IV administration via infusion. Drug substance ALN-VSPDS01 consists of two siRNAs (ALN-12115 targeting KSP and ALN-3133 targeting VEGF) in an equimolar ratio. The drug product is packaged in mL glass vials with a fill volume of 5 mL.

The following terminology is used herein:

| Drug Substance | siRNA Duplexes | Single Strand Intermediates |
|---|---|---|
| ALN-VSPDS01 | ALN-12115* | Sense: A-19562 |
|  |  | Antisense: A-19563 |
|  | ALN-3133** | Sense: A-3981 |
|  |  | Antisense: A-3982 |

*Alternate names = AD-12115, AD12115;
**Alternate names = AD-3133, AD3133

9.1 Preparation of drug substance ALN-VSPDS01

The two siRNA components of drug substance ALN-VSPDS01, ALN-12115 and ALN-3133, are chemically synthesized using commercially available synthesizers and raw materials. The manufacturing process consists of synthesizing the two single strand oligonucleotides of each duplex (A 19562 sense and A 19563 antisense of ALN 12115 and A 3981 sense and A 3982 antisense of ALN 3133) by conventional solid phase oligonucleotide synthesis using phosphoramidite chemistry and 5' O dimethoxytriphenylmethyl (DMT) protecting group with the 2' hydroxyl protected with tert butyldimethylsilyl (TBDMS) or the 2' hydroxyl replaced with a 2' methoxy group (2' OMe). Assembly of an oligonucleotide chain by the phosphoramidite method on a solid support such as controlled pore glass or polystyrene. The cycle consists of 5' deprotection, coupling, oxidation, and capping. Each coupling reaction is carried out by activation of the appropriately protected ribo, 2' OMe, or deoxyribonucleoside amidite using 5 (ethylthio) 1H tetrazole reagent followed by the coupling of the free 5' hydroxyl group of a support immobilized protected nucleoside or oligonucleotide. After the appropriate number of cycles, the final 5' protecting group is removed by acid treatment. The crude oligonucleotide is cleaved from the solid support by aqueous methylamine treatment with concomitant removal of the cyanoethyl protecting group as well as nucleobase protecting groups. The 2' O TBDMS group is then cleaved using a hydrogen fluoride containing reagent to yield the crude oligoribonucleotide, which is purified using strong anion exchange high performance liquid chromatography (HPLC) followed by desalting using ultrafiltration. The purified single strands are analyzed to confirm the correct molecular weight, the molecular sequence, impurity profile and oligonucleotide content, prior to annealing into the duplexes. The annealed duplex intermediates ALN 12115 and ALN 3133 are either lyophilized and stored at 20° C. or mixed in 1:1 molar ratio and the solution is lyophilized to yield drug substance ALN VSPDS01. If the duplex intermediates were stored as dry powder, they are redissolved in water before mixing. The equimolar ratio is achieved by monitoring the mixing process by an HPLC method.

Figure 16:
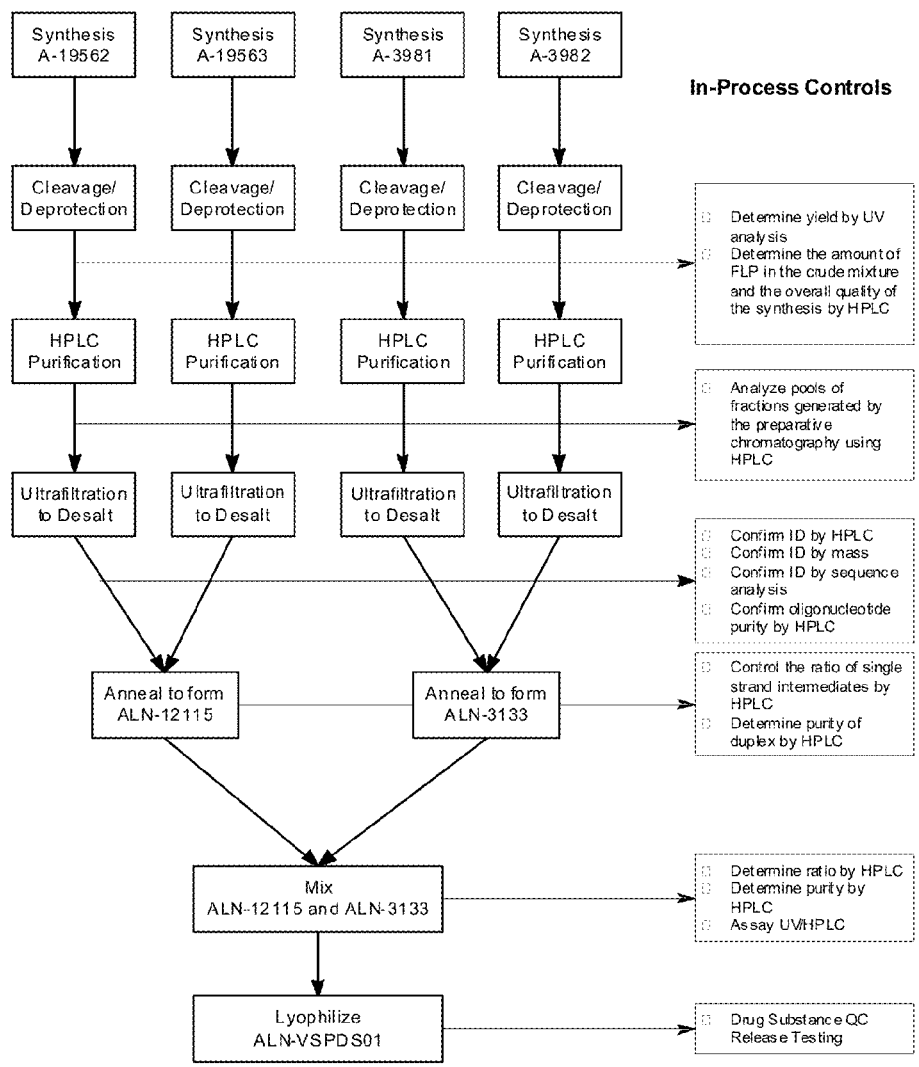
FIG. 16 is a flow diagram illustrating the manufacturing process of ALN-VSPDS01.

The manufacturing process flow diagram is shown in FIG. 16.

Example specifications are shown in Table 16a.

The results of up to 12 month stability testing for ALN-VSPDS01 drug substance are shown in Tables 16c. The assay methods were chosen to assess physical property (appearance, pH, moisture), purity (by SEC and denaturing anion exchange chromatography) and potency (by denaturing anion exchange chromatography [AX-HPLC]).

TABLE 16a

Example specifications for ALN-VSPDS01

| Test | Method | Acceptance Criteria |
|---|---|---|
| Appearance | Visual | White to off-white powder |
| Identity, ALN-VSPDS01 ALN-3133 ALN-12115 | Duplex AX-HPLC | Duplex retention times are consistent with those of reference standards |
| Identity, ALN-VSPDS01 | MS | Molecular weight of single strands are within the following ranges: A-3981: 6869-6873 Da A-3982: 7305-7309 Da A-19562: 6762-6766 Da A-19563: 6675-6679 Da |
| Sodium counter ion (% w/w on anhydrous basis) | Flame AAS or ICP-OES | Report data |
| ALN-VSPDS01 assay | Denaturing AX-HPLC | 90-110% |
| Purity of ALN-VSPDS01 | SEC | ≥90.0 area % |
| Single strand purity, ALN-VSPDS01 | Denaturing AX-HPLC | Report data Report area % for total impurities |
| siRNA molar ratio | Duplex AX-HPLC | 1.0 ± 0.1 |
| Moisture content | Karl Fischer titration | ≤15% |
| Residual solvents Acetonitrile Ethanol Isopropanol | HS-Capillary GC | ≤410 ppm ≤5000 ppm ≤5000 ppm |
| pH of 1% solution | USP <791> | Report data |
| Heavy metals As, Cd, Cu, Cr, Fe, Ni, Pb, Sn | ICP-MS | Report data |
| Bacterial endotoxins | USP <85> | ≤0.5 EU/mg |
| Bioburden | Modified USP <61> | <100 CFU/g |

TABLE 16b

Stability of drug substance

Lot No.: A05M07001N    Study Storage Conditions: −20° C. (Storage Condition)

| Test | Method | Acceptance Criteria | Results Initial | 1 Month | 3 Months | 6 Months | 12 Months |
|---|---|---|---|---|---|---|---|
| Appearance | Visual | White to off-white powder | Pass | Pass | Pass | Pass | Pass |
| pH | USP <791> | Report data | 6.7 | 6.4 | 6.6 | 6.4 | 6.8 |
| Moisture content (% w/w) | Karl Fischer titration | ≤15% | 3.6* | 6.7 | 6.2 | 5.6 | 5.0 |
| Purity (area %) | SEC | ≥90.0 area % | 95 | 95 | 94 | 92 | 95 |
| A-3981 (sense) (area %) | Denaturing AX-HPLC | Report data | 24 | 23 | 23 | 23 | 23 |
| A-3982 (antisense) (area %) | Denaturing AX-HPLC | Report data | 23 | 23 | 23 | 23 | 24 |
| A-19562 (sense) (area %) | Denaturing AX-HPLC | Report data | 22 | 21 | 21 | 21 | 21 |
| A-19563 (antisense) (area %) | Denaturing AX-HPLC | Report data | 23 | 22 | 22 | 22 | 22 |

9.2 Preparation of drug product ALN-VSP02 (SNALP-VSP)

Figure 17:
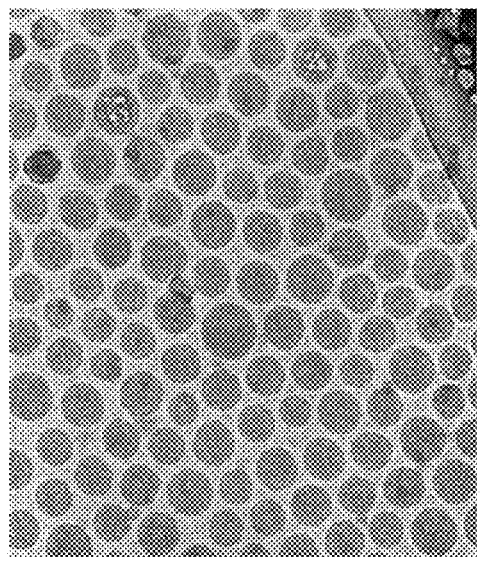
FIG. 17 is a cryo-transmission electron microscope (cryo-TEM) image of ALN-VSP02.

ALN VSP02, is a sterile formulation of the two siRNAs (in a 1:1 molar ratio) with lipid excipients in isotonic buffer. The lipid excipients associate with the two siRNAs, protect them from degradation in the circulatory system, and aid in their delivery to the target tissue. The specific lipid excipients and the quantitative proportion of each (shown in Table 17) have been selected through an iterative series of experiments comparing the physicochemical properties, stability, pharmacodynamics, pharmacokinetics, toxicity and product manufacturability of numerous different formulations. The excipient DLinDMA is a titratable aminolipid that is positively charged at low pH, such as that found in the endosome of mammalian cells, but relatively uncharged at the more neutral pH of whole blood. This feature facilitates the efficient encapsulation of the negatively charged siRNAs at low pH, preventing formation of empty particles, yet allows for adjustment (reduction) of the particle charge by replacing the formulation buffer with a more neutral storage buffer prior to use. Cholesterol and the neutral lipid DPPC are incorporated in order to provide physicochemical stability to the particles. The polyethyleneglycol lipid conjugate PEG2000 C DMA aids drug product stability, and provides optimum circulation time for the proposed use. ALN VSP02 lipid particles have a mean diameter of approximately 80-90 nm with low polydispersity values. A representative cryo transmission electron microscope (cryo TEM) image is shown in FIG. 17. At neutral pH, the particles are essentially uncharged, with Zeta Potential values of less than 6 mV. There is no evidence of empty (non loaded) particles based on the manufacturing process.

TABLE 17

Quantitative Composition of ALN-VSP02

| Component, grade | Proportion (mg/mL) |
|---|---|
| ALN-VSPDS01, cGMP | 2.0* |
| DLinDMA (1,2-Dilinoleyloxy-N,N-dimethyl-3-aminopropane), cGMP | 7.3 |
| DPPC (R-1,2-Dipalmitoyl-sn-glycero-3-phosphocholine), cGMP | 1.1 |
| Cholesterol, Synthetic, cGMP | 2.8 |
| PEG2000-C-DMA (3-N-[(ω-Methoxy poly(ethylene glycol) 2000) carbamoyl]-1,2-dimyristyloxy-propylamine), cGMP | 0.8 |
| Phosphate Buffered Saline, cGMP | q.s. |

*The 1:1 molar ratio of the two siRNAs in the drug product is maintained throughout the size distribution of the drug product particles.

Figure 18:
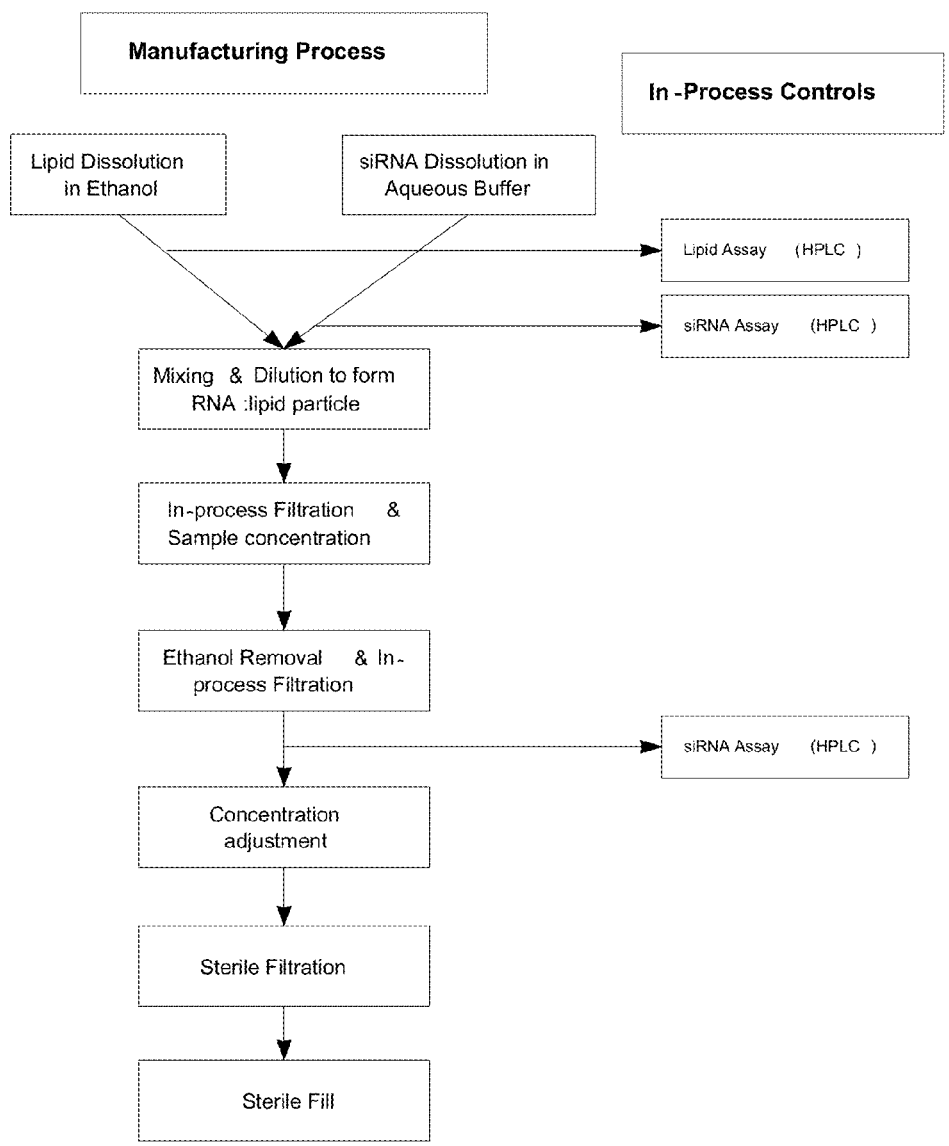
FIG. 18 is a flow diagram illustrating the manufacturing process of ALN-VSP02.

Solutions of lipid (in ethanol) and ALN VSPDS01 drug substance (in aqueous buffer) are mixed and diluted to form a colloidal dispersion of siRNA lipid particles with an average particle size of approximately 80-90 nm. This dispersion is then filtered through 0.45/0.2 μm filters, concentrated, and diafiltered by Tangential Flow Filtration. After in process testing and concentration adjustment to 2.0 mg/mL, the product is sterile filtered, aseptically filled into glass vials, stoppered, capped and placed at 5±3° C. The ethanol and all aqueous buffer components are USP grade; all water used is USP Sterile Water For Injection grade. Representative ALN-VSP02 process is shown in flow diagram in FIG. 18.

TABLE 18a

Example ALN-VSP02 specifications

| Test | Analytical Procedure | Acceptance Criteria |
|---|---|---|
| Appearance | Visual | White to off-white, homogeneous opalescent liquid, no foreign particles |
| pH | USP <791> | 6.8-7.8 |
| Osmolality | USP <785> | 250-350 mOsm/kg |
| Identity, ALN-VSPDS01 ALN-3133 ALN-12115 | Duplex Anion Exchange (AX)-HPLC | Retention times consistent with those of reference standards |
| Identity, ALN-VSPDS01 A-3981 A-3982 A-19562 A-19563 | Denaturing AX-HPLC | Retention times consistent with those of reference standards |
| Lipid identity DLinDMA PEG$_{2000}$-C-DMA DPPC Cholesterol | Reversed Phase (RP)-HPLC with Evaporative Light Scattering (ELS) detection | Retention times consistent with those of reference standards |
| ALN-VSPDS01 label claim (Strength/Potency) | Denaturing AX-HPLC | 1.7-2.3 mg/mL |
| Duplex molar ratio | Duplex AX-HPLC | 1.0 ± 0.1 |
| DLinDMA content | RP-HPLC with ELS detection | 5.6-10.3 mg/mL |
| PEG$_{2000}$-C-DMA content | RP-HPLC with ELS detection | 0.6-1.1 mg/mL |
| DPPC content | RP-HPLC with ELS detection | 0.8-1.5 mg/mL |
| Cholesterol content | RP-HPLC with ELS detection | 2.1-3.9 mg/mL |
| Total lipid:ALN-VSPDS01 ratio | Calculated from total lipid assay and label claim for drug substance | 4.9-8.1 mg/mg |
| ALN-VSPDS01 encapsulation | Fluorometric assay | ≥90.0% |
| Purity | Denaturing AX-HPLC | ≥80.0 area % |
| Impurity profile | Denaturing AX-HPLC | Report retention times (relative to A-19563) and area % for all peaks ≥0.20% |
| Residual ethanol | USP <467> | ≤5000 ppm |
| Residual EDTA | Ion Pairing (IP)-HPLC with UV detection | ≤2000 μg/mL |
| Particle size Z average | Dynamic light scattering | 60-120 nm |
| Polydispersity | Dynamic light scattering | ≤0.15 |

TABLE 18a-continued

Example ALN-VSP02 specifications

| Test | Analytical Procedure | Acceptance Criteria |
|---|---|---|
| Particle size distribution | Dynamic light scattering | Report data |
| $D_{10}$ | | |
| $D_{50}$ | | |
| $D_{90}$ | | |
| Particulate matter | Modified USP <788> | |
| ≥25 μm | | ≤300 per container |
| ≥10 μm | | ≤3000 per container |
| Bacterial endotoxins | Modified USP <85> | ≤5.0 EU/mL |
| Sterility | USP <71> | Pass |
| Volume in container | USP <1> | ≥5.0 mL |
| Dose uniformity | USP <905> | Pass |
| Heavy metal analysis | Inductive Coupled Plasma Mass Spectrometry (ICP-MS) | Report data |

9.4 Container/Closure System

The ALN VSP02 drug product is packaged in 10 mL glass vials with a fill volume of 5 mL. The container closure system is comprised of a USP/EP Type I borosilicate glass vial, a teflon faced butyl rubber stopper and an aluminum flip off cap. The drug product will be stored at 5±3° C.

9.5 Stability of Drug Product ALN-VSP02

Stability data (25° C./60% RH) are given in Table 18b and 18c.

TABLE 18b

Example ALN-VSPO2 stability at storage conditions

| | Lot No.: IC097 | | Study Storage Conditions: 2-8° C. Results | | | | | |
|---|---|---|---|---|---|---|---|---|
| Test | Method | Acceptance Criteria | Initial | 1 Month | 2 Months | 3 Months | 4 Months | 6 Months |
| Appearance | Visual | White to off-white, homogeneous opalescent liquid, no foreign particles | Pass | Pass | Pass | Pass | Pass | Pass |
| pH | USP <791> | 6.8-7.8 | 7.4 | 7.4 | 7.4 | 7.3 | 7.4 | 7.3 |
| Osmolality | USP <791> | 250-350 mOsm/kg | 308 | 307 | 305 | 306 | 309 | 305 |
| ALN-VSPDS01 Identity, ALN-3133 ALN-12115 | Duplex AX-HPLC | Retention times consistent with those of reference standards | Pass | Pass | Pass | Pass | Pass | Pass |
| ALN-VSPDS01 Identity, A-3981 A-3982 A-19562 A-19563 | Denaturing AX-HPLC | Retention times consistent with those of reference standards | Pass | Pass | Pass | Pass | Pass | Pass |
| Lipid identity, DLinDMA PEGr000-C-DMA DPPC Cholesterol | RP-HPLC with ELS Detection | Retention times consistent with those of reference standards | Pass | Pass | Pass | Pass | Pass | Pass |
| ALN-VSPDS01 strength/potency | Denaturing AX-HPLC | 1.7-2.3 mg/mL | 2.1 | 2.2 | 2.1 | 2.1 | 2.1 | 2.1 |
| Duplex molar ratio | Duplex AX-HPLC | 1.0 ± 0.1 | 1.0 | 1.0 | 1.0 | 1.0 | 1.0 | 1.0 |
| DLinDMA content | RP-HPLC with ELS Detection | 5.6-10.3 mg/mL | 9.1 | 9.4 | 9.1 | 9.6 | 9.1 | 9.2 |
| Cholesterol content | RP-HPLC with ELS Detection | 2.1-3.9 mg/mL | 3.4 | 3.5 | 3.4 | 3.5 | 3.4 | 3.5 |

TABLE 18b-continued

Example ALN-VSPO2 stability at storage conditions

Lot No.: IC097 — Study Storage Conditions: 2-8° C. Results

| Test | Method | Acceptance Criteria | Initial | 1 Month | 2 Months | 3 Months | 4 Months | 6 Months |
|---|---|---|---|---|---|---|---|---|
| DPPC content | RP-HPLC with ELS Detection | 0.8-1.5 mg/mL | 1.3 | 1.3 | 1.4 | 1.4 | 1.2 | 1.3 |
| $PEG_{2000}$-C-DMA content | RP-HPLC with ELS Detection | 0.6-1.1 mg/mL | 1.0 | 1.0 | 1.0 | 1.1 | 1.0 | 1.0 |
| Total lipid: ALN-VSPDS01 ratio | Calculation | 4.9-8.1 mg/mg | 7.0 | 6.9 | 7.1 | 7.4 | 7.0 | 7.1 |
| ALN-VSPDS01 encapsulation | Fluorometric assay | ≥90.0% | 95.9 | 96.5 | 94.4 | 98.1 | 97.8 | 96.4 |
| Purity | Denaturing AX-HPLC | ≥80.0% | 90.7 | 89.6 | 90.8 | 91.3 | 92.4 | 90.8 |
| Particle size, Z-average | Light scattering | 60-120 nm | 86 | 87 | 87 | 87 | 87 | 87 |
| Polydispersity | Light scattering | ≤0.15 | 0.02 | 0.03 | 0.02 | 0.03 | 0.03 | 0.03 |
| Particle size distribution, $D_{10}$ | Light scattering | Report data (nm) | 56 | 56 | 56 | 56 | 56 | 56 |
| Particle size distribution, $D_{50}$ | Light scattering | Report data (nm) | 76 | 77 | 77 | 77 | 78 | 77 |
| Particle size distribution, $D_{90}$ | Light scattering | Report data (nm) | 110 | 112 | 112 | 113 | 112 | 113 |
| Particulate matter, ≥25 μm ≥10 μm | Modified USP <788> | (per container) ≤300 ≤3000 | 18 48 | NS | NS | NS | NS | 3 11 |
| Bacterial endotoxins | USP <85> | ≤5.0 EU/mL | 0.50 | NS | NS | NS | NS | NS |
| Sterility | USP <71> | Pass | Pass | NS | NS | NS | NS | NS |

TABLE 18c

Example ALN-VSPO2 stability at 25° C./ambient humidity

Lot No.: IC097 — Study Storage Conditions: 25° C./ambient humidity Results

| Test | Method | Acceptance Criteria | Initial | 1 Month | 2 Months | 3 Months | 4 Months | 6 Months |
|---|---|---|---|---|---|---|---|---|
| Appearance | Visual | White to off-white, homogeneous opalescent liquid, no foreign particles | Pass | Pass | Pass | Pass | Pass | Pass |
| pH | USP <791> | 6.8-7.8 | 7.4 | 7.3 | 7.2 | 7.1 | 7.2 | 7.1 |
| Osmolality | USP <785> | 250-350 mOsm/kg | 308 | 306 | 304 | 307 | 307 | 304 |
| ALN-VSPDS01 Identity, ALN-3133 ALN-12115 | Duplex AX-HPLC | Retention times consistent with those of reference standards | Pass | Pass | Pass | Pass | Pass | Pass |

TABLE 18c-continued

Example ALN-VSPO2 stability at 25° C./ambient humidity

| | Lot No.: IC097 | | Study Storage Conditions: 25° C./ambient humidity Results | | | | | |
|---|---|---|---|---|---|---|---|---|
| Test | Method | Acceptance Criteria | Initial | 1 Month | 2 Months | 3 Months | 4 Months | 6 Months |
| ALN-VSPDS01 Identity, A-3981 A-3982 A-19562 A-19563 | Denaturing AX-HPLC | Retention times consistent with those of reference standards | Pass | Pass | Pass | Pass | Pass | Pass |
| Lipid identity, DLinDMA $PEG_{2000}$-C-DMA DPPC Cholesterol | RP-HPLC with ELS Detection | Retention times consistent with those of reference standards | Pass | Pass | Pass | Pass | Pass | Pass |
| ALN-VSPDS01 strength/potency | Denaturing AX-HPLC | 1.7-2.3 mg/mL | 2.1 | 2.1 | 2.0 | 2.0 | 2.0 | 2.0 |
| Duplex molar ratio | Duplex AX-HPLC | 1.0 ± 0.1 | 1.0 | 1.0 | 1.0 | 1.0 | 1.0 | 1.0 |
| DLinDMA content | RP-HPLC with ELS Detection | 5.6-10.3 mg/mL | 9.1 | 9.6 | 9.0 | 9.3 | 9.2 | 9.3 |
| Cholesterol content | RP-HPLC with ELS Detection | 2.1-3.9 mg/mL | 3.4 | 3.5 | 3.4 | 3.5 | 3.4 | 3.5 |
| DPPC content | RP-HPLC with ELS Detection | 0.8-1.5 mg/mL | 1.3 | 1.3 | 1.3 | 1.2 | 1.2 | 1.1 |
| $PEG_{2000}$-C-DMA content | RP-HPLC with ELS Detection | 0.6-1.1 mg/mL | 1.0 | 1.0 | 1.0 | 1.1 | 1.0 | 1.0 |
| Total lipid: ALN-VSPDS01 ratio | Calculation | 4.9-8.1 mg/mg | 7.0 | 7.3 | 7.4 | 7.6 | 7.4 | 7.5 |
| ALN-VSPDS01 encapsulation | Fluorometric assay | ≥90.0% | 95.9 | 97.2 | 94.6 | 97.9 | 97.9 | 96.7 |
| Purity | Denaturing AX-HPLC | ≥80.0% | 90.7 | 88.0 | 88.9 | 88.4 | 89.0 | 85.3 |
| Particle size, Z-average | Light scattering | 60-120 nm | 86 | 85 | 86 | 89 | 87 | 87 |
| Polydispersity | Light scattering | ≤0.15 | 0.02 | 0.05 | 0.03 | 0.04 | 0.04 | 0.03 |
| Particle size distribution, $D_{10}$ | Light scattering | Report data (nm) | 56 | 54 | 56 | 58 | 56 | 57 |
| Particle size distribution, $D_{50}$ | Light scattering | Report data (nm) | 76 | 75 | 77 | 79 | 77 | 78 |
| Particle size distribution, $D_{90}$ | Light scattering | Report data (nm) | 110 | 110 | 111 | 116 | 113 | 113 |
| Particulate matter, ≥25 μm ≥10 μm | Modified USP <788> | (per container) ≤300 ≤3000 | 18 48 | NS | NS | NS | NS | 1 16 |
| Bacterial endotoxins | USP <85> | ≤5.0 EU/mL | 0.50 | NS | NS | NS | NS | <0.50 |
| Sterility | USP <71> | Pass | Pass | NS | NS | NS | NS | Pass |

Example 10

In Vitro Efficacy of ALN-VSP02 in Human Cancer Cell Lines

The efficacy of ALN-VSP02 treatment in human cancer cell lines was determined via measurement of KSP mRNA, VEGF mRNA, and cell viability after treatment. IC50 (nM) values determined for KSP and VEGF in each cell line.

TABLE 19

| cell lines | |
|---|---|
| Cell line tested | ATCC cat number |
| HELA | ATCC Cat N: CCL-2 |
| KB | ATCC Cat N: CCL-17 |
| HEP3B | ATCC Cat N: HB-8064 |
| SKOV-3 | ATCC Cat N: HTB-77 |
| HCT-116 | ATCC Cat N: CCL-247 |
| HT-29 | ATCC Cat N: HTB-38 |
| PC-3 | ATCC Cat N: CRL-1435 |
| A549 | ATCC Cat N: CCL-185 |
| MDA-MB-231 | ATCC Cat N: HTB-26 |

Cells were plated in 96 well plates in complete media at day 1 to reach a density of 70% on day 2. On day 2 media was replaced with Opti-MEM reduced serum media (Invitrogen Cat N: 11058-021) and cells were transfected with either ALN-VSP02 or control SNALP-Luc with concentration range starting at 1.8 μM down to 10 μM. After 6 hours the media was changed to complete media. Three replicate plates for each cell line for each experiment was done.

Cells were harvested 24 hours after transfection. KSP levels were measured using bDNA; VEGF mRNA levels were measured using human TaqMan assay.

Viability was measured using Cell Titer Blue reagent (Promega Cat N: G8080) at 48 and/or 72 h following manufacturer's recommendations.

As shown in Table 20, nM concentrations of VSP02 are effective in reducing expression of both KSP and VEGF in multiple human cell lines. Viability of treated cells was not

TABLE 20

| Results | | |
|---|---|---|
| Cell line | IC50 (nM) KSP | IC50 (nM) VEGF |
| HeLa | 8.79 | 672 |
| SKOV-3 | 142 | 1347 |
| HCT116 | 31.6 | 27.5 |
| Hep3B | 1.3 | 14.5 |
| HT-29 | 262 | ND |
| PC3 | 127 | ND |
| KB | 50.6 | ND |
| A549 | 201 | ND |
| MB231 | 187 | ND |

Example 11

Anti-Tumor Efficacy of VSP SNALP Vs. Sorafenib in Established Hep3B Intrahepatic Tumors The anti-tumor effects of multi-dosing VSP SNALP verses Sorafenib in scid/beige mice bearing established Hep3B intrahepatic tumors was studied. Sorafenib is a small molecule inhibitor of protein kinases approved for treatment of hepatic cellular carcinoma (HCC).

Tumors were established by intrahepatic seeding in scid/beige mice as described herein. Treatment was initiated 11 days post-seeding. Mice were treated with Sorafenib and a control siRNA-SNALP, Sorafenib and VSP siRNA-SNALP, or VSP siRNA-SNALP only. Control mice were treated with buffers only (DMSO for Sorafenib and PBS for siRNA-SNALP). Sorafenib was administered intraparenterally from Mon to Fri for three weeks, at mg/kg according to body weight for a total of 15 injections. Sorafenib was administered a minimum of 1 hour after SNALP injections. The siRNA-SNALPS were administered intravenously via the lateral tail vein according at 3 mg/kg based on the most recently recorded body weight (10 ml/kg) for 3 weeks (total of 6 doses) on days 1, 4, 7, 10, 14, and 17.

Mice were euthanized based on an assessment of tumor burden including progressive weight loss and clinical signs including condition, abdominal distension/discoloration and mobility.

Figure 19:
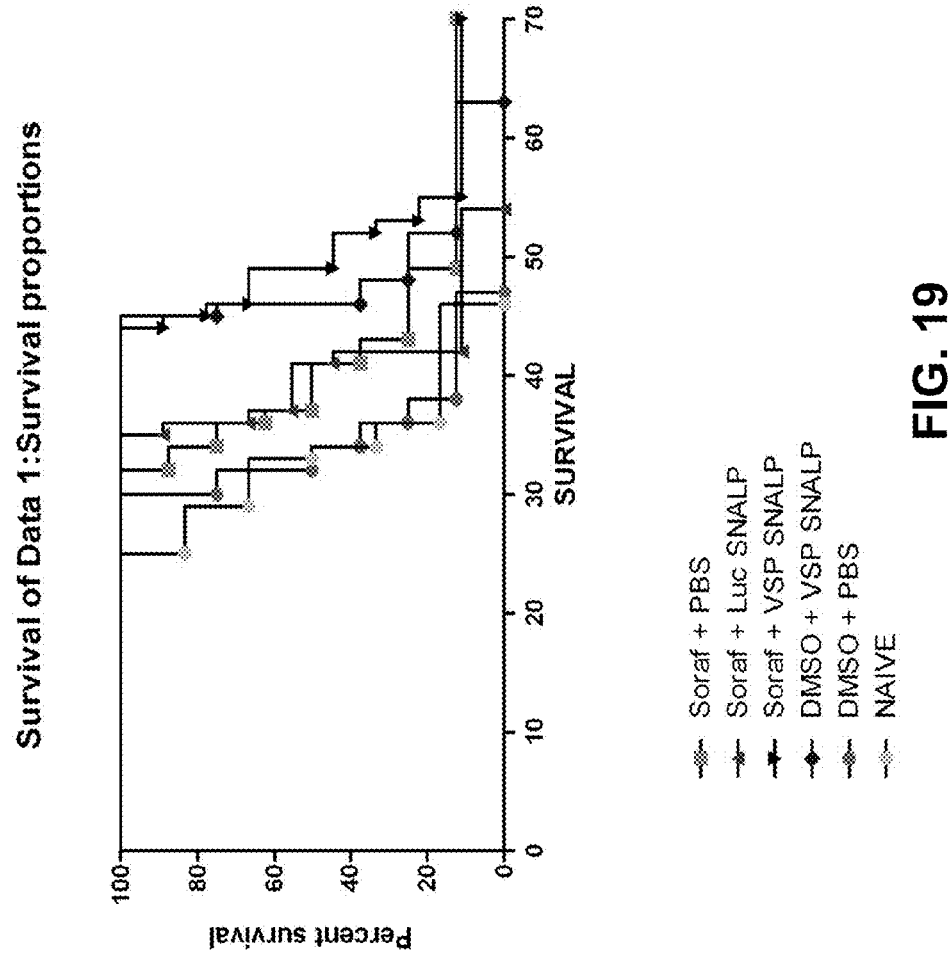
FIG. 19 is a graph illustrating the effects on survival of administration SNALP formulated siRNA and Sorafenib.

The percent survival data are shown in FIG. 19. Co-administration of VSP siRNA-SNALP with Sorafenib increased survival proportion compared to administration of Sorafenib or VSP siRNA-SNALP alone. VSP siRNA-SNALP increased survival proportion compared to Sorafenib.

Example 12

In Vitro Efficacy of VSP Using Variants of AD-12115 and AD-3133

Two sets of duplexes targeted to Eg5/KSP and VEGF were designed and synthesized. Each set included duplexes tiling 10 nucleotides in each direction of the target sites for either AD-12115 and AD-3133.

Sequences of the target, sense strand, and antisense strand for each duplex are shown in the Table below.

Each duplex is assayed for inhibition of expression using the assays described herein.

The duplexes are administered alone and/or in combination, e.g., an Eg5/KSP dsRNA in combination with a VEGF dsRNA. In some embodiments, the dsRNA are administered in a SNALP formulation as described herein.

TABLE 21

Sequences of dsRNA targeted to VEGF and Eg5/KSP (tiling)

| Duplex ID | target gene | target sequence 5' to 3' | SEQ ID NO: | Sense Strand Antisense strand 5' to 3' | SEQ ID NO: |
|---|---|---|---|---|---|
| AD-20447.1 | VEGFA | ACCAAGGCCAGCACAUAGG | 2264 | AccAAGGccAGcAcAuAGGTsT | 2304 |
| | | | | CCuAUGUGCUGGCCUUGGUTsT | 2305 |

TABLE 21-continued

Sequences of dsRNA targeted to VEGF and Eg5/KSP (tiling)

| Duplex ID | target gene | target sequence 5' to 3' | SEQ ID NO: | Sense Strand Antisense strand 5' to 3' | SEQ ID NO: |
|---|---|---|---|---|---|
| AD-20448.1 | VEGFA | CCAAGGCCAGCACAUAGGA | 2265 | ccAAGGccAGcAcAuAGGATsT<br>UCCuAUGUGCUGGCCUUGGTsT | 2306<br>2307 |
| AD-20449.1 | VEGFA | CCAAGGCCAGCACAUAGGA | 2266 | ccAAGGccAGcAcAuAGGATsT<br>CUCCuAUGUGCUGGCCUUGTsT | 2308<br>2309 |
| AD-20450.1 | VEGFA | AAGGCCAGCACAUAGGAGA | 2267 | AAGGccAGcAcAuAGGAGATsT<br>UCUCCuAUGUGCUGGCCUUTsT | 2310<br>2311 |
| AD-20451.1 | VEGFA | AGGCCAGCACAUAGGAGAG | 2268 | AGGccAGcAcAuAGGAGAGTsT<br>CUCUCCuAUGUGCUGGCCUTsT | 2312<br>2313 |
| AD-20452.1 | VEGFA | GGCCAGCACAUAGGAGAGA | 2269 | GGccAGcAcAuAGGAGAGATsT<br>UCUCUCCuAUGUGCUGGCCTsT | 2314<br>2315 |
| AD-20453.1 | VEGFA | GCCAGCACAUAGGAGAGAU | 2270 | GccAGcAcAuAGGAGAGAuTsT<br>AUCUCUCCuAUGUGCUGGCTsT | 2316<br>2317 |
| AD-20454.1 | VEGFA | CCAGCACAUAGGAGAGAUG | 2271 | ccAGcAcAuAGGAGAGAuGTsT<br>cAUCUCUCCuAUGUGCUGGTsT | 2318<br>2319 |
| AD-20455.1 | VEGFA | CAGCACAUAGGAGAGAUGA | 2272 | cAGcAcAuAGGAGAGAuGATsT<br>UcAUCUCUCCuAUGUGCUGTsT | 2320<br>2321 |
| AD-20456.1 | VEGFA | AGCACAUAGGAGAGAUGAG | 2273 | AGcAcAuAGGAGAGAuGAGTsT<br>CUcAUCUCUCCuAUGUGCUTsT | 2322<br>2323 |
| AD-20457.1 | VEGFA | CACAUAGGAGAGAUGAGCU | 2274 | cAcAuAGGAGAGAuGAGcuTsT<br>AGCUcAUCUCUCCuAUGUGTsT | 2324<br>2325 |
| AD-20458.1 | VEGFA | ACAUAGGAGAGAUGAGCUU | 2275 | AcAuAGGAGAGAuGAGcuuTsT<br>AAGCUcAUCUCUCCuAUGUTsT | 2326<br>2327 |
| AD-20459.1 | VEGFA | CAUAGGAGAGAUGAGCUUC | 2276 | cAuAGGAGAGAuGAGcuucTsT<br>GAAGCUcAUCUCUCCuAUGTsT | 2328<br>2329 |
| AD-20460.1 | VEGFA | AUAGGAGAGAUGAGCUUCC | 2277 | AuAGGAGAGAuGAGcuuccTsT<br>GGAAGCUcAUCUCUCCuAUTsT | 2330<br>2331 |
| AD-20461.1 | VEGFA | UAGGAGAGAUGAGCUUCCU | 2278 | uAGGAGAGAuGAGcuuccuTsT<br>AGGAAGCUcAUCUCUCCuATsT | 2332<br>2333 |
| AD-20462.1 | VEGFA | AGGAGAGAUGAGCUUCCUA | 2279 | AGGAGAGAuGAGcuuccuATsT<br>uAGGAAGCUcAUCUCUCCUTsT | 2334<br>2335 |
| AD-20463.1 | VEGFA | GGAGAGAUGAGCUUCCUAC | 2280 | GGAGAGAuGAGcuuccuAcTsT<br>GuAGGAAGCUcAUCUCUCCTsT | 2336<br>2337 |
| AD-20464.1 | VEGFA | GAGAGAUGAGCUUCCUACA | 2281 | GAGAGAuGAGcuuccuAcATsT<br>UGuAGGAAGCUcAUCUCUCTsT | 2338<br>2339 |
| AD-20465.1 | VEGFA | AGAGAUGAGCUUCCUACAG | 2282 | AGAGAuGAGcuuccuAcAGTsT<br>CUGuAGGAAGCUcAUCUCUTsT | 2340<br>2341 |
| AD-20466.1 | VEGFA | GAGAUGAGCUUCCUACAGC | 2283 | GAGAuGAGcuuccuAcAGcTsT<br>GCUGuAGGAAGCUcAUCUCTsT | 2342<br>2343 |
| AD-20467.1 | KSP | AUGUUCCUUAUCGAGAAUC | 2284 | AuGuuccuuAucGAGAAucTsT<br>GAUUCUCGAuAAGGAAcAUTsT | 2344<br>2345 |
| AD-20468.1 | KSP | UGUUCCUUAUCGAGAAUCU | 2285 | uGuuccuuAucGAGAAucuTsT<br>AGAUUCUCGAuAAGGAAcATsT | 2346<br>2347 |
| AD-20469.1 | KSP | GUUCCUUAUCGAGAAUCUA | 2286 | GuuccuuAucGAGAAucuATsT<br>uAGAUUCUCGAuAAGGAACTsT | 2348<br>2349 |
| AD-20470.1 | KSP | UUCCUUAUCGAGAAUCUAA | 2287 | uuccuuAucGAGAAucuAATsT<br>UuAGAUUCUCGAuAAGGAATsT | 2350<br>2351 |
| AD-20471.1 | KSP | UCCUUAUCGAGAAUCUAAA | 2288 | uccuuAucGAGAAucuAAATsT<br>UUuAGAUUCUCGAuAAGGATsT | 2352<br>2353 |

TABLE 21-continued

Sequences of dsRNA targeted to VEGF and Eg5/KSP (tiling)

| Duplex ID | target gene | target sequence 5' to 3' | SEQ ID NO: | Sense Strand Antisense strand 5' to 3' | SEQ ID NO: |
|---|---|---|---|---|---|
| AD-20472.1 | KSP | CCUUAUCGAGAAUCUAAAC | 2289 | ccuuAucGAGAAucuAAAcTsT GUUuAGAUUCUCGAuAAGGTsT | 2354 2355 |
| AD-20473.1 | KSP | CUUAUCGAGAAUCUAAACU | 2290 | cuuAucGAGAAucuAAAcuTsT AGUUuAGAUUCUCGAuAAGTsT | 2356 2357 |
| AD-20474.1 | KSP | UUAUCGAGAAUCUAAACUA | 2291 | uuAucGAGAAucuAAAcuATsT uAGUUuAGAUUCUCGAuAATsT | 2358 2359 |
| AD-20475.1 | KSP | UAUCGAGAAUCUAAACUAA | 2292 | uAucGAGAAucuAAAcuAATsT UuAGUUuAGAUUCUCGAuATsT | 2360 2361 |
| AD-20476.1 | KSP | AUCGAGAAUCUAAACUAAC | 2293 | AucGAGAAucuAAAcuAAcTsT GUuAGUUuAGAUUCUCGAUTsT | 2362 2363 |
| AD-20477.1 | KSP | CGAGAAUCUAAACUAACUA | 2294 | cGAGAAucuAAAcuAAcuATsT uAGUuAGUUuAGAUUCUCGTsT | 2364 2365 |
| AD-20478.1 | KSP | GAGAAUCUAAACUAACUAG | 2295 | GAGAAucuAAAcuAAcuAGTsT CuAGUuAGUUuAGAUUCUCTsT | 2366 2367 |
| AD-20479.1 | KSP | AGAAUCUAAACUAACUAGA | 2296 | AGAAucuAAAcuAAcuAGATsT UCuAGUuAGUUuAGAUUCUTsT | 2368 2369 |
| AD-20480.1 | KSP | GAAUCUAAACUAACUAGAA | 2297 | GAAucuAAAcuAAcuAGAATsT UUCuAGUuAGUUuAGAUUCTsT | 2370 2371 |
| AD-20481.1 | KSP | AAUCUAAACUAACUAGAAU | 2298 | AAucuAAAcuAAcuAGAAuTsT AUUCuAGUuAGUUuAGAUUTsT | 2372 2373 |
| AD-20482.1 | KSP | AUCUAAACUAACUAGAAUC | 2299 | AucuAAAcuAAcuAGAAucTsT GAUUCuAGUuAGUUuAGAUTsT | 2374 2375 |
| AD-20483.1 | KSP | UCUAAACUAACUAGAAUCC | 2300 | ucuAAAcuAAcuAGAAuccTsT GGAUUCuAGUuAGUUuAGATsT | 2376 2377 |
| AD-20484.1 | KSP | CUAAACUAACUAGAAUCCU | 2301 | cuAAAcuAAcuAGAAuccuTsT AGGAUUCuAGUuAGUUuAGTsT | 2378 2379 |
| AD-20485.1 | KSP | UAAACUAACUAGAAUCCUC | 2302 | uAAAcuAAcuAGAAuccucTsT GAGGAUUCuAGUuAGUUuATsT | 2380 2381 |
| AD-20486.1 | KSP | AAACUAACUAGAAUCCUCC | 2303 | AAAcuAAcuAGAAuccuccTsT GGAGGAUUCuAGUuAGUUUTsT | 2382 2383 |

Example 13

VEGF Targeted dsRNA with a Single Blunt End

A set duplexes targeted to VEGF were designed and synthesized. The set included duplexes tiling 10 nucleotides in each direction of the target sites for AD-3133. Each duplex includes a 2 base overhang at the end corresponding to the 3' end of the antisense strand and no overhang, e.g., a blunt end, at the end corresponding to the 5' end of the antisense strand.

The sequences of each strand of these duplexes are shown in the following table.

Each duplex is assayed for inhibition of expression using the assays described herein. The VEGF duplexes are administered alone and/or in combination with an Eg5/KSP dsRNA (e.g., AD-12115). In some embodiments, the dsRNA are administered in a SNALP formulation as described herein.

TABLE 22

Target sequences of blunt ended dsRNA targeted to VEGF

| duplex ID | SEQ ID NO: | VEGF target sequence 5' to 3' | position on VEGF gene |
|---|---|---|---|
| AD-20447.1 | 2384 | ACCAAGGCCAGCACAUAGG | 1365 |
| AD-20448.1 | 2385 | CCAAGGCCAGCACAUAGGA | 1366 |
| AD-20449.1 | 2386 | CAAGGCCAGCACAUAGGAG | 1367 |
| AD-20450.1 | 2387 | AAGGCCAGCACAUAGGAGA | 1368 |
| AD-20451.1 | 2388 | AGGCCAGCACAUAGGAGAG | 1369 |
| AD-20452.1 | 2389 | GGCCAGCACAUAGGAGAGA | 1370 |
| AD-20453.1 | 2390 | GCCAGCACAUAGGAGAGAU | 1371 |

TABLE 22-continued

Target sequences of blunt ended dsRNA targeted to VEGF

| duplex ID | SEQ ID NO: | VEGF target sequence 5' to 3' | position on VEGF gene |
|---|---|---|---|
| AD-20454.1 | 2391 | CCAGCACAUAGGAGAGAUG | 1372 |
| AD-20455.1 | 2392 | CAGCACAUAGGAGAGAUGA | 1373 |
| AD-20456.1 | 2393 | AGCACAUAGGAGAGAUGAG | 1374 |
| AD-20457.1 | 2394 | CACAUAGGAGAGAUGAGCU | 1376 |
| AD-20458.1 | 2395 | ACAUAGGAGAGAUGAGCUU | 1377 |
| AD-20459.1 | 2396 | CAUAGGAGAGAUGAGCUUC | 1378 |
| AD-20460.1 | 2397 | AUAGGAGAGAUGAGCUUCC | 1379 |
| AD-20461.1 | 2398 | UAGGAGAGAUGAGCUUCCU | 1380 |
| AD-20462.1 | 2399 | AGGAGAGAUGAGCUUCCUA | 1381 |
| AD-20463.1 | 2400 | GGAGAGAUGAGCUUCCUAC | 1382 |
| AD-20464.1 | 2401 | GAGAGAUGAGCUUCCUACA | 1383 |
| AD-20465.1 | 2402 | AGAGAUGAGCUUCCUACAG | 1384 |
| AD-20466.1 | 2403 | GAGAUGAGCUUCCUACAGC | 1385 |

TABLE 23

Strand sequences of blunt ended dsRNA targeted to VEGF

| duplex ID | Sense strand (5' to 3') | SEQ ID NO: | Antisense strand (5' to 3') | SEQ ID NO: |
|---|---|---|---|---|
| AD-20447.1 | ACCAAGGCCAGCACAUAGGAG | 2404 | CUCCUAUGUGCUGGCCUUGGUGA | 2424 |
| AD-20448.1 | CCAAGGCCAGCACAUAGGAGA | 2405 | UCUCCUAUGUGCUGGCCUUGGUG | 2425 |
| AD-20449.1 | CAAGGCCAGCACAUAGGAGAG | 2406 | CUCUCCUAUGUGCUGGCCUUGGU | 2426 |
| AD-20450.1 | AAGGCCAGCACAUAGGAGAGA | 2407 | UCUCUCCUAUGUGCUGGCCUUGG | 2427 |
| AD-20451.1 | AGGCCAGCACAUAGGAGAGAU | 2408 | AUCUCUCCUAUGUGCUGGCCUUG | 2428 |
| AD-20452.1 | GGCCAGCACAUAGGAGAGAUG | 2409 | CAUCUCUCCUAUGUGCUGGCCUU | 2429 |
| AD-20453.1 | GCCAGCACAUAGGAGAGAUGA | 2410 | UCAUCUCUCCUAUGUGCUGGCCU | 2430 |
| AD-20454.1 | CCAGCACAUAGGAGAGAUGAG | 2411 | CUCAUCUCUCCUAUGUGCUGGCC | 2431 |
| AD-20455.1 | CAGCACAUAGGAGAGAUGAGC | 2412 | GCUCAUCUCUCCUAUGUGCUGGC | 2432 |
| AD-20456.1 | AGCACAUAGGAGAGAUGAGCU | 2413 | AGCUCAUCUCUCCUAUGUGCUGG | 2433 |
| AD-20457.1 | CACAUAGGAGAGAUGAGCUUC | 2414 | GAAGCUCAUCUCUCCUAUGUGCU | 2434 |
| AD-20458.1 | ACAUAGGAGAGAUGAGCUUCC | 2415 | GGAAGCUCAUCUCUCCUAUGUGC | 2435 |
| AD-20459.1 | CAUAGGAGAGAUGAGCUUCCU | 2416 | AGGAAGCUCAUCUCUCCUAUGUG | 2436 |
| AD-20460.1 | AUAGGAGAGAUGAGCUUCCUA | 2417 | UAGGAAGCUCAUCUCUCCUAUGU | 2437 |
| AD-20461.1 | UAGGAGAGAUGAGCUUCCUAC | 2418 | GUAGGAAGCUCAUCUCUCCUAUG | 2438 |
| AD-20462.1 | AGGAGAGAUGAGCUUCCUACA | 2419 | UGUAGGAAGCUCAUCUCUCCUAU | 2439 |
| AD-20463.1 | GGAGAGAUGAGCUUCCUACAG | 2420 | CUGUAGGAAGCUCAUCUCUCCUA | 2440 |
| AD-20464.1 | GAGAGAUGAGCUUCCUACAGC | 2421 | GCUGUAGGAAGCUCAUCUCUCCU | 2441 |
| AD-20465.1 | AGAGAUGAGCUUCCUACAGCA | 2422 | UGCUGUAGGAAGCUCAUCUCUCC | 2442 |
| AD-20466.1 | GAGAUGAGCUUCCUACAGCAC | 2423 | GUGCUGUAGGAAGCUCAUCUCUC | 2443 |

Example 14

Inhibition of Eg5/KSP and VEGF Expression in Humans

A human subject is treated with a pharmaceutical composition, e.g., ALNVSP02, having both a SNALP formulated dsRNA targeted to a Eg5/KSP gene and a SNALP formulated dsRNA targeted to a VEGF gene to inhibit expression of the Eg5/KSP and VEGF genes.

A subject in need of treatment is selected or identified. The subject can be in need of cancer treatment, e.g., liver cancer.

At time zero, a suitable first dose of the composition is subcutaneously administered to the subject. The composition is formulated as described herein. After a period of time, the subject's condition is evaluated, e.g., by measurement of tumor growth, measuring serum AFP levels, and the like. This measurement can be accompanied by a measurement of Eg5/KSP and/or VEGF expression in said subject, and/or the products of the successful siRNA-targeting of Eg5/KSP and/or VEGF mRNA. Other relevant criteria can also be measured. The number and strength of doses are adjusted according to the subject's needs.

After treatment, the subject's condition is compared to the condition existing prior to the treatment, or relative to the condition of a similarly afflicted but untreated subject.

Those skilled in the art are familiar with methods and compositions in addition to those specifically set out in the present disclosure which will allow them to practice this invention to the full scope of the claims hereinafter appended.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09006197B2). An electronic copy of the "Sequence Listing" will also be available from the USPTO upon request and payment of the fee set forth in 37 CFR 1.19(b)(3).

We claim:

1. A composition comprising a first double-stranded ribonucleic acid (dsRNA) for inhibiting the expression of a human kinesin family member 11 (Eg5/KSP) gene in a cell and a second dsRNA for inhibiting expression of a human VEGF in a cell, wherein:
   both said first and said second dsRNA are formulated in a stable nucleic acid lipid particle (SNALP) wherein said SNALP comprises DLinDMA, cholesterol, DPPC, and PEG2000-C-DMA;
   said first dsRNA consists of a first sense strand and a first antisense strand, and said first sense strand comprises a first sequence and said first antisense strand comprises a second sequence complementary to at least 15 contiguous nucleotides of SEQ ID NO:1311 (5'-UCGAGAAU-CUAAACUAACU-3'), wherein said first sequence is complementary to said second sequence and wherein said first dsRNA is between 15 and 30 base pairs in length; and
   said second dsRNA consists of a second sense strand and a second antisense strand, said second sense strand comprising a third sequence and said second antisense strand comprising a fourth sequence complementary to at least 15 contiguous nucleotides of SEQ ID NO:1538 (5'-GCACAUAGGAGAGAUGAGCUU-3'), wherein said third sequence is complementary to said fourth sequence and wherein each strand is between 15 and 30 base pairs in length.

2. The composition of claim 1, wherein the first antisense strand comprises a second sequence complementary to SEQ ID NO:1311 (5'-UCGAGAAUCUAAACUAACU-3') and the second antisense strand comprises a fourth sequence complementary to SEQ ID NO:1538 (5'-GCACAUAG-GAGAUGAGCUU-3').

3. The composition of claim 1, wherein the first dsRNA consists of a sense strand consisting of SEQ ID NO:1534 (5'-UCGAGAAUCUAAACUAACUTT-3') and an antisense strand consisting of SEQ ID NO:1535 (5'-AGUUAGUUUA-GAUUCUCGATT-3') and the second dsRNA consists of a sense strand consisting of SEQ ID NO:1536 (5'-GCA-CAUAGGAGAGAUGAGCUU-3'), and an antisense strand consisting of SEQ ID NO:1537 (5'-AAGCUCAUCUCUC-CUAUGUGCUG-3').

4. The composition of claim 3, wherein each strand is modified as follows to include a 2'-O-methyl ribonucleotide as indicated by a lower case letter "c" or "u" and a phosphorothioate as indicated by a lower case letter "s":
   the first dsRNA consists of a sense strand consisting of
   SEQ ID NO:1240 (5'-ucGAGAAucuAAAcuAAcuTsT-3')
   and an antisense strand consisting of
   SEQ ID NO:1241 (5'-AGUuAGUUuAGAUUCUC-GATsT);
   the second dsRNA consists of a sense strand consisting of
   SEQ ID NO:1242 (5'-GcAcAuAGGAGAGAuGAG-CUsU-3')
   and an antisense strand consisting of
   SEQ ID NO:1243 (5'-AAGCUcAUCUCUCCuAuGuG-CusG-3').

5. The composition of claim 1, 2, or 3, wherein said first and second dsRNA comprises at least one modified nucleotide.

6. The composition of claim 5, wherein said modified nucleotide is chosen from the group of: a 2'-O-methyl modified nucleotide, a nucleotide comprising a 5'-phosphorothioate group, and a terminal nucleotide linked to a cholesteryl derivative or dodecanoic acid bisdecylamide group.

7. The composition of claim 5, wherein said modified nucleotide is chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

8. The composition of claim 1, 2, or 3, wherein said first and second dsRNA each comprise at least one 2'-O-methyl modified ribonucleotide and at least one nucleotide comprising a 5'-phosphorothioate group.

9. The composition of claim 1 or 2, wherein each strand of each dsRNA is 19-23 bases in length.

10. The composition of claim 1 or 2, wherein each strand of each dsRNA is 21-23 bases in length.

11. The composition of claim 1 or 2, wherein each strand of the first dsRNA is 21 bases in length and the sense strand of the second dsRNA is 21 bases in length and the antisense strand of the second dsRNA is 23 bases in length.

12. The composition of claim 1, 2, 3, or 4, wherein the first and second dsRNA are present in an equimolar ratio.

13. The composition of claim 1, 2, 3, or 4, comprising the components in the proportions listed in Table 17.

14. The composition of claim 1, 2, 3, or 4, wherein said composition, upon contact with a cell expressing Eg5, inhibits expression of Eg5 by at least 40, 50, 60, 70, 80, or by at least 90%.

15. The composition of claim 1, 2, 3, or 4, wherein said composition, upon contact with a cell expressing VEGF, inhibits expression of VEGF by at least 40, 50, 60, 70, 80, or by at least 90%.

16. The composition of claim 1, 2, 3, or 4, wherein administration of said composition to a cell decreases expression of both Eg5 and VEGF in said cell.

17. The composition of claim 16, wherein the composition is administered in a nM concentration.

18. The composition of claim 1, 2, 3, or 4, wherein administration of said composition to a cell increases mono-aster formation in the cell.

19. The composition of claim 1, 2, 3, or 4, wherein administration of said composition to a mammal results in at least one effect selected from the group consisting of prevention of tumor growth, reduction in tumor growth, or prolonged survival in said mammal.

20. The composition of claim 19, wherein said effect is measured using at least one assay selected from the group consisting of determination of body weight, determination of organ weight, visual inspection, mRNA analysis, serum AFP analysis and survival monitoring.

21. The composition of claim 1, 2, 3, or 4, further comprising Sorafenib.

22. The composition of claim 1 or 2, wherein the first dsRNA contains two overhangs and the second dsRNA contains an overhang at the 3' of the antisense and a blunt end at the 5' end of the antisense strand.

23. A method for inhibiting the expression of Eg5/KSP and VEGF in a cell comprising administering any of the compositions of claim 1, 2, 3, or 4 to the cell.

24. A method for preventing tumor growth, reducing tumor growth, or prolonging survival in a mammal in need of treatment for cancer comprising administering the composition of claim 1, 2, 3, or 4 to said mammal.

25. The method of claim 24, wherein said mammal has liver cancer.

26. The method of claim 24, wherein said mammal is a human with liver cancer.

27. The method of claim 23, further comprising administering Sorafenib.

\* \* \* \* \*